United States Patent
Yu et al.

(10) Patent No.: US 10,906,905 B2
(45) Date of Patent: Feb. 2, 2021

(54) FIVE-MEMBERED HETEROARYL RING BRIDGED RING DERIVATIVE, PREPARATION METHOD THEREFOR AND MEDICAL USE THEREOF

(71) Applicants: Jiangsu Hengrui Medicine Co., Ltd., Lianyungang (CN); SHANGHAI HENGRUI PHARMACEUTICAL CO., LTD., Shanghai (CN)

(72) Inventors: Shanghai Yu, Shanghai (CN); Fanglong Yang, Shanghai (CN); Jingjing Yan, Shanghai (CN); Xiao Wu, Shanghai (CN); Feng He, Shanghai (CN); Weikang Tao, Shanghai (CN)

(73) Assignees: Jiangsu Hengrui Medicine Co., Ltd., Lianyungang (CN); Shanghai Hengrui Pharmaceutical Co., Ltd., Shanghai (CN)

(*) Notice: Subject to any disclaimer, the term of this patent is extended or adjusted under 35 U.S.C. 154(b) by 0 days.

(21) Appl. No.: 16/340,063

(22) PCT Filed: Oct. 13, 2017

(86) PCT No.: PCT/CN2017/106052
§ 371 (c)(1),
(2) Date: Apr. 5, 2019

(87) PCT Pub. No.: WO2018/068759
PCT Pub. Date: Apr. 19, 2018

(65) Prior Publication Data
US 2020/0055852 A1    Feb. 20, 2020

(30) Foreign Application Priority Data

Oct. 14, 2016  (CN) .......................... 2016 1 0899026
Aug. 11, 2017  (CN) .......................... 2017 1 0685501

(51) Int. Cl.
| C07D 471/18 | (2006.01) |
| A61K 31/439 | (2006.01) |
| C07D 471/08 | (2006.01) |
| C07D 519/00 | (2006.01) |

(52) U.S. Cl.
CPC ......... C07D 471/08 (2013.01); C07D 519/00 (2013.01)

(58) Field of Classification Search
CPC .............................. C07D 471/18; A61K 31/439
See application file for complete search history.

(56) References Cited

U.S. PATENT DOCUMENTS

| 2010/0160280 A1 | 6/2010 | Allen |
| 2012/0095075 A1 | 4/2012 | Manoharan |
| 2014/0005183 A1 | 1/2014 | Galatsis |
| 2014/0134133 A1 | 5/2014 | Xi |
| 2015/0284362 A1 | 10/2015 | Bersot |

FOREIGN PATENT DOCUMENTS

| CN | 103925731 | 4/2013 |
| CN | 104177390 | 12/2014 |
| CN | 105175294 | 12/2015 |
| JP | 2011079782 A | 4/2011 |
| WO | WO2004111046 A2 | 12/2004 |
| WO | WO2005092894 A1 | 10/2005 |
| WO | WO2006052568 A2 | 5/2006 |
| WO | WO2007018818 A1 | 2/2007 |
| WO | WO2009155527 A2 | 12/2009 |
| WO | WO2010059943 A2 | 5/2010 |
| WO | WO2010132509 A2 | 11/2010 |
| WO | WO2012000595 A1 | 1/2012 |
| WO | WO2012002680 A2 | 1/2012 |
| WO | WO2012086735 A1 | 6/2012 |
| WO | WO2013009140 A2 | 1/2013 |

(Continued)

OTHER PUBLICATIONS

Golub, Molecular Classificaiton of Cancer, 1999, Science, vol. 531, p. 531-537. (Year: 1999).*

(Continued)

*Primary Examiner* — Karen Cheng
(74) *Attorney, Agent, or Firm* — Morrison & Foerster LLP

(57) ABSTRACT

The present invention relates to a five-membered heteroaryl ring bridged ring derivative, a preparation method therefor and the medical use thereof. In particular, the present invention relates to a new five-membered heteroaryl ring bridged ring derivative as shown in formula (I), a preparation method therefor and a pharmaceutical composition comprising the derivative, and the use thereof as a therapeutic agent, in particular as a TGF-β inhibitor, and the use in the preparation of a drug for treating, preventing or reducing cancers mediated by the over-expression of TGF-β, wherein the definition of each substituent in the general formula (I) is the same as defined in the description.

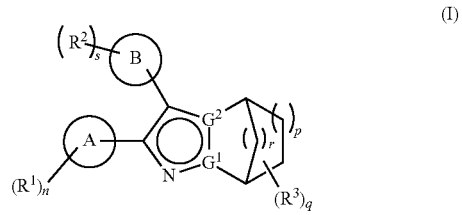

20 Claims, No Drawings

(56) References Cited

FOREIGN PATENT DOCUMENTS

| WO | WO2013101974 A1 | 7/2013 |
| WO | WO2014022128 A1 | 2/2014 |
| WO | WO2014210255 A1 | 12/2014 |
| WO | WO2015039172 A1 | 3/2015 |
| WO | WO2015103137 A1 | 7/2015 |
| WO | WO2016106266 A1 | 6/2016 |

OTHER PUBLICATIONS

Targeted Cancer Therapies Fact Sheet, http://www.cancer.gov/about-cancer/treatment/types/targeted-therapies/targeted-therapies-fact-sheet, accessed Dec. 8, 2015 (Year: 2015).*

'Cancer Prevention Overview', http://www.cancer.gov/cancertopics/pdq/prevention/overview/patient, accessed Nov. 14, 2012 (Year: 2012).*

Gordon, Role of transforming growth factor-b superfamily signaling pathways in human disease, 2008, Biochimica et Biophysica Acta, vol. 1782, p. 197-228 (Year: 2008).*

Alexandrow, M.G.et al. (Apr. 1, 1995). "Transforming Growth Factor β and Cell Cycle Regulation," Cancer Res. 55:1452-1457.

Bitzer, M. et al. (1998). "Transforming Growth Factor-β in Renal Disease," Kidney Blood Press. Res. 21:1-12.

Border, W.A. et al. (Jul. 26, 1990). "Suppression of Experimental Glomerulonephritis by Antiserum Against Transforming Growth Factor β1," Nature 340:371-374.

Brea, R. J. et al. (2005). "Methyl-Blocked Dimeric α,γ,-Peptide Nanotube Segments: Formation of a Peptide Heterodimer Through Backbone-Backbone Interactions," Angew. Chem. Int. Ed. 44:5710-5713.

Hojo, M. et al. (Feb. 11, 1999). "Cyclosporine Induces Cancer Progression by a Cell-Autonomous Mechanism," Nature 397:530-534.

Kottler, U. B. et al. (2005, e-pub. Oct. 31, 2004). "Comparative Effects of TGF-β1 and TGF-β2 on Extracellular Matrix Production, Proliferation, Migration, and Collagen Contraction of Human Tenon's Capsule Fibroblasts in Pseudoexfoliation and Primary Open-Angle Glaucoma," Exp. Eye Res.80:121-134.

Liu, C. et al. (Sep. 29, 2014). "Discovery of New Imidazole Derivatives Containing the 2,4-Dienone Motif with Broad-Spectrum Antifungal and Antibacterial Activity," Molecules 19:15653-15672.

Maehara, Y. et al. (1999). "Role of Transforming Growth Factor-β1 in Invasion and Metastasis in Gastric Carcinoma," J. Clin. Oncol. 17:607-614.

Massagué, J. (1990). "The Transforming Growth Factor-β Family," Ann. Rev, Cell. Biol. 6:594-641.

McCaffrey, T.A. et al. (Dec. 1995). "Decreased Type II/Type I TGF-β Receptor Ratio in Cells Derived From Human Atherosclerotic Lesions. Conversion From an Antiproliferative to Profibrotic Response to TGF-β1," J. Clin. Invest. 96:2667-2675.

Patel, R.V. et al. (2012). "Combination of Bioactive Moieties with Different Heteroatom(s): Application of the Suzuki Cross-Coupling Reaction," Heteroatom Chemistry 23(4):399-410.

Picht, G. et al. (2001). "Transforming Growth Factor β2 Levels in the Aqueous Humor in Different Types of Glaucoma and the Relation to Filtering Bleb Development," Graefe's Arch. Clin. Exp. Ophthalmol 239:199-207.

Picon, A. et al, (Jun. 1998). "A Subset of Metastatic Human Colon Cancers Expresses Elevated Levels of Transforming Growth Factor β1," Cancer Epidemiol. Biomarkers Prev.7:497-504.

Roberts, A.B. et al. (1993). "Physiological Actions and Clinical Applications of Transforming Growth Factorβ (TGF-3)," Growth Factor 8: 1-9.

Saltis, J. et al. (1996). "Regulation and Interaction of Transforming Growth Factor-β With Cardiovascular Cells: Implications for Development and Disease," Clin. Exp. Pharmacol. Physiol. 23:193-200.

Takagi, J. et al. (2013, e-pub. Nov. 3, 2012). "Syntheses of (4,4,5,5-tetramethyl-1,3,2-dioxaborolan-2-yl)arenes Through Pd-Catalyzed Borylation of Arylbromides With the Successive Use of 2,2"-bis(1,3,2-benzodioxaborole) and Pinacol," Tetrahedron Letters54(2):166-169.

Ting, R. et al. (2008, e-pub. May 20, 2008). "Substituent Effects on Aryltrifluoroborate Solvolysis in Water: Implications for Suzuki-Miyaura Coupling and the Design of Stable 18F-Labeled Aryltrifluoroborates for Use in PET Imaging," J. Org. Chem. 73:4662-4670.

* cited by examiner

FIVE-MEMBERED HETEROARYL RING BRIDGED RING DERIVATIVE, PREPARATION METHOD THEREFOR AND MEDICAL USE THEREOF

CROSS REFERENCE TO RELATED APPLICATIONS

This application is a national stage application under 35 U.S.C. § 371 of International Application No.: PCT/CN2017/106052, filed internationally on Oct. 13, 2017, which claims priority benefit to Chinese Application No.: 201610899026.3, filed Oct. 14, 2016 and Chinese Application No.: 201710685501.1, filed Aug. 11, 2017.

FIELD OF THE INVENTION

The present invention belongs to the field of medicine, and relates to a novel five-membered heteroaryl ring fused bridge ring derivative, a preparation method thereof and a pharmaceutical composition comprising the same, as well as a use thereof as a therapeutic agent, in particular as a TGF-β inhibitor, and a use thereof in the preparation of a medicament for treating, preventing or reducing cancer mediated by TGF-β overexpression.

BACKGROUND OF THE INVENTION

Transforming Growth Factor 0 (TGF-β) is a member of the superfamily of dimeric polypeptide growth factors that includes, for example, activins, inhibins, bone morphogenetic proteins (BMPs), growth differentiation factors (GDFs) and Müllerian-inhibiting substance (MIS).

TGF-β has three isoforms of TGF-β1, TGF-β2, and TGF-β3, which are involved in the regulation of cell proliferation and differentiation, wound healing, extracellular matrix production, and immunosuppression. See, for example, Massague, J. Ann. Rev, Cell. Biol. 6: 594-641 (1990); Roberts, A. B. Peptide Growth Factor and Their receptors, 95: 419-472 Berlin: Springer-Verlag (1990); Roberts, A. B. and Sporn M. B. Growth Factor 8: 1-9 (1993); and Alexandrow, M. G., Moses, H. L. Cancer Res. 55:1452-1457 (1995). Three isoforms of TGFβ are present in most cells along with their receptors. Each TGFβ isoform is synthesized as a precursor protein that is cleaved intracellularly into a C-terminal region (latency associated peptide, LAP) and an N-terminal part, called mature or active TGF-β. LAP typically non-covalently bonds to mature TGF-β prior to secretion from cells. The LAP-TGFβ complex cannot bind to the TGFβ receptor, and is not biologically active. TGF-β is generally released (and is active) from the complex by a variety of mechanisms including, for example, interaction with thrombospondin-1 or plasmin. TGF-β1 transduces signals through two highly conserved single transmembrane serine/threonine kinases, i.e. the type I (ALK5) and type II TGF-β receptors. Upon ligand induced oligomerization, the type II receptor hyperphosphorylates serine/threonine residues in the GS region of the ALK5, which leads to activation of the ALK5 by creating a binding site for Smad proteins. The activated ALK5 in turn phosphorylates Smad2 and Smad3 proteins at the C-terminal SSXS-motif, thereby causing their dissociation from the receptor and heteromeric complex formation with Smad4. Smad complexes translocate to the nucleus, assemble with specific DNA-binding co-factors and co-modulators to finally activate transcription of extracellular matrix components and inhibitors of matrix-degrading proteases.

The hyperactivity of the TGF-β signaling pathway is responsible for many human diseases such as excessive deposition of extracellular matrices, abnormally high levels of inflammatory responses, fibrotic disorders, and progressive cancer. The tumor cells and the stromal cells within the tumors in late stages of various cancers generally overexpress TGF-β. This leads to stimulation of angiogenesis and cell motility, suppression of the immune system, and increased interaction of tumor cells with the extracellular matrix (e.g., Hojo, M. et al., Nature 397: 530-534 (1999)). Consequently, the tumor cells become more invasive and metastasize to distant organs (e.g., Maehara, Y. et al., J. Clin. Oncol. 17: 607-614 (1999); Picon, A. et al., Cancer Epidemiol. Biomarkers Prev. 7: 497-504 (1998)).

Numerous experimental animal studies demonstrate an association between glomerular expression of TGF-β and fibrosis, including the Thy-1 rat model of proliferative glomerulonephritis, anti-GBM glomerulonephritis in rabbits, and the 5/6 nephrectomy rat model of focal segmental glomerulosclerosis, as has been reviewed recently (e.g., Bitzer, M. et al., Kidney Blood Press. Res. 21: 1-12 (1998)). Neutralizing antibody to TGF-β improves glomerular histology in the Thy-1 nephritis model (e.g., Border, W. A. et al., Nature 346: 371-374 (1990)).

TGF-β1 and its receptors are overexpressed in injured blood vessels and in fibroproliferative vascular lesions, leading to overproduction of extracellular matrix (e.g., Saltis, J. et al., Clin. Exp. Pharmacol. Physiol. 23: 193-200 (1996); McCaffrey, T. A. et al., J. Clin. Invest. 96: 2667-2675 (1995)).

TGF-β2 levels are increased in most of the eyes with juvenile glaucoma in the aqueous humor of eyes and in nearly half of the eyes with primary open-angle glaucoma (POAG) (e.g., Picht, G. et al., Graefes Arch. Clin. Exp. Ophthalmol. 239: 199-207 (2001)). Both TGF-β1 and TGF-β2 isoforms are reported to increase extracellular matrix production in cultured human Tenon's capsule fibroblasts derived from patients with pseudoexfoliation glaucoma and POAG (e.g., Kottler, U. B. et al., Exp. Eye Res. 80: 121-134 (2005)).

It is therefore desirable to develop inhibitors of TGF-β family members to prevent and/or treat diseases involving such signaling pathways. Patent applications that disclose the modulators (e.g., antagonists) of the TGF-β family member receptors include WO2004111046, WO2012000595, WO2012002680, WO2013009140, WO2016106266.

The inventors hope to develop a new generation of TGF-β receptor kinase inhibitors with high efficacy and low toxicity, so as to achieve better therapeutic results and meet the needs of the market. The present invention provides a novel structure of a TGF-β receptor kinase inhibitor, and it is found that a compound of such a structure has good activity and exhibits excellent TGF-β receptor inhibitory activity.

SUMMARY OF THE INVENTION

The object of the present invention is to provide a compound of formula (I), or a tautomer, mesomer, racemate, enantiomer, diastereomer thereof, or mixture thereof, or a pharmaceutically acceptable salt thereof,

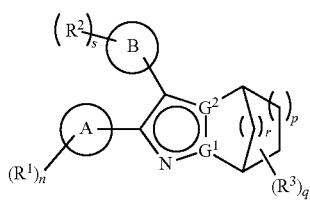

wherein:

is heteroaryl;

$G^1$ and $G^2$ are each N or C, and when $G^1$ is N, $G^2$ is C; and when $G^1$ is C, $G^2$ is N;

ring A is aryl or heteroaryl;

ring B is selected from the group consisting of aryl, heteroaryl and heterocyclyl;

each $R^1$ is identical or different and each is independently selected from the group consisting of hydrogen, halogen, alkyl, alkoxy, haloalkyl, hydroxy, hydroxyalkyl, cyano, amino, nitro, cycloalkyl and heterocyclyl;

each $R^2$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, oxo, —$OR^4$, —$C(O)R^4$, —$C(O)OR^4$, —$NHC(O)OR^4$, —$O(CH_2)_xOR^4$, —$NH(CH_2)_xOR^4$, —$NR^5R^6$, —$O(CH_2)_xC(O)NR^5R^6$, —$NH(CH_2)_xNR^5R^6$ and —$C(O)NR^5R^6$, wherein the alkyl, alkoxy, cycloalkyl, heterocyclyl, aryl and heteroaryl are each independently optionally substituted by one or more substituents selected from the group consisting of hydrogen, alkyl, alkoxy, halogen, haloalkyl, hydroxy, hydroxyalkyl, cyano, amino, nitro, cycloalkyl, heterocyclyl, aryl, heteroaryl, —$OR^7$, —$C(O)R^7$, —$C(O)OR^7$, —$S(O)_mR^7$, —$S(O)_mNR^8R^9$, —$NR^8R^9$ and —$C(O)NR^8R^9$;

each $R^3$ is identical or different and each is independently selected from the group consisting of hydrogen, halogen, alkyl, alkoxy, haloalkyl, hydroxy, hydroxyalkyl, amino, cyano and nitro;

$R^4$ is selected from the group consisting of hydrogen, alkyl, haloalkyl, amino, alkenyl, alkynyl, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

$R^5$ and $R^6$ are each independently selected from the group consisting of hydrogen, alkyl, haloalkyl, alkoxy, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl, heteroaryl, —$NR^8R^9$, —$C(O)R^7$, —$C(O)OR^7$, —$S(O)_mNR^8R^9$ and —$S(O)_mR^7$;

$R^7$ is selected from the group consisting of hydrogen, alkyl, haloalkyl, hydroxyalkyl, amino, alkenyl, alkynyl, cycloalkyl, heterocyclyl, aryl and heteroaryl;

$R^8$ and $R^9$ are each independently selected from the group consisting of hydrogen, alkyl, haloalkyl, cycloalkyl, heterocyclyl, aryl and heteroaryl;

n is 0, 1 or 2;
s is 0, 1 or 2;
r is 1 or 2;
p is 0, 1 or 2;
q is 0, 1 or 2;
m is 0, 1 or 2; and
x is 0, 1, 2, 3 or 4.

In a preferred embodiment of the present invention, the compound of formula (I) is a compound of formula (II):

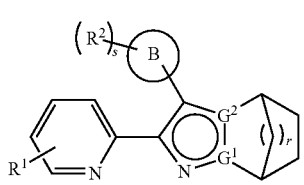

or a tautomer, mesomer, racemate, enantiomer, diastereomer thereof, or mixture thereof, or a pharmaceutically acceptable salt thereof, wherein:

ring B, $G^1$, $G^2$, $R^1$, $R^2$, s and r are as defined in formula (I).

In a preferred embodiment of the present invention, the compound of formula (I) is a compound of formula (II-1):

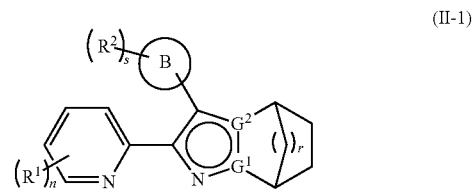

or a tautomer, mesomer, racemate, enantiomer, diastereomer thereof, or mixture thereof, or a pharmaceutically acceptable salt thereof, wherein:

ring B, $G^1$, $G^2$, $R^1$, $R^2$, s, n and r are as defined in claim 1.

In a preferred embodiment of the present invention, in the compound of formula (I), $R^1$ is alkyl or halogen, preferably methyl, ethyl, chlorine, bromine or fluorine.

In a preferred embodiment of the present invention, in the compound of formula (I), ring B is selected from the group consisting of:

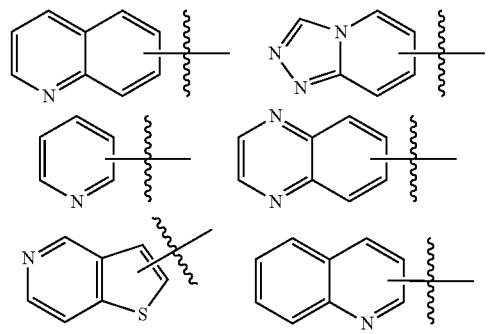

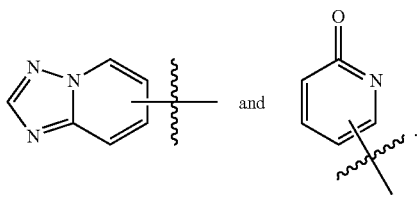

In a preferred embodiment of the present invention, the compound of formula (I) is a compound of formula (III) or (IV):

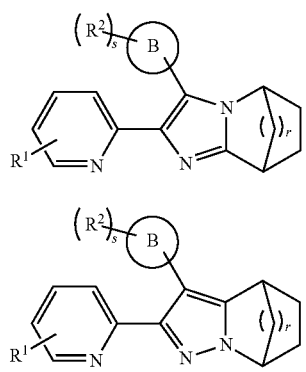

(III)

(IV)

or a tautomer, mesomer, racemate, enantiomer, diastereomer thereof, or mixture thereof, or a pharmaceutically acceptable salt thereof, wherein:

ring B, $R^1$, $R^2$, s and r are as defined in formula (I).

In a preferred embodiment of the present invention, the compound of formula (I) is a compound of formula (V) or (VI):

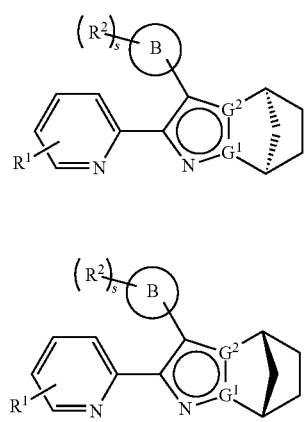

(V)

(VI)

or a tautomer, mesomer, racemate, enantiomer, diastereomer thereof, or mixture thereof, or a pharmaceutically acceptable salt thereof, wherein:

ring B, $G^1$, $G^2$, $R^1$, $R^2$ and s are as defined in formula (I).

In a preferred embodiment of the present invention, the compound of formula (V) is a compound of formula (V-1) or (V-2):

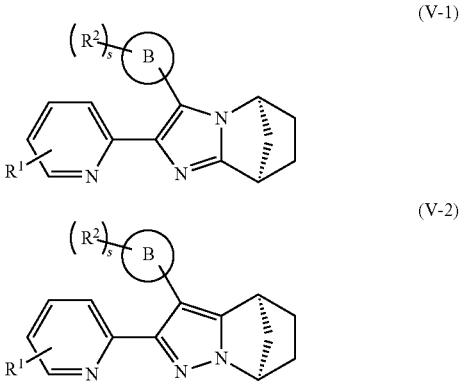

(V-1)

(V-2)

or a tautomer, mesomer, racemate, enantiomer, diastereomer thereof, or mixture thereof, or a pharmaceutically acceptable salt thereof, wherein:

ring B, $R^1$, $R^2$ and s are as defined in formula (I).

In a preferred embodiment of the present invention, the compound of formula (VI) is a compound of formula (VI-1) or (VI-2):

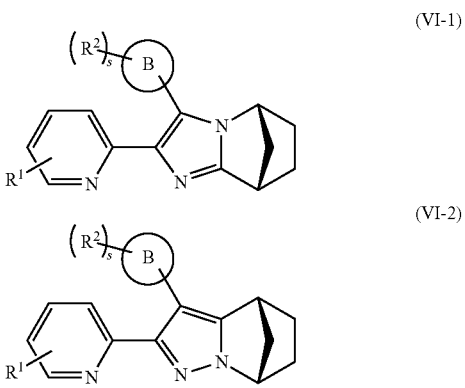

(VI-1)

(VI-2)

or a tautomer, mesomer, racemate, enantiomer, diastereomer thereof, or mixture thereof, or a pharmaceutically acceptable salt thereof, wherein:

ring B, $R^1$, $R^2$ and s are as defined in formula (I).

The compound of the present invention includes all conformational isomers thereof, e.g., cis-isomers and trans-isomers; and all optical isomers and stereoisomers and mixtures thereof. The compound of the present invention has asymmetric centers, and therefore there are different enantiomeric and diastereomeric isomers. The present invention relates to the use of the compound of the present invention, and the pharmaceutical composition applying and comprising the same, and the therapeutic method thereof. The present invention relates to the use of all such tautomers and mixtures thereof.

Typical compounds of the present invention include, but are not limited to the following:

| Example No. | Structure |
|---|---|
| 1 | 6-(2-(6-methylpyridin-2-yl)-5,6,7,8-tetrahydro-5,8-methanoimidazo[1,2-a]pyridin-3-yl)quinoline-4-carboxamide |
| 1-1 | 6-((5S,8R)-2-(6-methylpyridin-2-yl)-5,6,7,8-tetrahydro-5,8-methanoimidazo[1,2-a]pyridin-3-yl)quinoline-4-carboxamide |
| 1-2 | 6-((5R,8S)-2-(6-methylpyridin-2-yl)-5,6,7,8-tetrahydro-5,8-methanoimidazo[1,2-a]pyridin-3-yl)quinoline-4-carboxamide |
| 2 | 6-(2-(6-methylpyridin-2-yl)-5,6,7,8-tetrahydro-5,8-methanoimidazo[1,2-a]pyridin-3-yl)-[1,2,4]triazolo[4,3-a]pyridine-3-carboxamide |
| 2-1 | 6-((5S,8R)-2-(6-methylpyridin-2-yl)-5,6,7,8-tetrahydro-5,8-methanoimidazo[1,2-a]pyridin-3-yl)-[1,2,4]triazolo[4,3-a]pyridine-3-carboxamide |
| 2-2 | 6-((5R,8S)-2-(6-methylpyridin-2-yl)-5,6,7,8-tetrahydro-5,8-methanoimidazo[1,2-a] |

| Example No. | Structure |
|---|---|
| | pyridin-3-yl)-[1,2,4]triazolo[4,3-a]pyridine-3-carboxamide |
| 3 | 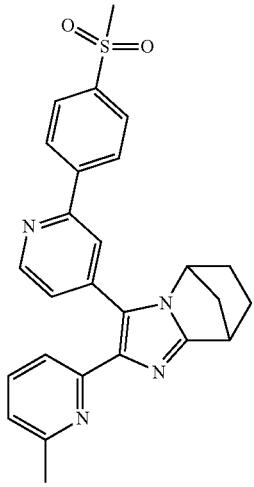<br>3<br><br>2-(6-methylpyridin-2-yl)-3-(2-(4-(methylsulfonyl)phenyl)pyridin-4-yl)-5,6,7,8-tetrahydro-5,8-methanoimidazo[1,2-a]pyridine |
| 3-1 | 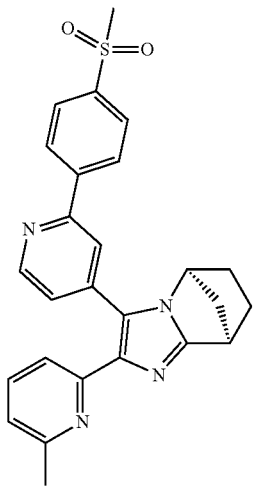<br>3-1<br><br>(5S,8R)-2-(6-methylpyridin-2-yl)-3-(2-(4-(methylsulfonyl)phenyl)pyridin-4-yl)-5,6,7,8-tetrahydro-5,8-methanoimidazo[1,2-a]pyridine |
| 3-2 | 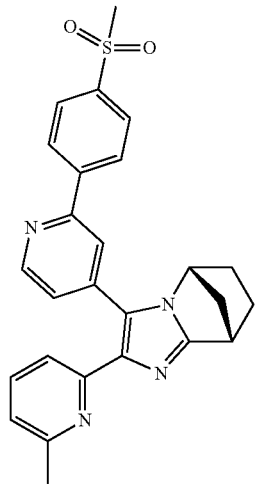<br>3-2<br><br>(5R,8S)-2-(6-methylpyridin-2-yl)-3-(2-(4-(methylsulfonyl)phenyl)pyridin-4-yl)-5,6,7,8-tetrahydro-5,8-methanoimidazo[1,2-a]pyridine |
| 4 | 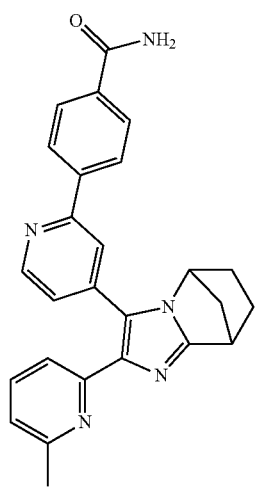<br>4<br><br>4-(4-(2-(6-methylpyridin-2-yl)-5,6,7,8-tetrahydro-5,8-methanoimidazo[1,2-a]pyridin-3-yl)pyridin-2-yl)benzamide |

| Example No. | Structure |
|---|---|
| 4-1 | 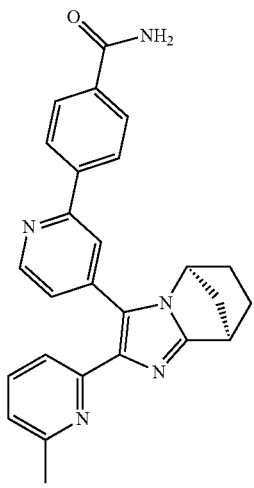<br>4-1<br>4-(4-((5S,8R)-2-(6-methylpyridin-2-yl)-5,6,7,8-tetrahydro-5,8-methanoimidazo[1,2-a]pyridin-3-yl)pyridin-2-yl)benzamide |
| 4-2 | 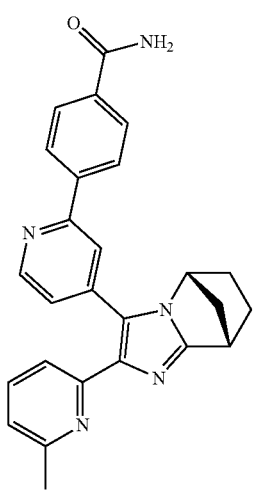<br>4-2<br>4-(4-((5R,8S)-2-(6-methylpyridin-2-yl)-5,6,7,8-tetrahydro-5,8-methanoimidazo[1,2-a]pyridin-3-yl)pyridin-2-yl)benzamide |

| Example No. | Structure |
|---|---|
| 5 | 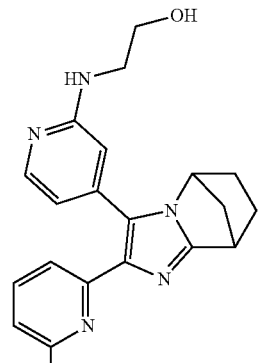<br>5<br>2-((4-(2-(6-methylpyridin-2-yl)-5,6,7,8-tetrahydro-5,8-methanoimidazo[1,2-a]pyridin-3-yl)pyridin-2-yl)amino)ethanol |
| 5-1 | 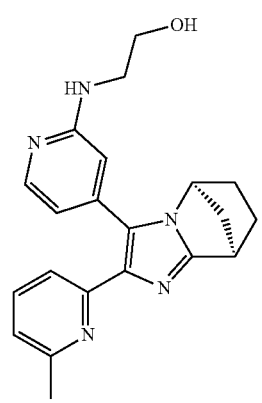<br>5-1<br>2-((4-((5S,8R)-2-(6-methylpyridin-2-yl)-5,6,7,8-tetrahydro-5,8-methanoimidazo[1,2-a]pyridin-3-yl)pyridin-2-yl)amino)ethanol |
| 5-2 | 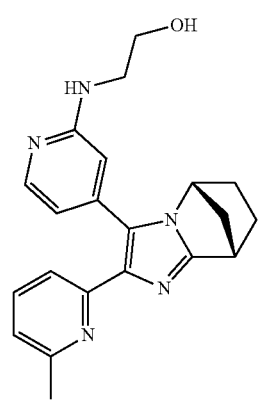<br>5-2<br>2-((4-((5R,8S)-2-(6-methylpyridin-2-yl)-5,6,7,8-tetrahydro-5,8-methanoimidazo[1,2-a]pyridin-3-yl)pyridin-2-yl)amino)ethanol |

| Example No. | Structure |
|---|---|
| 6 | 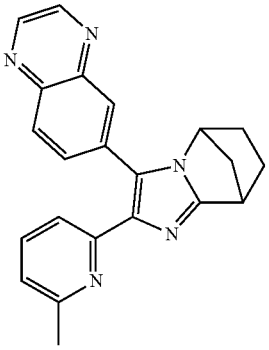<br>6<br>2-(6-methylpyridin-2-yl)-3-(quinoxalin-6-yl)-5,6,7,8-tetrahydro-5,8-methanoimidazo[1,2-a]pyridine |
| 6-1 | 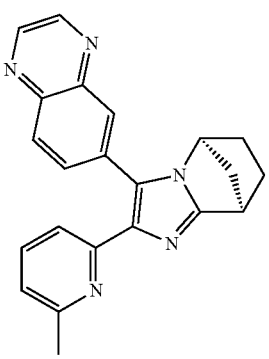<br>6-1<br>(5S,8R)-2-(6-methylpyridin-2-yl)-3-(quinoxalin-6-yl)-5,6,7,8-tetrahydro-5,8-methanoimidazo[1,2-a]pyridine |
| 6-2 | 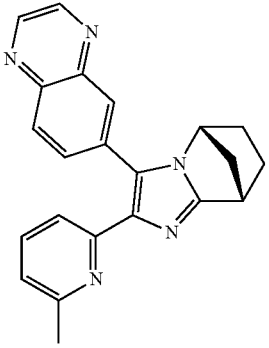<br>6-2<br>(5R,8S)-2-(6-methylpyridin-2-yl)-3-(quinoxalin-6-yl)-5,6,7,8-tetrahydro-5,8-methanoimidazo[1,2-a]pyridine |
| 7 | 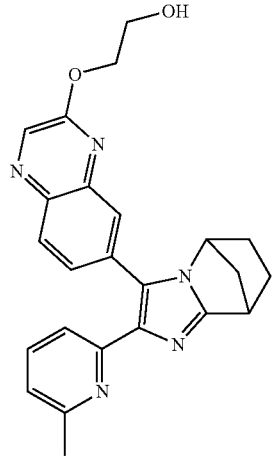<br>7<br>2-((7-2-(6-methylpyridin-2-yl)-5,6,7,8-terahydro-5,8-methanoimidazo[1,2-a]pyridin-3-yl)quinoxalin-2-yl)oxy)ethanol |
| 8 | 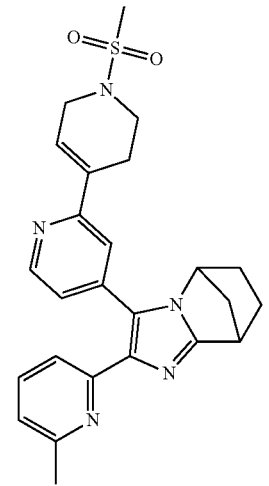<br>8<br>2-(6-methylpyridin-2-yl)-3-(1'-(methylsulfonyl)-1',2',3',6',-tetrahydro-[2,4'-bipyridin]-4-yl)-5,6,7,8-tetrahydro-5,8-methanoimidazo[1,2-a]pyridine |
| 9 | 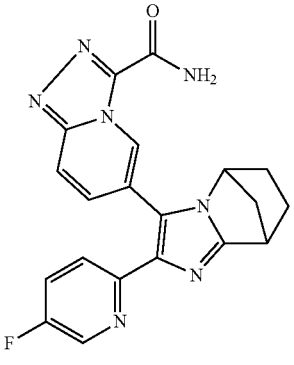<br>9 |

| Example No. | Structure |
|---|---|
| | 6-(2-(5-fluoropyridin-2-yl)-5,6,7,8-tetrahydro-5,8-methanoimidazo[1,2-a]pyridin-3-yl)-[1,2,4]triazolo[4,3-a]pyridine-3-carboxamide |
| 9-1 | 9-1 |
| | 6-((5S,8R)-2-(5-fluoropyridin-2-yl)-5,6,7,8-tetrahydro-5,8-methanoimidazo[1,2-a]pyridin-3-yl)-[1,2,4]triazolo[4,3-a]pyridine-3-carboxamide |
| 9-2 | 9-2 |
| | 6-((5R,8S)-2-(5-fluoropyridin-2-yl)-5,6,7,8-tetrahydro-5,8-methanoimidazo[1,2-a]pyridin-3-yl)-[1,2,4]triazolo[4,3-a]pyridine-3-carboxamide |
| 10 | 10 |
| | 2-(2-(6-methylpyridin-2-yl)-5,6,7,8-tetrahydro-5,8-methanoimidazo[1,2-a]pyridin-3-yl)thieno[3,2-c]pyridine |
| 11 | 11 |
| | 3-([1,2,4]triazolo[1,5-a]pyridin-6-yl)-2-(6-methylpyridin-2-yl)-5,6,7,8-tetrahydro-5,8-methanoimidazo[1,2-a]pyridine |
| 12 | 12 |
| | 3-(2-(1-methyl-1H-pyrazol-4-yl)pyridin-4-yl)-2-(6-methylpyridin-2-yl)-5,6,7,8-tetrahydro-5,8-methanoimidazo[1,2-a]pyridine |
| 12-1 | 12-1 |
| | 3-((5S,8R)-2-(1-methyl-1H-pyrazol-4-yl)pyridin-4-yl)-2-(6-methylpyridin-2-yl)-5,6,7,8-tetrahydro-5,8-methanoimidazo[1,2-a]pyridine |

| Example No. | Structure |
|---|---|
| 12-2 | 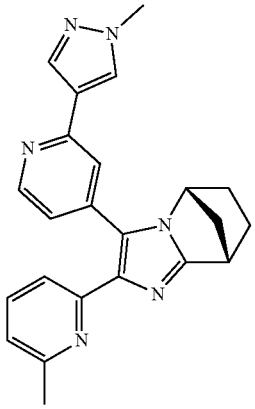<br>12-2<br>3-((5R,8S)-2-(1-methyl-1H-pyrazol-4-yl)pyridin-4-yl)-2-(6-methylpyridin-2-yl)-5,6,7,8-tetrahydro-5,8-methanoimidazol[1,2-a]pyridine |
| 13 | 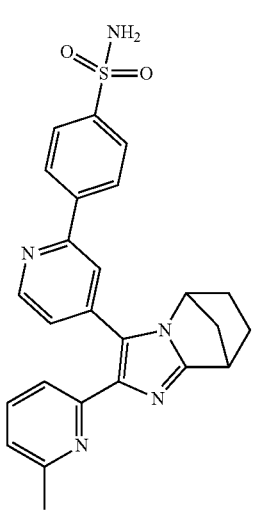<br>13<br>4-(4-(2-(6-methylpyridin-2-yl)-5,6,7,8-tetrahydro-5,8-methanoimidazo[1,2-a]pyridin-3-yl)pyridin-2-yl)benzenesulfonamide |
| 13-1 | 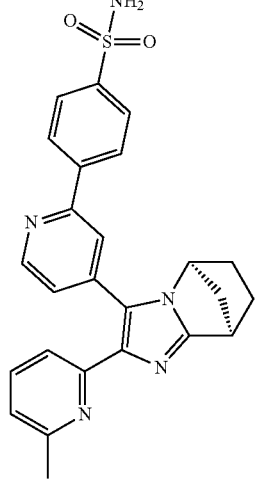<br>13-1<br>4-(4-((5S,8R)-2-(6-methylpyridin-2-yl)-5,6,7,8-tetrahydro-5,8-methanoimidazo[1,2-a]pyridin-3-yl)pyridin-2-yl)benzenesulfonamide |
| 13-2 | 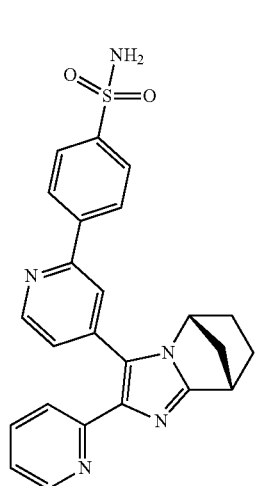<br>13-2<br>4-(4-((5R,8S)-2-(6-methylpyridin-2-yl)-5,6,7,8-tetrahydro-5,8-methanoimidazo[1,2-a]pyridin-3-yl)pyridin-2-yl)benzenesulfonamide |

| Example No. | Structure |
|---|---|
| 14 | 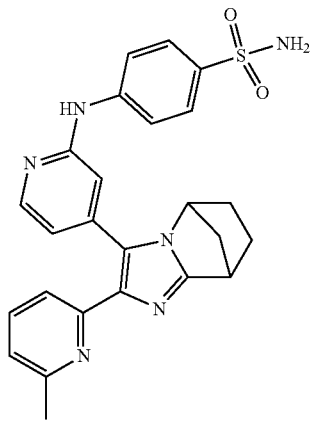

14

4-((4-(2-(6-methylpyridin-2-yl)-5,6,7,8-tetrahydro-5,8-methanoimidazo[1,2-a]pyridin-3-yl)pyridin-2-yl)amino)benzenesulfonamide |
| 15 | 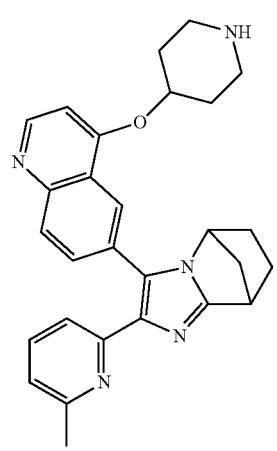

15

2-(6-methylpyridin-2-yl)-3-(4-(piperidin-4-yloxy)quinolin-6-yl)-5,6,7,8-tetrahydro-5,8-methanoimidazo[1,2-a]pyridine |
| 16 | 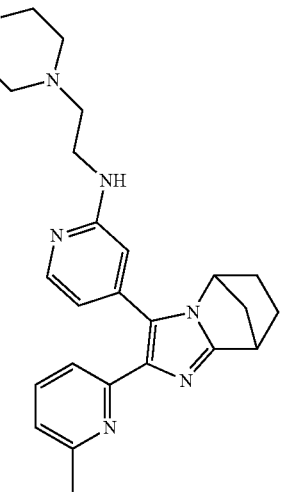

16

4-(2-(6-methylpyridin-2-yl)-5,6,7,8-tetrahydro-5,8-methanoimidazo[1,2-a]pyridin-3-yl)-N-(2-morpholinoethyl)pyridin-2-amine |
| 16-1 | 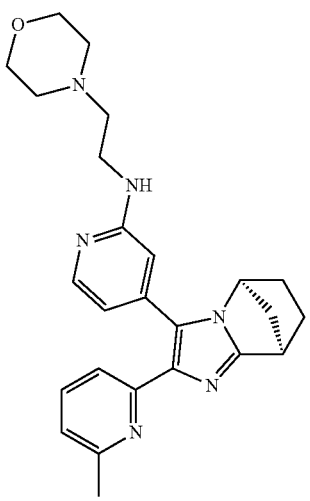

16-1

4-((5S,8R)-2-(6-methylpyridin-2-yl)-5,6,7,8-tetrahydro-5,8-methanoimidazo[1,2-a]pyridin-3-yl)-N-(2-morpholinoethyl)pyridin-2-amine |

| Example No. | Structure |
|---|---|
| 16-2 | 16-2<br>4-((5R,8S)-2-(6-methylpyridin-2-yl)-5,6,7,8-tetrahydro-5,8-methanoimidazo[1,2-a]pyridin-3-yl)-N-(2-morpholinoethyl)pyridin-2-amine |
| 17 | 17<br>4-(4-(2-(6-methylpyridin-2-yl)-5,6,7,8-tetrahydro-5,8-methanoimidazo[1,2-a]pyridin-3-yl)pyridin-2-yl)-N-(tetrahydro-2H-pyran-4-yl)benzamide |

| Example No. | Structure |
|---|---|
| 17-1 | 17-1<br>4-(4-((5S,8R)-2-(6-methylpyridin-2-yl)-5,6,7,8-tetrahydro-5,8-methanoimidazo[1,2-a]pyridin-3-yl)pyridin-2-yl)-N-(tetrahydro-2H-pyran-4-yl)benzamide |
| 17-2 | 17-2<br>4-(4-((5R,8S)-2-(6-methylpyridin-2-yl)-5,6,7,8-tetrahydro-5,8-methanoimidazo[1,2-a]pyridin-3-yl)pyridin-2-yl)-N-(tetrahydro-2H-pyran-4-yl)benzamide |

| Example No. | Structure |
|---|---|
| 18 | 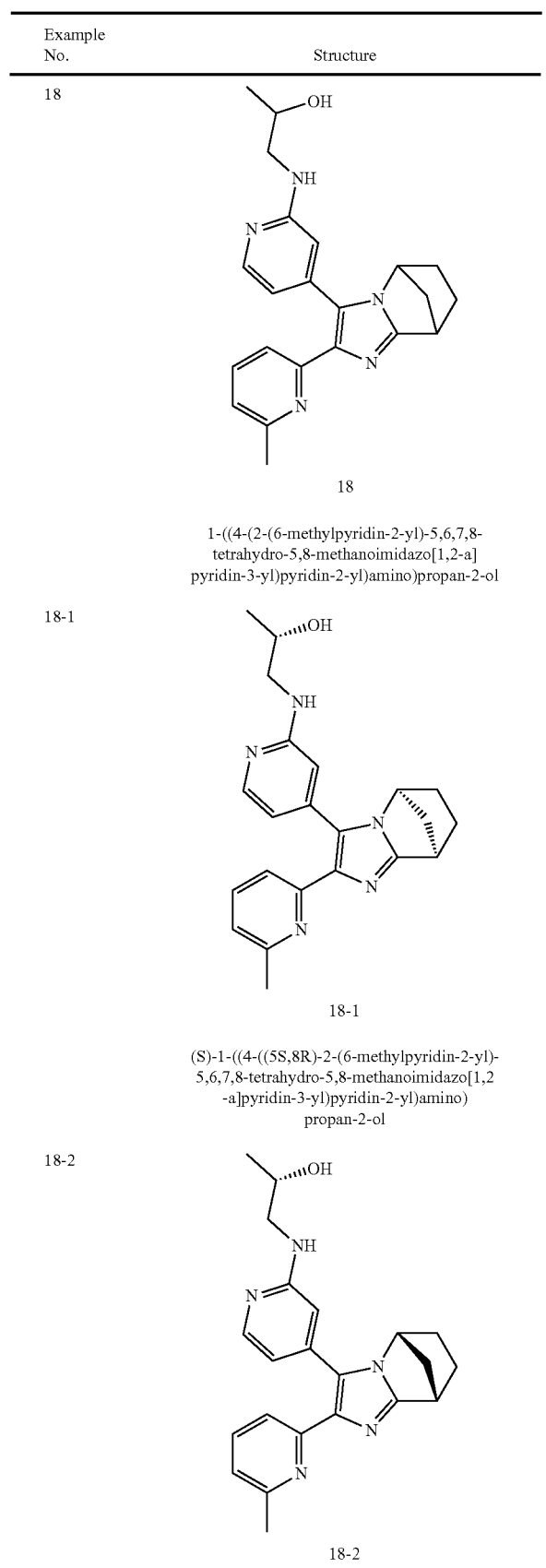
1-((4-(2-(6-methylpyridin-2-yl)-5,6,7,8-tetrahydro-5,8-methanoimidazo[1,2-a]pyridin-3-yl)pyridin-2-yl)amino)propan-2-ol |
| 18-1 | (S)-1-((4-((5S,8R)-2-(6-methylpyridin-2-yl)-5,6,7,8-tetrahydro-5,8-methanoimidazo[1,2-a]pyridin-3-yl)pyridin-2-yl)amino)propan-2-ol |
| 18-2 | |

| Example No. | Structure |
|---|---|
|  | (S)-1-((4-((5R,8S)-2-(6-methylpyridin-2-yl)-5,6,7,8-tetrahydro-5,8-methanoimidazo[1,2-a]pyridin-3-yl)pyridin-2-yl)amino)propan-2-ol |
| 19 | 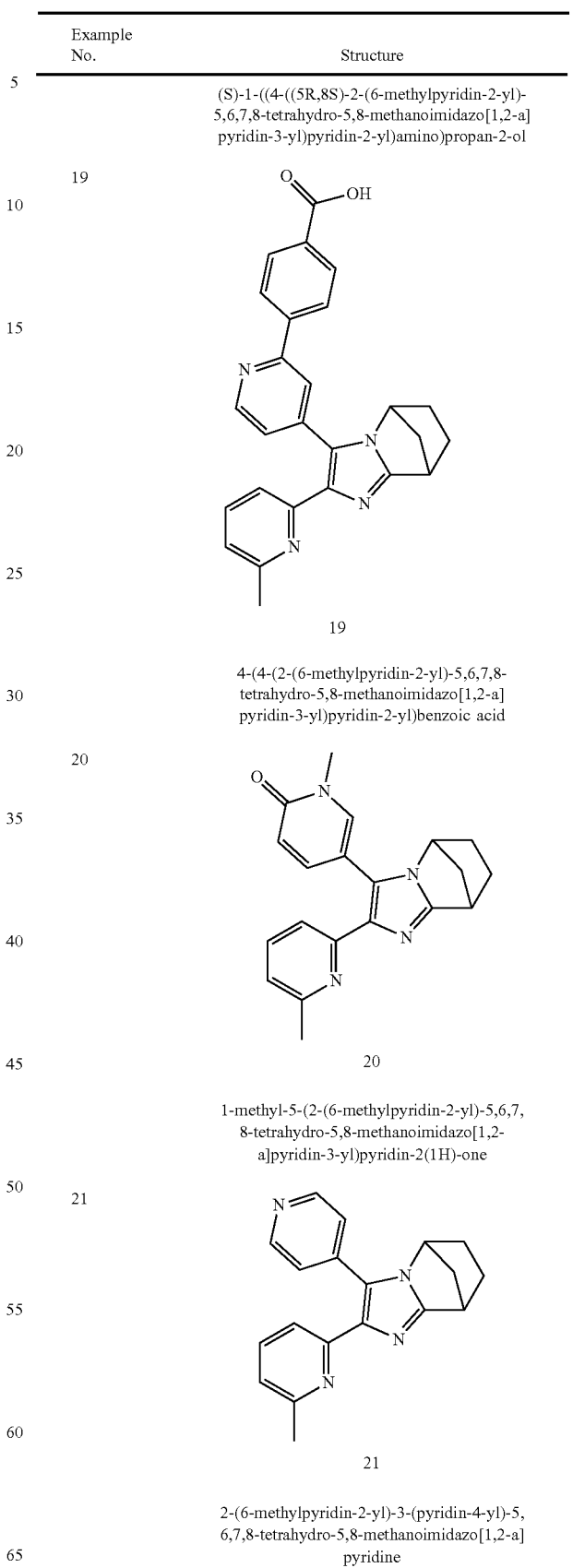
4-(4-(2-(6-methylpyridin-2-yl)-5,6,7,8-tetrahydro-5,8-methanoimidazo[1,2-a]pyridin-3-yl)pyridin-2-yl)benzoic acid |
| 20 | 1-methyl-5-(2-(6-methylpyridin-2-yl)-5,6,7,8-tetrahydro-5,8-methanoimidazo[1,2-a]pyridin-3-yl)pyridin-2(1H)-one |
| 21 | 2-(6-methylpyridin-2-yl)-3-(pyridin-4-yl)-5,6,7,8-tetrahydro-5,8-methanoimidazo[1,2-a]pyridine |

| Example No. | Structure |
|---|---|
| 22 | *[structure 22]* |

22

3-(2-fluoropyridin-4-yl)-2-(6-methylpyridin-2-yl)-5,6,7,8-tetrahydro-5,8-methanoimidazo[1,2-a]pyridine

| Example No. | Structure |
|---|---|
| 23 | *[structure 23]* |

23

3-((4-(2-(6-methylpyridin-2-yl)-5,6,7,8-tetrahydro-5,8-methanoimidazo[1,2-a]pyridin-3-yl)pyridin-2-yl)amino)propane-1,2-diol

| 23-1 | *[structure 23-1]* |

23-1

| Example No. | Structure |
|---|---|
|  | (S)-3-((4-((5S,8R)-2-(6-methylpyridin-2-yl)-5,6,7,8-tetrahydro-5,8-methanoimidazo[1,2-a]pyridin-3-yl)pyridin-2-yl)amino)propane-1,2-diol |
| 23-2 | *[structure 23-2]* |

23-2

(S)-3-((4-((5R,8S)-2-(6-methylpyridin-2-yl)-5,6,7,8-tetrahydro-5,8-methanoimidazo[1,2-a]pyridin-3-yl)pyridin-2-yl)amino)propane-1,2-diol

| 24 | *[structure 24]* |

24

$N^1$, $N^1$-dimethyl-$N^2$-(4-(2-(6-methylpyridin-2-yl)-5,6,7,8-tetrahydro-5,8-methanoimidazo[1,2-a]pyridin-3-yl)pyridin-2-yl)ethane-1,2-diamine

| Example No. | Structure |
|---|---|
| 24-1 | 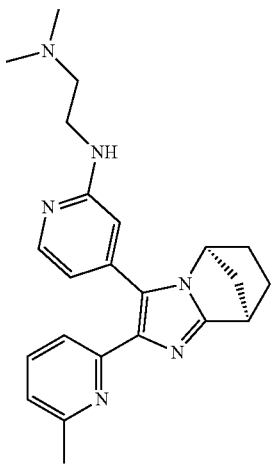<br>24-1<br>N$^1$, N$^1$-dimethyl-N$^2$-(4-((5S,8R)-2-(6-methylpyridin-2-yl)-5,6,7,8-tetrahydro-5,8-methanoimidazo[1,2-a]pyridin-3-yl)pyridin-2-yl)ethane-1,2-diamine |
| 24-2 | 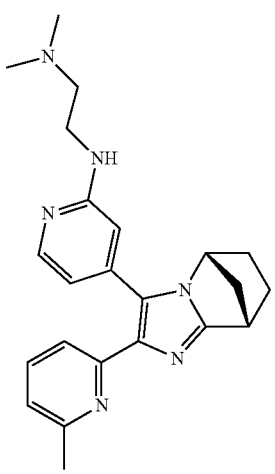<br>24-2<br>N$^1$,N$^1$-dimethyl-N$^2$-(4-((5R,8S)-2-(6-methylpyridin-2-yl)-5,6,7,8-tetrahydro-5,8-methanoimidazo[1,2-a]pyridin-3-yl)pyridin-2-yl)ethane-1,2-diamine |

| Example No. | Structure |
|---|---|
| 25 | 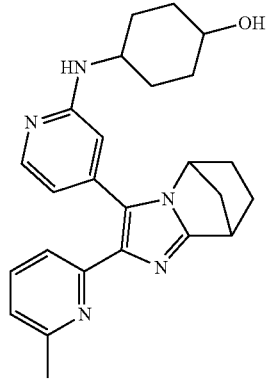<br>25<br>4-((4-(2-(6-methylpyridin-2-yl)-5,6,7,8-tetrahydro-5,8-methanoimidazo[1,2-a]pyridin-3-yl)pyridin-2-yl)amino)cyclohexanol |
| 26 | 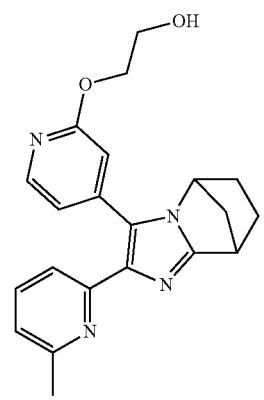<br>26<br>2-((4-(2-(6-methylpyridin-2-yl)-5,6,7,8-tetrahydro-5,8-methanoimidazo[1,2-a]pyridin-3-yl)pyridin-2-yl)oxy)ethanol |
| 27 | 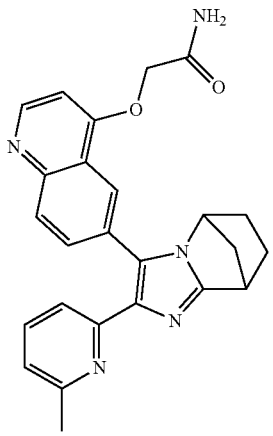<br>27<br>2-((6-(2-(6-methylpyridin-2-yl)-5,6,7,8-tetrahydro-5,8-methanoimidazo[1,2-a]pyridin-3-yl)quinolin-4-yl)oxy)acetamide |

-continued

| Example No. | Structure |
|---|---|
| 28 | 28<br>tert-butyl4-(2-(6-methylpyridin-2-yl)-5,6,7,8-tetrahydro-5,8-methanoimidazo[1,2-a]pyridin-3-yl)quinoline-6-carboxylate |
| 29 | 29<br>4-(2-(6-methylpyridin-2-yl)-5,6,7,8-tetrahydro-5,8-methanoimidazo[1,2-a]pyridin-3-yl)quinoline-6-carboxamide |
| 30 | 30<br>4-(2-(6-methylpyridin-2-yl)-5,6,7,8-tetrahydro-5,8-methanoimidazo[1,2-a]pyridin-3-yl)nicotinamide |

-continued

| Example No. | Structure |
|---|---|
| 30-1 | 30-1<br>4-((5S,8R)-2-(6-methylpyridin-2-yl)-5,6,7,8-tetrahydro-5,8-methanoimidazo[1,2-a]pyridin-3-yl)nicotinamide |
| 30-2 | 30-2<br>4-((5R,8S)-2-(6-methylpyridin-2-yl)-5,6,7,8-tetrahydro-5,8-methanoimidazo[1,2-a]pyridin-3-yl)nicotinamide |
| 31 | 31<br>tert-butyl(4-(2-(6-methylpyridin-2-yl)-5,6,7,8-tetrahydro-5,8-methanoimidazo[1,2-a]pyridin-3-yl)pyridin-2-yl)carbamate |

| Example No. | Structure |
|---|---|
| 32 | 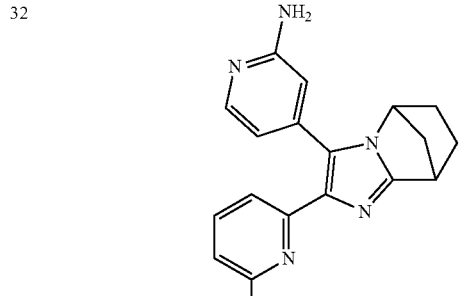<br>32<br>4-(2-(6-methylpyridin-2-yl)-5,6,7,8-tetrahydro-5,8-methanoimidazo[1,2-a]pyridin-3-yl)pyridin-2-amine |
| 33 | 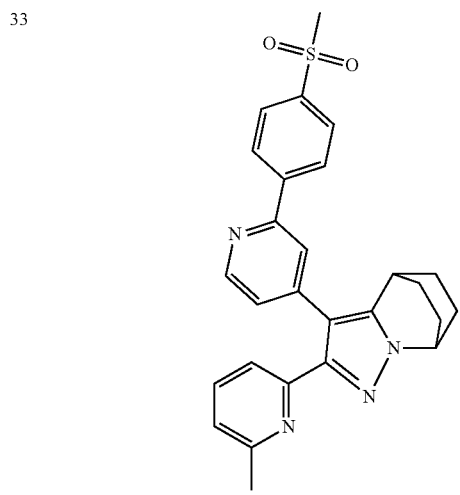<br>33<br>2-(6-methylpyridin-2-yl)-3-(2-(4-(methylsulfonyl)phenyl)pyridin-4-yl)-4,5,6,7-tetrahydro-4,7-ethanopyrazolo[1,5-a]pyridine |
| 34 | 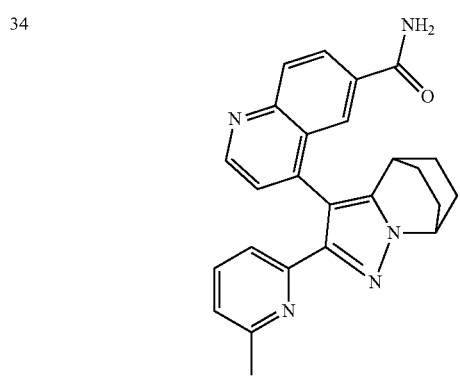<br>34<br>4-(2-(6-methylpyridin-2-yl)-4,5,6,7-tetrahydro-4,7-ethanopyrazolo[1,5-a]pyridin-3-yl)quinoline-6-carboxamide |
| 35 | 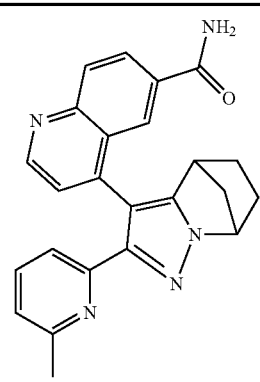<br>35<br>4-(2-(6-methylpyridin-2-yl)-4,5,6,7-tetrahydro-4,7-methanopyrazolo[1,5-a]pyridin-3-yl)quinoline-6-carboxamide |
| 35-1 | 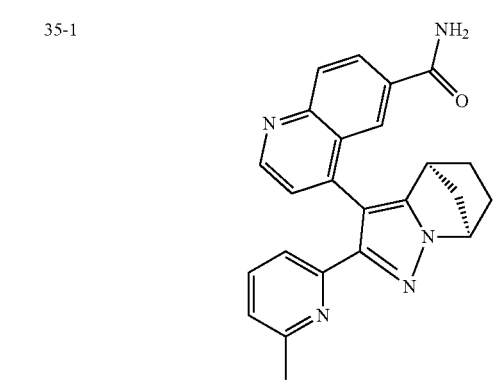<br>35-1<br>4-((4S,7R)-2-(6-methylpyridin-2-yl)-4,5,6,7-tetrahydro-4,7-methanopyrazoloa][1,5-pyridin-3-yl)quinoline-6-carboxamide |
| 35-2 | 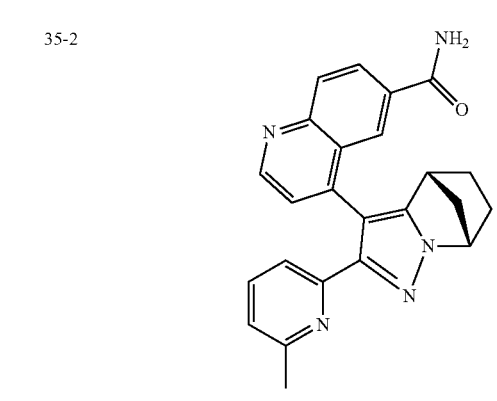<br>35-2<br>4-((4R,7S)-2-(6-methylpyridin-2-yl)-4,5,6,7-tetrahydro-4,7-methanopyrazolo[1,5-a]pyridin-3-yl)quinoline-6-carboxamide |

| Example No. | Structure |
|---|---|
| 36 | 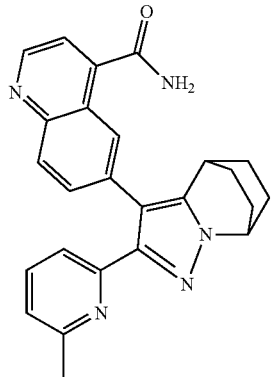<br>36<br>6-(2-(6-methylpyridin-2-yl)-4,5,6,7-tetrahydro-4,7-ethanopyrazolo[1,5-a]pyridin-3-yl)quinoline-4-carboxamide |
| 37 | 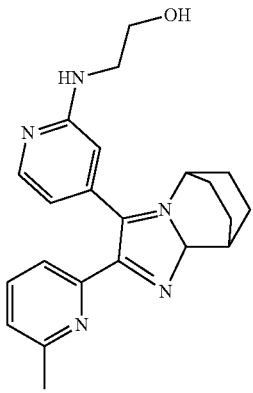<br>37<br>2-((4-(2-(6-methylpyridin-2-yl)-4,5,6,7-tetrahydro-4,7-ethanopyrazolo[1,5-a]pyridin-3-yl)pyridin-2-yl)amino)ethanol |
| 38 | 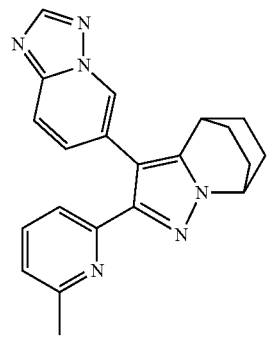<br>38<br>3-([1,2,4]triazolo[1,5-a]pyridin-6-yl)-2-(6-methylpyridin-2-yl)-4,5,6,7-tetrahydro-4,7-ethanopyrazolo[1,5-a]pyridine |

| Example No. | Structure |
|---|---|
| 39 | 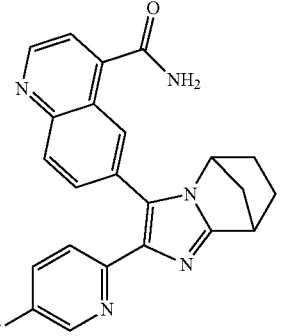<br>39<br>6-(2-(5-fluoropyridin-2-yl)-5,6,7,8-tetrahydro-5,8-methanoimidazo[1,2-a]pyridin-3-yl)quinoline-4-carboxamide |
| 39-1 | 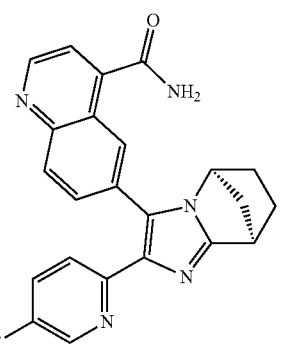<br>39-1<br>6-((5S,8R)-2-(5-fluoropyridin-2-yl)-5,6,7,8-tetrahydro-5,8-methanoimidazo[1,2-a]pyridin-3-yl)quinoline-4-carboxamide |
| 39-2 | 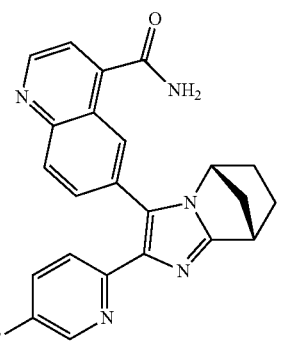<br>39-2<br>6-((5R,8S)-2-(5-fluoropyridin-2-yl)-5,6,7,8-tetrahydro-5,8-methanoimidazo[1,2-a]pyridin-3-yl)quinoline-4-carboxamide |

| Example No. | Structure |
|---|---|
| 40 | 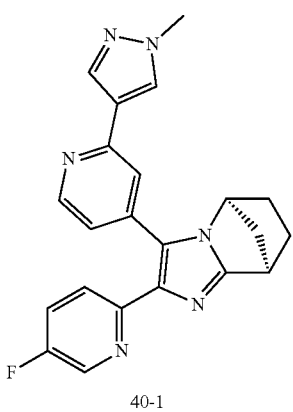 [SMILES: Cn1cc(-c2cc(-c3c(-c4ccc(F)cn4)nc4n3[C@H]3CC[C@@H]4C3)ccn2)cn1]<br>40<br>2-(5-fluoropyridin-2-yl)-3-(2-(1-methyl-1H-pyrazol-4-yl)pyridin-4-yl)-5,6,7,8-tetrahydro-5,8-methanoimidazo[1,2-a]pyridine |
| 40-1 | 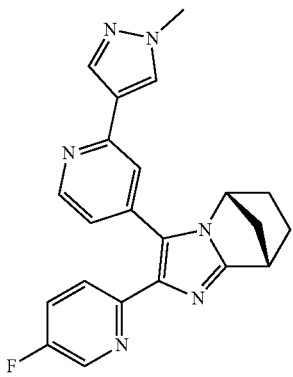<br>40-1<br>(5S,8R)-2-(5-fluoropyridin-2-yl)-3-(2-(1-methyl-1H-pyrazol-4-yl)pyridin-4-yl)-5,6,7,8-tetrahydro-5,8-methanoimidazo[1,2-a]pyridine |
| 40-2 | (5R,8S)-2-(5-fluoropyridin-2-yl)-3-(2-(1-methyl-1H-pyrazol-4-yl)pyridin-4-yl)-5,6,7,8-tetrahydro-5,8-methanoimidazo[1,2-a]pyridine |

| Example No. | Structure |
|---|---|
| 41 | 41<br>4-(4-(2-(5-fluoropyridin-2-yl)-5,6,7,8-tetrahydro-5,8-methanoimidazo[1,2-a]pyridin-3-yl)pyridin-2-yl)benzamide |
| 41-1 | 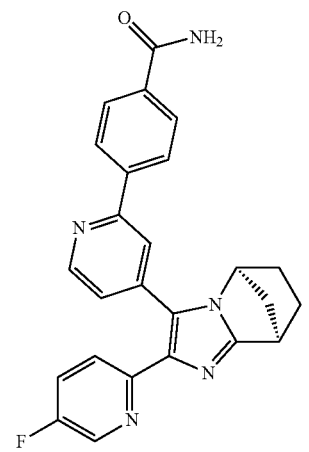<br>41-1<br>4-(4-((5S,8R)-2-(5-fluoropyridin-2-yl)-5,6,7,8-tetrahydro-5,8-methanoimidazo[1,2-a]pyridin-3-yl)pyridin-2-yl)benzamide |

| Example No. | Structure |
|---|---|
| 41-2 | 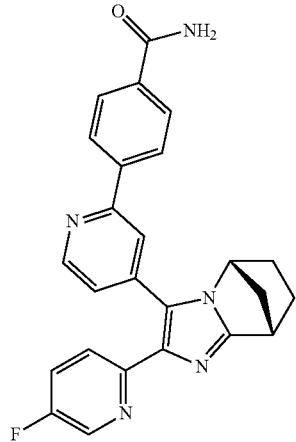<br>41-2<br>4-(4-((5R,8S)-2-(5-fluoropyridin-2-yl)-5,6,7,8-tetrahydro-5,8-methanoimidazo[1,2-a]pyridin-3-yl)pyridin-2-yl)benzamide |
| 42 | 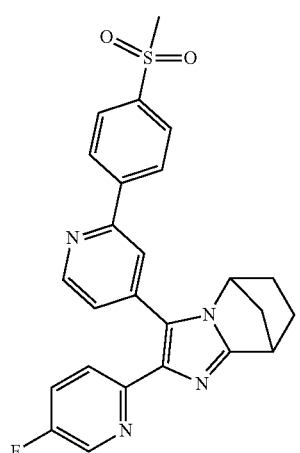<br>42<br>2-(5-fluoropyridin-2-yl)-3-(2-(4-(methylsulfonyl)phenyl)pyridin-4-yl)-5,6,7,8-tetrahydro-5,8-methanoimidazo[1,2-a]pyridine |

| Example No. | Structure |
|---|---|
| 42-1 | 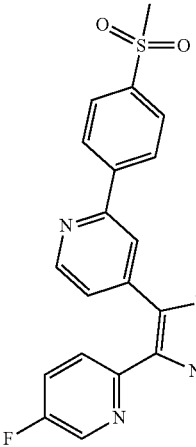<br>42-1<br>(5S,8R)-2-(5-fluoropyridin-2-yl)-3-(2-(4-(methylsulfonyl)phenyl)pyridin-4-yl)-5,6,7,8-tetrahydro-5,8-methanoimidazo[1,2-a]pyridine |
| 42-2 | 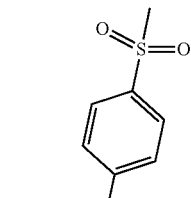<br>42-2<br>(5R,8S)-2-(5-fluoropyridin-2-yl)-3-(2-(4-(methylsulfonyl)phenyl)pyridin-4-yl)-5,6,7,8-tetrahydro-5,8-methanoimidazo[1,2-a]pyridine |

| Example No. | Structure |
|---|---|
| 43 | 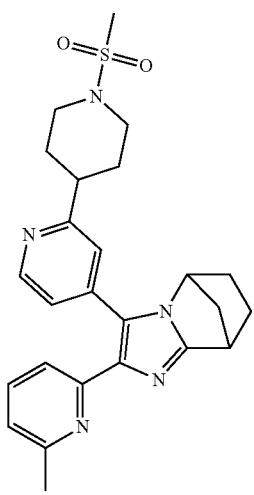

43

2-(6-methylpyridin-2-yl)-3-(2-(1-(methylsulfonyl)-1H-pyrazol-4-yl)pyridin-4-yl)-5,6,7,8-tetrahydro-5,8-methanoimidazo[1,2-a]pyridine |
| 44 |

2-(6-methylpyridin-2-yl)-3-(2-(1-(methylsulfonyl)piperidin-4-yl)pyridin-4-yl)-5,6,7,8-tetrahydro-5,8-methanoimidazo[1,2-a]pyridine |

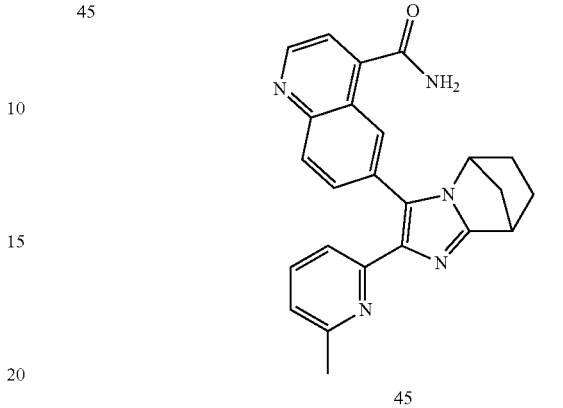

| Example No. | Structure |
|---|---|
| 45 |

45

6-(2-(pyridin-2-yl)-5,6,7,8-tetrahydro-5,8-methanoimidazo[1,2-a]pyridin-3-yl)quinoline-4-carboxamide |
| 45-1 | 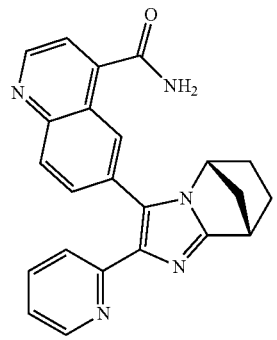

45-1

6-((5S,8R)-2-(pyridin-2-yl)-5,6,7,8-tetrahydro-5,8-methanoimidazo[1,2-a]pyridin-3-yl)quinoline-4-carboxamide |
| 45-2 |

45-2

6-((5R,8S)-2-(pyridin-2-yl)-5,6,7,8-tetrahydro-5,8-methanolmidazo[1,2-a]pyridin-3-yl)quinoline-4-carboxamide |

| Example No. | Structure |
|---|---|
| 46 | 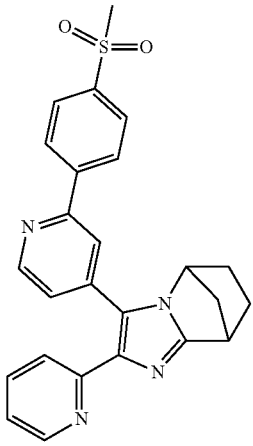<br>46<br>3-(2-(4-(methylsulfonyl)phenyl)pyridin-4-yl)-2-(pyridin-2-yl)-5,6,7,8-tetrahydro-5,8-methanoimidazo[1,2-a]pyridine |
| 46-1 | 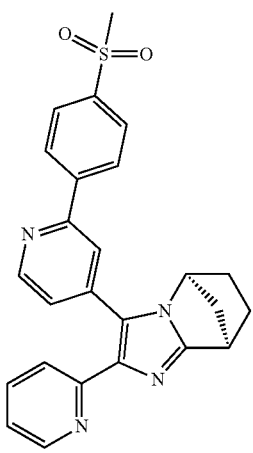<br>46-1<br>(5S,8R)-3-(2-(4-(methylsulfonyl)phenyl)pyridin-4-yl)-2-(pyridin-2-yl)-5,6,7,8-tetrahydro-5,8-methanoimidazo[1,2-a]pyridine |

| Example No. | Structure |
|---|---|
| 46-2 | 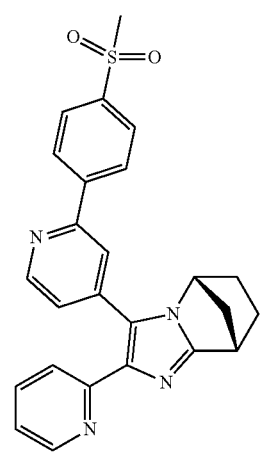<br>46-2<br>(5R,8S)-3-(2-(4-(methylsulfonyl)phenyl)pyridin-4-yl)-2-(pyridin-2-yl)-5,6,7,8-tetrahydro-5,8-methanoimidazo[1,2-a]pyridine |
| 47 | 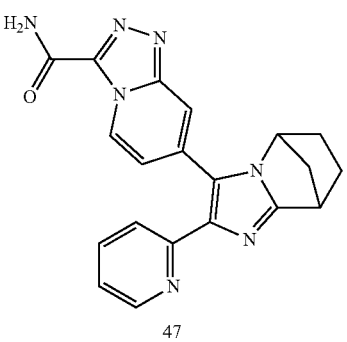 [SMILES: NC(=O)c1nnc2cc(-c3c(-c4ccccn4)nc4n3C3CCC4C3)ccn12]<br>47<br>7-(2-(pyridin-2-yl)-5,6,7,8-tetrahydro-5,8-methanoimidazo[1,2-a]pyridin-3-yl)-[1,2,4]triazolo[4,3-a]pyridine-3-carboxamide |
| 47-1 | 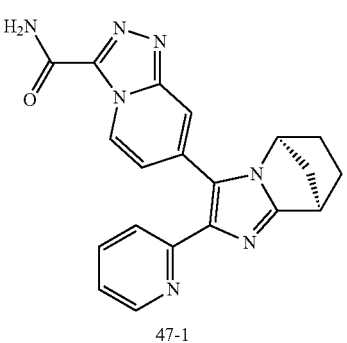<br>47-1<br>7-((5S,8R)-2-(pyridin-2-yl)-5,6,7,8-tetrahydro-5,8-methanoimidazo[1,2-a]pyridin-3-yl)-[1,2,4]triazolo[4,3-a]pyridine-3-carboxamide |

| Example No. | Structure |
|---|---|
| 47-2 | 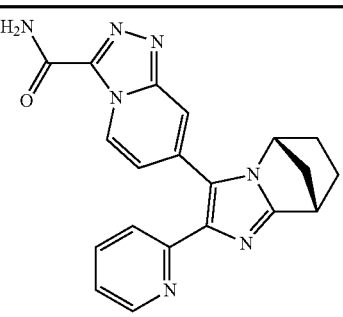<br>47-2<br>7-((5R,8S)-2-(pyridin-2-yl)-5,6,7,8-tetrahydro-5,8-methanoimidazo[1,2-a]pyridin-3-yl)-[1,2,4]triazolo[4,3-a]pyridine-3-carboxamide | or a tautomer, mesomer, racemate, enantiomer, diastereomer thereof, or mixture thereof, or a pharmaceutically acceptable salt thereof.

In another aspect, the present invention relates to a compound of formula (I-B):

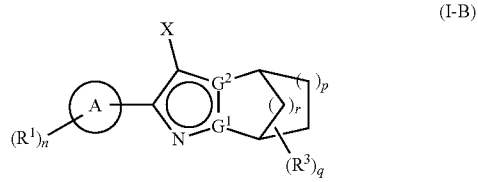 (I-B)

or a tautomer, mesomer, racemate, enantiomer, diastereomer thereof, or mixture thereof, or a pharmaceutically acceptable salt thereof, wherein:

X is halogen;

ring A, $G^1$, $G^2$, $R^1$, $R^3$, r, p, n and q are as defined in formula (I).

In a preferred embodiment of the present invention, the compound of formula (I-B) is a compound of formula (I-Bb):

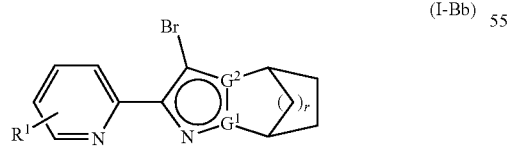 (I-Bb)

wherein:

$G^1$, $G^2$, $R^1$ and r are as defined in formula (I).

In a preferred embodiment of the present invention, the compound of formula (I-B) is a compound of formula (I-Bc):

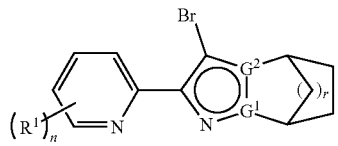 (I-Bc)

wherein:

$G^1$, $G^2$, $R^1$, n and r are as defined in claim 1.

In a preferred embodiment of the present invention, the compound of formula (I-Bb) is a compound of formula (I-Bb-1) or (I-Bb-2):

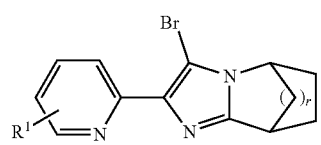 (I-Bb-1)

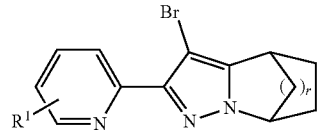 (I-Bb-2)

wherein:

$R^1$ and r are as defined in formula (I).

The compounds of formula (I-B) include, but are not limited to the following:

| Example No. | Structure and name |
|---|---|
| 1f | 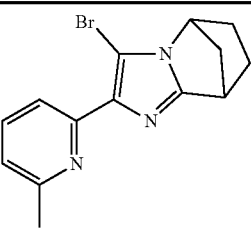<br>1f<br>3-bromo-2-(6-methylpyridin-2-yl)-5,6,7,8-tetrahydro-5,8-methanoimidazo[1,2-a]pyridine 1f |
| 1f-1 | 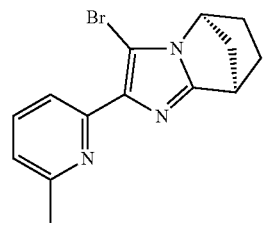<br>1f-1<br>(5S,8R)-3-bromo-2-(6-methylpyridin-2-yl)-5,6,7,8-tetrahydro-5,8-methanoimidazo[1,2-a]pyridine 1f-1 |

| Example No. | Structure and name |
|---|---|
| 1f-2 | 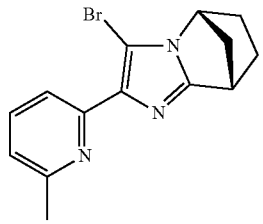<br>1f-2<br>(5R,8S)-3-bromo-2-(6-methylpyridin-2-yl)-5,6,7,8-tetrahydro-5,8-methanoimidazo[1,2-a]pyridine 1f-2 |
| 9d | 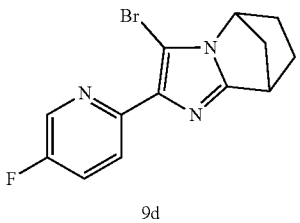 [SMILES: Fc1ccc(-c2nc3n(c2Br)C2CCC3C2)nc1]<br>9d<br>3-bromo-2-(5-fluoropyridin-2-yl)-5,6,7,8-tetrahydro-5,8-methanoimidazo[1,2-a]pyridine 9d |
| 39c-1 | 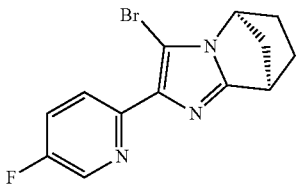<br>39c-1<br>(5S,8R)-3-bromo-2-(5-fluoropyridin-2-yl)-5,6,7,8-tetrahydro-5,8-methanoimidazo[1,2-a]pyridine 39c-1 |
| 39c-2 | 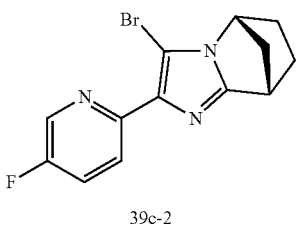 [SMILES: Fc1ccc(-c2nc3n(c2Br)[C@@H]2CC[C@H]3C2)nc1]<br>39c-2<br>(5R,8S)-3-bromo-2-(5-fluoropyridin-2-yl)-5,6,7,8-tetrahydro-5,8-methanoimidazo[1,2-a]pyridine 39c-2 |
| 33i | 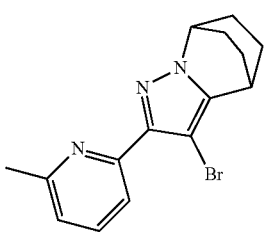<br>33i<br>3-bromo-2-(6-methylpyridin-2-yl)-4,5,6,7-tetrahydro-4,7-ethanopyrazolo[1,5-a]pyridine 33i |
| 35e | 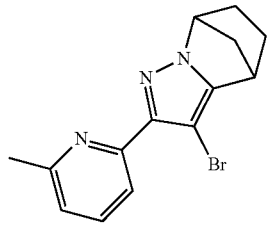<br>35e<br>3-bromo-2-(6-methylpyridin-2-yl)-4,5,6,7-tetrahydro-4,7-methanopyrazolo[1,5-a]pyridine 35e |
| 35e-1 | 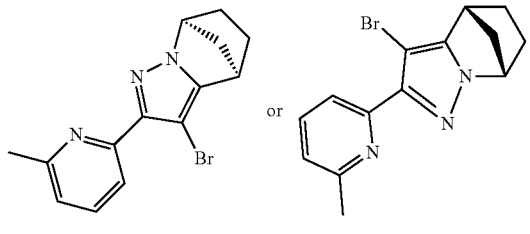<br>35e-1<br>(4R,7S)-3-bromo-2-(6-methylpyridin-2-yl)-4,5,6,7-tetrahydro-4,7-methanopyrazolo[1,5-a]pyridine 35e-1 |
| 35e-2 | 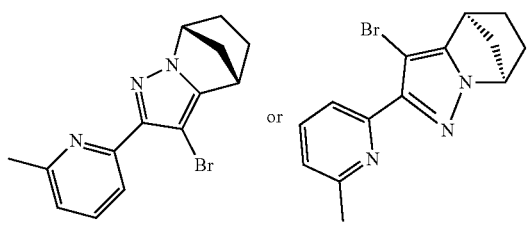<br>35e-2<br>(4S,7R)-3-bromo-2-(6-methylpyridin-2-yl)-4,5,6,7-tetrahydro-4,7-methanopyrazolo[1,5-a]pyridine 35e-2 |
| 45b | 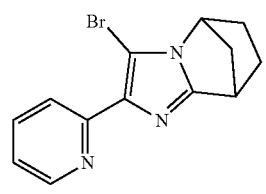<br>45b<br>3-bromo-2-(pyridin-2-yl)-5,6,7,8-tetrahydro-5,8-methanoimidazo[1,2-a]pyridine 45b |

| Example No. | Structure and name |
|---|---|
| 45b-1 | 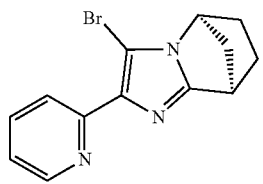<br>45b-1<br>(5S,8R)-3-bromo-2-(pyridin-2-yl)-5,6,7,8-tetrahydro-5,8-methanoimidazo[1,2-a]pyridine 45b-1 |
| 45b-2 | 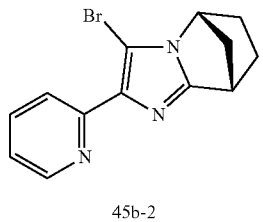 [SMILES: Brc1c(-c2ccccn2)nc2n1[C@@H]1CC[C@H]2C1]<br>45b-2<br>(5R,8S)-3-bromo-2-(pyridin-2-yl)-5,6,7,8-tetrahydro-5,8-methanoimidazo[1,2-a]pyridine 45b-2 |

In another aspect, the present invention relates to a method for preparing the compound of formula (I), comprising a step of:

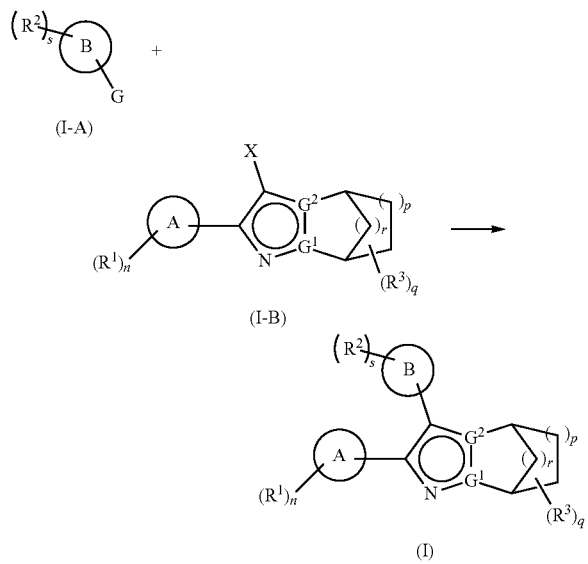

subjecting a compound of formula (I-A) and a compound of formula (I-B) to a Suzuki reaction under an alkaline condition in the presence of a catalyst to obtain the compound of formula (I), wherein:
G is selected from the group consisting of halogen,

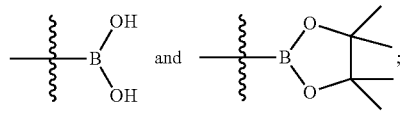

X is halogen, and preferably chlorine or bromine;
ring A, ring B, $G^1$, $G^2$, $R^1$~$R^3$, r, p, n, s and q are as defined in formula (I).

In another aspect, the present invention relates to a pharmaceutical composition comprising a therapeutically effective amount of the compound of formula (I), or a tautomer, mesomer, racemate, enantiomer, diastereomer thereof, or mixture thereof, or a pharmaceutically acceptable salt thereof, and one or more pharmaceutically acceptable carriers, diluents or excipients. The present invention also relates to a method for preparing the aforementioned composition, comprising a step of mixing the compound of formula (I), or a tautomer, mesomer, racemate, enantiomer, diastereomer thereof, or mixture thereof, or a pharmaceutically acceptable salt thereof, with one or more pharmaceutically acceptable carriers, diluents or excipients.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for inhibiting the TGF-β and/or activin (especially human TGF-β and/or activin) signaling pathway.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for treating, preventing or reducing the metastasis of tumor cells, particularly human tumor cells.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for treating, preventing or reducing cancer mediated by TGF-β overexpression, particularly in the preparation of a medicament for treating, preventing, or reducing cancer mediated by TGF-β overexpression by inhibiting the human TGF-β signaling pathway.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same, in the preparation of a medicament for treating, preventing or reducing a disease (especially in human) selected from the group consisting of vascular injury, glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, cystic fibrosis, interstitial lung disease, acute lung injury, adult respiratory distress syndrome, myelodysplastic syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, intimal thickening, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, glaucoma, high intraocular pressure, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, radiation-induced fibrosis, thrombosis, tumor metastasis growth, multiple myeloma, melanoma, glioma, glioblastomas, leukemia, sarcomas, leiomyomas, mesothelioma, breast cancer, cervical cancer, lung cancer, stomach cancer, rectal cancer, colon cancer, pancreatic cancer, brain cancer, skin cancer, oral cancer, prostate cancer, bone cancer, kidney cancer, ovarian cancer, bladder cancer and liver cancer.

The present invention further relates to a method for treating, preventing or reducing the metastasis of human tumor cells, comprising administering to a patient in need thereof a therapeutically effective amount of the compound of formula (I), or a tautomer, mesomer, racemate, enantiomer, diastereomer thereof, or mixture thereof, or a pharmaceutically acceptable salt thereof, or the pharmaceutical composition comprising the same.

The present invention further relates to a method for treating, preventing or reducing cancer mediated by TGF-β overexpression, in particular a method for treating, preventing or reducing cancer mediated by TGF-β overexpression by inhibiting the TGF-β signaling pathway, comprising administering to a patient in need thereof a therapeutically effective amount of the compound of formula (I), or a tautomer, mesomer, racemate, enantiomer, diastereomer thereof, or mixture thereof, or a pharmaceutically acceptable salt thereof, or the pharmaceutical composition comprising the same.

The present invention further relates to a method for treating, preventing or reducing a disease (especially in human) selected from the group consisting of vascular injury, glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, cystic fibrosis, interstitial lung disease, acute lung injury, adult respiratory distress syndrome, myelodysplastic syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, intimal thickening, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, glaucoma, high intraocular pressure, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, radiation-induced fibrosis, thrombosis, tumor metastasis growth, multiple myeloma, melanoma, glioma, glioblastomas, leukemia, sarcomas, leiomyomas, mesothelioma, breast cancer, cervical cancer, lung cancer, stomach cancer, rectal cancer, colon cancer, pancreatic cancer, brain cancer, skin cancer, oral cancer, prostate cancer, bone cancer, kidney cancer, ovarian cancer, bladder cancer and liver cancer, comprising administering to a patient in need thereof a therapeutically effective amount of the compound of formula (I), or a tautomer, mesomer, racemate, enantiomer, diastereomer thereof, or mixture thereof, or a pharmaceutically acceptable salt thereof, or the pharmaceutical composition comprising the same.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use as a medicament.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use as a TGF-β receptor kinase inhibitor.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating, preventing or reducing the metastasis of tumor cells, particularly human tumor cells.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating, preventing or reducing cancer mediated by TGF-β overexpression, in particular in treating, preventing or reducing cancer mediated by TGF-β overexpression by inhibiting the TGF-β signaling pathway.

The present invention further relates to the compound of formula (I), or a tautomer, mesomer, racemate, enantiomer, diastereomer thereof, or mixture thereof, or a pharmaceutically acceptable salt thereof, or the pharmaceutical composition comprising the same, for use in treating, preventing or reducing a disease (especially in human) selected from the group consisting of vascular injury, glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, cystic fibrosis, interstitial lung disease, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, intimal thickening, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, glaucoma, high intraocular pressure, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, radiation-induced fibrosis, thrombosis, tumor metastasis growth, multiple myeloma, melanoma, glioma, glioblastomas, leukemia, sarcomas, leiomyomas, mesothelioma, breast cancer, cervical cancer, lung cancer, stomach cancer, rectal cancer, colon cancer, pancreatic cancer, brain cancer, skin cancer, oral cancer, prostate cancer, bone cancer, kidney cancer, ovarian cancer, bladder cancer and liver cancer.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any known method in the art for the preparation of pharmaceutical composition. Such composition can contain one or more ingredients selected from the group consisting of sweeteners, flavoring agents, colorants and preservatives, in order to provide a pleasing and palatable pharmaceutical preparation. Tablets contain the active ingredient in admixture with nontoxic pharmaceutically acceptable excipients suitable for the manufacture of tablets.

An aqueous suspension contains the active ingredient in admixture with excipients suitable for the manufacture of an aqueous suspension.

An oil suspension can be formulated by suspending the active ingredient in a vegetable oil. The oil suspension can contain a thickener. The aforementioned sweeteners and flavoring agents can be added to provide a palatable formulation. These compositions can be preserved by adding an antioxidant.

The active ingredient in admixture with the dispersants or wetting agents, suspending agent or one or more preservatives can be prepared as a dispersible powder or granule suitable for the preparation of an aqueous suspension by adding water. Suitable dispersants or wetting agents and suspending agents are exemplified by those already mentioned above. Additional excipients, such as sweeteners, flavoring agents and colorants, can also be added. These compositions can be preserved by adding an antioxidant.

The pharmaceutical composition of the present invention can also be in the form of an oil-in-water emulsion. The oil phase can be a vegetable oil. Suitable emulsifying agents can be naturally occurring phosphatides. The emulsion can also contain sweeteners, flavoring agents, preservatives and antioxidants. Such formulations can also contain demulcents, preservatives, colorants, and antioxidants.

The pharmaceutical composition of the present invention can be in the form of a sterile injectable aqueous solution. The sterile injectable formulation can be a sterile injectable oil-in-water microemulsion in which the active ingredient is dissolved in the oil phase.

The pharmaceutical composition of the present invention can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium.

The compound of the present invention can be administered in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug.

It is well known to those skilled in the art that the dosage of a drug depends on a variety of factors including but not limited to, the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, —$OR^7$, —$C(O)R^7$, —$C(O)OR^7$, —$S(O)_mR^7$, —$NR^8R^9$ and —$C(O)NR^8R^9$.

The term "cycloalkyl" refers to a saturated or partially unsaturated monocyclic or polycyclic hydrocarbon group having 3 to 20 carbon atoms, preferably 3 to 12 carbon atoms, more preferably 3 to 10 carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

The term "spiro cycloalkyl" refers to a 5 to 20 membered polycyclic group with rings connected through one shared carbon atom (called a spiro atom), wherein the rings can contain one or more double bonds, but none of the rings has a completely conjugated π-electron system. The spiro cycloalkyl is preferably 6 to 14 membered spiro cycloalkyl, and more preferably 7 to 10 membered spiro cycloalkyl. According to the number of the spiro atoms shared between the rings, the spiro cycloalkyl can be divided into mono-spiro cycloalkyl, di-spiro cycloalkyl, or poly-spiro cycloalkyl, and the spiro cycloalkyl is preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

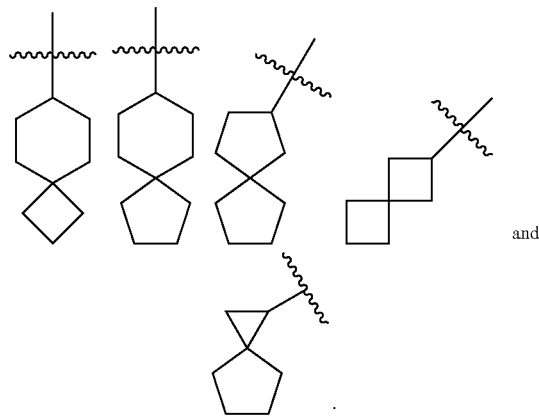

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated π-electron system. The fused cycloalkyl is preferably 6 to 14 membered fused cycloalkyl, and more preferably 7 to 10 membered fused cycloalkyl. According to the number of membered rings, the fused cycloalkyl can be divided into bicyclic, tricyclic, tetracyclic or polycyclic fused cycloalkyl, and the fused cycloalkyl is preferably bicyclic or tricyclic fused cycloalkyl, and more preferably 5-membered/5-membered, or 5-membered/6-membered bicyclic fused cycloalkyl. Non-limiting examples of fused cycloalkyl include:

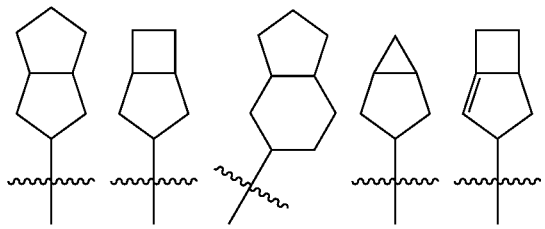

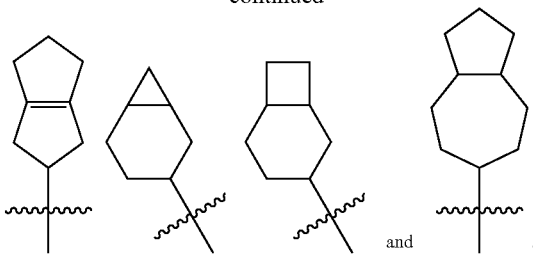

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated π-electron system. The bridged cycloalkyl is preferably 6 to 14 membered bridged cycloalkyl, and more preferably 7 to 10 membered bridged cycloalkyl. According to the number of membered rings, the bridged cycloalkyl can be divided into bicyclic, tricyclic, tetracyclic or polycyclic bridged cycloalkyl, and the bridged cycloalkyl is preferably bicyclic, tricyclic or tetracyclic bridged cycloalkyl, and more preferably bicyclic or tricyclic bridged cycloalkyl. Non-limiting examples of bridged cycloalkyls include:

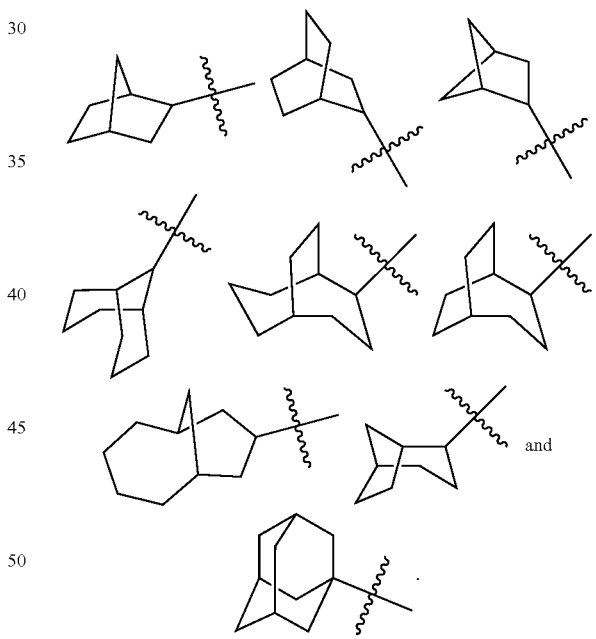

The ring of cycloalkyl can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, —OR$^7$, —C(O)R$^7$, —C(O)OR$^7$, —S(O)$_m$R$^7$, —NR$^8$R$^9$ and —C(O)NR$^8$R$^9$.

The term "heterocyclyl" refers to a 3 to 20 membered saturated or partially unsaturated monocyclic or polycyclic hydrocarbon group, wherein one or more ring atoms are heteroatoms selected from the group consisting of N, O, and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms, and more preferably 3 to 10 ring atoms. Non-limiting examples of monocyclic heterocyclyl include pyrrolidinyl, tetrahydropyranyl, 1,2,3,6-tetrahydropyridyl, piperidinyl, piperazinyl, morpholinyl, thiomorpholinyl, homopiperazinyl and the like. Polycyclic heterocyclyl includes a heterocyclyl having a spiro ring, fused ring or bridged ring.

The term "spiro heterocyclyl" refers to a 5 to 20 membered polycyclic heterocyclyl with rings connected through one shared atom (called a spiro atom), wherein one or more ring atoms are heteroatoms selected from the group consisting of N, O, and $S(O)_m$ (wherein m is an integer of 0 to 2), with the remaining ring atoms being carbon atoms, where the rings can contain one or more double bonds, but none of the rings has a completely conjugated π-electron system. The spiro heterocyclyl is preferably 6 to 14 membered spiro heterocyclyl, and more preferably 7 to 10 membered spiro heterocyclyl. According to the number of the spiro atoms shared between the rings, the spiro heterocyclyl can be divided into mono-spiro heterocyclyl, di-spiro heterocyclyl, or poly-spiro heterocyclyl, and the spiro heterocyclyl is preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

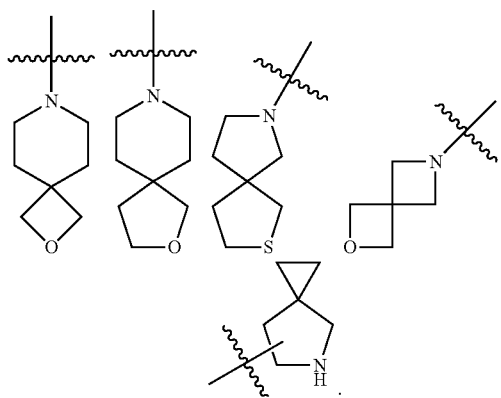

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O, and $S(O)_m$ (wherein m is an integer of 0 to 2), with the remaining ring atoms being carbon atoms. The fused heterocyclyl is preferably 6 to 14 membered fused heterocyclyl, and more preferably 7 to 10 membered fused heterocyclyl. According to the number of membered rings, the fused heterocyclyl can be divided into bicyclic, tricyclic, tetracyclic or polycyclic fused heterocyclyl, and the fused heterocyclyl is preferably bicyclic or tricyclic fused heterocyclyl, and more preferably 5-membered/5-membered, or 5-membered/6-membered bicyclic fused heterocyclyl. Non-limiting examples of fused heterocyclyl include:

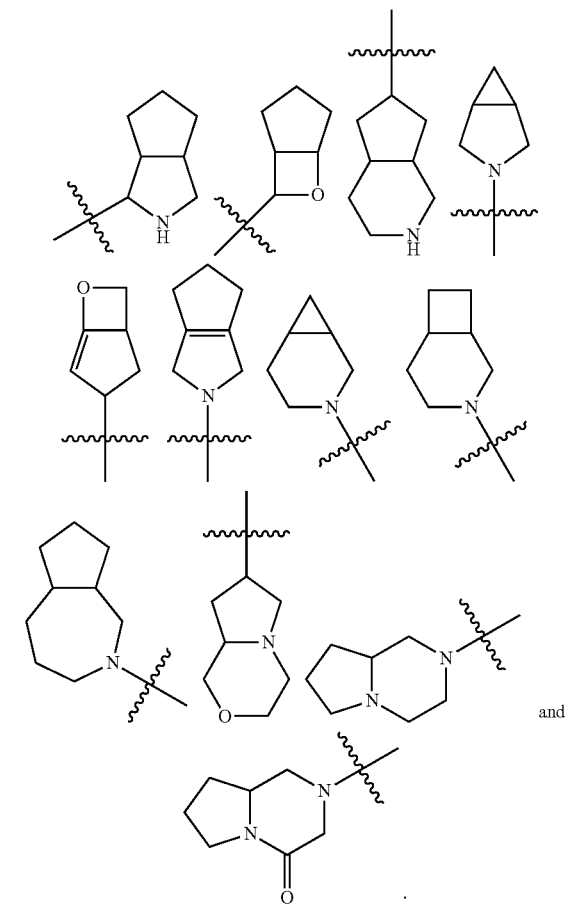

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O, and $S(O)_m$ (wherein m is an integer of 0 to 2), with the remaining ring atoms being carbon atoms. The bridged heterocyclyl is preferably 6 to 14 membered bridged heterocyclyl, and more preferably 7 to 10 membered bridged heterocyclyl. According to the number of membered rings, the bridged heterocyclyl can be divided into bicyclic, tricyclic, tetracyclic or polycyclic bridged heterocyclyl, and the bridged heterocyclyl is preferably bicyclic, tricyclic or tetracyclic bridged heterocyclyl, and more preferably bicyclic or tricyclic bridged heterocyclyl. Non-limiting examples of bridged heterocyclyls include:

The ring of heterocyclyl can be fused to the ring of aryl, heteroaryl or cycloalkyl, wherein the ring bound to the parent structure is heterocyclyl. Non-limiting examples include:

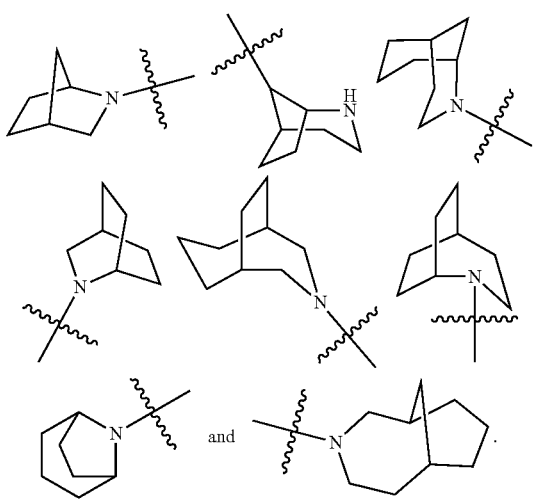

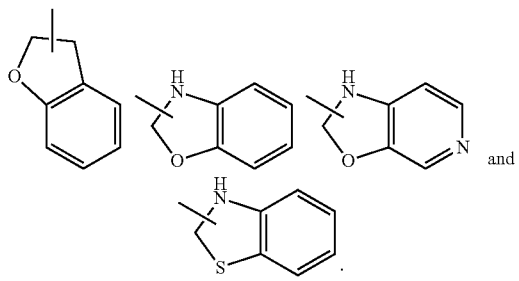

The heterocyclyl can be optionally substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, —OR$^7$, —C(O)R$^7$, —C(O)OR$^7$, —S(O)$_m$R$^7$, —NR$^8$R$^9$ and —C(O)NR$^8$R$^9$.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably 6 to 10 membered aryl, for example, phenyl and naphthyl. The ring of aryl can be fused to the ring of heteroaryl, heterocyclyl or cycloalkyl, wherein the ring bound to the parent structure is aryl ring. Non-limiting examples include:

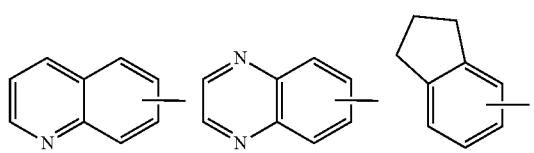

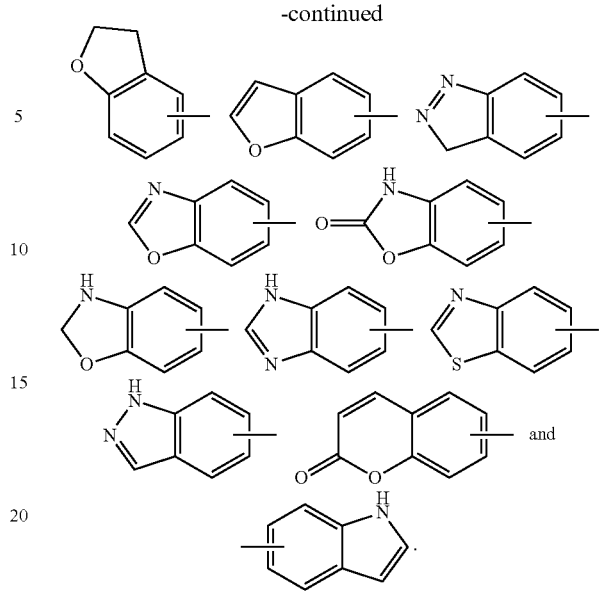

The aryl can be substituted or unsubstituted. When substituted, the substituent group(s) is preferably one or more group(s) independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, —OR$^7$, —C(O)R$^7$, —C(O)OR$^7$, —S(O)$_m$R$^7$, —NR$^8$R$^9$ and —C(O)NR$^8$R$^9$.

The term "heteroaryl" refers to a 5 to 14 membered heteroaromatic system having 1 to 4 heteroatoms selected from the group consisting of O, S and N. The heteroaryl is preferably 5 to 10 membered heteroaryl, more preferably 5 or 6 membered heteroaryl, for example, furanyl, thienyl, pyridyl, pyrrolyl, N-alkylpyrrolyl, pyrimidinyl, pyrazinyl, imidazolyl, pyrazolyl, tetrazolyl, and the like. The ring of heteroaryl can be fused to the ring of aryl, heterocyclyl or cycloalkyl, wherein the ring bound to the parent structure is heteroaryl ring. Non-limiting examples include:

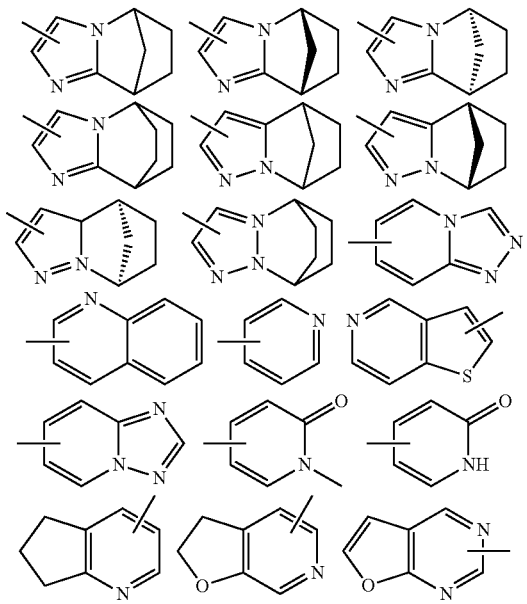

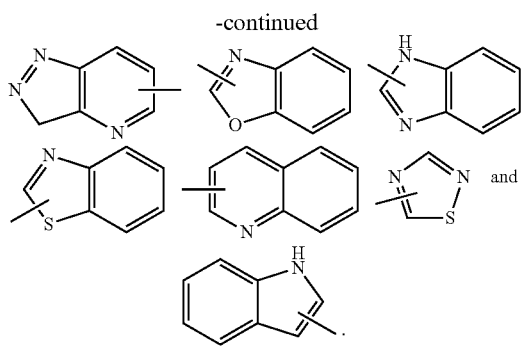

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, —$OR^7$, —$C(O)R^7$, —$C(O)OR^7$, —$S(O)_mR^7$, —$NR^8R^9$ and —$C(O)NR^8R^9$.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, amino, nitro, cyano, cycloalkyl, heterocyclyl, aryl, heteroaryl, cycloalkoxy, heteroalkoxy, cycloalkylthio, heterocyclylthio, —$OR^7$, —$C(O)R^7$, —$C(O)OR^7$, —$S(O)_mR^7$, —$NR^8R^9$ and —$C(O)NR^8R^9$.

The term "hydroxy" refers to an —OH group.

The term "halogen" refers to fluorine, chlorine, bromine or iodine.

The term "amino" refers to a —$NH_2$ group.

The term "cyano" refers to a —CN group.

The term "nitro" refers to a —$NO_2$ group.

The term "oxo" refers to an =O group.

The term "hydroxyalkyl" refers to an alkyl group by hydroxy(s), wherein the alkyl is as defined above.

The term "haloalkyl" refers to an alkyl group substituted by one or more halogens, wherein alkyl is as defined above.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not, be present, and such a description includes the situation of the heterocyclyl being substituted by an alkyl and the heterocyclyl being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

m and $R^7$ to $R^9$ are as defined in the compound of formula (I).

Synthesis Method of the Compound of the Present Invention

In order to achieve the object of the present invention, the present invention applies the following technical solutions:

Scheme 1
A method for preparing the compound of formula (I) of the present invention or a tautomer, mesomer, racemate, enantiomer, diastereomer thereof, or mixture thereof, or a pharmaceutically acceptable salt thereof, comprises the following steps of:

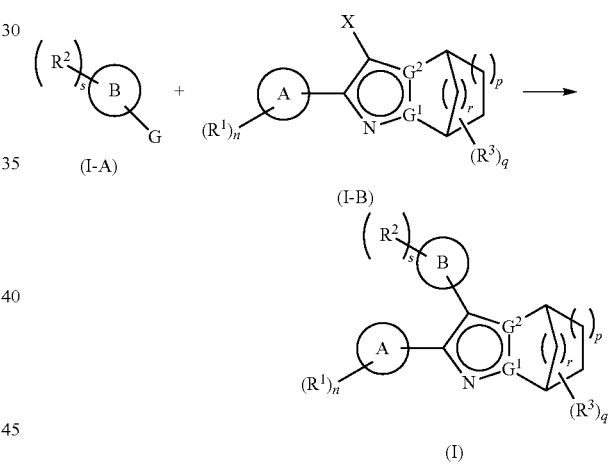

A method for preparing the compound of formula (I) of the present invention or a tautomer, mesomer, racemate, enantiomer, diastereomer thereof, or mixture thereof, or a pharmaceutically acceptable salt thereof, comprises the following steps of:

subjecting a compound of formula (I-A) and a compound of formula (I-B) to a Suzuki reaction under an alkaline condition in the presence of a catalyst to obtain the compound of formula (I).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide and potassium tert-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, palladium on carbon, Raney nickel, tetrakis(triphenylphosphine)palladium, palladium dichloride, palladium acetate, [1,1'-bis(diphenylphosphino)ferrocene]dichloropalladium, 1,1'-bis(diphenylphosphino)ferrocene palladium dichloride or tris(dibenzylideneacetone)dipalladium, and preferably [1,1'-bis(diphenylphosphino)ferrocene]dichloropalladium.

The above reactions are preferably carried out in a solvent. The solvent used includes, but not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

G is selected from the group consisting of halogen,

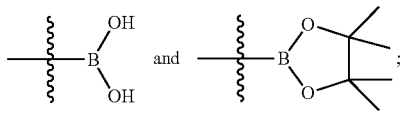

X is halogen, and preferably bromine;

ring A, ring B, $G^1$, $G^2$, $R^1$~$R^3$, r, p, n, s and q are as defined in formula (I).

A method for preparing the compound of formula (III) of the present invention or a tautomer, mesomer, racemate, enantiomer, diastereomer thereof, or mixture thereof, or a pharmaceutically acceptable salt thereof, comprises the following steps of:

Scheme II

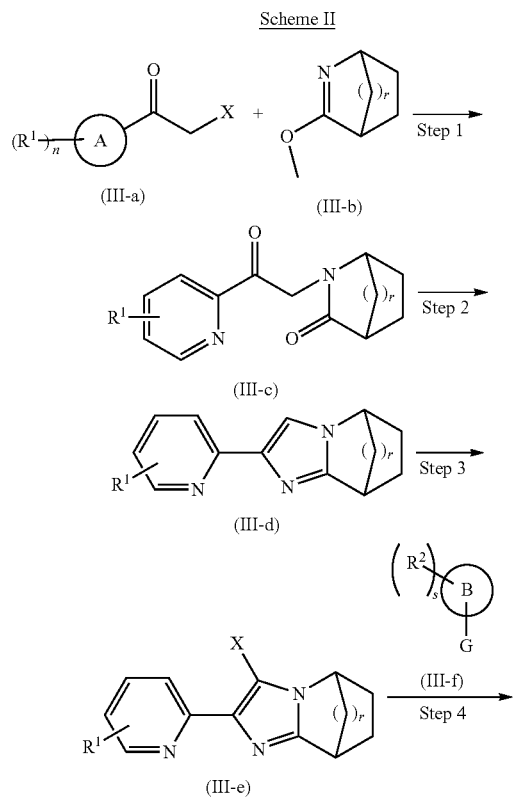

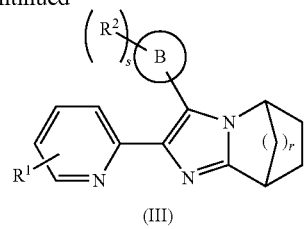

the first step reaction is a nucleophilic substitution reaction of a compound of formula (III-a) and a compound of (III-b) under high temperature to obtain a compound of formula (III-c);

the second step reaction is a cyclization reaction of the compound of formula (III-c) and ammonium acetate under an acidic condition to obtain a compound of formula (III-d);

the third step reaction is a halogenation reaction of the compound of formula (III-d) under an acidic condition to obtain a compound of formula (III-e);

the fourth step reaction is a Suzuki coupling reaction of the compound of formula (III-e) and a compound of (III-f) under an alkaline condition to obtain the compound of formula (III).

The reagent that provides an acidic condition includes, but is not limited to, pyridine hydrobromide, trifluoroacetic acid, formic acid, acetic acid, hydrochloric acid, sulfuric acid or methanesulfonic acid, and preferably acetic acid.

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide and potassium tert-butoxide. The inorganic bases include, but are not limited to, sodium hydride, potassium phosphate, sodium carbonate, potassium carbonate, potassium acetate, cesium carbonate, sodium hydroxide and lithium hydroxide.

The reagent that is used in the halogenation reaction includes, but is not limited to, liquid bromine, hydrogen bromide, N-bromosuccinimide (NBS), PBr₃, POBr₃, pyridine hydrobromide perbromide (PHP), 2,4,4,6-tetrabromo-2,5-cyclohexadienone (TBCO), diethyl bromomalonate and tetrabutylammonium bromide, N-chlorosuccinimide, PCl₃ and POCl₃.

The catalyst includes, but is not limited to, palladium on carbon, Raney nickel, tetrakis(triphenylphosphine)palladium, palladium dichloride, palladium acetate, [1,1'-bis(diphenylphosphino)ferrocene]dichloropalladium, 1,1'-bis(diphenylphosphino)ferrocene palladium dichloride or tris(dibenzylideneacetone)dipalladium, and preferably [1,1'-bis(diphenylphosphino)ferrocene]dichloropalladium.

The above reactions are preferably carried out in a solvent. The solvent used includes, but not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

X is halogen, and preferably bromine;

G is a leaving group selected from the group consisting of halogen,

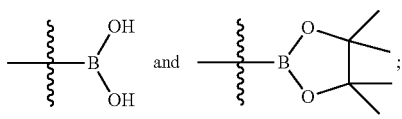

ring B, $R^1$, $R^2$, r and s are as defined in formula (I).

Scheme 3
A method for preparing the compound of formula (IV) of the present invention or a tautomer, mesomer, racemate, enantiomer, diastereomer thereof, or mixture thereof, or a pharmaceutically acceptable salt thereof, comprises the following steps of:

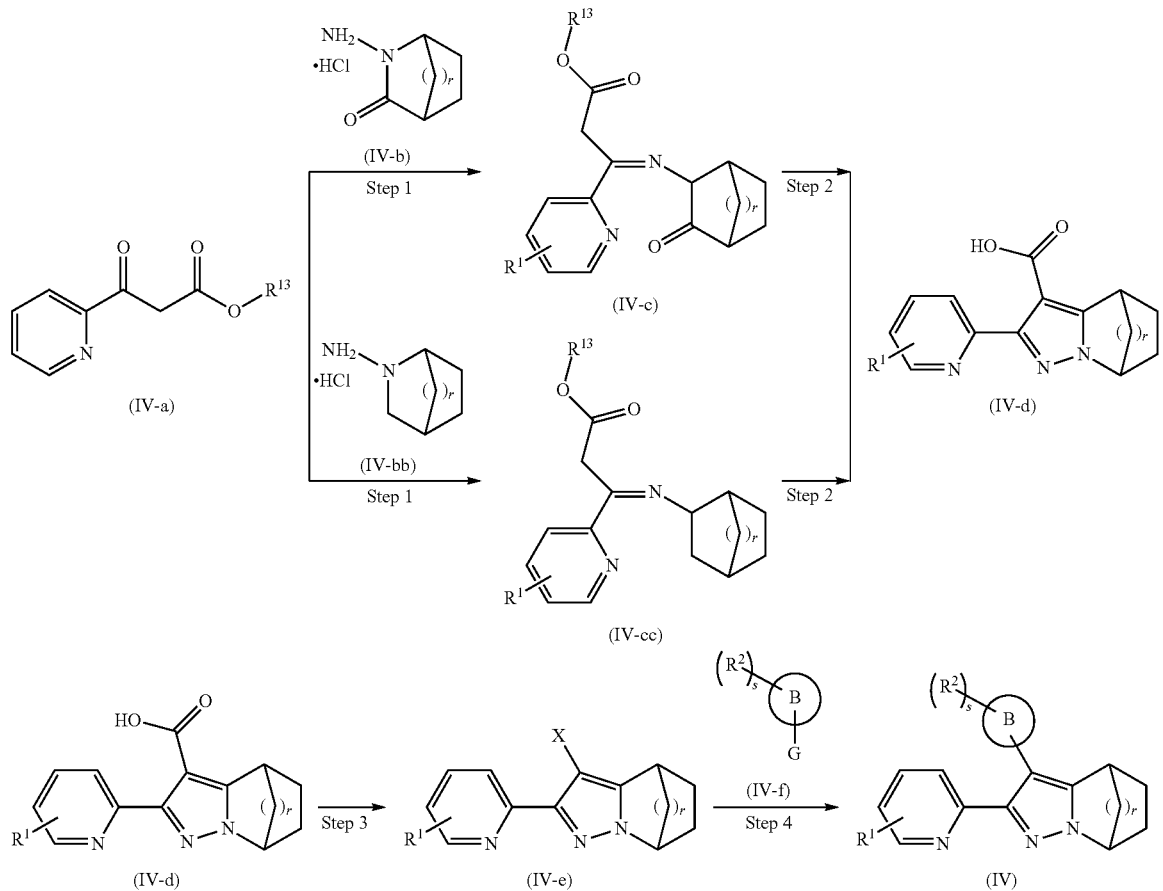

A method for preparing the compound of formula (IV) of the present invention or a tautomer, mesomer, racemate, enantiomer, diastereomer thereof, or mixture thereof, or a pharmaceutically acceptable salt thereof, comprises the following steps of:

the first step reaction is a reaction of a compound of formula (IV-a) and a compound of formula (IV-b) under an acidic condition to obtain a compound of formula (IV-c), or a reaction of a compound of formula (IV-a) and a compound of formula (IV-bb) under an acidic condition to obtain a compound of formula (IV-cc);

the second step reaction is a cyclization reaction of the compound of formula (IV-c) or the compound of formula (IV-cc) under an alkaline condition to obtain a compound of formula (IV-d);

the third step reaction is a halogenation reaction of the compound of formula (IV-d) under an acidic condition to obtain a compound of formula (IV-e);

the fourth step reaction is a Suzuki coupling reaction of the compound of formula (IV-e) and a compound of (IV-f) under an alkaline condition to obtain the compound of formula (IV).

The reagent that provides acidic an condition includes, but is not limited to, pyridine hydrobromide, trifluoroacetic acid, formic acid, acetic acid, hydrochloric acid, sulfuric acid or methanesulfonic acid, and preferably acetic acid.

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide and potassium tert-butoxide. The inorganic bases include, but are not limited to, sodium hydride, potassium phosphate, sodium carbonate, potassium carbonate, potassium acetate, cesium carbonate, sodium hydroxide and lithium hydroxide.

The reagent that is used in the halogenation reaction includes, but is not limited to, liquid bromine, hydrogen bromide, N-bromosuccinimide (NBS), $PBr_3$, $POBr_3$, pyridine hydrobromide perbromide (PHP), 2,4,4,6-tetrabromo-2,5-cyclohexadienone (TBCO), diethyl bromomalonate and tetrabutylammonium bromide, N-chlorosuccinimide, $PCl_3$ and $POCl_3$.

The catalyst includes, but is not limited to, palladium on carbon, Raney nickel, tetrakis(triphenylphosphine)palladium, palladium dichloride, palladium acetate, [1,1'-bis(diphenylphosphino)ferrocene]dichloropalladium, 1,1'-bis(diphenylphosphino)ferrocene palladium dichloride or tris(dibenzylideneacetone)dipalladium, and preferably [1,1'-bis(diphenylphosphino)ferrocene]dichloropalladium.

The above reactions are preferably carried out in a solvent. The solvent used includes, but not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

$R^{13}$ is selected from the group consisting of alkyl, cycloalkyl and heterocyclyl, preferably alkyl, and more preferably ethyl;

X is halogen, and preferably bromine;

G is a leaving group selected from the group consisting of halogen,

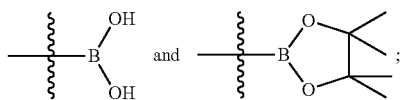

ring B, $R^1$, $R^2$, r and s are as defined in formula (I).

Scheme 4
A method for preparig the compound of formula (IV) of the present invention or a tautomer, racemate, enantiomer, diastereomer thereof, or mixture thereof, or a pharmaceutically acceptable salt thereof, comprises the following steps of:

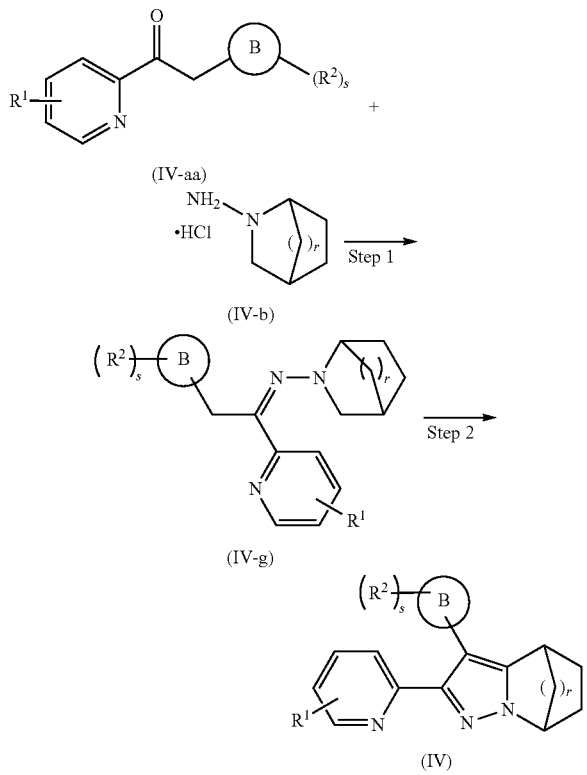

A method for preparing the compound of formula (IV) of the present invention or a tautomer, racemate, enantiomer, diastereomer thereof, or mixture thereof, or a pharmaceutically acceptable salt thereof, comprises the following steps of:

the first step reaction is a reaction of a compound of formula (IV-aa) and a compound of formula (IV-b) under an acidic condition to obtain a compound of formula (IV-g);

the second step reaction is a cyclization reaction of the compound of formula (IV-g) under an alkaline condition to obtain the compound of formula (IV).

The reagent that provides an acidic condition includes, but is not limited to, pyridine hydrobromide, trifluoroacetic acid, formic acid, acetic acid, hydrochloric acid, sulfuric acid or methanesulfonic acid, and preferably acetic acid.

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, sodium tert-butoxide and potassium tert-butoxide. The inorganic bases include, but are not limited to, sodium hydride, potassium phosphate, sodium carbonate, potassium carbonate, potassium acetate, cesium carbonate, sodium hydroxide and lithium hydroxide.

The above reactions are preferably carried out in a solvent. The solvent used includes, but not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

ring B, $R^1$, $R^2$, r and s are as defined in formula (I).

PREFERRED EMBODIMENTS

The present invention will be further described with reference to the following examples, but the examples should not be considered as limiting the scope of the present invention.

EXAMPLES

The structures of the compounds were identified by nuclear magnetic resonance (NMR) and/or mass spectrometry (MS). NMR shifts (δ) are given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard was tetramethylsilane (TMS).

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column), and a Waters 2695-2996 high pressure liquid chromatography spectrometer (Gimini C18 150×4.6 mm chromatographic column).

Chiral HPLC was determined on a LC-10A vp (Shimadzu) or SFC-analytical (Berger Instruments Inc.).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for column chromatography.

Prep Star SD-1 (Varian Instruments Inc.) or SFC-multigram (Berger Instruments Inc.) was used for chiral preparative column chromatography.

The average kinase inhibition rates and $IC_{50}$ values were determined by a NovoStar ELISA (BMG Co., Germany).

The known starting materials of the present invention can be prepared by the methods known in the art, or can be purchased from ABCR GmbH & Co. KG, Acros Organnics, Aldrich Chemical Company, Accela ChemBio Inc., or Dari chemical Company, etc.

Unless otherwise stated, the reactions were carried out under nitrogen atmosphere or argon atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reactions were performed on a Parr 3916EKX hydrogenation instrument and a Qinglan QL-500 hydrogen generator or HC2-SS hydrogenation instrument.

In hydrogenation reactions, the reaction system was generally vacuumed and filled with hydrogen, with the above operation was repeated three times.

CEM Discover-S 908860 type microwave reactor was used in microwave reactions.

Unless otherwise stated, the solution refers to an aqueous solution.

Unless otherwise stated, the reaction temperature is room temperature from 20° C. to 30° C.

The reaction process in the examples was monitored by thin layer chromatography (TLC), and the developing solvent system used in the reactions included: A: system of dichloromethane and methanol, B: system of n-hexane and ethyl acetate, C: system of dichloromethane and acetone, D: system of petroleum ether and ethyl acetate. The ratio of the volume of the solvent was adjusted according to the polarity of the compounds.

The elution system for purification of the compounds by column chromatography and thin layer chromatography included: A: system of dichloromethane and methanol, B: system of n-hexane and ethyl acetate, C: system of dichloromethane and acetone, D: system of petroleum ether and ethyl acetate. The ratio of the volume of the solvent was adjusted according to the polarity of the compounds, and a small quantity of alkaline reagent such as triethylamine or acidic reagent such as acetic acid can also be added for adjustment.

Example 1

6-(2-(6-Methylpyridin-2-yl)-5,6,7,8-tetrahydro-5,8-methanoimidazo[1,2-a]pyridin-3-yl) quinoline-4-carboxamide 1

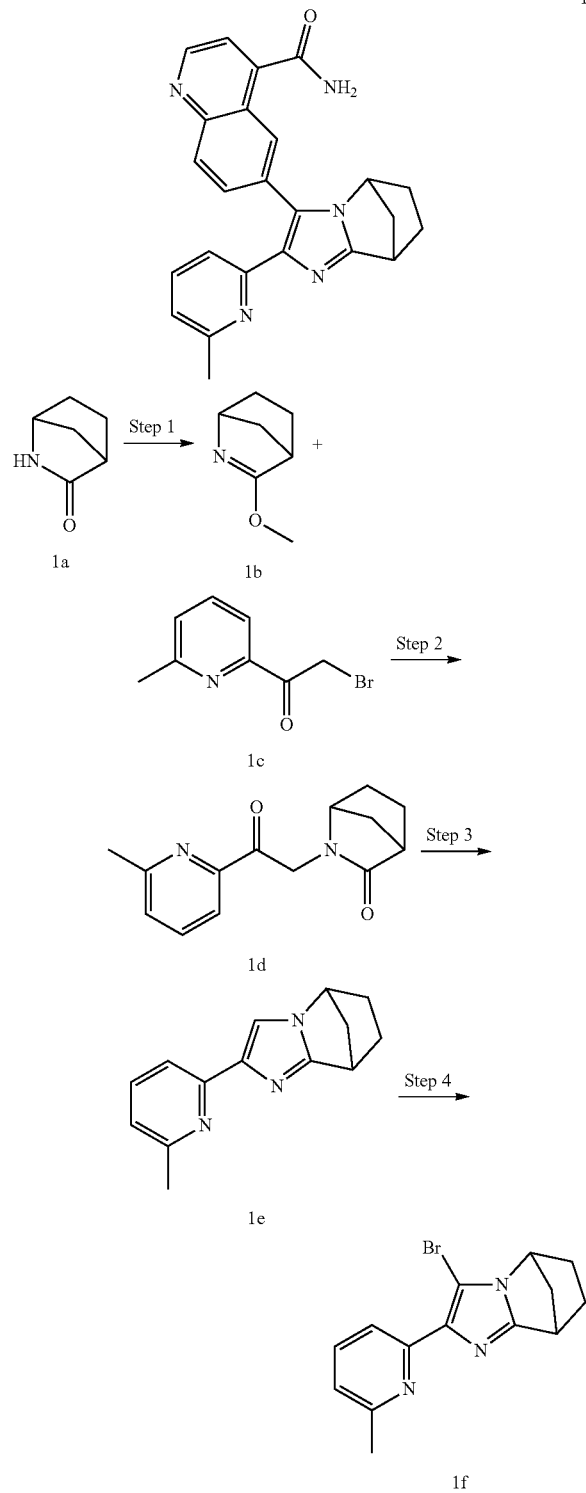

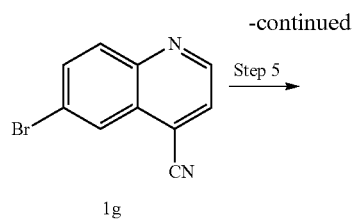

1g

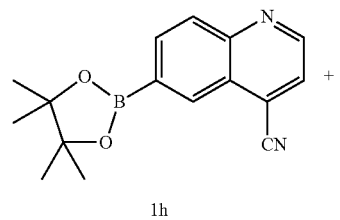

1h

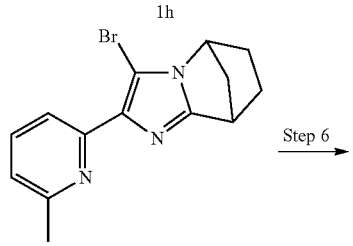

1f

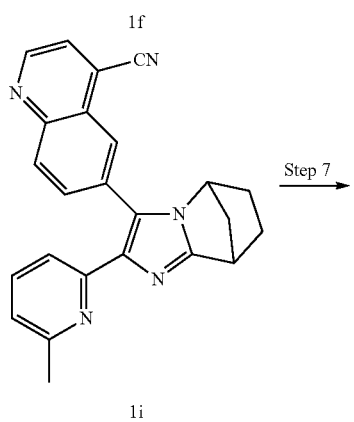

1i

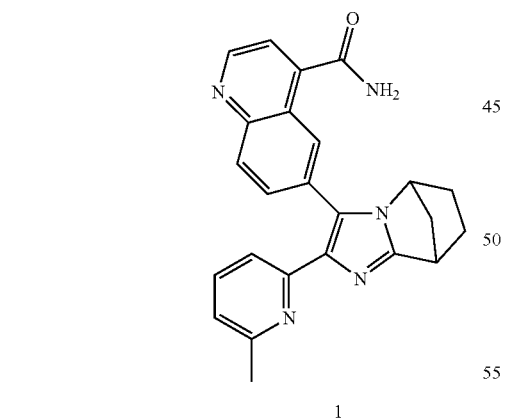

1

Step 1

3-Methoxy-2-azabicyclo[2.2.1]hept-2-ene 1b

2-Azabicyclo[2.2.1]heptan-3-one 1a (2.5 g, 22.494 mmol, prepared according to the known method disclosed in "*Angewandte Chemie, International Edition,* 2005, 44(35), 5710-5713") was dissolved in 40 mL of dichloromethane, then trimethyltetrafluoroborate (3.66 g, 24.744 mmol) was added. After stirring for 12 hours, the reaction solution was added with saturated sodium bicarbonate solution and extracted with dichloromethane. The organic phases were combined, dried over anhydrous sodium sulfate and filtered. The filtrate was concentrated under reduced pressure to obtain the crude title compound 1b (2.5 g), which was used directly in the next step without purification.

Step 2

2-(2-(6-Methylpyridin-2-yl)-2-oxoethyl)-2-azabicyclo[2.2.1]heptan-3-one 1d

Compound 1c (600 mg, 2.802 mmol) and the crude compound 1b (702 mg, 5.606 mmol) were dissolved in 5 mL of N,N-dimethylformamide, then the reaction solution was warmed up to 55° C. and stirred for 5 hours. The reaction solution was cooled to room temperature, added with water, and extracted with ethyl acetate. The organic phases were combined, dried over anhydrous sodium sulfate and filtered. The filtrate was concentrated under reduced pressure to obtain the crude title compound 1d (685 mg), which was used directly in the next step without purification.

Step 3

2-(6-Methylpyridin-2-yl)-5,6,7,8-tetrahydro-5,8-methanoimidazo[1,2-a]pyridine 1e The crude compound 1d (685 mg, 2.8 mmol) and ammonium acetate (2.16 g, 2.8 mmol) were dissolved in 3 mL of acetic acid, then the reaction solution was warmed up to 100° C. and stirred for 12 hours. The reaction solution was cooled to room temperature and concentrated under reduced pressure. Saturated sodium bicarbonate solution was then added dropwise to the resulting residue until the pH is 7. The reaction solution was extracted with dichloromethane, then the organic phases were combined, dried over anhydrous sodium sulfate and filtered. The filtrate was concentrated under reduced pressure, and the resulting residue was purified by silica gel column chromatography with elution system A to obtain the title compound 1e (600 mg, yield: 95%).

Step 4

3-Bromo-2-(6-methylpyridin-2-yl)-5,6,7,8-tetrahydro-5,8-methanoimidazo[1,2-a]pyridine 1f Compound 1e (500 mg, 2.22 mmol) was dissolved in 20 mL of dichloromethane, then liquid bromine (390 mg, 2.44 mmol) was added. After stirring for 2 hours, the reaction solution was added with saturated sodium bicarbonate solution and extracted with dichloromethane. The organic phases were combined, dried over anhydrous sodium sulfate and filtered. The filtrate was concentrated under reduced pressure to obtain the crude title compound 1f (600 mg), which was used directly in the next step without purification.

Step 5

6-(4,4,5,5-Tetramethyl-1,3,2-dioxaborolan-2-yl)quinoline-4-carbonitrile 1h

6-Bromoquinoline-4-carbonitrile 1g (550 mg, 2.36 mmol, prepared according to the method disclosed in the patent application "WO2014022128"), bis(pinacolato)diboron (898.91 mg, 3.54 mmol), potassium acetate (926.41 mg, 9.44 mmol) and [1,1'-bis(diphenylphosphino)ferrocene]dichloropalladium (350.11 mg, 0.47 mmol) were dissolved in 10 mL of 1,4-dioxane, then the reaction solution was warmed up to 90° C. and stirred for 12 hours. The reaction solution was cooled to room temperature, and concentrated under reduced pressure. The resulting residue was purified by silica gel column chromatography with elution system B to obtain the title compound 1h (520 mg, yield: 78.66%).

Step 6

6-(2-(6-Methylpyridin-2-yl)-5,6,7,8-tetrahydro-5,8-methanoimidazo[1,2-a]pyridin-3-yl) quinoline-4-carbonitrile 1i Compound 1f (300 mg, 0.968 mmol), compound 1h (414 mg, 1.479 mmol), [1,1'-bis(diphenylphosphino)ferrocene]dichloropalladium (72 mg, 0.099 mmol) and potassium carbonate (408 mg, 2.958 mmol) were dissolved in 10 mL of a mixed solvent of 1,4-dioxane and water (V/V=4:1), then the reaction solution was warmed up to 85° C. and stirred for 12 hours. The reaction solution was cooled to room temperature, and concentrated under reduced pressure. The resulting residue was purified by silica gel column chromatography with elution system B to obtain the title compound 1i (160 mg, yield: 43%).

Step 7

Compound 1i (30 mg, 0.079 mmol) was dissolved in 3 mL of dimethyl sulfoxide, then 0.2 mL of hydrogen peroxide solution (30%) and potassium carbonate (33 mg, 0.283 mmol) were added. After stirring at room temperature for 2 hours, the reaction solution was concentrated under reduced pressure. The resulting residue was purified by high performance liquid chromatography to obtain the title compound 1 (15 mg, yield: 48.4%).

MS m/z (ESI): 396.2 [M+1]

$^1$H NMR (400 MHz, CDCl$_3$) δ 8.97 (d, 1H), 8.49 (d, 1H), 8.12 (d, 1H), 8.00 (dd, 1H), 7.64-7.54 (m, 3H), 6.99 (d, 1H), 6.18 (s, 1H), 5.95 (s, 1H), 4.97 (s, 1H), 3.69 (d, 1H), 2.39 (s, 3H), 2.37 (s, 1H), 2.09-2.02 (m, 1H), 1.99-1.91 (m, 2H), 1.56-1.55 (m, 1H), 1.46-1.42 (m, 1H).

Example 1-1

6-((5S,8R)-2-(6-Methylpyridin-2-yl)-5,6,7,8-tetrahydro-5,8-methanoimidazo[1,2-a]pyridin-3-yl)quinoline-4-carboxamide 1-1

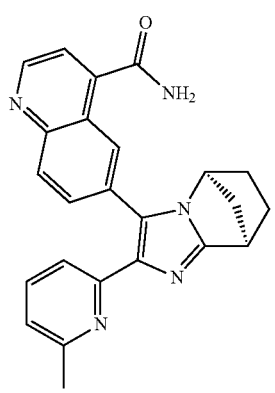

1-1

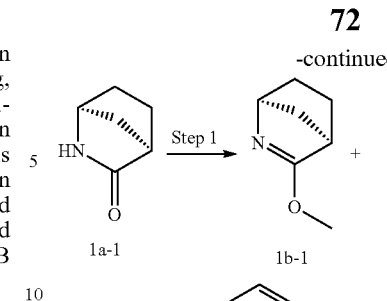

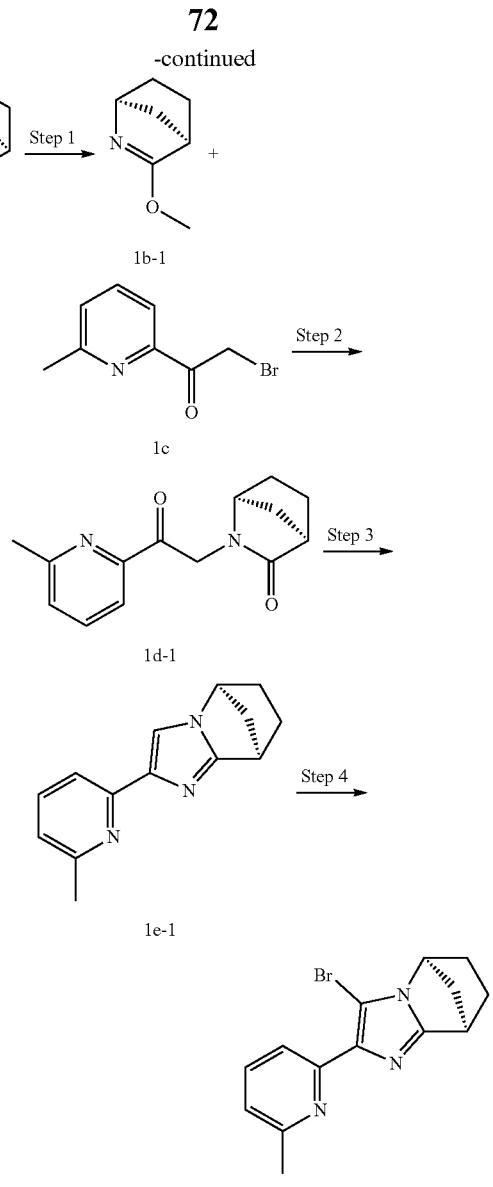

-continued

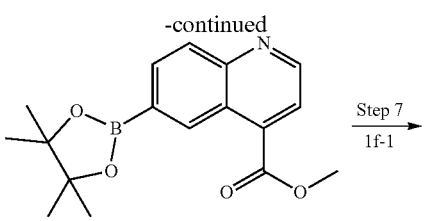

→ Step 7
1f-1

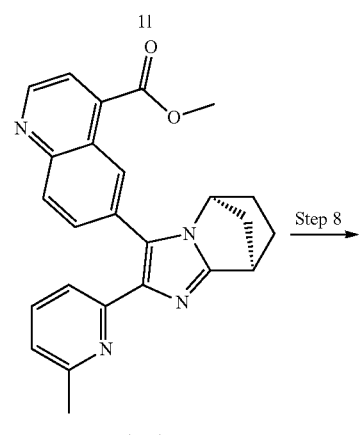

1m-1

→ Step 8

1-1

Step 1

(1S,4R)-3-Methoxy-2-azabicyclo[2.2.1]hept-2-ene 1b-1

(1S,4R)-2-Azabicyclo[2.2.1]heptan-3-one 1a-1 (50 g, 449.88 mmol, prepared according to the method disclosed in the patent application "US20150284362") was dissolved in 400 mL of dichloromethane, then trimethyltetrafluoroborate (86.5 g, 584.85 mmol) was added. After stirring at room temperature for 48 hours, the reaction solution was added with saturated sodium bicarbonate solution and extracted with dichloromethane. The organic phases were combined, dried over anhydrous sodium sulfate and filtered. The filtrate was concentrated under reduced pressure to obtain the crude title compound 1b-1 (47 g), which was used directly in the next step without purification.

Step 2

(1S,4R)-2-(2-(6-Methylpyridin-2-yl)-2-oxoethyl)-2-azabicyclo[2.2.1]heptan-3-one 1d-1

2-Bromo-1-(6-methylpyridin-2-yl)ethanone 1c (40 g, 186.86 mmol, prepared according to the method disclosed in the patent application "WO2013009140") and the crude compound 1b-1 (46.78 g, 373.73 mmol) were dissolved in 300 mL of N,N-dimethylformamide, then the reaction solution was warmed up to 50° C. and stirred for 12 hours. The reaction solution was cooled to room temperature, and concentrated under reduced pressure to obtain the crude title compound 1d-1 (45.649 g), which was used directly in the next step without purification.

Step 3

(5S,8R)-2-(6-Methylpyridin-2-yl)-5,6,7,8-tetra-hydro-5,8-methanoimidazo[1,2-a]pyridine 1e-1

The crude compound 1d-1 (35 g, 143.27 mmol) and ammonium acetate (110.43 g, 1432.7 mmol) were dissolved in 250 mL of acetic acid, then the reaction solution was warmed up to 110° C. and stirred for 12 hours. The reaction solution was cooled to room temperature and concentrated under reduced pressure. Saturated sodium bicarbonate solution was then added dropwise to the resulting residue until the pH was 7. The reaction solution was extracted with dichloromethane, then the organic phases were combined, dried over anhydrous sodium sulfate and filtered. The filtrate was concentrated under reduced pressure, and the resulting residue was purified by silica gel column chromatography with elution system B to obtain the title compound 1e-1 (12 g, yield: 37.18%).

Step 4

(5S,8R)-3-Bromo-2-(6-methylpyridin-2-yl)-5,6,7,8-tetrahydro-5,8-methanoimidazo[1,2-a]pyridine 1f-1

Compound 1e-1 (6 g, 26.63 mmol) was dissolved in 100 mL of dichloromethane, then liquid bromine (4.26 g, 26.63 mmol) was added. After stirring at room temperature for 1 hours, the reaction solution was added with saturated sodium bicarbonate solution and extracted with dichloromethane. The organic phases were combined, dried over anhydrous sodium sulfate and filtered. The filtrate was concentrated under reduced pressure, and the resulting residue was purified by silica gel column chromatography with elution system A to obtain the title compound 1f-1 (6.6 g, yield: 81.47%).

Step 5

Methyl 6-bromoquinoline-4-carboxylate 1k

6-Bromoquinoline-4-carboxylic acid 1j (3.5 g, 13.89 mmol) was dissolved in 50 mL of methanol, then thionyl chloride (1.65 g, 13.89 mmol) was added. The reaction solution was warmed up to reflux and stirred for 12 hours. The reaction solution was cooled to room temperature, and concentrated under reduced pressure to obtain the crude title compound 1k (3.7 g), which was used directly in the next step without purification.

Step 6

Methyl 6-(4,4,5,5-tetramethyl-1,3,2-dioxaborolan-2-yl)quinoline-4-carboxylate 1l The crude compound 1k (3.69 g, 13.87 mmol), bis(pinacolato)diboron (5.28 g, 20.8 mmol), potassium acetate (2.72 g, 27.73 mmol) and [1,1'-bis(diphenylphosphino)ferrocene]

dichloropalladium (1014.8 mg, 1.39 mmol) were dissolved in 30 mL of 1,4-dioxane, then the reaction solution was warmed up to 80° C. and stirred for 12 hours. The reaction solution was cooled to room temperature, and concentrated under reduced pressure. The resulting residue was purified by silica gel column chromatography with elution system B to obtain the title compound 1l (4.3 g, yield: 99.02%).

Step 7

Methyl 6-((5S,8R)-2-(6-methylpyridin-2-yl)-5,6,7,8-tetrahydro-5,8-methanoimidazo[1,2-a]pyridin-3-yl)quinoline-4-carboxylate 1m-1

Compound 1l (2.32 g, 7.4 mmol), compound 1f-1 (1.5 g, 4.93 mmol), [1,1'-bis(diphenylphosphino)ferrocene]dichloropalladium (0.36 g, 0.49 mmol) and potassium carbonate (1.36 g, 9.86 mmol) were dissolved in 24 mL of a mixed solvent of 1,4-dioxane and water (V/V=5:1), then the reaction solution was warmed up to 80° C. and stirred for 12 hours. The reaction solution was cooled to room temperature, and concentrated under reduced pressure. The resulting residue was purified by silica gel column chromatography with elution system B to obtain the title compound 1m-1 (1 g, yield: 49.41%).

Step 8

6-((5S,8R)-2-(6-Methylpyridin-2-yl)-5,6,7,8-tetrahydro-5,8-methanoimidazo[1,2-a]pyridin-3-yl)quinoline-4-carboxamide 1-1

Compound 1m (1 g, 2.44 mmol) was dissolved in 80 mL of 7 M ammonia in methanol, then the reaction solution was warmed up to 100° C. and stirred in a sealed tube for 12 hours. The reaction solution was cooled to room temperature, and concentrated under reduced pressure. The resulting residue was purified by high performance liquid chromatography to obtain the title compound 1-1 (750 mg, yield: 77.85%).
MS m/z (ESI): 396.4 [M+1]
$^1$H NMR (400 MHz, CDCl$_3$) δ 8.98 (d, 1H), 8.48 (d, 1H), 8.11 (d, 1H), 8.01 (dd, 1H), 7.62 (d, 1H), 7.58-7.53 (m, 2H), 6.99 (d, 1H), 6.26 (s, 1H), 6.00 (s, 1H), 4.97 (s, 1H), 3.68 (d, 1H), 2.39 (s, 3H), 2.37 (s, 1H), 2.12-2.08 (m, 1H), 2.01-1.98 (m, 1H), 1.91 (d, 1H), 1.56-1.52 (m, 1H), 1.46-1.43 (m, 1H).

Example 1-2

6-((5R,8S)-2-(6-Methylpyridin-2-yl)-5,6,7,8-tetrahydro-5,8-methanoimidazo[1,2-a]pyridin-3-yl)quinoline-4-carboxamide 1-2

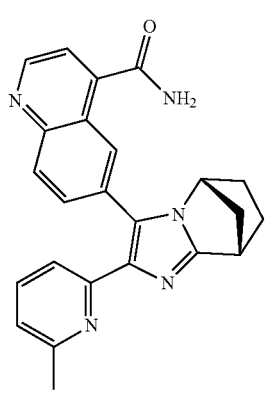

1-2

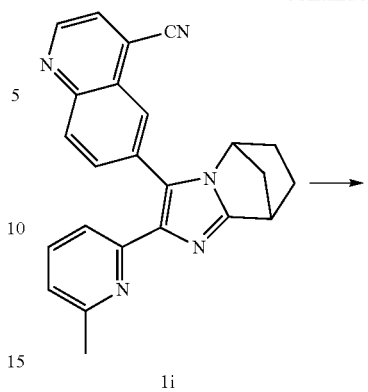

1i

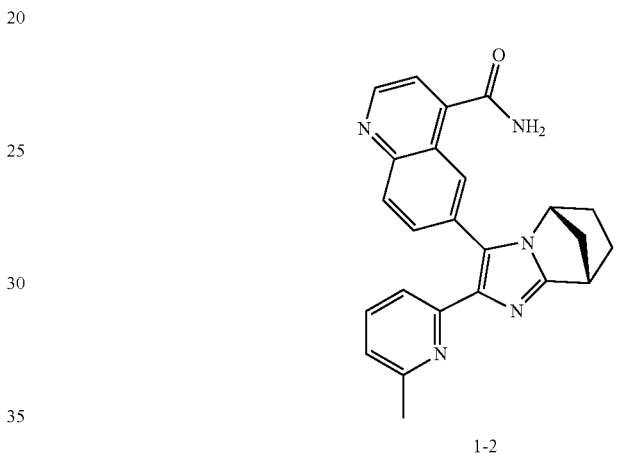

1-2

Compound 1i (100 mg, 0.424 mmol) was dissolved in 3 mL of dimethyl sulfoxide, then 0.5 mL of hydrogen peroxide solution (30%) and potassium carbonate (117 mg, 0.848 mmol) were added. After stirring at room temperature for 1 hours, the reaction solution was concentrated under reduced pressure, and the resulting residue was purified by chiral preparation method (separation conditions: chiral preparative column CHIRALPAK OD 21.5×250 mm, 5 μm, mobile phase: ethanol (containing 0.1% diethylamine)/n-hexane=20/80 (v/v); flow rate: 50 mL/min). The corresponding fractions were collected and concentrated under reduced pressure to obtain the title compound 1-2 (52 mg, yield: 31%).

MS m/z (ESI): 396.4 [M+1]

Chiral HPLC analysis method: retention time 23.287 minutes (chromatographic column: CHIRALPAK OD 4.6× 150 mm 5 m; mobile phase: ethanol (containing 0.1% diethylamine)/n-hexane=10/90 (v/v));

$^1$H NMR (400 MHz, CDCl$_3$) δ 8.99 (d, 1H), 8.49 (d, 1H), 8.12 (d, 1H), 8.02 (dd, 1H), 7.64-7.54 (m, 3H), 6.99 (d, 1H), 6.17 (s, 1H), 5.95 (s, 1H), 4.97 (s, 1H), 3.69 (d, 1H), 2.39 (s, 3H), 2.37 (s, 1H), 2.12-2.09 (m, 1H), 2.01-1.98 (m, 1H), 1.91 (d, 1H), 1.59-1.54 (m, 1H), 1.47-1.42 (m, 1H).

Example 2

6-(2-(6-Methylpyridin-2-yl)-5,6,7,8-tetrahydro-5,8-methanoimidazo[1,2-a]pyridin-3-yl) [1,2,4]triazolo[4,3-a]pyridine-3-carboxamide 2

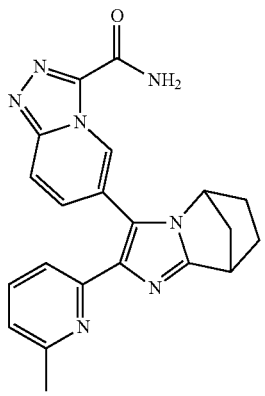

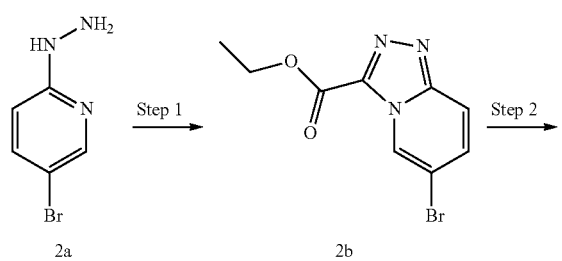

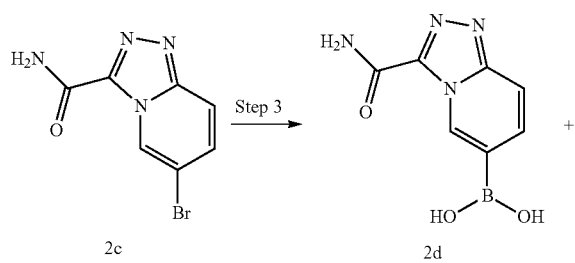

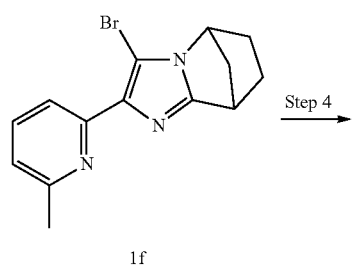

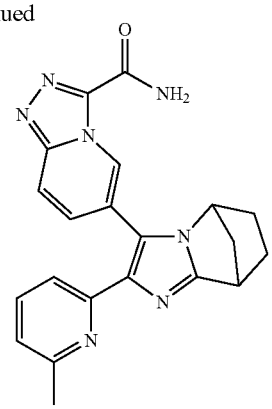

2

Step 1

Ethyl 6-bromo-[1,2,4]triazolo[4,3-a]pyridine-3-carboxylate 2b

5-Bromo-2-hydrazinylpyridine 2a (4 g, 21.27 mmol, prepared according to the method disclosed in the patent application "US20140134133") and ethyl 2-oxoacetate (2.17 g, 21.27 mmol) were dissolved in 60 mL of methanol, then the reaction solution was warmed up to 60° C. and stirred for 1 hours. The reaction solution was cooled to room temperature, and concentrated under reduced pressure. 60 mL of 1,4-dioxane was added to the resulting residue, then (diacetoxyiodo)benzene (7.81 g, 24.24 mmol) was added slowly. After stirring at room temperature for 18 hours, the reaction solution was concentrated under reduced pressure, and the resulting residue was purified by silica gel column chromatography with elution system B to obtain the title compound 2b (500 mg, yield: 8.7%).

Step 2

6-Bromo-[1,2,4]triazolo[4,3-a]pyridine-3-carboxamide 2c

Compound 2b (4.5 g, 17.57 mmol) was dissolved in 33.75 mL of 7 M ammonia in methanol, then the reaction solution was warmed up to 50° C. and stirred in a sealed tube for 2 hours. The reaction solution was cooled to room temperature, and concentrated under reduced pressure to obtain the crude title compound 2c (4.2 g), which was used directly in the next step without purification.

Step 3

(3-Carbamoyl-[1,2,4]triazolo[4,3-a]pyridin-6-yl) boronic acid 2d

The crude compound 2c (4.2 g, 17.42 mmol), bis(pinacolato)diboron (6.64 g, 26.14 mmol), potassium acetate (4.28 g, 43.56 mmol) and [1,1'-bis(diphenylphosphino)ferrocene]dichloropalladium (1.29 g, 1.74 mmol) were dissolved in 80 mL of 1,4-dioxane, then the reaction solution was warmed up to 80° C. and stirred for 3 hours. The reaction solution was cooled to room temperature, and concentrated under reduced pressure. The resulting residue was purified by silica gel column chromatography with elution system A to obtain the title compound 2d (2.6 g, yield: 72.4%).

Step 4

6-((5S,8R)-2-(6-Methylpyridin-2-yl)-5,6,7,8-tetrahydro-5,8-methanoimidazo[1,2-a]pyridin-3-yl)-[1,2,4]triazolo[4,3-a]pyridine-3-carboxamide 2

Compound 1f (60 mg, 0.2 mmol), compound 2d (60.94 mg, 0.3 mmol), [1,1'-bis(diphenylphosphino)ferrocene]dichloropalladium (14.63 mg, 0.02 mmol) and potassium carbonate (54.52 mg, 0.39 mmol) were dissolved in 5 mL of a mixed solvent of 1,4-dioxane and water (V/V=4:1), then the reaction solution was warmed up to 80° C. and stirred for 12 hours. The reaction solution was cooled to room temperature, filtered, and the filtrate was concentrated under reduced pressure. The resulting residue was purified by high performance liquid chromatography to obtain the title compound 2 (19 mg, yield: 26.3%).

MS m/z (ESI): 386.5 [M+1]

Example 2-1

6-((5S,8R)-2-(6-Methylpyridin-2-yl)-5,6,7,8-tetrahydro-5,8-methanoimidazo[1,2-a]pyridin-3-yl)[1,2,4]triazolo[4,3-a]pyridine-3-carboxamide 2-1

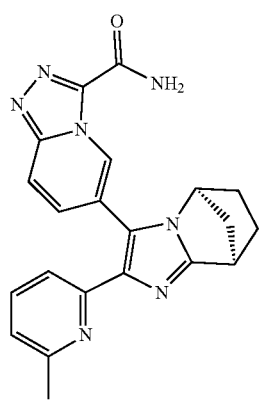

In accordance with the synthetic route of Example 2, the starting compound 1f used in Step 3 was replaced with compound 1f-1, accordingly, the title compound 2-1 (20 mg, yield: 26.31%) was prepared.

MS m/z (ESI): 386.5 [M+1]

$^1$H NMR (400 MHz, CDCl$_3$) δ 9.57 (t, 1H), 7.86 (dd, 1H), 7.76 (dd, 2H), 7.62 (t, 1H), 7.46 (s, 1H), 7.01 (d, 1H), 5.77 (s, 1H), 4.89 (s, 1H), 3.73 (d, 1H), 2.42 (d, 1H), 2.37 (s, 3H), 2.15-2.12 (m, 1H), 2.05-2.02 (m, 1H), 1.93 (d, 1H), 1.59-1.54 (m, 1H), 1.47-1.42 (m, 1H).

Example 2-2

6-((5R,8S)-2-(6-Methylpyridin-2-yl)-5,6,7,8-tetrahydro-5,8-methanoimidazo[1,2-a]pyridin-3-yl)[1,2,4]triazolo[4,3-a]pyridine-3-carboxamide 2-2

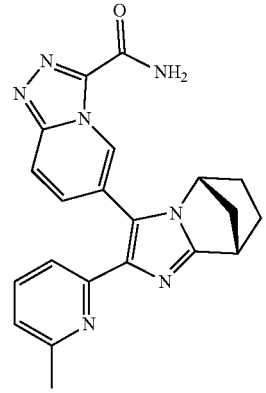

In accordance with the synthetic route of Example 2, chiral preparation was carried out (separation conditions: chiral preparative column CHIRALPAK AS 20×250 mm, 5 m; mobile phase: ethanol (containing 0.1% diethylamine)/n-hexane=20/80 (v/v); flow rate: 15 mL/min). The corresponding fractions were collected and concentrated under reduced pressure to obtain the title compound 2-2 (30 mg).

MS m/z (ESI): 386.5 [M+1]

Chiral HPLC analysis method: retention time 7.486 minutes, chiral purity: 99.5% (chromatographic column: CHIRALPAK AD 4.6×150 mm 5 m; mobile phase: methanol/ethanol (containing 0.1% diethylamine)/n-hexane=10/10/80 (v/v/v));

$^1$H NMR (400 MHz, CD$_3$OD) δ 9.56 (s, 1H), 7.87 (d, 1H), 7.68 (t, 2H), 7.60 (d, 1H), 7.10 (d, 1H), 5.00 (s, 1H), 3.65 (d, 1H), 2.37 (d, 1H), 2.31 (s, 3H), 2.23-2.16 (m, 1H), 2.10-1.98 (m, 2H), 1.42-1.35 (m, 2H).

Example 3

2-(6-Methylpyridin-2-yl)-3-(2-(4-(methylsulfonyl)phenyl)pyridin-4-yl)-5,6,7,8-tetrahydro-5,8-methanoimidazo[1,2-a]pyridine 3

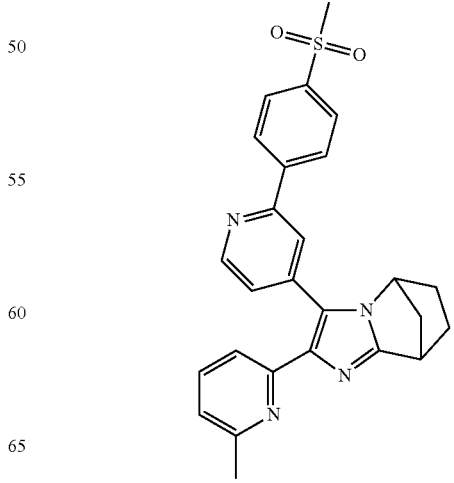

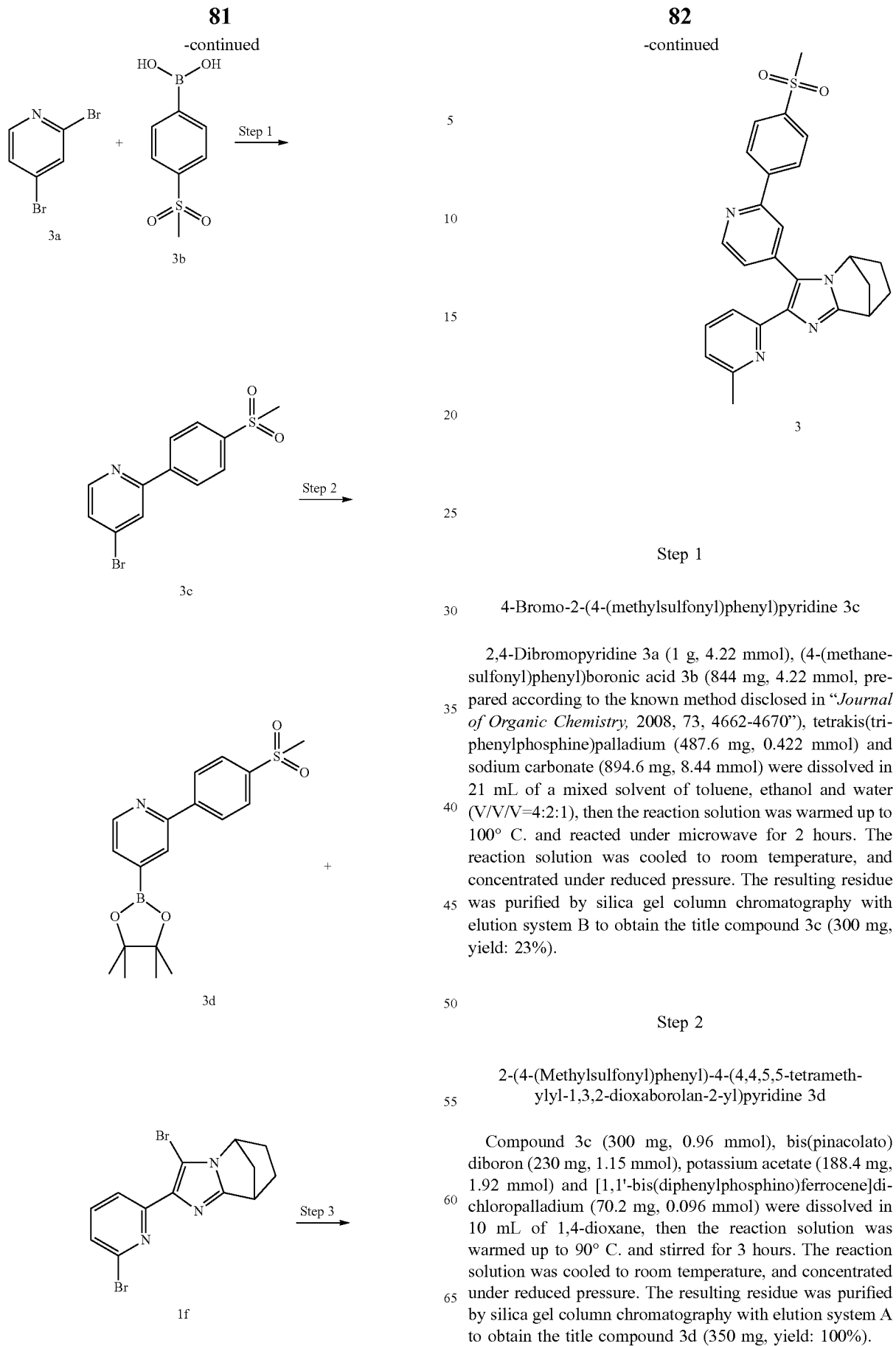

Step 1

4-Bromo-2-(4-(methylsulfonyl)phenyl)pyridine 3c 2,4-Dibromopyridine 3a (1 g, 4.22 mmol), (4-(methanesulfonyl)phenyl)boronic acid 3b (844 mg, 4.22 mmol, prepared according to the known method disclosed in "*Journal of Organic Chemistry*, 2008, 73, 4662-4670"), tetrakis(triphenylphosphine)palladium (487.6 mg, 0.422 mmol) and sodium carbonate (894.6 mg, 8.44 mmol) were dissolved in 21 mL of a mixed solvent of toluene, ethanol and water (V/V/V=4:2:1), then the reaction solution was warmed up to 100° C. and reacted under microwave for 2 hours. The reaction solution was cooled to room temperature, and concentrated under reduced pressure. The resulting residue was purified by silica gel column chromatography with elution system B to obtain the title compound 3c (300 mg, yield: 23%).

Step 2

2-(4-(Methylsulfonyl)phenyl)-4-(4,4,5,5-tetramethylyl-1,3,2-dioxaborolan-2-yl)pyridine 3d Compound 3c (300 mg, 0.96 mmol), bis(pinacolato)diboron (230 mg, 1.15 mmol), potassium acetate (188.4 mg, 1.92 mmol) and [1,1'-bis(diphenylphosphino)ferrocene]dichloropalladium (70.2 mg, 0.096 mmol) were dissolved in 10 mL of 1,4-dioxane, then the reaction solution was warmed up to 90° C. and stirred for 3 hours. The reaction solution was cooled to room temperature, and concentrated under reduced pressure. The resulting residue was purified by silica gel column chromatography with elution system A to obtain the title compound 3d (350 mg, yield: 100%).

Step 3

(5S,8R)-2-(6-Methylpyridin-2-yl)-3-(2-(4-(methylsulfonyl)phenyl)pyridin-4-yl)-5,6,7,8-tetrahydro-5,8-methanoimidazo[1,2-a]pyridine 3

Compound 1f (50 mg, 0.16 mmol), compound 3d (91.09 mg, 0.254 mmol), [1,1'-bis(diphenylphosphino)ferrocene]dichloropalladium (24.385 mg, 0.0329 mmol) and potassium carbonate (68.153 mg, 0.4931 mmol) were dissolved in 5 mL of a mixed solvent of 1,4-dioxane and water (V/V=4:1), then the reaction solution was warmed up to 100° C. and stirred for 12 hours. The reaction solution was cooled to room temperature, and filtered through celite. The filter cake was washed with ethyl acetate, and the filtrate was concentrated under reduced pressure. The resulting residue was purified by high performance liquid chromatography to obtain the title compound 3 (21 mg, yield: 24.5%).

MS m/z (ESI): 457.4 [M+1]

$^1$H NMR (400 MHz, CD$_3$OD) δ 8.70 (d, 1H), 8.18 (d, 2H), 8.08 (d, 3H) 7.73 (t, 1H), 7.58-7.52 (m, 2H), 7.19 (d, 1H), 5.10 (s, 1H), 3.66 (s, 1H), 3.19 (s, 3H), 2.45 (d, 1H), 2.35 (s, 3H), 2.25-2.15 (m, 1H), 2.04-2.02 (m, 2H), 1.45-1.25 (m, 2H).

Example 3-1

(5S,8R)-2-(6-Methylpyridin-2-yl)-3-(2-(4-(methylsulfonyl)phenyl)pyridin-4-yl)-5,6,7,8-tetrahydro-5,8-methanoimidazo[1,2-a]pyridine 3-1

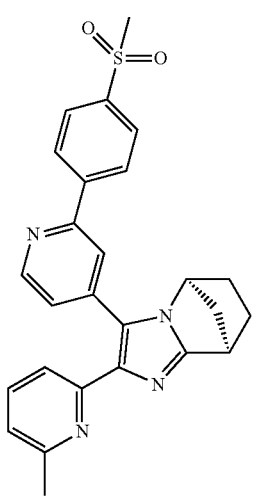

3-1

In accordance with the synthetic route of Example 3, the starting compound 1f used in Step 3 was replaced with compound 1f-1, accordingly, the title compound 3-1 (20 mg, yield: 24.52%) was prepared.

MS m/z (ESI): 457.4 [M+1]

$^1$H NMR (400 MHz, CD$_3$OD) δ 8.70 (d, 1H), 8.18 (d, 2H), 8.08 (d, 3H) 7.73 (t, 1H), 7.58-7.52 (m, 2H), 7.19 (d, 1H), 5.10 (s, 1H), 3.66 (s, 1H), 3.19 (s, 3H), 2.45 (d, 1H), 2.35 (s, 3H), 2.25-2.15 (m, 1H), 2.04-2.02 (m, 2H), 1.45-1.25 (m, 2H).

Example 3-2

(5R,8S)-2-(6-Methylpyridin-2-yl)-3-(2-(4-(methylsulfonyl)phenyl)pyridin-4-yl)-5,6,7,8-tetrahydro-5,8-methanoimidazo[1,2-a]pyridine 3-2

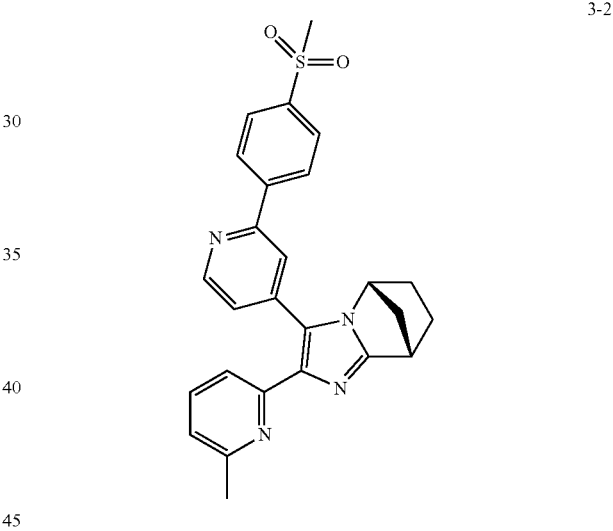

3-2

Compound 3 was separated chirally (separation conditions: chiral preparative column CHIRALPAK OD 21.5× 250 mm, 5 m; mobile phase: ethanol=100 (v/v); flow rate: 7.0 mL/min). The corresponding fractions were collected and concentrated under reduced pressure to obtain the title compound 3-2 (51 mg).

MS m/z (ESI): 457.4 [M+1]

Chiral HPLC analysis method: retention time 8.488 minutes (chromatographic column: CHIRALPAK OD 4.6×150 mm 5 m; mobile phase: ethanol/n-hexane=60/40 (v/v));

$^1$H NMR (400 MHz, CD$_3$OD) δ 8.70 (d, 1H), 8.18 (d, 2H), 8.08 (d, 3H) 7.73 (t, 1H), 7.58-7.52 (m, 2H), 7.19 (d, 1H), 5.10 (s, 1H), 3.66 (s, 1H), 3.19 (s, 3H), 2.45 (d, 1H), 2.35 (s, 3H), 2.25-2.15 (m, 1H), 2.04-2.02 (m, 2H), 1.45-1.25 (m, 2H).

Example 4

4-(4-(2-(6-Methylpyridin-2-yl)-5,6,7,8-tetrahydro-5,8-methanoimidazo[1,2-a]pyridin-3-yl)pyridin-2-yl)benzamide 4

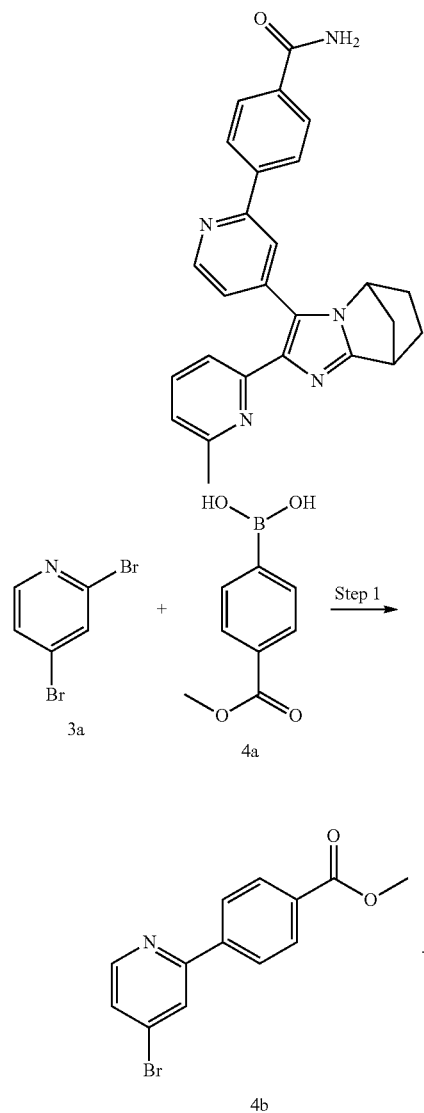

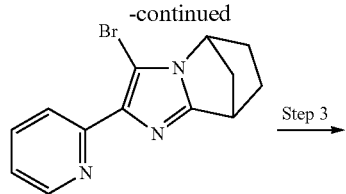

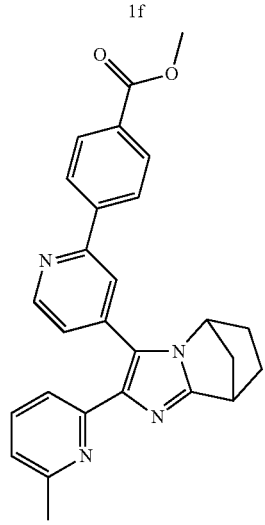

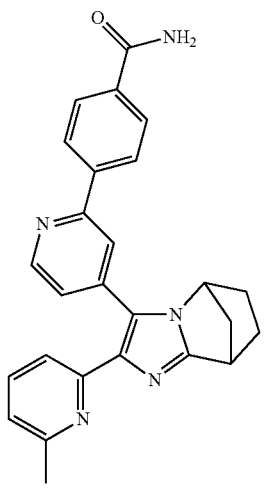

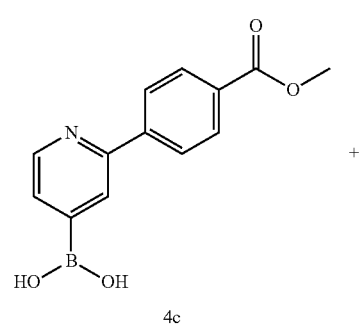

Step 1

Methyl 4-(4-bromopyridin-2-yl)benzoate 4b

Compound 3a (1 g, 4.22 mmol), (4-(methoxycarbonyl)phenyl)boronic acid 4a (759.72 mg, 4.22 mmol), tetrakis(triphenylphosphine)palladium (487.8 mg, 0.422 mmol) and sodium carbonate (894.85 mg, 8.44 mmol) were dissolved in 14 mL of a mixed solvent of toluene, ethanol and water (V/V/V=4:2:1), then the reaction solution was warmed up to 100° C. and reacted under microwave for 1 hours. The reaction solution was cooled to room temperature, and concentrated under reduced pressure. The resulting residue

87 was purified by silica gel column chromatography with elution system B to obtain the title compound 4b (220 mg, yield: 17.84%).

Step 2

(2-(4-(Methoxycarbonyl)phenyl)pyridin-4-yl)boronic acid 4c

Compound 4b (310 mg, 1.06 mmol), bis(pinacolato)diboron (404.21 mg, 1.59 mmol), potassium acetate (208.29 mg, 2.12 mmol) and [1,1'-bis(diphenylphosphino)ferrocene]dichloropalladium (78.716 mg, 0.106 mmol) were dissolved in 10 mL of 1,4-dioxane, then the reaction solution was warmed up to 90° C. and stirred for 2 hours. The reaction solution was cooled to room temperature, and concentrated under reduced pressure to obtain the crude title compound 4c (272 mg), which was used directly in the next step without purification.

Step 3

Methyl 4-(4-(2-(6-methylpyridin-2-yl)-5,6,7,8-tetrahydro-5,8-methanoimidazo[1,2-a]pyridin-3-yl)pyridin-2-yl)benzoate 4d Compound 1f (200 mg, 0.658 mmol), the crude compound 4c (202.81 mg, 0.789 mmol), [1,1'-bis(diphenylphosphino)ferrocene]dichloropalladium (48.771 mg, 0.0657 mmol) and potassium carbonate (272.61 mg, 1.972 mmol) were dissolved in 12 mL of a mixed solvent of 1,4-dioxane and water (V/V=5:1), then the reaction solution was warmed up to 100° C. and stirred for 12 hours. The reaction solution was cooled to room temperature, filtered, and the filtrate was concentrated under reduced pressure. The resulting residue was purified by silica gel column chromatography with elution system B to obtain the title compound 4d (180 mg, yield: 62.72%).

Step 4

4-(4-(2-(6-Methylpyridin-2-yl)-5,6,7,8-tetrahydro-5,8-methanoimidazo[1,2-a]pyridin-3-yl)pyridin-2-yl)benzamide 4

Compound 4d (30 mg, 0.07 mmol) was dissolved in 10 mL of 7 M ammonia in methanol, then the reaction solution was warmed up to 110° C. and stirred in a sealed tube for 12 hours. The reaction solution was cooled to room temperature, and concentrated under reduced pressure. The resulting residue was purified by high performance liquid chromatography to obtain the title compound 4 (10 mg, yield: 33.4%).

MS m/z (ESI): 422.6 [M+1]

$^1$H NMR (400 MHz, CD$_3$OD) δ 8.68 (d, 1H), 8.04-8.02 (m, 1H), 8.00 (s, 4H) 7.75 (t, 1H), 7.56 (d, 1H), 7.52-7.49 (dd, 1H), 7.20 (d, 1H), 5.10 (s, 1H), 3.68 (m, 1H), 2.42 (d, 1H), 2.36 (s, 3H), 2.25-2.15 (m, 1H), 2.10-2.00 (m, 2H), 1.45-1.35 (m, 2H).

88

Examples 4-1, 4-2

4-(4-((5S,8R)-2-(6-Methylpyridin-2-yl)-5,6,7,8-tetrahydro-5,8-methanoimidazo[1,2-a]pyridin-3-yl)pyridin-2-yl)benzamide 4-1

4-(4-((5R,8S)-2-(6-Methylpyridin-2-yl)-5,6,7,8-tetrahydro-5,8-methanoimidazo[1,2-a]pyridin-3-yl)pyridin-2-yl)benzamide 4-2

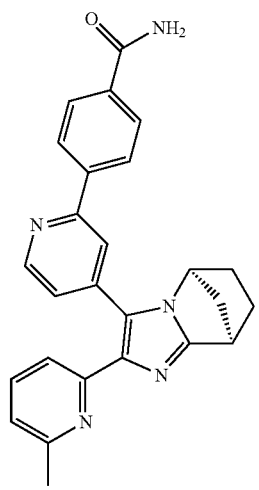

4-1

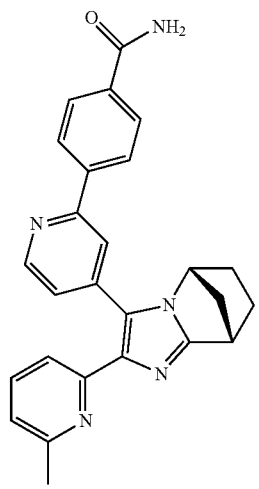

4-2

Compound 4 (150 mg, 0.344 mmol) was dissolved in 10 mL of 7 M ammonia in methanol, then the reaction solution was warmed up to 110° C. and stirred in a sealed tube for 12 hours. The reaction solution was cooled to room temperature, and concentrated under reduced pressure. The resulting residue was purified by chiral preparation (separation conditions: chiral preparative column CHIRALPAK OD 21.5× 250 mm, 5 μm, mobile phase: ethanol (containing 0.1% diethylamine)=100 (v); flow rate: 7 mL/min). The corresponding fractions were collected and concentrated under reduced pressure to obtain the title compounds (30 mg, 35 mg).

Compound in a single configuration (with shorter retention time):

MS m/z (ESI): 422.2 [M+1]

Chiral HPLC analysis method: retention time 4.058 minutes (chromatographic column: CHIRALPAK OD 4.6×150 mm 5 m; mobile phase: ethanol (containing 0.1% diethylamine)/n-hexane=40/60 (v/v));

$^1$H NMR (400 MHz, CD$_3$OD) δ 8.68 (d, 1H), 8.03-8.00 (m, 5H), 7.74 (t, 1H), 7.57-7.50 (m, 2H), 7.20 (d, 1H), 5.11 (s, 1H), 3.68 (s, 1H), 2.42 (d, 1H), 2.36 (s, 3H), 2.21 (s, 1H), 2.03 (d, 2H), 1.41-1.31 (m, 2H).

Compound in a single configuration (with longer retention time):

MS m/z (ESI): 422.2 [M+1]

Chiral HPLC analysis method: retention time 7.204 minutes (chromatographic column: CHIRALPAK OD 4.6×150 mm 5 m; mobile phase: ethanol (containing 0.1% diethylamine)/n-hexane=40/60 (v/v));

$^1$H NMR (400 MHz, CD$_3$OD) δ 8.68 (d, 1H), 8.03-8.00 (m, 5H), 7.74 (t, 1H), 7.57-7.50 (m, 2H), 7.20 (d, 1H), 5.11 (s, 1H), 3.68 (s, 1H), 2.42 (d, 1H), 2.36 (s, 3H), 2.21 (s, 1H), 2.03 (d, 2H), 1.41-1.31 (m, 2H).

Example 5

2-((4-(2-(6-Methylpyridin-2-yl)-5,6,7,8-tetrahydro-5,8-methanoimidazo[1,2-a]pyridin-3-yl)pyridin-2-yl)amino)ethanol 5

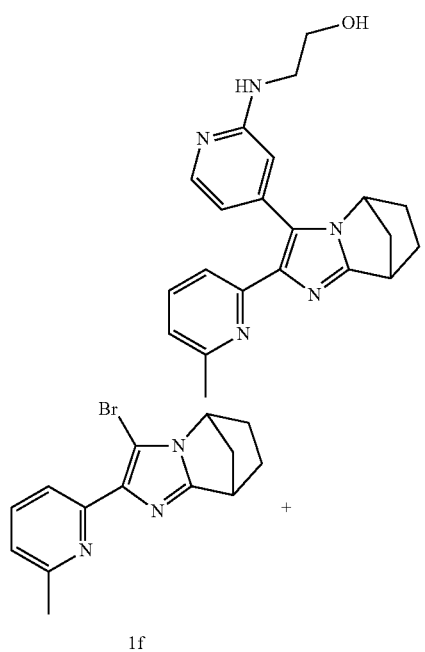

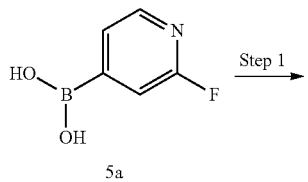

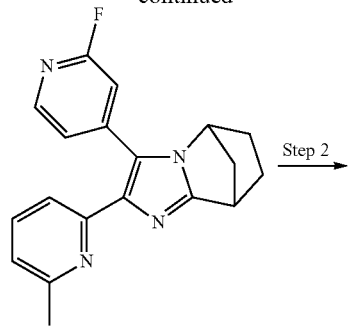

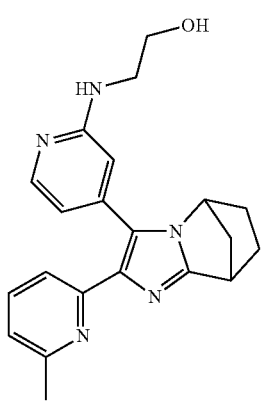

Step 1

(5S,8R)-3-(2-Fluoropyridin-4-yl)-2-(6-methylpyridin-2-yl)-5,6,7,8-tetrahydro-5,8-methanoimidazo[1,2-a]pyridine 5b (2-Fluoropyridin-4-yl)boronic acid 5a (48.64 mg, 0.35 mmol, prepared according to the method disclosed in the patent application "WO2015103137"), compound 1f (70 mg, 0.23 mmol), [1,1'-bis(diphenylphosphino)ferrocene]dichloropalladium (17.07 mg, 0.023 mmol) and potassium carbonate (63.61 mg, 0.46 mmol) were dissolved in 5 mL of a mixed solvent of 1,4-dioxane and water (V/V=4:1), then the reaction solution was warmed up to 80° C. and stirred for 12 hours. The reaction solution was cooled to room temperature, and concentrated under reduced pressure. The resulting residue was purified by silica gel column chromatography with elution system A to obtain the title compound 5b (70 mg, yield: 94.95%).

Step 2

2-((4-((5S,8R)-2-(6-Methylpyridin-2-yl)-5,6,7,8-tetrahydro-5,8-methanoimidazo[1,2-a]pyridin-3-yl)pyridin-2-yl)amino)ethanol 5

Compound 5b (50 mg, 0.16 mmol) and aminoethanol (476.65 mg, 7.8 mmol) were added to a flask, then the reaction solution was warmed up to 110° C. and stirred for 2 hours. The reaction solution was cooled to room temperature, and concentrated under reduced pressure. The resulting residue was purified by high performance liquid chromatography to obtain the title compound 5 (15 mg, yield: 26%).

MS m/z (ESI): 362.5 [M+1]

¹H NMR (400 MHz, CDCl₃) δ 8.04 (d, 1H), 7.49 (t, 1H), 7.19 (d, 1H), 6.97 (d, 1H), 6.51 (d, 1H), 6.30 (s, 1H), 4.75 (s, 1H), 3.87-3.85 (m, 2H), 3.77-3.75 (m, 1H), 3.59 (d, 1H), 3.51-3.48 (m, 1H), 2.47 (t, 3H), 2.22 (d, 1H), 1.97-1.90 (m, 2H), 1.81-1.77 (m, 2H), 1.13-1.11 (m, 1H), 0.93-0.90 (m, 1H).

Example 5-1

2-((4-((5S,8R)-2-(6-Methylpyridin-2-yl)-5,6,7,8-tetrahydro-5,8-methanoimidazo[1,2-a]pyridin-3-yl)pyridin-2-yl)amino)ethanol 5-1

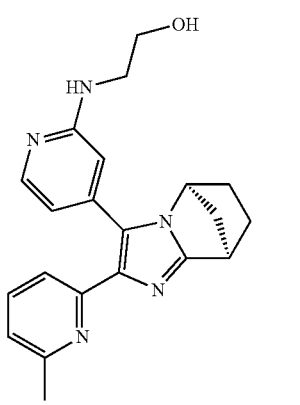

5-1

In accordance with the synthetic route of Example 5, the starting compound 1f used in Step 1 was replaced with compound 1f-1, accordingly, the title compound 5-1 (20 mg, yield: 35.45%) was prepared.

MS m/z (ESI): 362.3 [M+1]

¹H NMR (400 MHz, CDCl₃) δ 8.06 (d, 1H), 7.48 (t, 1H), 7.15 (d, 1H), 6.97 (d, 1H), 6.48 (d, 1H), 6.24 (s, 1H), 4.75 (s, 1H), 3.87-3.83 (m, 3H), 3.60 (d, 1H), 3.44-3.40 (m, 1H), 2.47 (s, 3H), 2.26 (d, 1H), 1.90-1.72 (m, 4H), 1.05-1.02 (m, 1H), 0.79-0.76 (m, 1H).

Example 6

2-(6-Methylpyridin-2-yl)-3-(quinoxalin-6-yl)-5,6,7,8-tetrahydro-5,8-methanoimidazo[1,2-a]pyridine 6

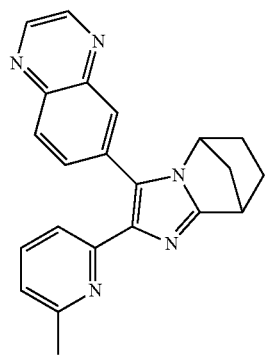

6

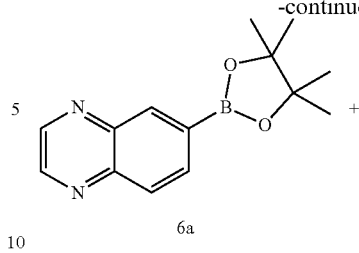

6a

1f

6

Compound 1f (900 mg, 2.959 mmol), 6-(4,4,5,5-tetramethyl-1,3,2-dioxaborolan-2-yl)quinoxaline 6a (985 mg, 3.846 mmol, prepared according to the method disclosed in the patent application "WO2010059943"), [1,1'-bis(diphenylphosphino)ferrocene]dichloropalladium (216 mg, 0.296 mmol) and sodium carbonate (941 mg, 8.877 mmol) were dissolved in 18 mL of a mixed solvent of glycol dimethyl ether and water (V/V=5:1), then the reaction solution was warmed up to 80° C. and stirred for 24 hours. The reaction solution was cooled to room temperature, added with water, and extracted with ethyl acetate. The organic phases were combined, dried over anhydrous sodium sulfate and filtered. The filtrate was concentrated under reduced pressure, and the resulting residue was purified by silica gel column chromatography with elution system A to obtain the title compound 6 (560 mg, yield: 54%).

MS m/z (ESI): 354.3 [M+1]

¹H NMR (400 MHz, CD₃OD) δ 9.01 (d, 2H), 8.37 (d, 1H), 8.30 (d, 1H), 8.01 (d, 1H), 7.83 (t, 1H), 7.43 (d, 1H), 7.36 (d, 1H), 5.16 (s, 1H), 3.98 (d, 1H), 2.69 (s, 3H), 2.56 (d, 1H), 2.39-2.36 (m, 1H), 2.20-2.16 (m, 2H), 1.60-1.55 (m, 2H).

Examples 6-1, 6-2

(5S,8R)-2-(6-Methylpyridin-2-yl)-3-(quinoxalin-6-yl)-5,6,7,8-tetrahydro-5,8-methanoimidazo[1,2-a]pyridine 6-1

(5R,8S)-2-(6-Methylpyridin-2-yl)-3-(quinoxalin-6-yl)-5,6,7,8-tetrahydro-5,8-methanoimidazo[1,2-a]pyridine 6-2

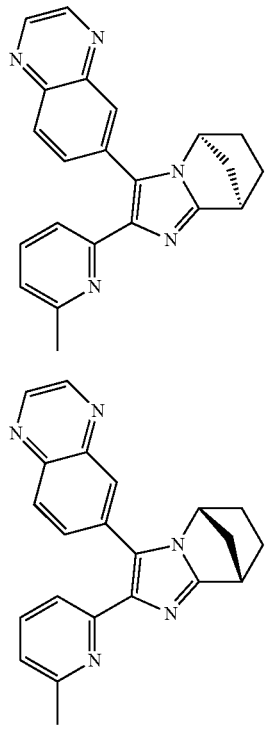

6-1

6-2

Compound 6 was separated chirally (560 mg, 1.58 mmol) (separation conditions: chromatographic column: Superchiral S-OZ (Chiralway), 2 cm I.D.×25 cm Length, 5 μm; mobile phase: carbon dioxide/ethanol=50/50 (v/v); flow rate: 50 g/min). The corresponding fractions were collected and concentrated under reduced pressure to obtain the title compounds (240 mg, 245 mg).

Compound in a single configuration (with shorter retention time):

MS m/z (ESI): 354.4 [M+1]

Chiral HPLC analysis method: retention time 3.747 minutes (chromatographic column: CHIRALPAK IB 4.6×150 mm 5 m; mobile phase: ethanol (containing 0.1% diethylamine)/n-hexane=30/70 (v/v));

$^1$H NMR (400 MHz, CDCl$_3$) δ 8.91 (t, 2H), 8.20 (d, 1H), 8.08 (d, 1H), 7.92-7.88 (dd, 1H), 7.70 (t, 1H), 7.52 (d, 1H), 7.15 (d, 1H), 5.08 (s, 1H), 3.69 (d, 1H), 2.42 (d, 1H), 2.33 (s, 3H), 2.23-2.21 (m, 1H), 2.05-2.02 (m, 2H), 1.44-1.38 (m, 2H).

Compound in a single configuration (with longer retention time):

MS m/z (ESI): 354.4 [M+1]

Chiral HPLC analysis method: retention time 5.327 minutes (chromatographic column: CHIRALPAK IB 4.6×150 mm 5 m; mobile phase: ethanol (containing 0.1% diethylamine)/n-hexane=30/70 (v/v));

$^1$H NMR (400 MHz, CDCl$_3$) δ 8.91 (t, 2H), 8.20 (d, 1H), 8.08 (d, 1H), 7.92-7.88 (dd, 1H), 7.70 (t, 1H), 7.52 (d, 1H), 7.15 (d, 1H), 5.08 (s, 1H), 3.69 (d, 1H), 2.42 (d, 1H), 2.33 (s, 3H), 2.23-2.21 (m, 1H), 2.05-2.02 (m, 2H), 1.44-1.38 (m, 2H).

Example 7

2-((7-(2-(6-Methylpyridin-2-yl)-5,6,7,8-tetrahydro-5,8-methanoimidazo[1,2-a]pyridin-3-yl)quinoxalin-2-yl)oxy)ethanol 7

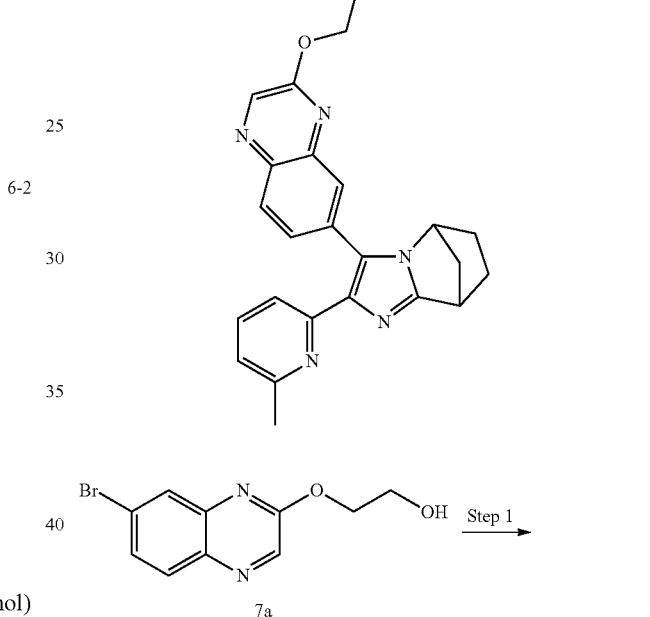

7

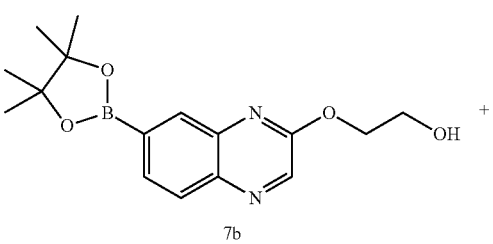

7a

7b

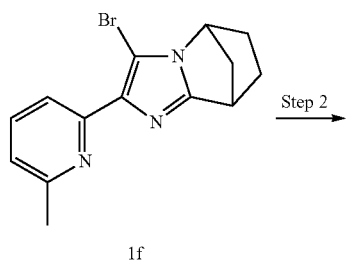

1f

95

-continued

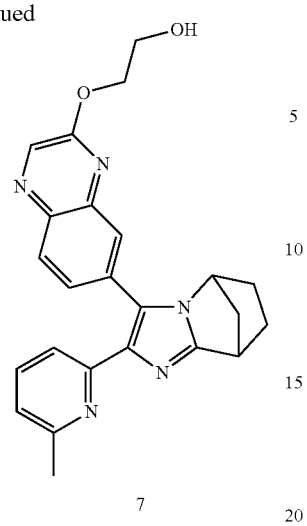

7

Step 1

2-((7-(4,4,5,5-tetramethyl-1,3,2-dioxaborolan-2-yl)quinoxalin-2-yl)oxy)ethanol 7b 2-((7-Bromoquinoxalin-2-yl)oxy)ethanol 7a (400 mg, 1.48 mmol, prepared according to the method disclosed in the patent application "WO2005092894"), bis(pinacolato)diboron (451 mg, 1.78 mmol), potassium acetate (290 mg, 2.96 mmol) and [1,1'-bis(diphenylphosphino)ferrocene]dichloropalladium (54 mg, 0.074 mmol) were dissolved in 5 mL of 1,4-dioxane, then the reaction solution was warmed up to 90° C. and stirred for 2 hours. The reaction solution was cooled to room temperature, added with 50 mL of water, and extracted with ethyl acetate (50 mL×2). The organic phases were combined, dried over anhydrous sodium sulfate and filtered. The filtrate was concentrated under reduced pressure, and the resulting residue was purified by silica gel column chromatography with elution system B to obtain the title compound 7b (249 mg, yield: 53%).

Step 2

2-((7-(2-(6-Methylpyridin-2-yl)-5,6,7,8-tetrahydro-5,8-methanoimidazo[1,2-a]pyridin-3-yl)quinoxalin-2-yl)oxy)ethanol 7

Compound 7b (103 mg, 0.328 mmol), compound 1f (50 mg, 0.164 mmol), [1,1'-bis(diphenylphosphino)ferrocene]dichloropalladium (24 mg, 0.033 mmol) and potassium carbonate (67 mg, 0.442 mmol) were dissolved in 6 mL of a mixed solvent of 1,4-dioxane and water (V/V=5:1), then the reaction solution was warmed up to 100° C. and stirred for 1 hours. The reaction solution was cooled to room temperature, filtered through celite, and the filtrate was concentrated under reduced pressure. The resulting residue was purified by high performance liquid chromatography to obtain the title compound 7 (20 mg, yield: 29.8%).

MS m/z (ESI): 414.4 [M+1]

$^1$H NMR (400 MHz, CD$_3$OD) δ 8.51 (d, 1H), 7.96 (d, 2H), 7.70-7.60 (m, 2H), 7.44 (d, 1H), 7.15 (d, 1H), 5.10 (s, 1H), 4.59 (t, 2H), 3.98 (t, 2H), 3.68 (s, 1H), 2.43 (d, 1H), 2.37 (s, 3H), 2.25-2.15 (m, 1H), 2.10-2.00 (m, 2H), 1.45-1.35 (m, 2H).

96

Example 8

2-(6-Methylpyridin-2-yl)-3-(1'-(methylsulfonyl)-1',2',3',6'-tetrahydro-[2,4'-bipyridin]-4-yl)-5,6,7,8-tetrahydro-5,8-methanoimidazo[1,2-a]pyridine 8

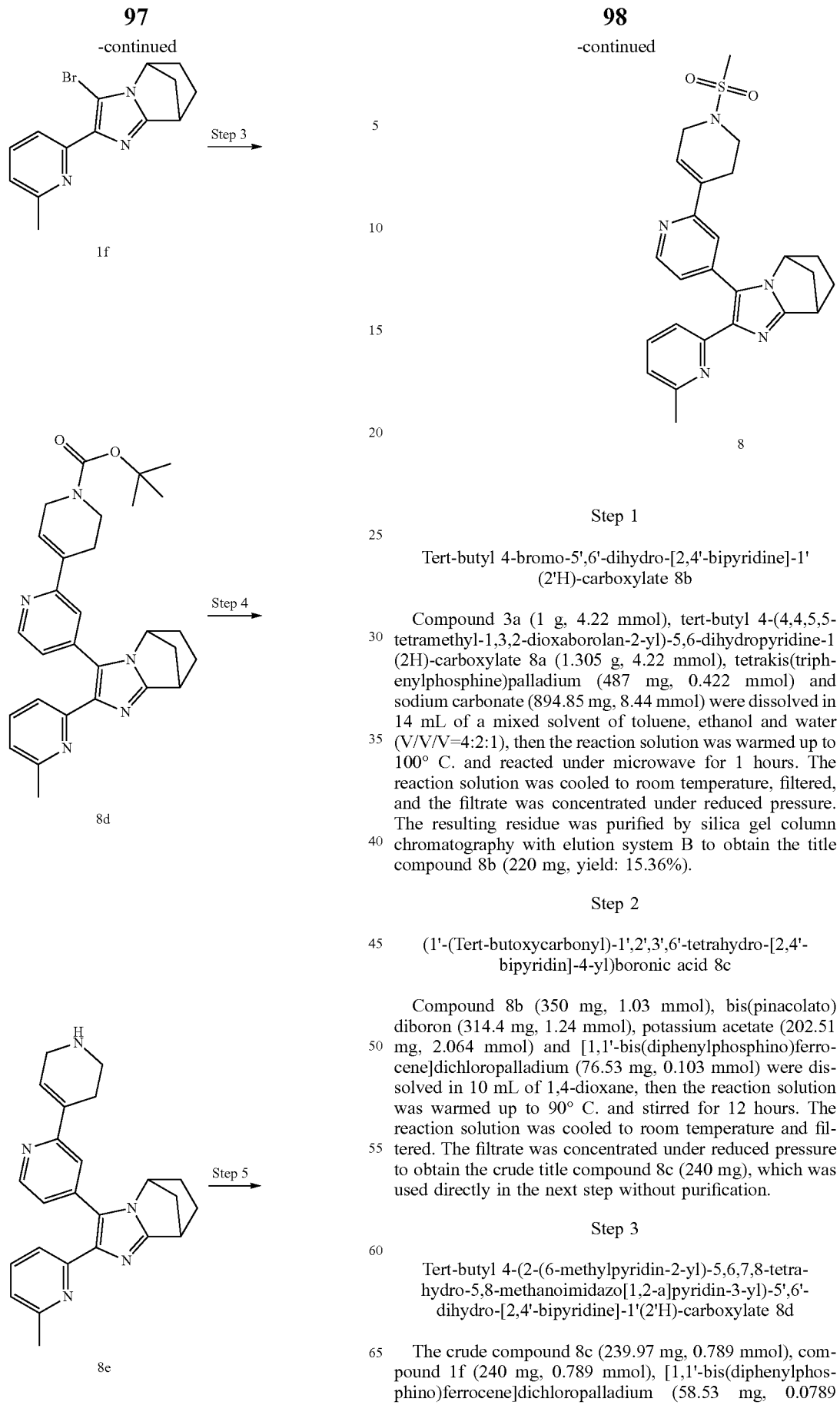

Step 1

Tert-butyl 4-bromo-5',6'-dihydro-[2,4'-bipyridine]-1'(2'H)-carboxylate 8b

Compound 3a (1 g, 4.22 mmol), tert-butyl 4-(4,4,5,5-tetramethyl-1,3,2-dioxaborolan-2-yl)-5,6-dihydropyridine-1(2H)-carboxylate 8a (1.305 g, 4.22 mmol), tetrakis(triphenylphosphine)palladium (487 mg, 0.422 mmol) and sodium carbonate (894.85 mg, 8.44 mmol) were dissolved in 14 mL of a mixed solvent of toluene, ethanol and water (V/V/V=4:2:1), then the reaction solution was warmed up to 100° C. and reacted under microwave for 1 hours. The reaction solution was cooled to room temperature, filtered, and the filtrate was concentrated under reduced pressure. The resulting residue was purified by silica gel column chromatography with elution system B to obtain the title compound 8b (220 mg, yield: 15.36%).

Step 2

(1'-(Tert-butoxycarbonyl)-1',2',3',6'-tetrahydro-[2,4'-bipyridin]-4-yl)boronic acid 8c Compound 8b (350 mg, 1.03 mmol), bis(pinacolato)diboron (314.4 mg, 1.24 mmol), potassium acetate (202.51 mg, 2.064 mmol) and [1,1'-bis(diphenylphosphino)ferrocene]dichloropalladium (76.53 mg, 0.103 mmol) were dissolved in 10 mL of 1,4-dioxane, then the reaction solution was warmed up to 90° C. and stirred for 12 hours. The reaction solution was cooled to room temperature and filtered. The filtrate was concentrated under reduced pressure to obtain the crude title compound 8c (240 mg), which was used directly in the next step without purification.

Step 3

Tert-butyl 4-(2-(6-methylpyridin-2-yl)-5,6,7,8-tetrahydro-5,8-methanoimidazo[1,2-a]pyridin-3-yl)-5',6'-dihydro-[2,4'-bipyridine]-1'(2'H)-carboxylate 8d The crude compound 8c (239.97 mg, 0.789 mmol), compound 1f (240 mg, 0.789 mmol), [1,1'-bis(diphenylphosphino)ferrocene]dichloropalladium (58.53 mg, 0.0789 mmol) and potassium carbonate (218.09 mg, 1.578 mmol) were dissolved in 16.5 mL of a mixed solvent of 1,4-dioxane and water (V/V=10:1), then the reaction solution was warmed up to 100° C. and stirred for 12 hours. The reaction solution was cooled to room temperature, filtered through celite, and the filtrate was concentrated under reduced pressure. The resulting residue was purified by silica gel column chromatography with elution system B to obtain the title compound 8d (300 mg, yield: 78.63%).

Step 4

2-(6-Methylpyridin-2-yl)-3-(1',2',3',6'-tetrahydro-[2,4'-bipyridin]-4-yl)-5,6,7,8-tetrahydro-5,8-methano-imidazo[1,2-a]pyridine 8e Compound 8d (200 mg, 0.414 mmol) was dissolved in 10 mL of dichloromethane, then 6 mL of trifluoroacetic acid was added. After stirring at room temperature for 12 hours, the reaction solution was added with saturated sodium carbonate solution to adjust the pH to about 8, and extracted with dichloromethane. The organic phases were combined, dried over anhydrous sodium sulfate and filtered. The filtrate was concentrated under reduced pressure to obtain the crude title compound 8e (150 mg), which was used directly in the next step without purification.

Step 5

2-(6-Methylpyridin-2-yl)-3-(1'-(methylsulfonyl)-1',2',3',6'-tetrahydro-[2,4'-bipyridin]-4-yl)-5,6,7,8-tetra-hydro-5,8-methanoimidazo[1,2-a]pyridine 8

The crude compound 8e (20 mg, 0.0522 mmol) was dissolved in 5 mL of dichloromethane, then 0.03 mL of N,N-diisopropylethylamine was added, followed by addition of methanesulfonyl chloride (8.96 mg, 0.08 mmol). After stirring at room temperature for 1 hours, the reaction solution was concentrated under reduced pressure. The resulting residue was purified by high performance liquid chromatography to obtain the title compound 8 (4 mg, yield: 15.95%).

MS m/z (ESI): 462.2 [M+1]

$^1$H NMR (400 MHz, CD$_3$OD) δ 8.52 (d, 1H), 7.73 (t, 1H), 7.62 (s, 1H), 7.51 (d, 1H), 7.38-7.21 (m, 1H), 7.20 (d, 1H), 6.58 (s, 1H), 5.05 (s, 1H), 4.64 (s, 1H), 4.01-3.99 (m, 2H), 3.66 (s, 1H), 3.51 (t, 2H), 2.92 (s, 3H), 2.72 (s, 2H), 2.41 (s, 3H), 2.21-2.20 (m, 1H), 2.06-1.97 (m, 2H), 1.39-1.23 (m, 2H).

Example 9

6-(2-(5-Fluoropyridin-2-yl)-5,6,7,8-tetrahydro-5,8-methanoimidazo[1,2-a]pyridin-3-yl)-[1,2,4]triazolo[4,3-a]pyridine-3-carboxamide 9

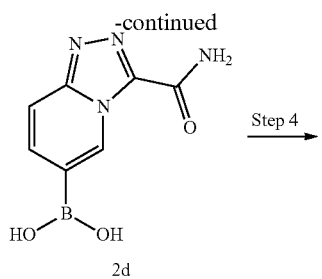

2d

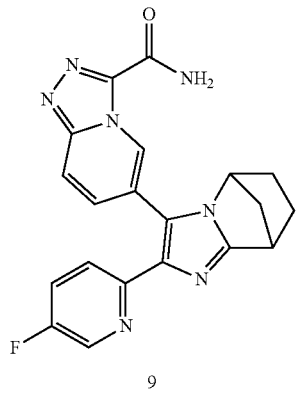 [SMILES: NC(=O)c1nnc2ccc(-c3c(-c4ccc(F)cn4)nc4n3C3CCC4C3)cn12]

9

Step 1

2-(2-(5-Fluoropyridin-2-yl)-2-oxoethyl)-2-azabicyclo[2.2.1]heptan-3-one 9b

2-Bromo-1-(5-fluoropyridin-2-yl)ethanone 9a (5.56 g, 44.41 mmol, prepared according to the known method disclosed in "Molecules, 2014, 19(10), 15653-15672") was dissolved in 15 mL of N,N-dimethylformamide, then compound 1b (4.2 g, 19.26 mmol) was added. After stirring at 50° C. for 18 hours under an argon atmosphere, the reaction solution was concentrated under reduced pressure to obtain the crude title compound 9b (4 g), which was used directly in the next step without purification.

Step 2

2-(5-Fluoropyridin-2-yl)-5,6,7,8-tetrahydro-5,8-methanoimidazo[1,2-a]pyridine 9c The crude compound 9b (4 g, 16.11 mmol) and ammonium acetate (12.42 g, 161.13 mmol) were dissolved in 20 mL of acetic acid, then the reaction solution was stirred at 110° C. for 4 hours. After the reaction was completed, the reaction solution was concentrated under reduced pressure. The resulting residue was dissolved in ethyl acetate, and washed with saturated sodium bicarbonate solution. The organic phase was dried over anhydrous sodium sulfate and filtered. The filtrate was concentrated under reduced pressure, and the resulting residue was purified by silica gel column chromatography with elution system B to obtain the title compound 9c (1.4 g, yield: 37.90%).

Step 3

3-Bromo-2-(5-fluoropyridin-2-yl)-5,6,7,8-tetrahydro-5,8-methanoimidazo[1,2-a]pyridine 9d Compound 9c (1.4 g, 6.11 mmol) was added to 25 mL of dichloromethane, the reaction solution was cooled to 0° C., liquid bromine (0.35 mL, 6.72 mmol) was added dropwise, and the reaction solution was stirred at 25° C. for 1.5 hours. After the reaction was completed, the reaction was quenched by adding 20 mL of saturated sodium sulfite solution under stirring for 10 minutes. The reaction solution was extracted with dichloromethane, then the organic phase was dried over anhydrous sodium sulfate and filtered. The filtrate was concentrated under reduced pressure, and the resulting residue was purified by silica gel column chromatography with elution system B to obtain the title compound 9d (1 g, yield: 53.14%).

Step 4

6-(2-(5-Fluoropyridin-2-yl)-5,6,7,8-tetrahydro-5,8-methanoimidazo[1,2-a]pyridin-3-yl)-[1,2,4]triazolo[4,3-a]pyridine-3-carboxamide 9

Compound 2d (60.16 mg, 0.29 mmol), compound 9d (90 mg, 0.29 mmol) and potassium carbonate (237.9 mg, 0.73 mmol) were dissolved in 10 mL of 1,4-dioxane and 1.5 mL of water. The reaction system was purged with argon three times. [1,1'-Bis(diphenylphosphino)ferrocene]dichloropalladium (19.33 mg, 0.3 mmol) was added, then the reaction solution was warmed up to 100° C. and stirred for 1 hours under an argon atmosphere. After the reaction was completed, the reaction was quenched by adding water under stirring. The reaction solution was extracted with ethyl acetate, then the organic phases were combined, dried over anhydrous sodium sulfate and filtered. The filtrate was concentrated under reduced pressure, and the resulting residue was purified by silica gel column chromatography with elution system B to obtain the title compound 9 (25 mg, yield: 20.71%).

MS m/z (ESI): 390.4 [M+1]

$^1$H NMR (400 MHz, CDCl$_3$) δ 9.62-9.60 (m, 1H), 8.25 (d, 1H), 8.03-8.00 (m, 1H), 7.89 (dd, 1H), 7.65 (dd, 1H), 7.53 (br, 1H), 7.48-7.43 (m, 1H), 5.89 (br, 1H), 4.87 (br, 1H), 3.73-3.72 (m, 1H), 2.41 (d, 1H), 2.19-2.12 (m, 1H), 2.05-1.96 (m, 1H), 1.94 (d, 1H), 1.56-1.51 (m, 1H), 1.43-1.36 (m, 1H).

Examples 9-1, 9-2

6-((5S,8R)-2-(5-Fluoropyridin-2-yl)-5,6,7,8-tetrahydro-5,8-methanoimidazo[1,2-a]pyridin-3-yl)-[1,2,4]triazolo[4,3-a]pyridine-3-carboxamide 9-1

6-((5R,8S)-2-(5-Fluoropyridin-2-yl)-5,6,7,8-tetrahydro-5,8-methanoimidazo[1,2-a]pyrid in-3-yl)-[1,2,4]triazolo[4,3-a]pyridine-3-carboxamide 9-2

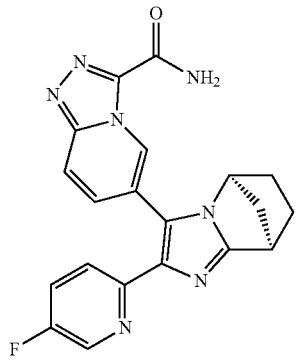

9-1

-continued 9-2

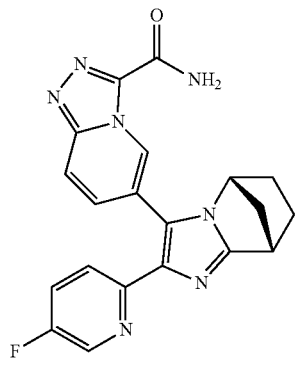

Compound 9 (17 mg, 0.044 mmol) was separated chirally (separation conditions: chiral preparative column Lux Amylose-1 (AD)21.2×250 mm, 5 m; mobile phase: ethanol (containing 0.1% diethylamine)/n-hexane=50/50 (v/v), flow rate: 15.0 mL/min). The corresponding fractions were collected and concentrated under reduced pressure to obtain the title compounds (8 mg, 8 mg).

Compound in a Single Configuration (with Shorter Retention Time):

MS m/z (ESI): 390.4 [M+1]

Chiral HPLC analysis method: retention time 6.631 minutes (chromatographic column: AD Phenomenex Lux Amylose-1 150×4.6 mm, 5 m; mobile phase: ethanol (containing 0.1% diethylamine)/n-hexane (containing 0.1% diethylamine)=40/60 (v/v));

MS m/z (ESI): 390.4 [M+1]

$^1$H NMR (400 MHz, CDCl$_3$) δ 9.60-96.2 (m, 1H), 8.25 (d, 1H), 8.03-8.00 (m, 1H), 7.89 (dd, 1H), 7.65 (dd, 1H), 7.53 (br, 1H), 7.48-7.43 (m, 1H), 5.89 (br, 1H), 4.87 (br, 1H), 3.73-3.72 (m, 1H), 2.41 (d, 1H), 2.19-2.12 (m, 1H), 2.05-1.96 (m, 1H), 1.94 (d, 1H), 1.56-1.51 (m, 1H), 1.43-1.36 (m, 1H).

Compound in a Single Configuration (with Longer Retention Time):

MS m/z (ESI): 390.4 [M+1]

Chiral HPLC analysis method: retention time 13.001 minutes (chromatographic column: AD Phenomenex Lux Amylose-1 150×4.6 mm, 5 m; mobile phase: ethanol (containing 0.1% diethylamine)/n-hexane (containing 0.1% diethylamine)=40/60 (v/v));

MS m/z (ESI): 390.4 [M+1]

$^1$H NMR (400 MHz, CDCl$_3$) δ 9.62-9.60 (m, 1H), 8.25 (d, 1H), 8.03-8.00 (m, 1H), 7.89 (dd, 1H), 7.65 (dd, 1H), 7.53 (br, 1H), 7.48-7.43 (m, 1H), 5.89 (br, 1H), 4.87 (br, 1H), 3.73-3.72 (m, 1H), 2.41 (d, 1H), 2.19-2.12 (m, 1H), 2.05-1.96 (m, 1H), 1.94 (d, 1H), 1.56-1.51 (m, 1H), 1.43-1.36 (m, 1H).

Example 10

2-(2-(6-Methylpyridin-2-yl)-5,6,7,8-tetrahydro-5,8-methanoimidazo[1,2-a]pyridin-3-yl) thieno[3,2-c]pyridine 10

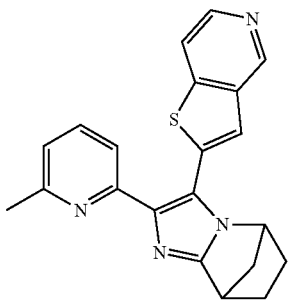

In accordance with the synthetic route of Example 1, the starting compound 1h used in Step 5 was replaced with thieno[3,2-c]pyridin-2-yl boronic acid (prepared according to the method disclosed in the patent application "WO2013101974"), accordingly, the title compound 10 (25 mg) was prepared.

MS m/z (ESI): 359.3 [M+1]

$^1$H NMR (400 MHz, CDCl$_3$) δ 9.65 (s, 1H), 8.66 (d, 1H), 8.32 (d, 1H), 8.09-7.90 (m, 2H), 7.75 (d, 1H), 7.40 (d, 1H), 5.18 (s, 1H), 4.07 (t, 1H), 2.76 (s, 3H), 2.54 (d, 1H), 2.32-2.30 (m, 1H), 2.21-2.18 (m, 1H), 2.09 (d, 1H), 1.69-1.66 (m, 1H), 1.59-1.57 (m, 1H).

Example 11

3-([1,2,4]Triazolo[1,5-a]pyridin-6-yl)-2-(6-methylpyridin-2-yl)-5,6,7,8-tetrahydro-5,8-methanoimidazo[1,2-a]pyridine 11

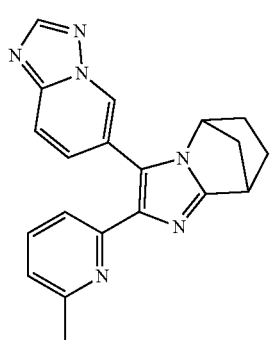

In accordance with the synthetic route of Example 1, the starting compound 1h used in Step 5 was replaced with 6-(4,4,5,5-tetramethyl-1,3,2-dioxaborolan-2-yl)-[1,2,4]triazole[1,5-a]pyridine (prepared according to the method disclosed in the patent application "WO2013009140"), accordingly, the title compound 11 (10 mg) was prepared.

MS m/z (ESI): 343.3 [M+1]

$^1$H NMR (400 MHz, CDCl$_3$) δ 9.14 (d, 1H), 8.42 (s, 1H), 7.80-7.71 (m, 3H), 7.59 (t, 1H), 6.99 (d, 1H), 4.84 (s, 1H), 3.72 (d, 1H), 2.41 (s, 3H), 2.34 (d, 1H), 2.14-2.11 (m, 1H), 2.04-1.92 (m, 2H), 1.55-1.54 (m, 1H), 1.41-1.40 (m, 1H).

Example 12

3-(2-(1-Methyl-1H-pyrazol-4-yl)pyridin-4-yl)-2-(6-methylpyridin-2-yl)-5,6,7,8-tetrahydro-5,8-methano-imidazo[1,2-a]pyridine 12

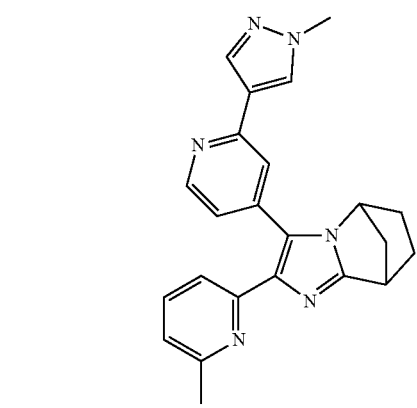

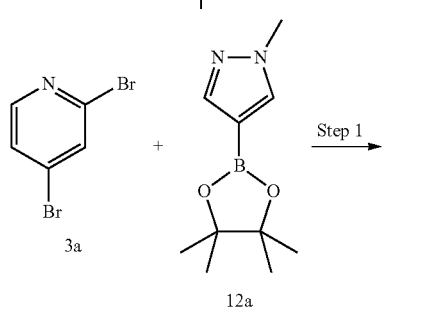

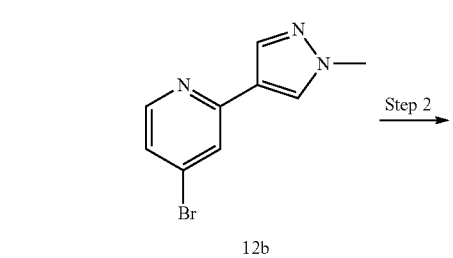

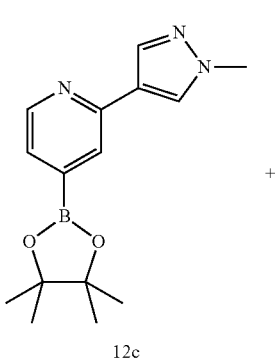

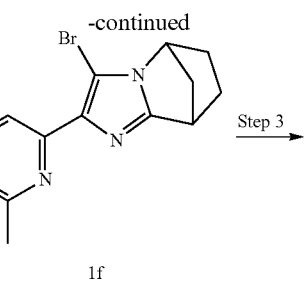

Step 1

4-Bromo-2-(1-methyl-1H-pyrazol-4-yl)pyridine 12b

Compound 3a (1 g, 4.22 mmol), 1-methyl-4-(4,4,5,5-tetramethyl-1,3,2-dioxaborolan-2-yl)-1H-pyrazole 12a (0.79 g, 0.90 mmol, prepared according to the method disclosed in the patent application "WO2009155527"), tetrakis(triphenylphosphine)palladium (0.49 g, 0.42 mmol) and sodium carbonate (0.89 mg, 8.44 mmol) were dissolved in 7 mL of a mixed solvent of toluene, ethanol and water (V/V/V=4:2:1), then the reaction solution was warmed up to 100° C. and reacted under microwave for 1 hours. After the reaction was completed, the reaction solution was concentrated under reduced pressure. The resulting residue was dissolved in ethyl acetate, and washed with water. The organic phase was dried over anhydrous sodium sulfate and filtered. The filtrate was concentrated under reduced pressure, and the resulting residue was purified by silica gel column chromatography with elution system B to obtain the title compound 12b (530 mg, yield: 52.74%).

Step 2

2-(1-Methyl-1H-pyrazol-4-yl)-4-(4,4,5,5-tetramethyl-1,3,2-dioxaborolan-2-yl)pyridine 12c Compound 12b (250 mg, 1.05 mmol), bis(pinacolato)diboron (319.98 mg, 1.26 mmol), potassium acetate (206.11 mg, 2.10 mmol) and [1,1'-bis(diphenylphosphino)ferrocene]dichloropalladium (77.89 mg, 0.11 mmol) were dissolved in 10 mL of 1,4-dioxane, then the reaction solution was warmed up to 80° C. and stirred for 5 hours. After the reaction was completed, the reaction solution of the title compound 12c, which was used directly in the next step without treatment, was obtained.

Step 3

3-(2-(1-Methyl-1H-pyrazol-4-yl)pyridin-4-yl)-2-(6-methylpyridin-2-yl)-5,6,7,8-tetrahydro-5,8-methano-imidazo[1,2-a]pyridine 12

Compound 1f (80 mg, 0.263 mmol), the above reaction solution of compound 12c, [1,1'-bis(diphenylphosphino)ferrocene]dichloropalladium (19.25 mg, 0.026 mmol) and potassium carbonate (109.05 mg, 0.79 mmol) were dissolved in 5 mL of a mixed solvent of 1,4-dioxane and water (V/V=4:1), then the reaction solution was warmed up to 80° C. and stirred for 12 hours. The reaction solution was cooled to room temperature, and filtered through celite. The filter cake was washed with ethyl acetate, and the filtrate was concentrated under reduced pressure. The resulting residue was purified by high performance liquid chromatography to obtain the title compound 12 (60 mg, yield: 59.65%).

MS m/z (ESI): 383.5 [M+1]

$^1$H NMR (400 MHz, CDCl$_3$) δ 8.58 (d, 1H), 7.96 (s, 1H), 7.91 (s, 1H), 7.78 (s, 1H), 7.61-7.58 (m, 2H), 7.26 (d, 1H), 7.02 (d, 1H), 4.88 (s, 1H), 4.00 (s, 3H), 3.70 (d, 1H), 2.44 (s, 3H), 2.37 (d, 1H), 2.12-2.09 (m, 1H), 2.00-1.98 (m, 1H), 1.92 (d, 1H), 1.57-1.51 (m, 1H), 1.41-1.39 (m, 1H).

Examples 12-1, 12-2

(5S,8R)-3-(2-(1-Methyl-1H-pyrazol-4-yl)pyridin-4-yl)-2-(6-methylpyridin-2-yl)-5,6,7,8-tetrahydro-5,8-methanoimidazo[1,2-a]pyridine 12-1

(5R,8S)-3-(2-(1-Methyl-1H-pyrazol-4-yl)pyridin-4-yl)-2-(6-methylpyridin-2-yl)-5,6,7,8-tetrahydro-5,8-methanoimidazo[1,2-a]pyridine 12-2

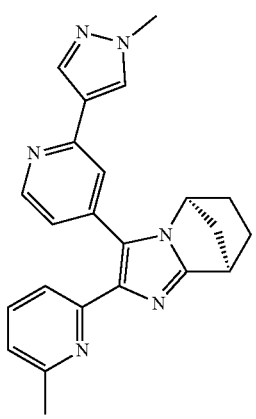

12-1

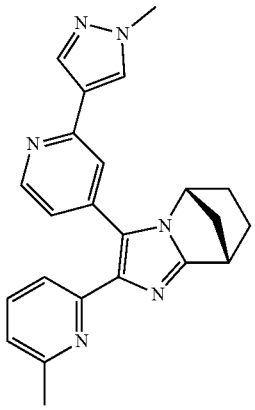

12-2

Compound 12 (60 mg, 0.157 mmol) was separated chirally (separation conditions: chiral preparative column CHIRALPAK OD 21.5×250 mm, 5 m; mobile phase: ethanol (containing 0.1% diethylamine)/n-hexane=50/50 (v/v), flow rate: 12 mL/min). The corresponding fractions were collected and concentrated under reduced pressure to obtain the title compounds (20 mg, 20 mg).

Compound in a single configuration (with shorter retention time):

MS m/z (ESI): 383.5 [M+1]

Chiral HPLC analysis method: retention time 2.955 minutes (chromatographic column: CHIRALPAK OD 4.6×150 mm 5 m; mobile phase: ethanol (containing 0.1% diethylamine)/n-hexane=60/40 (v/v));

$^1$H NMR (400 MHz, CDCl$_3$) δ 8.58 (d, 1H), 7.96 (s, 1H), 7.91 (s, 1H), 7.78 (s, 1H), 7.61-7.58 (m, 2H), 7.26 (d, 1H), 7.02 (d, 1H), 4.88 (s, 1H), 4.00 (s, 3H), 3.70 (d, 1H), 2.44 (s, 3H), 2.37 (d, 1H), 2.12-2.09 (m, 1H), 2.00-1.98 (m, 1H), 1.92 (d, 1H), 1.57-1.51 (m, 1H), 1.41-1.39 (m, 1H).

Compound in a single configuration (with longer retention time):

MS m/z (ESI): 383.5 [M+1]

Chiral HPLC analysis method: retention time 4.695 minutes (chromatographic column: CHIRALPAK OD 4.6×150 mm 5 m; mobile phase: ethanol (containing 0.1% diethylamine)/n-hexane=60/40 (v/v));

$^1$H NMR (400 MHz, CDCl$_3$) δ 8.58 (d, 1H), 7.96 (s, 1H), 7.91 (s, 1H), 7.78 (s, 1H), 7.61-7.58 (m, 2H), 7.26 (d, 1H), 7.02 (d, 1H), 4.88 (s, 1H), 4.00 (s, 3H), 3.70 (d, 1H), 2.44 (s, 3H), 2.37 (d, 1H), 2.12-2.09 (m, 1H), 2.00-1.98 (m, 1H), 1.92 (d, 1H), 1.57-1.51 (m, 1H), 1.41-1.39 (m, 1H).

Example 13-1

4-(4-((5S,8R)-2-(6-Methylpyridin-2-yl)-5,6,7,8-tetrahydro-5,8-methanoimidazo[1,2-a]pyridin-3-yl)pyridin-2-yl)benzenesulfonamide 13-1

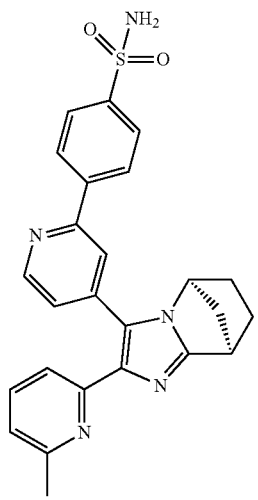

13-1

In accordance with the synthetic route of Example 3, the starting compound 3b used in Step 1 was replaced with 4-(4,4,5,5-tetramethyl-1,3,2-dioxaborolan-2-yl)benzenesulfonamide (prepared according to the known method disclosed in "Tetrahedron Letters, 2013, 54(2), 166-169"), accordingly, the title compound 13-1 (10 mg) was prepared.

MS m/z (ESI): 458.4 [M+1]

$^1$H NMR (400 MHz, CD$_3$OD) δ 8.70-8.68 (d, 1H), 8.09-8.01 (m, 5H), 7.76-7.74 (m, 1H), 7.71-7.58 (m, 2H), 7.21-7.19 (d, 1H), 5.11 (s, 1H), 3.68 (m, 1H), 2.42-2.40 (d, 1H), 2.35 (s, 3H), 2.25-2.15 (m, 1H), 2.05-2.02 (m, 2H), 1.37-1.31 (m, 2H).

Example 14

4-((4-(2-(6-Methylpyridin-2-yl)-5,6,7,8-tetrahydro-5,8-methanoimidazo[1,2-a]pyridin-3-yl)pyridin-2-yl)amino)benzenesulfonamide 14

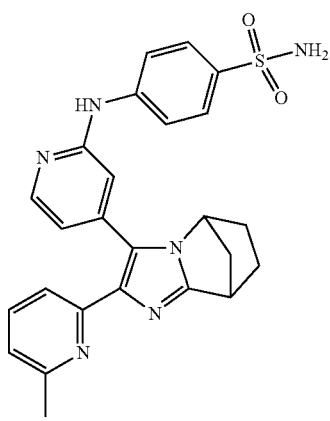

14

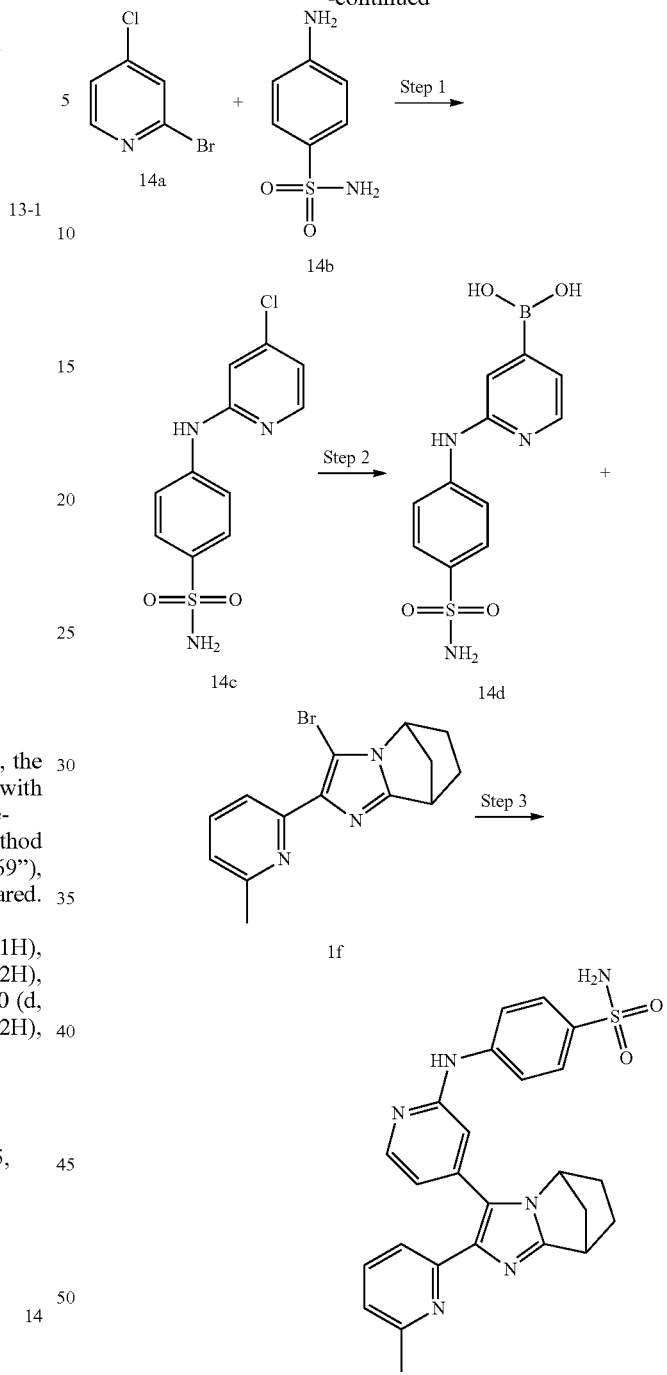

Step 1

4-((4-Chloropyridin-2-yl)amino)benzenesulfonamide 14c

2-Bromo-4-chloropyridine 14a (576 mg, 2.993 mmol), 4-aminobenzenesulfonamide 14b (515.42 mg, 2.99 mmol, prepared according to the method disclosed in the patent application "CN105175294"), 4,5-bis(diphenylphosphino)-9,9-dimethylxanthene (173.19 mg, 0.299 mmol), cesium carbonate (1.462 g, 4.49 mmol) and palladium acetate (67.199 mg, 0.299 mmol) were dissolved in 10 mL of 1,4-dioxane, then the reaction solution was warmed up to 90° C. and stirred for 12 hours. The reaction solution was cooled to room temperature, filtered, and the filtrate was concentrated under reduced pressure. The resulting residue was purified by silica gel column chromatography with elution system A to obtain the title compound 14c (230 mg, yield: 27.08%).

Step 2

(2-((4-Sulfamoylphenyl)amino)pyridin-4-yl)boronic acid 14d

Compound 14c (50 mg, 0.176 mmol), potassium acetate (25.94 mg, 0.264 mmol), 2-dicyclohexylphosphine-2',6'-dimethoxy-biphenyl (7.235 mg, 0.0176 mmol), bis(pinacolato)diboron (89.5 mg, 0.352 mmol) and tris(dibenzylideneacetone)dipalladium (8.6 mg, 0.0088 mmol) were dissolved in 5 mL of 1,4-dioxane, then the reaction solution was warmed up to 100° C. and stirred for 3 hours. The reaction solution was cooled to room temperature, filtered, and the filtrate was concentrated under reduced pressure. The resulting residue was purified by silica gel column chromatography with elution system A to obtain the title compound 14d (35 mg, yield: 67.76%).

Step 3

4-((4-(2-(6-Methylpyridin-2-yl)-5,6,7,8-tetrahydro-5, 8-methanoimidazo[1,2-a]pyridin-3-yl)pyridin-2-yl) amino)benzenesulfonamide 14

Compound 14d (35 mg, 0.119 mmol), compound 1f (36 mg, 0.119 mmol), [1,1'-bis(diphenylphosphino)ferrocene] dichloropalladium (8.86 mg, 0.0119 mmol) and potassium carbonate (33 mg, 0.239 mmol) were dissolved in 6 mL of a mixed solvent of 1,4-dioxane and water (V/V=5:1), then the reaction solution was warmed up to 100° C. and stirred for 12 hours. The reaction solution was cooled to room temperature, filtered through celite, and the filtrate was concentrated under reduced pressure. The resulting residue was purified by high performance liquid chromatography to obtain the title compound 14 (10 mg, yield: 17%).

MS m/z (ESI): 473.4 [M+1]

$^1$H NMR (400 MHz, CD$_3$OD) δ 8.40 (d, 1H), 7.95 (t, 1H), 7.83 (s, 4H), 7.51-7.47 (m, 2H), 7.02-7.00 (m, 2H), 5.15 (s, 1H), 3.91 (s, 1H), 2.71 (s, 3H), 2.48-2.31 (m, 2H), 2.19-2.14 (m, 2H), 1.55-1.52 (m, 2H).

Example 15

2-(6-Methylpyridin-2-yl)-3-(4-(piperidin-4-yloxy) quinolin-6-yl)-5,6,7,8-tetrahydro-5,8-methanoimidazo[1,2-a]pyridine 15

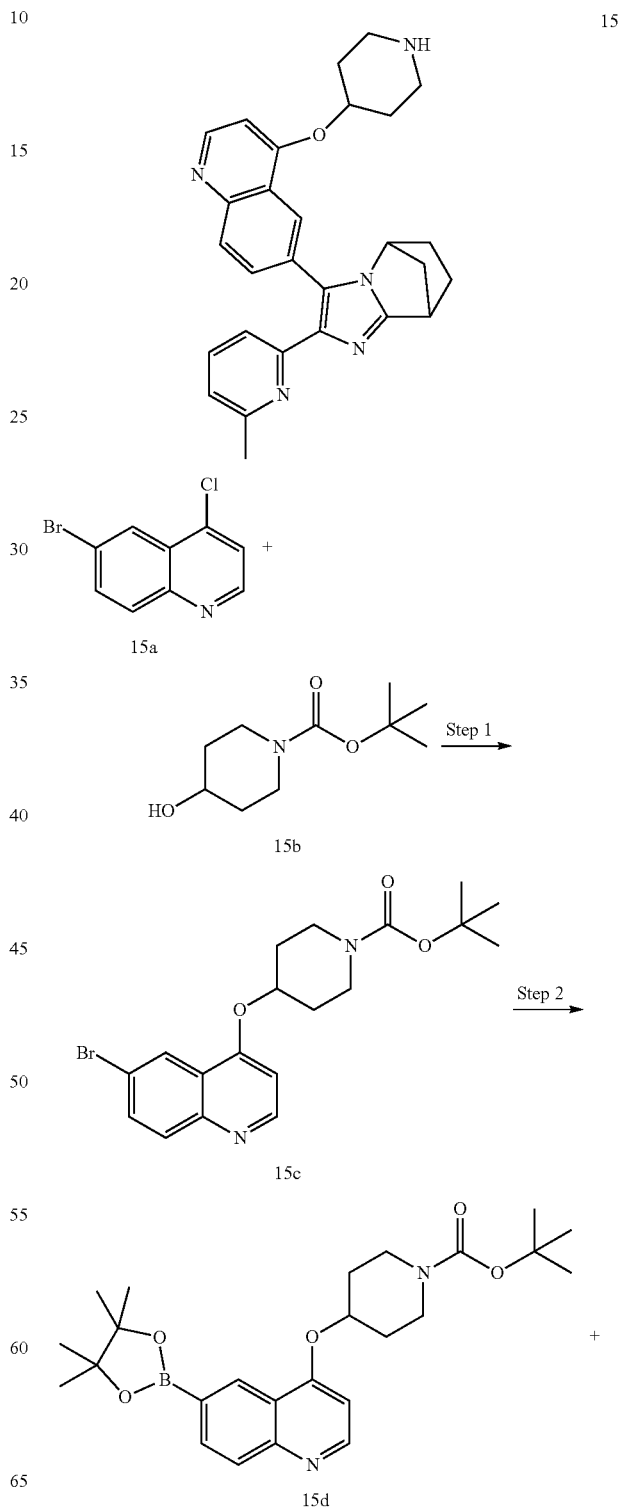

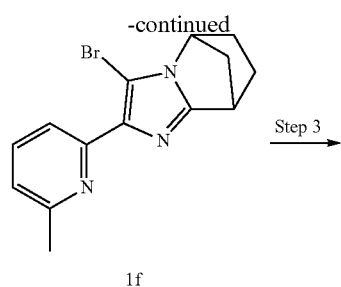

1f

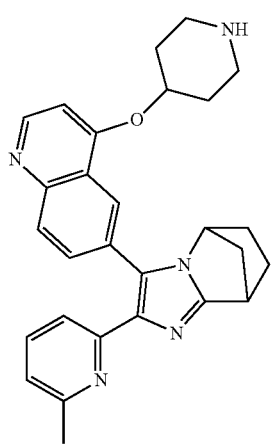

15e

15

Step 1

Tert-butyl 4-((6-bromoquinolin-4-yl)oxy)piperidine-1-carboxylate 15c

Tert-butyl 4-hydroxypiperidine-1-carboxylate 15b (166 mg, 0.826 mmol) and sodium hydride (99 mg, 2.48 mmol, 60%) were dissolved in 5 mL of N,N-dimethylformamide, then the reaction solution was stirred at room temperature for 30 minutes. 6-Bromo-4-chloroquinoline 15a (200 mg, 0.826 mmol) was added, and the reaction solution was stirred at room temperature for 2 hours. The reaction solution was added with 10 mL of water, and extracted with ethyl acetate (20 mL×2). The organic phases were combined, dried over anhydrous sodium sulfate and filtered. The filtrate was concentrated under reduced pressure to obtain the crude title compound 15c (230 mg), which was used directly in the next step without purification.

Step 2

Tert-butyl 4-((6-(4,4,5,5-tetramethyl-1,3,2-dioxaborolan-2-yl)quinolin-4-yl)oxy)piperidine-1-carboxylate 15d The crude compound 15c (302 mg, 0.746 mmol), potassium acetate (146 mg, 1.492 mmol), [1,1'-bis(diphenylphosphino)ferrocene]dichloropalladium (27 mg, 0.037 mmol) and bis(pinacolato)diboron (227 mg, 0.896 mmol) were dissolved in 5 mL of 1,4-dioxane, then the reaction solution was warmed up to 90° C. and stirred for 2 hours. The reaction solution was cooled to room temperature, added with 20 mL of water, and extracted with ethyl acetate (50 mL×2). The organic phases were combined, dried over anhydrous sodium sulfate and filtered. The filtrate was concentrated under reduced pressure, and the resulting residue was purified by silica gel column chromatography with elution system B to obtain the title compound 15b (100 mg, yield: 29.4%).

Step 3

Tert-butyl 4-((6-(2-(6-methylpyridin-2-yl)-5,6,7,8-tetrahydro-5,8-methanoimidazo[1,2-a]pyridin-3-yl)quinolin-4-yl)oxy)piperidine-1-carboxylate 15e Compound 15d (100 mg, 0.22 mmol), compound 1f (44.6 mg, 0.147 mmol), [1,1'-bis(diphenylphosphino)ferrocene]dichloropalladium (21 mg, 0.03 mmol) and potassium carbonate (60 mg, 0.441 mmol) were dissolved in 5 mL of a mixed solvent of 1,4-dioxane and water (V/V=4:1), then the reaction solution was warmed up to 100° C. and stirred for 1 hours. The reaction solution was cooled to room temperature, added with 50 mL of ethyl acetate, and washed with water (30 mL). The organic phase was dried over anhydrous sodium sulfate and filtered. The filtrate was concentrated under reduced pressure, and the resulting residue was purified by high performance liquid chromatography to obtain the title compound 15e (30 mg, yield: 37.5%).

Step 4

2-(6-Methylpyridin-2-yl)-3-(4-(piperidin-4-yloxy)quinolin-6-yl)-5,6,7,8-tetrahydro-5,8-methanoimidazo[1,2-a]pyridine 15

Compound 15e (30 mg, 0.054 mmol) was dissolved in 4 mL of dichloromethane, then 1 mL of trifluoroacetic acid was added. After stirring at room temperature for 2 hours, the reaction solution was added with saturated sodium bicarbonate solution and extracted with ethyl acetate (50 mL×2). The organic phases were combined, dried over anhydrous sodium sulfate and filtered. The filtrate was concentrated under reduced pressure, and the resulting residue was purified by high performance liquid chromatography to obtain the title compound 15 (8 mg, yield: 33.3%).

MS m/z (ESI): 452.5 [M+1]

¹H NMR (400 MHz, CDCl₃) δ 9.13 (d, 1H), 8.70 (s, 1H), 8.29-8.24 (dd, 2H), 8.02 (t, 1H), 7.75 (d, 1H), 7.70 (d, 1H), 7.68 (d, 1H), 5.45-5.32 (m, 2H), 5.12 (s, 1H), 3.98 (s, 1H), 3.55-3.42 (m, 2H), 2.66 (s, 3H), 2.56 (d, 1H), 2.43-2.32 (m, 3H), 2.31-2.20 (m, 2H), 2.16 (d, 2H), 1.61-1.52 (m, 2H), 1.35-1.27 (m, 2H).

Example 16-1

4-((5S,8R)-2-(6-Methylpyridin-2-yl)-5,6,7,8-tetrahydro-5,8-methanoimidazo[1,2-a]pyridin-3-yl)-N-(2-morpholinoethyl)pyridin-2-amine 16-1

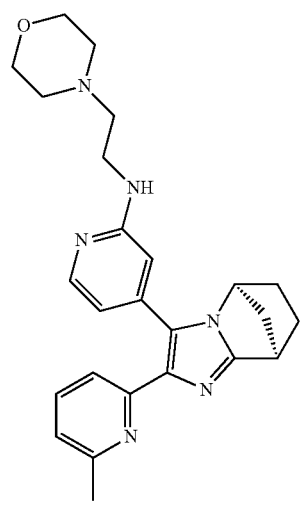

16-1

In accordance with the synthetic route of Example 5, the starting compound aminoethanol used in Step 2 was replaced with 2-morpholinylethylamine, accordingly, the title compound 16-1 (10 mg) was prepared.

MS m/z (ESI): 431.3 [M+1]

¹H NMR (400 MHz, CDCl₃) δ 8.13 (d, 1H), 7.46-7.54 (m, 2H), 7.02 (d, 1H), 6.69 (d, 2H), 5.16 (s, 1H), 4.85 (s, 1H), 3.75 (t, 4H), 3.68 (d, 1H), 3.39-3.34 (m, 2H), 2.65 (t, 2H), 2.53-2.51 (m, 7H), 2.33 (d, 1H), 2.10-2.07 (m, 1H), 1.98-1.95 (m, 2H), 1.57-1.54 (m, 2H).

Example 17

4-(4-(2-(6-Methylpyridin-2-yl)-5,6,7,8-tetrahydro-5,8-methanoimidazo[1,2-a]pyridin-3-yl)pyridin-2-yl)-N-(tetrahydro-2H-pyran-4-yl)benzamide 17

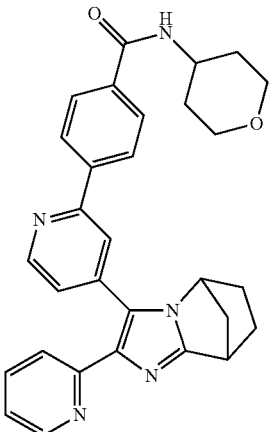

17

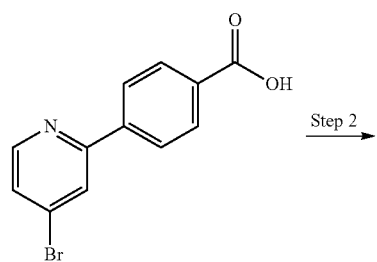

4b

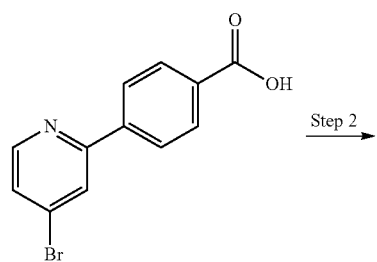

17a

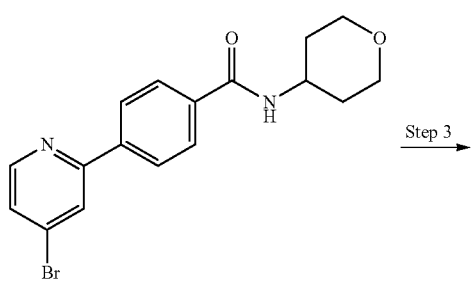

17b

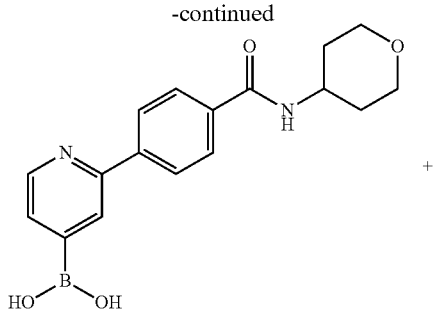

17c

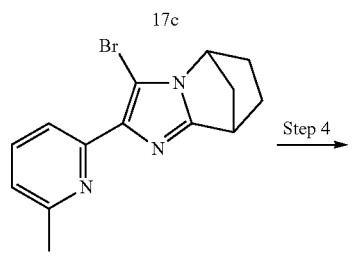

1f

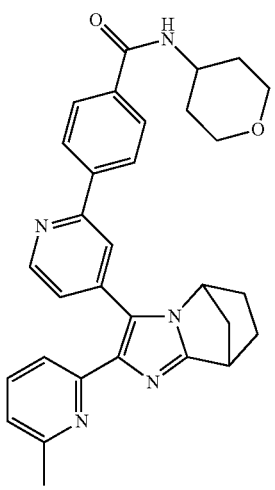

17

Step 1

4-(4-Bromopyridin-2-yl)benzoic acid 17a

Compound 4b (100 mg, 0.342 mmol) was dissolved in 7 mL of a mixed solvent of methanol and water (V/V=5:2), then sodium hydroxide (68.46 mg, 1.712 mmol) was added. After stirring at room temperature for 12 hours, the reaction solution was added with 2 M hydrochloric acid to adjust the pH to acidic, and extracted with dichloromethane three times. The organic phases were combined, dried over anhydrous sodium sulfate and filtered. The filtrate was concentrated under reduced pressure to obtain the crude title compound 17a (90 mg), which was used directly in the next step without purification.

Step 2

4-(4-Bromopyridin-2-yl)-N-(tetrahydro-2H-pyran-4-yl)benzamide 17b

The crude compound 17a (100 mg, 0.36 mmol) and thionyl chloride (2138.98 mg, 17.98 mmol) were added to a flask, then the reaction solution was warmed up to 80° C. and stirred for 2 hours. The reaction solution was cooled to room temperature and concentrated under reduced pressure. 10 mL of dichloromethane was added to the resulting residue. 4-Aminotetrahydropyran (54.56 mg, 0.54 mmol) was dissolved in 3 mL of dichloromethane, and slowly added to the above reaction solution. After stirring at room temperature for 2 hours, the reaction solution was concentrated under reduced pressure to obtain the crude title compound 17b (129 mg), which was used directly in the next step without purification.

Step 3

(2-(4-((Tetrahydro-2H-pyran-4-yl)carbamoyl)phenyl)pyridin-4-yl)boronic acid 17c

Bis(triphenylphosphine)palladium dichloride (21.37 mg, 0.03 mmol), potassium acetate (59.77 mg, 0.61 mmol), the crude compound 17b (110 mg, 0.3 mmol) and bis(pinacolato)diboron (92.79 mg, 0.37 mmol) were dissolved in 5 mL of 1,4-dioxane, then the reaction solution was warmed up to 90° C. and stirred for 2 hours. The reaction solution was cooled to room temperature and concentrated under reduced pressure. The resulting residue was added with 10 mL of water, and extracted with ethyl acetate (20 mL×2). The organic phases were combined, dried over anhydrous sodium sulfate and filtered. The filtrate was concentrated under reduced pressure, and the resulting residue was purified by silica gel column chromatography with elution system B to obtain the title compound 17c (70 mg, yield: 70.48%).

Step 4

4-(4-(2-(6-Methylpyridin-2-yl)-5,6,7,8-tetrahydro-5,8-methanoimidazo[1,2-a]pyridin-3-yl)pyridin-2-yl)-N-(tetrahydro-2H-pyran-4-yl)benzamide 17

Compound 17c (48.25 mg, 0.148 mmol), compound 1f (30 mg, 0.099 mmol), [1,1'-bis(diphenylphosphino)ferrocene]dichloropalladium (7.32 mg, 0.001 mmol) and potassium carbonate (27.26 mg, 0.197 mmol) were dissolved in 5 mL of a mixed solvent of 1,4-dioxane and water (V/V=4:1), then the reaction solution was warmed up to 90° C. and stirred for 12 hours. The reaction solution was cooled to room temperature, added with 10 mL of water, and extracted with ethyl acetate (20 mL×2). The organic phases were combined, dried over anhydrous sodium sulfate and filtered. The filtrate was concentrated under reduced pressure, and the resulting residue was purified by high performance liquid chromatography to obtain the title compound 17 (23 mg, yield: 26.29%).

MS m/z (ESI): 506.5 [M+1]

$^1$H NMR (400 MHz, CD$_3$OD) δ 8.68 (d, 1H), 8.02-7.93 (m, 5H), 7.73 (t, 1H), 7.57 (d, 1H), 7.50 (d, 1H), 7.20 (d, 1H), 5.11 (s, 1H), 4.20-4.10 (m, 1H), 4.01 (d, 2H), 3.68 (s, 1H), 3.55 (t, 2H), 2.48 (d, 1H), 2.36 (s, 3H), 2.25-2.15 (m, 1H), 2.10-2.00 (m, 2H), 1.96-1.85 (m, 2H), 1.75-1.65 (m, 2H), 1.45-1.30 (m, 2H).

Examples 17-1, 17-2

4-(4-((5S,8R)-2-(6-Methylpyridin-2-yl)-5,6,7,8-tetrahydro-5,8-methanoimidazo[1,2-a]pyridin-3-yl)pyridin-2-yl)-N-(tetrahydro-2H-pyran-4-yl)benzamide 17-1

4-(4-((5R,8S)-2-(6-Methylpyridin-2-yl)-5,6,7,8-tetrahydro-5,8-methanoimidazo[1,2-a]pyridin-3-yl)pyridin-2-yl)-N-(tetrahydro-2H-pyran-4-yl)benzamide 17-2

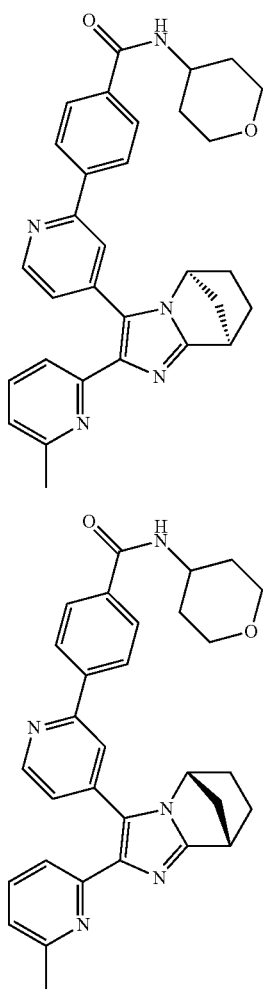

Compound 17 (23 mg, 0.045 mmol) was separated chirally (separation conditions: chiral preparative column CHIRALPAK OD 21.5×250 mm, 5 m; mobile phase: ethanol/n-hexane=50/50 (v/v), flow rate: 10 mL/min). The corresponding fractions were collected and concentrated under reduced pressure to obtain the title compounds (8 mg, 10 mg).

Compound in a single configuration (with longer retention time):

MS m/z (ESI): 506.5 [M+1]

Chiral HPLC analysis method: retention time 9.196 minutes (chromatographic column: CHIRALPAK OD 4.6×150 mm 5 m; mobile phase: ethanol (containing 0.1% diethylamine)/n-hexane=30/70 (v/v));

$^1$H NMR (400 MHz, CD$_3$OD) δ 8.68 (d, 1H), 8.02-7.93 (m, 5H), 7.73 (t, 1H), 7.57 (d, 1H), 7.50 (d, 1H), 7.20 (d, 1H), 5.11 (s, 1H), 4.20-4.10 (m, 1H), 4.01 (d, 2H), 3.68 (s, 1H) 3.55 (t, 2H), 2.48 (d, 1H), 2.36 (s, 3H), 2.25-2.15 (m, 1H), 2.10-2.00 (m, 2H), 1.96-1.85 (m, 2H), 1.75-1.65 (m, 2H), 1.45-1.30 (m, 2H).

Compound in a single configuration (with shorter retention time):

MS m/z (ESI): 506.5 [M+1]

Chiral HPLC analysis method: retention time 5.418 minutes (chromatographic column: CHIRALPAK OD 4.6×150 mm 5 m; mobile phase: ethanol (containing 0.1% diethylamine)/n-hexane=30/70 (v/v));

$^1$H NMR (400 MHz, CD$_3$OD) δ 8.68 (d, 1H), 8.02-7.93 (m, 5H), 7.73 (t, 1H), 7.57 (d, 1H), 7.50 (d, 1H), 7.20 (d, 1H), 5.11 (s, 1H), 4.20-4.10 (m, 1H), 4.01 (d, 2H), 3.68 (s, 1H) 3.55 (t, 2H), 2.48 (d, 1H), 2.36 (s, 3H), 2.25-2.15 (m, 1H), 2.10-2.00 (m, 2H), 1.96-1.85 (m, 2H), 1.75-1.65 (m, 2H), 1.45-1.30 (m, 2H).

Example 18-1

(S)-1-((4-((5S,8R)-2-(6-Methylpyridin-2-yl)-5,6,7,8-tetrahydro-5,8-methanoimidazo[1,2-a]pyridin-3-yl)pyridin-2-yl)amino)propan-2-ol 18-1

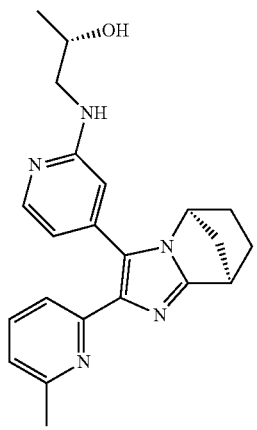

In accordance with the synthetic route of Example 5, the starting compound aminoethanol used in Step 2 was replaced with (S)-1-aminopropan-2-ol (prepared according to the method disclosed in the patent application "JP2011079782"), accordingly, the title compound 18-1 (20 mg) was prepared.

MS m/z (ESI): 376.5 [M+1]

$^1$H NMR (400 MHz, CDCl$_3$) δ 8.05 (d, 1H), 7.51 (t, 1H), 7.32 (d, 1H), 6.99 (d, 1H), 6.61 (dd, 1H), 6.48 (s, 1H), 5.65 (s, 1H), 4.78 (s, 1H), 4.08-4.12 (m, 1H), 3.63 (d, 1H), 3.48-3.52 (m, 1H), 3.35-3.38 (m, 1H), 2.50 (s, 3H), 2.52 (d, 2H), 1.98-2.02 (m, 2H), 1.82-1.86 (m, 2H), 1.28 (d, 3H).

Example 19

4-(4-(2-(6-Methylpyridin-2-yl)-5,6,7,8-tetrahydro-5,8-methanoimidazo[1,2-a]pyridin-3-yl)pyridin-2-yl)benzoic acid 19

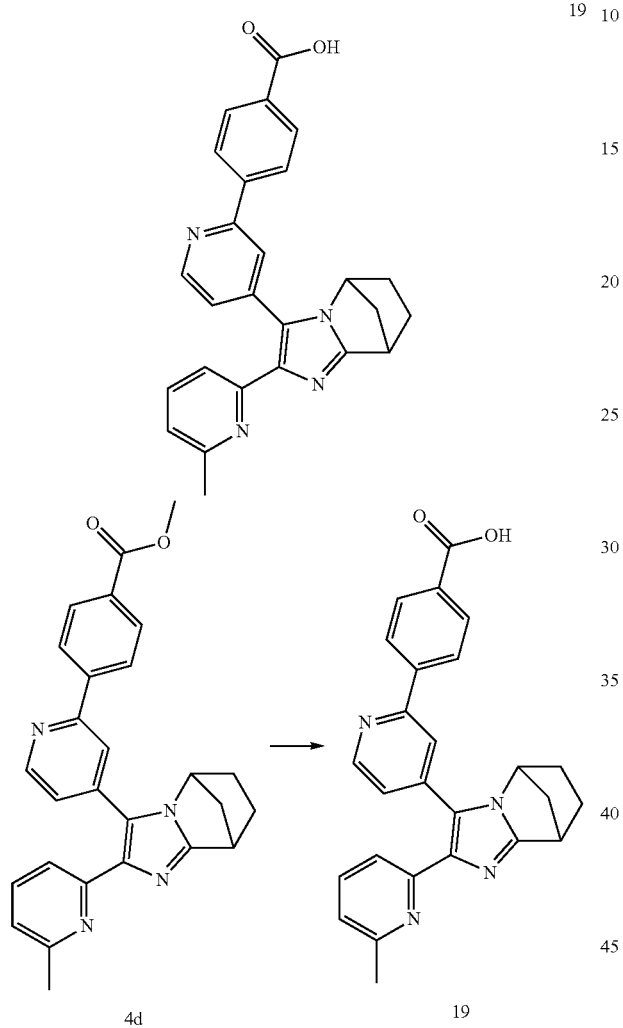

Compound 4d (30 mg, 0.069 mmol) was dissolved in 10 mL of methanol, then 4 mL of water and sodium hydroxide (27.5 mg, 0.687 mmol) were added. After stirring at room temperature for 12 hours, the reaction solution was adjusted until the pH was acidic, and extracted with dichloromethane. The organic phases were combined, dried over anhydrous sodium sulfate and filtered. The filtrate was concentrated under reduced pressure, and the resulting residue was purified by high performance liquid chromatography to obtain the title compound 19 (10 mg).

MS m/z (ESI): 423.2 [M+1]

$^1$H NMR (400 MHz, CD$_3$OD) δ 8.86 (d, 1H), 7.90-8.17 (m, 6H), 7.61 (d, 1H), 7.46 (d, 2H), 5.16 (s, 1H), 3.90 (s, 1H), 2.68 (s, 3H), 2.32-2.51 (m, 2H), 2.14 (d, 2H), 1.51 (s, 2H).

Example 20

1-Methyl-5-(2-(6-methylpyridin-2-yl)-5,6,7,8-tetrahydro-5,8-methanoimidazo[1,2-a]pyridin-3-yl)pyridin-2(1H)-one 20

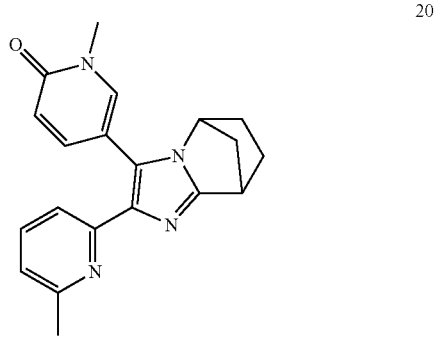 [SMILES: Cc1cccc(-c2nc3n(c2-c2ccc(=O)n(C)c2)C2CCC3C2)n1]

In accordance with the synthetic route of Example 7, the starting compound 7b used in Step 2 was replaced with 1-methyl-5-(4,4,5,5-tetramethyl-1,3,2-dioxaborolan-2-yl)pyridine-2(1H)-one (prepared according to the method disclosed in the patent application "WO2014210255"), accordingly, the title compound 20 (40 mg) was prepared.

MS m/z (ESI): 333.4 [M+1]

$^1$H NMR (400 MHz, CDCl$_3$) δ 8.06 (d, 1H), 7.72-7.70 (dd, 1H), 7.59 (t, 1H), 7.52 (dd, 1H), 7.00 (d, 1H), 6.65 (d, 1H), 4.74 (br, 1H), 3.68 (s, 3H), 2.48 (s, 3H), 2.33-2.31 (m, 1H), 2.13-2.07 (m, 1H), 2.02-1.96 (m, 1H), 1.92-1.89 (d, 1H), 1.53-1.48 (m, 1H), 1.40-1.29 (m, 2H).

Example 21

2-(6-Methylpyridin-2-yl)-3-(pyridin-4-yl)-5,6,7,8-tetrahydro-5,8-methanoimidazo[1,2-a]pyridine 21

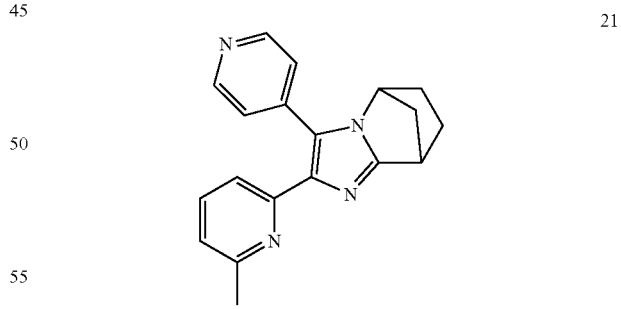

In accordance with the synthetic route of Example 7, the starting compound 7b used in Step 2 was replaced with pyridin-4-yl boronic acid (prepared according to the method disclosed in the patent application "CN104177390"), accordingly, the title compound 21 (30 mg) was prepared.

MS m/z (ESI): 303.2 [M+1]

$^1$H NMR (400 MHz, CD$_3$OD) δ 8.54 (d, 2H), 7.72 (t, 1H), 7.53-7.49 (m, 3H), 7.20 (d, 1H), 5.06 (s, 1H), 3.65 (s, 1H), 2.42-2.36 (m, 4H), 2.19-2.01 (m, 3H), 1.39-1.31 (m, 2H).

Example 22

3-(2-Fluoropyridin-4-yl)-2-(6-methylpyridin-2-yl)-5,6,7,8-tetrahydro-5,8-methanoimidazo[1,2-a]pyridine 22

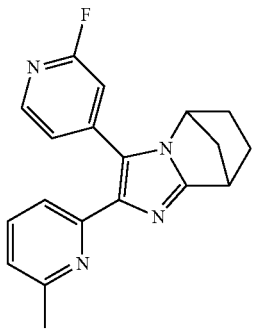

In accordance with the synthetic route of Example 7, the starting compound 7b used in Step 2 was replaced with compound 8a, accordingly, the title compound 22 (30 mg) was prepared.

MS m/z (ESI): 321.1 [M+1]

$^1$H NMR (400 MHz, CD$_3$OD) δ 8.19 (d, 1H), 7.73 (t, 1H), 7.54 (t, 1H), 7.37 (d, 1H), 7.27 (s, 1H), 7.20 (d, 1H), 5.07 (s, 1H), 3.66 (s, 1H), 2.41 (s, 3H), 2.38 (d, 1H), 2.21-2.17 (m, 1H), 2.06-2.00 (m, 2H), 1.38-1.29 (m, 2H).

Example 23-1

(S)-3-((4-((5S,8R)-2-(6-Methylpyridin-2-yl)-5,6,7,8-tetrahydro-5,8-methanoimidazo[1,2-a]pyridin-3-yl)pyridin-2-yl)amino)propane-1,2-diol 23-1

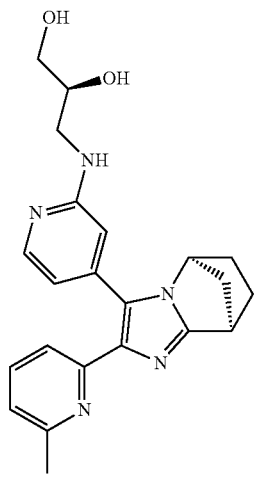

In accordance with the synthetic route of Example 5, the starting compound aminoethanol used in Step 2 was replaced with (S)-3-isopropylamine-1,2-diol (prepared according to the method disclosed in the patent application "US20120095075"), accordingly, the title compound 23-1 (20 mg) was prepared.

MS m/z (ESI): 392.5 [M+1]

$^1$H NMR (400 MHz, CDCl$_3$) δ 8.06 (d, 1H), 7.51 (t, 1H), 7.33 (d, 1H), 6.99 (d, 1H), 6.61 (dd, 1H), 6.49 (s, 1H), 5.81 (s, 1H), 4.78 (s, 1H), 4.13-4.09 (m, 1H), 3.64 (d, 1H), 3.50 (d, 1H), 3.39-3.32 (m, 1H), 2.50 (s, 3H), 2.27 (d, 1H), 2.05-1.99 (m, 4H), 1.90-1.83 (m, 3H).

Example 24-1

N$^1$,N$^1$-Dimethyl-N$^2$-(4-((5S,8R)-2-(6-methylpyridin-2-yl)-5,6,7,8-tetrahydro-5,8-methanoimidazo[1,2-a]pyridin-3-yl)pyridin-2-yl)ethane-1,2-diamine 24-1

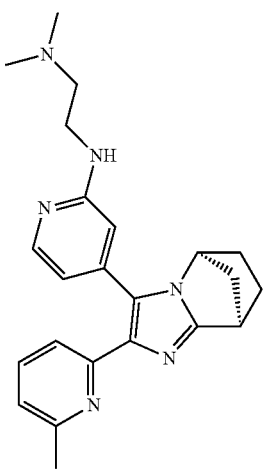

In accordance with the synthetic route of Example 5, the starting compound aminoethanol used in Step 2 was replaced with N,N-dimethylethane-1,2-diamine, accordingly, the title compound 24-1 (20 mg) was prepared.

MS m/z (ESI): 389.5[M+1]

$^1$H NMR (400 MHz, CDCl$_3$) δ 8.09 (d, 1H), 7.54 (t, 1H), 7.45 (d, 1H), 7.02 (d, 1H), 6.68 (dd, 1H), 6.63 (s, 1H), 5.43 (s, 1H), 4.85 (s, 1H), 3.67 (d, 1H), 3.42 (t, 2H), 2.64 (t, 2H), 2.53 (s, 3H), 2.33 (s, 6H), 2.07-2.05 (m, 2H), 1.95-1.87 (m, 4H).

Example 25

4-((4-(2-(6-Methylpyridin-2-yl)-5,6,7,8-tetrahydro-5,8-methanoimidazo[1,2-a]pyridin-3-yl)pyridin-2-yl)amino)cyclohexanol 25

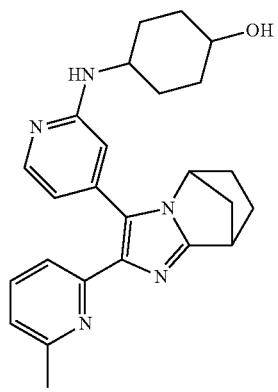

-continued

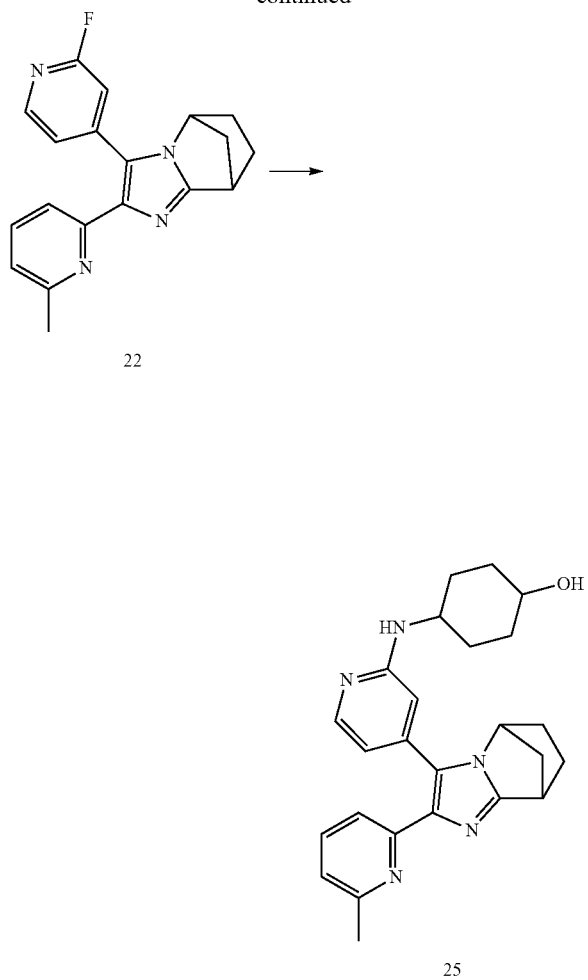

22

25

Compound 22 (30 mg, 0.094 mmol), 4-aminocyclohexanol (32 mg, 0.281 mmol) and cesium carbonate (91 mg, 0.281 mmol) were dissolved in 5 mL of dimethyl sulfoxide, then the reaction solution was warmed up to 120° C. and stirred for 12 hours. The reaction solution was cooled to room temperature, and concentrated under reduced pressure. The resulting residue was purified by high performance liquid chromatography to obtain the title compound 25 (6 mg, yield: 15%).

MS m/z (ESI): 416.3 [M+I]

$^1$H NMR (400 MHz, CDCl$_3$) δ 8.09 (d, 1H), 7.53 (t, 1H), 7.44 (d, 1H), 7.02 (d, 1H), 6.68 (dd, 1H), 6.51 (s, 1H), 4.85 (s, 1H), 4.51 (s, 1H), 3.67-3.72 (m, 2H), 3.48-3.46 (m, 1H), 2.54 (s, 3H), 2.35 (d, 1H), 2.10-1.87 (m, 5H), 1.58-1.55 (m, 1H), 1.41-1.26 (m, 8H).

Example 26

2-((4-(2-(6-Methylpyridin-2-yl)-5,6,7,8-tetrahydro-5,8-methanoimidazo[1,2-a]pyridin-3-yl)pyridin-2-yl)oxy)ethanol 26

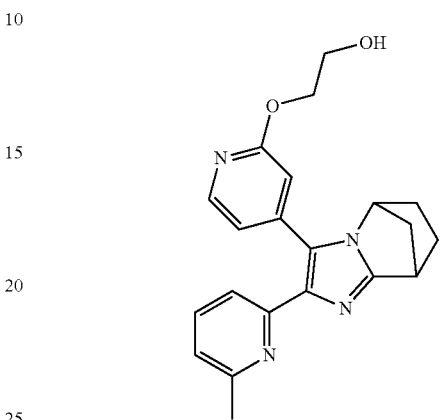

26

In accordance with the synthetic route of Example 25, the starting compound 4-aminocyclohexanol was replaced with ethylene glycol, accordingly, the title compound 26 (10 mg) was prepared.

MS m/z (ESI): 363.5 [M+1]

$^1$H NMR (400 MHz, CD$_3$OD) δ 8.09 (d, 1H), 7.71 (t, 1H) 7.43 (d, 1H), 7.19 (d, 1H), 6.96 (d, 1H), 6.91 (d, 1H), 5.10 (s, 1H), 4.37 (t, 2H), 3.88 (t, 2H), 3.68 (s, 1H), 2.44 (t, 3H), 2.35 (d, 1H), 2.20-2.15 (m, 1H), 2.10-1.98 (m, 2H), 1.49-1.30 (m, 2H).

Example 27

2-((6-(2-(6-Methylpyridin-2-yl)-5,6,7,8-tetrahydro-5,8-methanoimidazo[1,2-a]pyridin-3-yl)quinolin-4-yl)oxy)acetamide 27

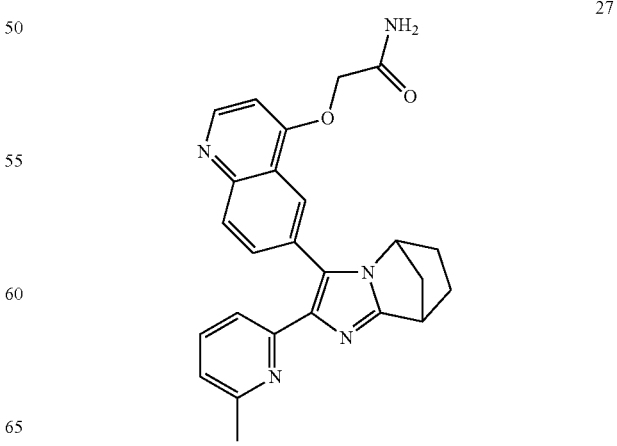

27

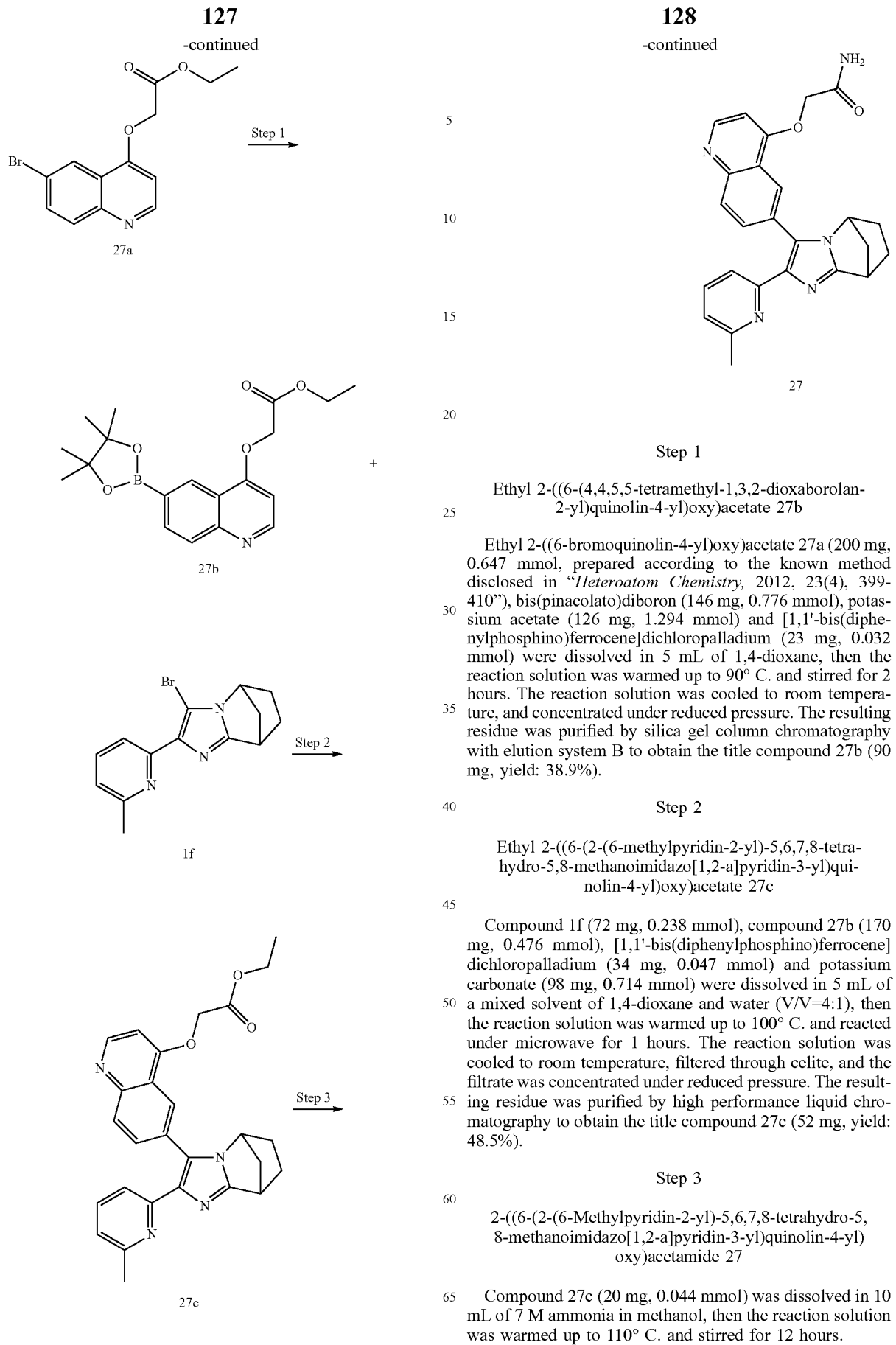

Step 1

Ethyl 2-((6-(4,4,5,5-tetramethyl-1,3,2-dioxaborolan-2-yl)quinolin-4-yl)oxy)acetate 27b Ethyl 2-((6-bromoquinolin-4-yl)oxy)acetate 27a (200 mg, 0.647 mmol, prepared according to the known method disclosed in "*Heteroatom Chemistry*, 2012, 23(4), 399-410"), bis(pinacolato)diboron (146 mg, 0.776 mmol), potassium acetate (126 mg, 1.294 mmol) and [1,1'-bis(diphenylphosphino)ferrocene]dichloropalladium (23 mg, 0.032 mmol) were dissolved in 5 mL of 1,4-dioxane, then the reaction solution was warmed up to 90° C. and stirred for 2 hours. The reaction solution was cooled to room temperature, and concentrated under reduced pressure. The resulting residue was purified by silica gel column chromatography with elution system B to obtain the title compound 27b (90 mg, yield: 38.9%).

Step 2

Ethyl 2-((6-(2-(6-methylpyridin-2-yl)-5,6,7,8-tetrahydro-5,8-methanoimidazo[1,2-a]pyridin-3-yl)quinolin-4-yl)oxy)acetate 27c Compound 1f (72 mg, 0.238 mmol), compound 27b (170 mg, 0.476 mmol), [1,1'-bis(diphenylphosphino)ferrocene]dichloropalladium (34 mg, 0.047 mmol) and potassium carbonate (98 mg, 0.714 mmol) were dissolved in 5 mL of a mixed solvent of 1,4-dioxane and water (V/V=4:1), then the reaction solution was warmed up to 100° C. and reacted under microwave for 1 hours. The reaction solution was cooled to room temperature, filtered through celite, and the filtrate was concentrated under reduced pressure. The resulting residue was purified by high performance liquid chromatography to obtain the title compound 27c (52 mg, yield: 48.5%).

Step 3

2-((6-(2-(6-Methylpyridin-2-yl)-5,6,7,8-tetrahydro-5,8-methanoimidazo[1,2-a]pyridin-3-yl)quinolin-4-yl)oxy)acetamide 27

Compound 27c (20 mg, 0.044 mmol) was dissolved in 10 mL of 7 M ammonia in methanol, then the reaction solution was warmed up to 110° C. and stirred for 12 hours.

The reaction solution was cooled to room temperature, and concentrated under reduced pressure. The resulting residue was purified by high performance liquid chromatography to obtain the title compound 27 (10 mg, yield: 53.4%).

MS m/z (ESI): 426.4 [M+1]

¹H NMR (400 MHz, CDCl₃) δ 8.50 (s, 1H), 8.01 (s, 1H), 7.82 (d, 1H), 7.68 (t, 1H), 7.55 (d, 1H), 7.46 (d, 1H), 7.12 (d, 1H), 6.38 (d, 1H), 5.06 (s, 1H), 4.62 (s, 2H), 3.66 (s, 1H), 2.39 (d, 1H), 2.36 (s, 3H), 2.21-2.10 (m, 1H), 2.06-1.95 (m, 2H), 1.42-1.30 (m, 2H).

Example 28

Tert-butyl 4-(2-(6-methylpyridin-2-yl)-5,6,7,8-tetrahydro-5,8-methanoimidazo[1,2-a]pyridin-3-yl) quinoline-6-carboxylate 28

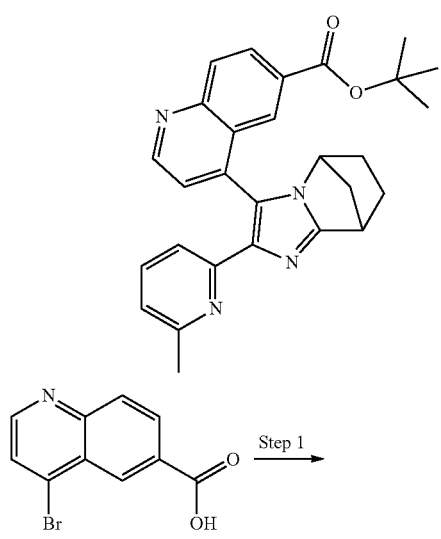

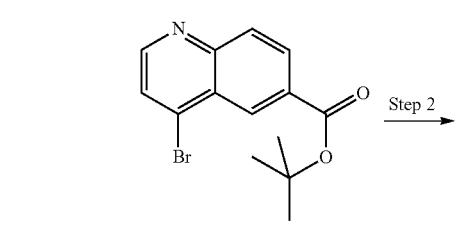

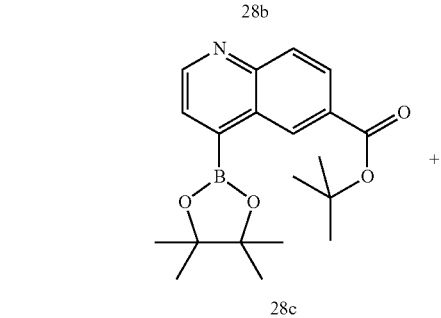

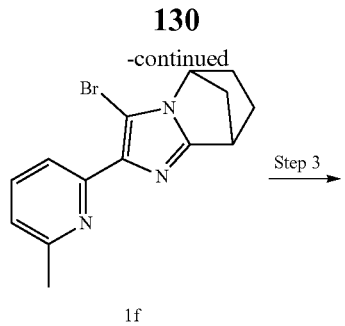

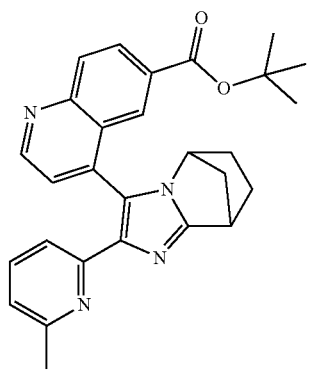

Step 1

Tert-butyl 4-bromoquinoline-6-carboxylate 28b

4-Bromoquinolin-6-carboxylic acid 28a (1.8 g, 7.141 mmol) was dissolved in 10 mL of N,N-dimethylformamide, followed by addition of N,N-carbonyldiimidazole (1.158 g, 7.141 mmol), then the reaction solution was warmed up to 40° C. and stirred for 1 hours. Tert-butanol (1.058 g, 14.282 mmol) and 1,8-diazabicyclo[5.4.0]undec-7-ene (2.177 g, 14.282 mmol) were added, then the reaction solution was warmed up to 80° C. and stirred for 12 hours. The reaction solution was cooled to room temperature, added with water, and extracted with ethyl acetate. The organic phases were combined, dried over anhydrous sodium sulfate and filtered. The filtrate was concentrated under reduced pressure, and the resulting residue was purified by silica gel column chromatography with elution system B to obtain the title compound 28b (900 mg, yield: 41%).

Step 2

Tert-butyl 4-(4,4,5,5-tetramethyl-1,3,2-dioxaborolan-2-yl)quinoline-6-carboxylate 28c Compound 28b (900 mg, 2.92 mmol), bis(pinacolato)diboron (1.11 g, 4.381 mmol), potassium acetate (858 mg, 8.76 mmol) and [1,1'-bis(diphenylphosphino)ferrocene]dichloropalladium (214 mg, 0.292 mmol) were dissolved in 10 mL of dimethyl sulfoxide, then the reaction solution was warmed up to 60° C. and stirred for 12 hours. The reaction solution was cooled to room temperature, and concentrated under reduced pressure. The resulting residue was purified by silica gel column chromatography with elution system B to obtain the title compound 28c (900 mg, yield: 90%).

Step 3

4-(2-(6-Methylpyridin-2-yl)-5,6,7,8-tetrahydro-5,8-methanoimidazo[1,2-a]pyridin-3-yl) quinoline-6-carboxylate 28

Compound 28c (61 mg, 0.171 mmol), compound 1f (40 mg, 0.131 mmol), sodium carbonate (42 mg, 0.393 mmol) and [1,1'-bis(diphenylphosphino)ferrocene]dichloropalladium (15 mg, 0.013 mmol) were dissolved in 6 mL of a mixed solvent of glycol dimethyl ether and water (V/V=5:1), then the reaction solution was warmed up to 80° C. and stirred for 12 hours. The reaction solution was cooled to room temperature, and concentrated under reduced pressure. The resulting residue was purified by high performance liquid chromatography to obtain the title compound 28 (10 mg, yield: 17%).

MS m/z (ESI): 453.4[M+1]

$^1$H NMR (400 MHz, CD$_3$OD) δ 9.01 (dd, 1H), 8.36 (d, 1H), 8.24-8.11 (m, 2H), 7.77-7.59 (m, 3H), 6.95 (dd, 1H), 5.17 (s, 1H), 3.76 (s, 1H), 2.69 (s, 3H), 2.48-2.41 (m, 2H), 2.25-2.21 (m, 2H), 2.09-2.01 (m, 2H), 1.50 (d, 9H).

Example 29

4-(2-(6-Methylpyridin-2-yl)-5,6,7,8-tetrahydro-5,8-methanoimidazo[1,2-a]pyridin-3-yl) quinoline-6-carboxamide 29

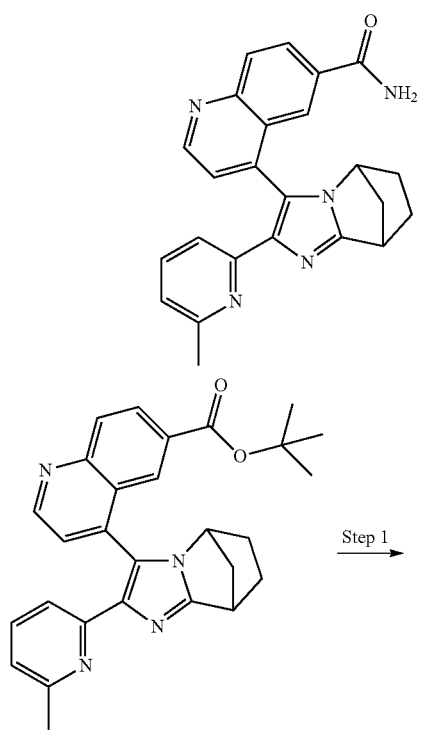

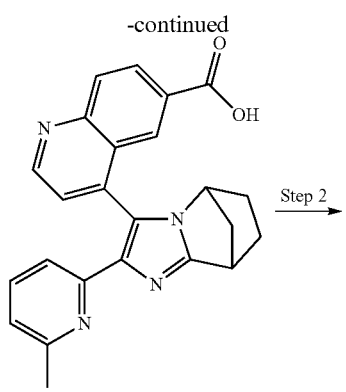

29a

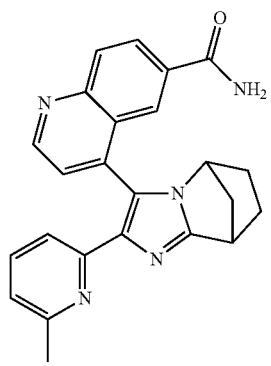

29

Step 1

4-(2-(6-Methylpyridin-2-yl)-5,6,7,8-methanoimidazo[1,2-a]pyridin-3-yl) quinoline-6-carboxylic acid 29a Compound 28 (80 mg, 0.177 mmol) was dissolved in 5 mL of dichloromethane, then 1.5 mL of trifluoroacetic acid was added. After stirring at room temperature for 12 hours, the reaction solution was concentrated under reduced pressure. The resulting residue was added with water, and extracted with ethyl acetate. The organic phases were combined, dried over anhydrous sodium sulfate and filtered. The filtrate was concentrated under reduced pressure to obtain the crude title compound 29a (50 mg), which was used directly in the next step without purification.

Step 2

4-(2-(6-Methylpyridin-2-yl)-5,6,7,8-tetrahydro-5,8-methanoimidazo[1,2-a]pyridin-3-yl) quinoline-6-carboxamide 29

The crude compound 29a (50 mg, 0.126 mmol), ammonium chloride (67 mg, 1.201 mmol), 1-ethyl-(3-dimethylaminopropyl)carbonyldiimide hydrochloride (36 mg, 0.189 mmol), 1-hydroxybenzotriazole (26 mg, 0.189 mmol) and N,N-diisopropylethylamine (49 mg, 0.378 mmol) were dissolved in 3 mL of N,N-dimethylformamide. After stirring at room temperature for 12 hours, the reaction solution was purified by high performance liquid chromatography to obtain the title compound 29 (10 mg, yield: 20%).

MS m/z (ESI): 396.4 [M+1]

$^1$H NMR (400 MHz, CD$_3$OD) δ 8.91 (t, 2H), 8.37 (d, 1H), 8.30 (d, 1H), 8.01 (dd, 1H), 7.82 (t, 1H), 7.43 (d, 1H), 7.34 (d, 1H), 5.17 (s, 1H), 3.98 (d, 1H), 2.69 (s, 3H), 2.56 (d, 1H), 2.39-2.35 (m, 1H), 2.20-2.16 (m, 2H), 1.60-1.55 (m, 2H).

Example 30

4-(2-(6-Methylpyridin-2-yl)-5,6,7,8-tetrahydro-5,8-methanoimidazo[1,2-a]pyridin-3-yl) nicotinamide 30

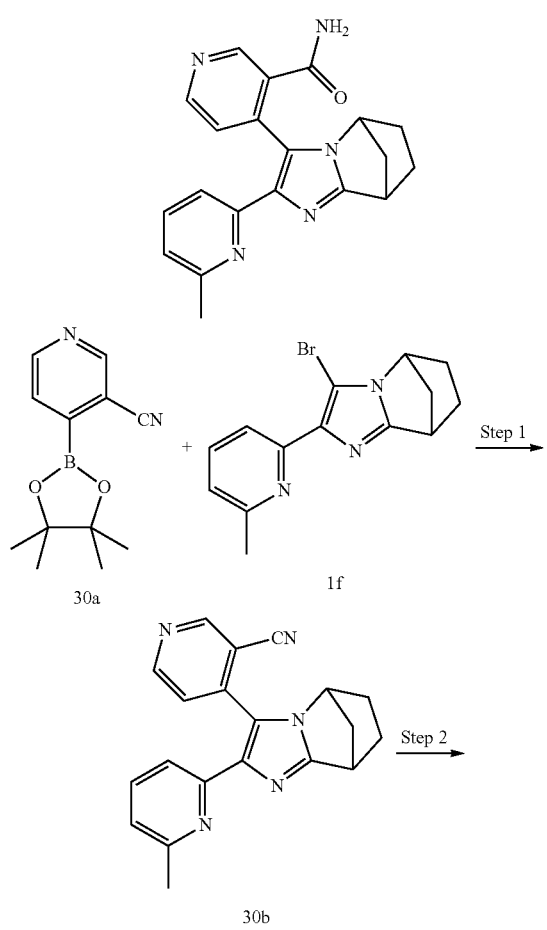

Step 1

4-(2-(6-Methylpyridin-2-yl)-5,6,7,8-tetrahydro-5,8-methanoimidazo[1,2-a]pyridin-3-yl) nicotinonitrile 30b 4-(4,4,5,5-Tetramethyl-1,3,2-dioxaborolan-2-yl)nicotinonitrile 30a (90.76 mg, 0.39 mmol, prepared according to the method disclosed in the patent application "WO2012086735"), compound 1f (60 mg, 0.2 mmol), [1,1'-bis(diphenylphosphino)ferrocene]dichloropalladium (14.43 mg, 0.02 mmol) and potassium carbonate (81.78 mg, 0.59 mmol) were dissolved in 5 mL of a mixed solvent of 1,4-dioxane and water (V/V=4:1), then the reaction solution was warmed up to 80° C. and stirred for 12 hours. The reaction solution was cooled to room temperature, and concentrated under reduced pressure. The resulting residue was purified by silica gel column chromatography with elution system B to obtain the title compound 30b (15 mg, yield: 23.23%).

Step 2

4-(2-(6-Methylpyridin-2-yl)-5,6,7,8-tetrahydro-5,8-methanoimidazo[1,2-a]pyridin-3-yl) nicotinamide 30

Compound 30b (15 mg, 0.05 mmol), hydrogen peroxide (15.58 mg, 0.46 mmol) and potassium carbonate (19 mg, 0.14 mmol) were dissolved in 1 mL of dimethyl sulfoxide. After stirring at room temperature for 2 hours, the reaction solution was purified by high performance liquid chromatography to obtain the title compound 30 (2 mg, yield: 12.39%).

MS m/z (ESI): 346.5[M+1]

$^1$H NMR (400 MHz, CDCl$_3$) δ 8.98 (dd, 2H), 8.57 (t, 1H), 7.71 (d, 1H), 7.59 (t, 1H), 6.99 (d, 1H), 6.46 (s, 1H), 5.93 (s, 1H), 4.81 (s, 1H), 3.70 (d, 1H), 2.39 (s, 3H), 2.36 (d, 1H), 2.08-2.20 (m, 1H), 1.81-1.97 (m, 2H), 1.50-1.52 (m, 1H), 1.34-1.35 (m, 1H).

Example 30-1

4-((5S,8R)-2-(6-Methylpyridin-2-yl)-5,6,7,8-tetrahydro-5,8-methanoimidazo[1,2-a]pyridin-3-yl)nicotinamide 30-1

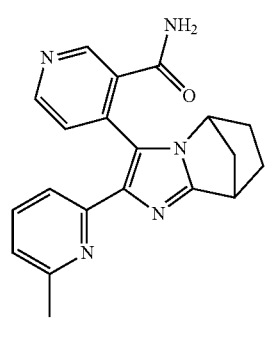

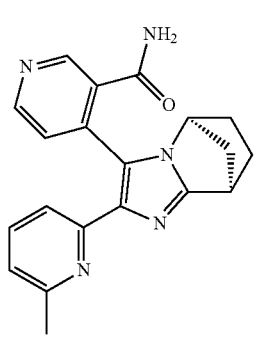

In accordance with the synthetic route of Example 30, the starting compound 1f used in Step 1 was replaced with compound 1f-1, accordingly, the title compound 30-1 (15 mg) was prepared.

MS m/z (ESI): 346.5 [M+1]

¹H NMR (400 MHz, CDCl₃) δ 8.99 (dd, 2H), 8.58 (t, 1H), 7.72 (d, 1H), 7.59 (t, 1H), 6.99 (d, 1H), 6.42 (s, 1H), 5.86 (s, 1H), 4.82 (s, 1H), 3.70 (d, 1H), 2.39 (s, 3H), 2.37 (d, 1H), 2.15-2.09 (m, 1H), 1.99-1.99 (m, 2H), 1.54-1.51 (m, 1H), 1.39-1.36 (m, 1H).

Example 31

Tert-butyl (4-(2-(6-methylpyridin-2-yl)-5,6,7,8-tetra-hydro-5,8-methanoimidazo[1,2-a]pyridin-3-yl)pyridin-2-yl)carbamate 31

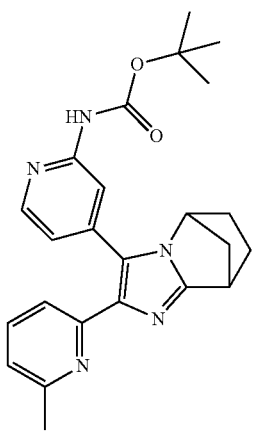

In accordance with the synthetic route of Example 8, the starting compound 8c used in Step 3 was replaced with tert-butyl (4-(4,4,5,5-tetramethyl-1,3,2-dioxaborolan-2-yl)pyridin-2-yl)carbamate (prepared according to the method disclosed in the patent application "WO2015039172"), accordingly, the title compound 31 (30 mg) was prepared.

MS m/z (ESI): 418.2 [M+1]

¹H NMR (400 MHz, CD₃OD) δ 8.17 (d, 1H), 8.02 (s, 1H), 7.71 (t, 1H), 7.46 (d, 1H), 7.19 (d, 1H), 7.04-7.02 (m, 1H), 5.12 (s, 1H), 3.65 (s, 1H), 2.44 (s, 3H), 2.39-2.02 (m, 4H), 1.53 (s, 9H), 1.42-1.31 (m, 2H).

Example 32

4-(2-(6-Methylpyridin-2-yl)-5,6,7,8-tetrahydro-5,8-methanoimidazo[1,2-a]pyridin-3-yl)pyridin-2-amine 32

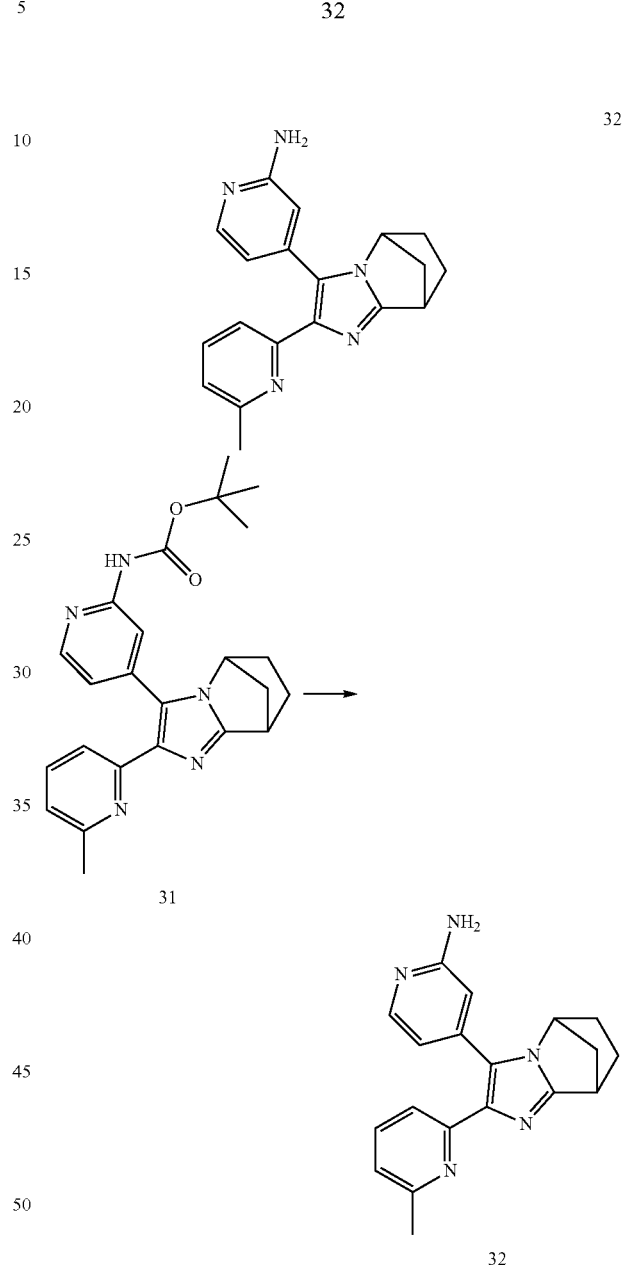

Compound 31 (50 mg, 0.12 mmol) was dissolved in 10 mL of dichloromethane, then 3 mL of trifluoroacetic acid was added. After stirring at 100° C. for 16 hours, the reaction solution was adjusted with saturated sodium bicarbonate solution until the pH was alkaline, and extracted with dichloromethane. The organic phases were combined, dried over anhydrous sodium sulfate and filtered. The filtrate was concentrated under reduced pressure, and the resulting residue was purified by high performance liquid chromatography to obtain the title compound 32 (20 mg).

MS m/z (ESI): 318.2 [M+1]

¹H NMR (400 MHz, CD₃OD) δ 7.86 (d, 1H), 7.70 (t, 1H), 7.41 (t, 1H), 7.18 (d, 1H), 6.69 (d, 1H), 6.61 (t, 1H), 5.22 (s,

1H), 3.64 (s, 1H), 2.68 (s, 3H), 2.47-2.46 (m, 1H), 2.34-2.32 (m, 1H), 2.07-1.99 (m, 2H), 1.39-1.32 (m, 2H).
Example 33
2-(6-Methylpyridin-2-yl)-3-(2-(4-(methylsulfonyl)phenyl)pyridin-4-yl)-4,5,6,7-tetrahydro-4,7-ethano-pyrazolo[1,5-a]pyridine 33
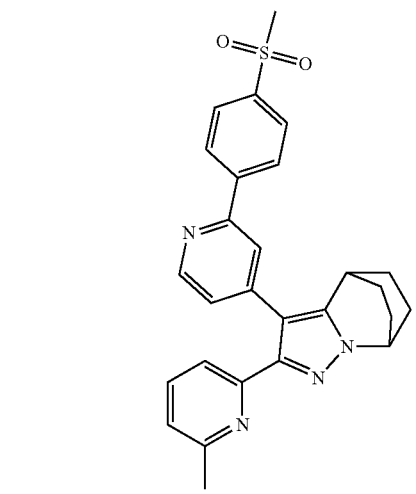
33
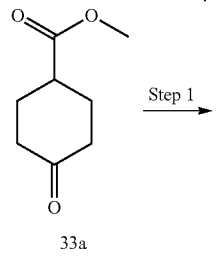
33a
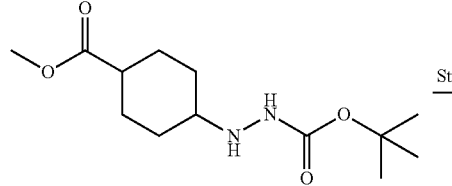
33b
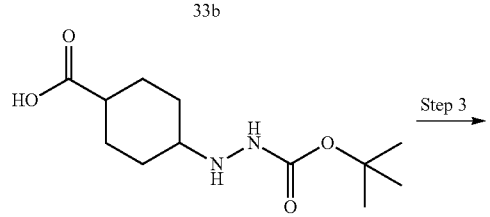
33c
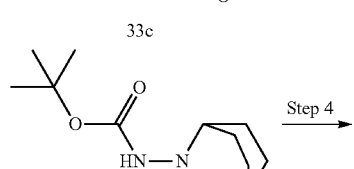
33d
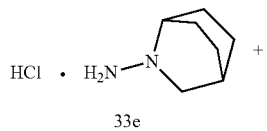
33e
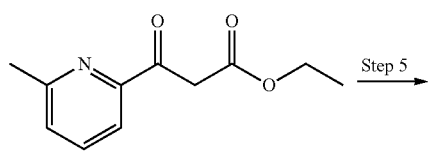
33f
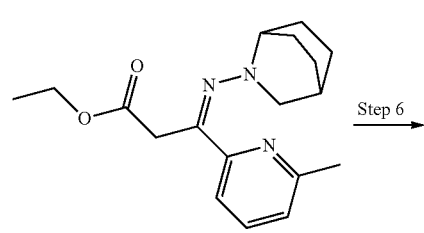
33g
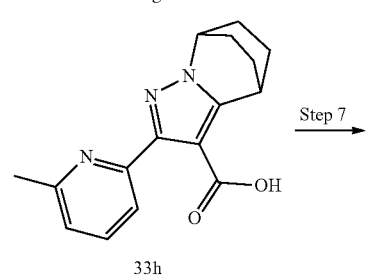
33h
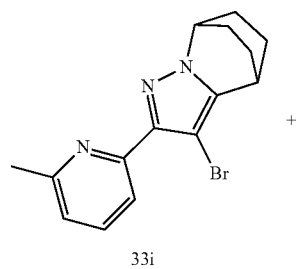
33i
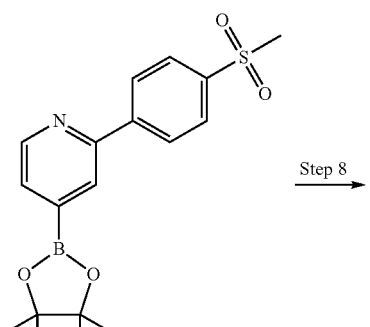
3d

139

-continued

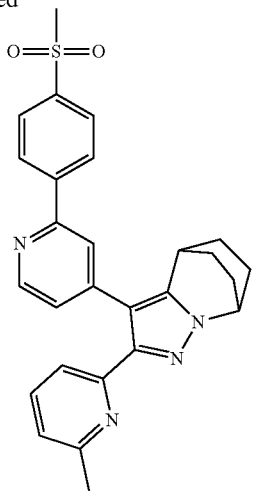

33

Step 1

Tert-butyl 2-(4-(methoxycarbonyl)cyclohexyl)hydrazinecarboxylate 33b Methyl 4-cyclohexanonecarboxylate 33a (2 g, 12.806 mmol), tert-butyl hydrazinecarboxylate (1.86 g, 14.286 mmol) and sodium triacetoxyborohydride (5.4 g, 25.612 mmol) were dissolved in 30 mL of dichloromethane, then 0.5 mL of acetic acid was added. After stirring at room temperature for 12 hours, the reaction solution was added with water, and extracted with dichloromethane. The organic phases were combined, dried over anhydrous sodium sulfate and filtered. The filtrate was concentrated under reduced pressure, and the resulting residue was purified by silica gel column chromatography with elution system B to obtain the title compound 33b (1.5 g, yield: 43%).

Step 2

4-(2-(Tert-butoxycarbonyl)hydrazinyl)cyclohexanecarboxylic acid 33c

Compound 33b (900 mg, 3.203 mmol) was dissolved in 10 mL of methanol, then 4 mL of 2 M sodium hydroxide solution was added. After stirring at room temperature for 3 hours, the reaction solution was added dropwise with 2 M hydrochloric acid until the pH was 5-6, and extracted with a mixed solvent of dichloromethane and methanol (V/V=10:1). The organic phases were combined, dried over anhydrous sodium sulfate and filtered. The filtrate was concentrated under reduced pressure to obtain the crude title compound 33c (750 mg), which was used directly in the next step without purification.

Step 3

Tert-butyl 2-azabicyclo[2.2.2]octan-2-ylcarbamate 33d

The crude compound 33c (750 mg, 2.903 mmol), 1-ethyl-(3-dimethylaminopropyl)carbonyldiimide hydrochloride (832 mg, 4.355 mmol), 1-hydroxybenzotriazole (588 mg, 4.355 mmol) and triethylamine (633 mg, 5.806 mmol) were dissolved in 10 mL of N,N-dimethylformamide. After stirring at room temperature for 12 hours, the reaction solution

140 was added with saturated sodium bicarbonate solution and extracted with dichloromethane. The organic phases were combined, dried over anhydrous sodium sulfate and filtered. The filtrate was concentrated under reduced pressure, and the resulting residue was purified by silica gel column chromatography with elution system B to obtain the title compound 33d (490 mg, yield: 70%).

Step 4

2-Azabicyclo[2.2.2]octan-2-amine hydrochloride 33e

Compound 33d (490 mg, 2.039 mmol) was dissolved in 5 mL of 4 M hydrogen chloride in 1,4-dioxane. After stirring at room temperature for 3 hours, the reaction solution was concentrated under reduced pressure to obtain the crude title compound 33e (300 mg), which was used directly in the next step without purification.

Step 5

Ethyl 3-(2-azabicyclo[2.2.2]octan-2-ylimino)-3-(6-methylpyridin-2-yl)propanoate 33g The crude compound 33e (350 mg, 1.981 mmol), ethyl 3-(6-methylpyridin-2-yl)-3-oxopropanoate 33f (452 mg, 2.179 mmol, prepared according to the method disclosed in the patent application "WO2006052568") and p-toluenesulfonic acid (34 mg, 0.198 mmol) were dissolved in 10 mL of pyridine, then 100 mg of 4 Å molecular sieve was added. After stirring at room temperature for 12 hours, the reaction solution was concentrated under reduced pressure, and the resulting residue was purified by silica gel column chromatography with elution system B to obtain the title compound 33g (300 mg, yield: 46%).

Step 6

2-(6-Methylpyridin-2-yl)-4,5,6,7-tetrahydro-4,7-ethanopyrazolo[1,5-a]pyridine-3-carboxylic acid 33h Compound 33g (1.3 g, 3.95 mmol) was dissolved in 20 mL of toluene, then sodium ethoxide (537.14 mg, 7.89 mmol) was added. The reaction solution was warmed up to 100° C. and stirred for 12 hours. The reaction solution was cooled to room temperature, and concentrated under reduced pressure. The resulting residue was added with 50 mL of ethyl acetate, washed with water and saturated sodium chloride solution successively, dried over anhydrous sodium sulfate and filtered. The filtrate was concentrated under reduced pressure to obtain the crude title compound 33h (1.1 g), which was used directly in the next step without purification.

Step 7

3-Bromo-2-(6-methylpyridin-2-yl)-4,5,6,7-tetrahydro-4,7-ethanopyrazolo[1,5-a]pyridine 33i The crude compound 33h (1.1 g, 3.88 mmol) was dissolved in 15 mL of N,N-dimethylformamide, then N-bromosuccinimide (1.38 g, 7.76 mmol) was added. The reaction solution was warmed up to 40° C. and stirred for 12 hours. The reaction solution was cooled to room temperature, and concentrated under reduced pressure. The resulting residue was purified by silica gel column chromatography with elution system B to obtain the title compound 33i (550 mg, yield: 44.52%).

Step 8

2-(6-Methylpyridin-2-yl)-3-(2-(4-(methylsulfonyl)phenyl)pyridin-4-yl)-4,5,6,7-tetrahydro-4,7-ethanopyrazolo[1,5-a]pyridine 33

Compound 33i (50 mg, 0.157 mmol), compound 3d (112.9 mg, 0.314 mmol), [1,1'-bis(diphenylphosphino)ferrocene]dichloropalladium (11.5 mg, 0.0157 mmol) and potassium carbonate (65.15 mg, 0.47 mmol) were dissolved in 2 mL of a mixed solvent of 1,4-dioxane and water (V/V=3:1), then the reaction solution was warmed up to 100° C. and reacted under microwave for 1 hours. The reaction solution was cooled to room temperature, and concentrated under reduced pressure. The resulting residue was purified by high performance liquid chromatography to obtain the title compound 33 (15 mg, yield: 20.08%).

MS m/z (ESI): 471.4 [M+1]

$^1$H NMR (400 MHz, CDCl$_3$) δ 8.69 (d, 1H), 8.12 (d, 2H), 8.05 (d, 2H), 7.80 (s, 1H), 7.60 (t, 1H), 7.42 (d, 1H), 7.29 (d, 1H), 7.13 (d, 1H), 4.92 (s, 1H), 3.54 (s, 1H), 3.13 (s, 3H), 2.52 (s, 3H), 2.04-1.19 (m, 6H), 1.76-1.71 (m, 2H).

Example 34

4-(2-(6-Methylpyridin-2-yl)-4,5,6,7-tetrahydro-4,7-ethanopyrazolo[1,5-a]pyridin-3-yl)quinoline-6-carboxamide 34

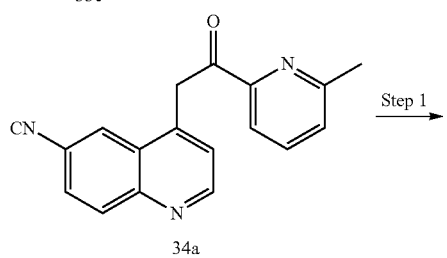

Step 1

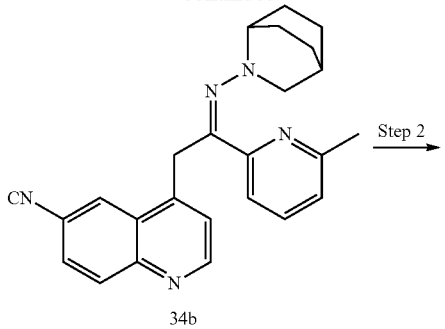

Step 2

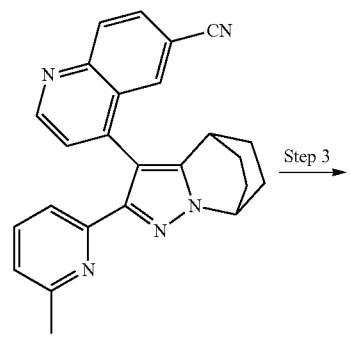

Step 3

34

Step 1

4-(2-(2-Azabicyclo[2.2.2]octan-2-ylimino)-2-(6-methylpyridin-2-yl)ethyl)quinoline-6-carbonitrile 34b The compound 33e (200 mg, 1.132 mmol), 4-(2-(6-methylpyridin-2-yl)-2-oxoethyl)quinoline-6-carbonitrile 34a (358 mg, 1.245 mmol, prepared according to the method disclosed in the patent application "WO2007018818") and p-toluenesulfonic acid (50 mg, 0.291 mmol) were dissolved in 5 mL of pyridine, then 200 mg of 4 Å molecular sieve was added. After stirring at room temperature for 12 hours, the reaction solution was concentrated under reduced pressure, and the resulting residue was purified by silica gel column chromatography with elution system B to obtain the title compound 34b (200 mg, yield: 43%).

Step 2

4-(2-(6-Methylpyridin-2-yl)-4,5,6,7-tetrahydro-4,7-ethanopyrazolo[1,5-a]pyridin-3-yl)quinoline-6-carbonitrile 34c Compound 34b (150 mg, 0.366 mmol) was dissolved in 4 mL of N,N-dimethylformamide, then sodium hydride (44 mg, 1.099 mmol, 60%) was added. The reaction solution was stirred at room temperature for 1 hours, followed by stirring at 100° C. for 12 hours. The reaction solution was cooled to room temperature, added with water, and extracted with dichloromethane. The organic phases were combined, dried over anhydrous sodium sulfate and filtered. The filtrate was concentrated under reduced pressure to obtain the crude title compound 34c (70 mg), which was used directly in the next step without purification.

Step 3

4-(2-(6-Methylpyridin-2-yl)-4,5,6,7-tetrahydro-4,7-ethanopyrazolo[1,5-a]pyridin-3-yl)quinoline-6-carboxamide 34

The crude compound 34c (70 mg, 0.179 mmol) was dissolved in 3 mL of dimethyl sulfoxide, then 0.3 mL of hydrogen peroxide solution (30%) and potassium carbonate (74 mg, 0.536 mmol) were added. After stirring at room temperature for 2 hours, the reaction solution was added with water, and extracted with ethyl acetate. The organic phases were combined, dried over anhydrous sodium sulfate and filtered. The filtrate was concentrated under reduced pressure, and the resulting residue was purified by high performance liquid chromatography to obtain the title compound 34 (20 mg, yield: 27%).

MS m/z (ESI): 410.4 [M+1]

$^1$H NMR (400 MHz, CDCl$_3$) δ 9.00 (d, 1H), 8.26 (d, 1H), 8.19 (d, 1H), 8.13 (dd, 1H), 7.56 (d, 1H), 7.38 (dd, 1H), 7.00 (dd, 2H), 5.98 (s, 1H), 5.50 (s, 1H), 4.99 (s, 1H), 3.28 (s, 1H), 2.38 (s, 3H), 2.09-1.93 (m, 6H), 1.78-1.76 (m, 2H).

Example 35

4-(2-(6-Methylpyridin-2-yl)-4,5,6,7-tetrahydro-4,7-methanopyrazolo[1,5-a]pyridin-3-yl)quinoline-6-carboxamide 35

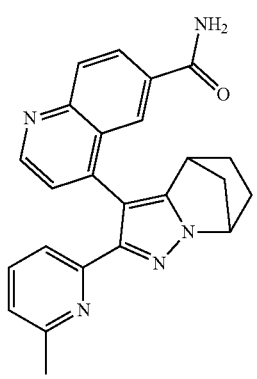

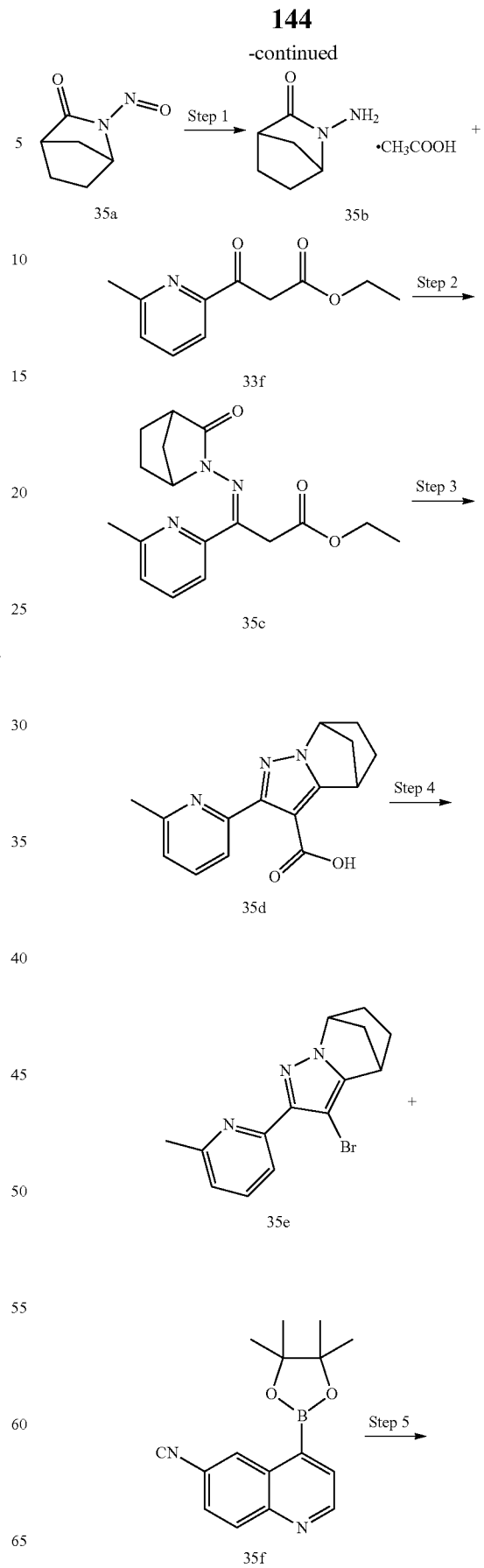

-continued

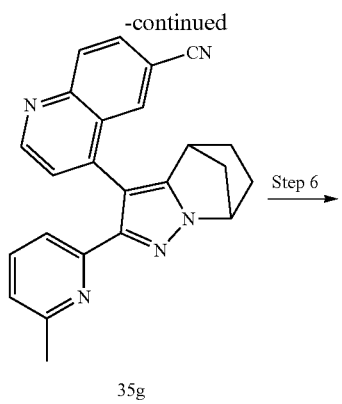

35g

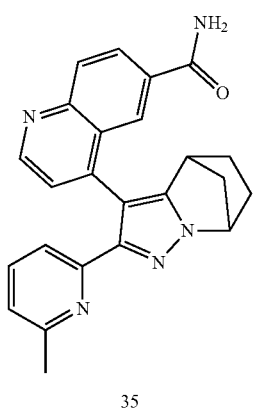

35

Step 1

2-Amino-2-azabicyclo[2.2.1]heptan-3-one acetate 35b

2-Nitroso-2-azabicyclo[2.2.1]heptan-3-one 35a (15 g, 107 mmol, prepared according to the method disclosed in the patent application "WO2010132509") was dissolved in 75 mL of acetic acid. The reaction solution was cooled to 0° C., and zinc powder (10.2 g, 159 mmol) was added. The reaction solution was slowly warmed up to room temperature and stirred until the reaction solution became grey, then the reaction was stopped. The reaction solution was filtered through silica gel. The filtrate was concentrated under reduced pressure to obtain the crude title compound 35b (22 g), which was used directly in the next step without purification.

Step 2

Ethyl 3-(6-methylpyridin-2-yl)-3-((3-oxoazabicyclo [2.2.1]heptan-2-yl)imino)propanoate 35c The crude compound 35b (5 g, 25.9 mmol) and compound 33f (7.2 g, 38.9 mmol) were dissolved in 100 mL of toluene, then p-toluenesulfonic acid (445 mg, 25.9 mmol) was added. The reaction solution was warmed up to 130° C. and stirred for 18 hours. The reaction solution was cooled to room temperature, added with saturated sodium bicarbonate solution, and extracted with ethyl acetate. The organic phases were combined, dried over anhydrous sodium sulfate and filtered. The filtrate was concentrated under reduced pressure, and the resulting residue was purified by silica gel column chromatography with elution system B to obtain the title compound 35c (5.9 g, yield: 72.8%).

Step 3

2-(6-Methylpyridin-2-yl)-4,5,6,7-tetrahydro-4,7-methanopyrazolo[1,5-a]pyridine-3-carboxylic acid 35d Compound 35c (2 g, 6.9 mmol) was dissolved in 50 mL of toluene, then sodium ethoxide (1.4 g, 20.9 mmol) was added. The reaction solution was warmed up to 100° C. and stirred for 16 hours. The reaction solution was cooled to room temperature, and water was added. 1 N hydrochloric acid was added dropwise until the pH was 5-6. The reaction solution was extracted with ethyl acetate, then the organic phases were combined, dried over anhydrous sodium sulfate and filtered. The filtrate was concentrated under reduced pressure to obtain the crude title compound 35d (1.4 g), which was used directly in the next step without purification.

Step 4

3-Bromo-2-(6-methylpyridin-2-yl)-4,5,6,7-tetrahydro-4,7-methanopyrazolo[1,5-a]pyridine 35e The crude compound 35d (600 mg, 2.23 mmol) was dissolved in 5 mL of N,N-dimethylformamide, then N-bromosuccinimide (422 mg, 2.45 mmol) was added.

After stirring at room temperature for 4 hours, the reaction solution was added with saturated sodium bicarbonate solution and extracted with ethyl acetate. The organic phases were combined, dried over anhydrous sodium sulfate and filtered. The filtrate was concentrated under reduced pressure, and the resulting residue was purified by silica gel column chromatography with elution system B to obtain the title compound 35e (610 mg, yield: 90.3%).

Step 5

4-(2-(6-Methylpyridin-2-yl)-4,5,6,7-tetrahydro-4,7-methanopyrazolo[1,5-a]pyridin-3-yl)quinoline-6-carbonitrile 35g Compound 35e (250 mg, 0.18 mmol), 4-(4,4,5,5-tetramethyl-1,3,2-dioxaborolan-2-yl)quinoline-6-carbonitrile 35f (278 mg, 0.989 mmol, prepared according to the method disclosed in the patent application "US20100160280"), [1,1'-bis(diphenylphosphino)ferrocene]dichloropalladium (30 mg, 0.041 mmol) and potassium carbonate (342 mg, 2.475 mmol) were dissolved in 5.5 mL of a mixed solvent of 1,4-dioxane and water (V/V=10:1), then the reaction solution was warmed up to 80° C. and stirred for 1 hours. The reaction solution was cooled to room temperature, added with water, and extracted with ethyl acetate. The organic phases were combined, dried over anhydrous sodium sulfate and filtered. The filtrate was concentrated under reduced pressure, and the resulting residue was purified by high performance liquid chromatography to obtain the title compound 35g (250 mg, yield: 80%).

Step 6

4-(2-(6-Methylpyridin-2-yl)-4,5,6,7-tetrahydro-4,7-methanopyrazolo[1,5-a]pyridin-3-yl)quinoline-6-carboxamide 35

Compound 35g (250 mg, 0.66 mmol) was dissolved in 3 mL of dimethyl sulfoxide, then 0.5 mL of hydrogen peroxide solution (30%) and potassium carbonate (273 mg, 1.98 mmol) were added. After stirring at room temperature for 1 hours, the reaction solution was added with water, and extracted with ethyl acetate. The organic phases were combined, dried over anhydrous sodium sulfate and filtered. The filtrate was concentrated under reduced pressure, and the resulting residue was purified by high performance liquid chromatography to obtain the title compound 35 (98 mg, yield: 37.6%).

MS m/z (ESI): 396.4 [M+1]

$^1$H NMR (400 MHz, CD$_3$OD) δ 8.88-8.87 (d, 1H), 8.40 (s, 1H), 8.16-8.09 (m, 2H), 7.60-7.56 (m, 1H), 7.69-7.46 (m, 2H), 7.05-7.03 (d, 1H), 5.08 (s, 1H), 6.65-3.63 (m, 1H), 3.37 (s, 1H), 2.68 (s, 3H), 2.44-2.41 (d, 1H), 2.16-2.12 (m, 2H), 2.06-2.03 (m, 1H), 1.56-1.51 (m, 1H), 1.45-1.40 (m, 1H), 0.92-0.90 (m, 1H).

Examples 35-1, 35-2

4-((4S,7R)-2-(6-Methylpyridin-2-yl)-4,5,6,7-tetrahydro-4,7-methanopyrazolo[1,5-a]pyridin-3-yl)quinoline-6-carboxamide 35-1

4-((4R,7S)-2-(6-Methylpyridin-2-yl)-4,5,6,7-tetrahydro-4,7-methanopyrazolo[1,5-a]pyridin-3-yl)quinoline-6-carboxamide 35-2

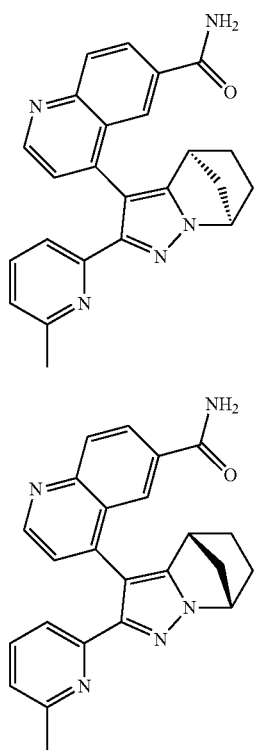

Compound 35 (98 mg, 0.247 mmol) was separated chirally (separation conditions: chromatographic column: Superchiral S-OJ (Chiralway), 2 cm I.D.×25 cm Length, 5 m; mobile phase: carbon dioxide/methanol=80/20 (v/v); flow rate: 50 g/min). The corresponding fractions were collected and concentrated under reduced pressure to obtain the title compounds (45 mg, 45 mg).

Compound in a single configuration (with shorter retention time):

MS m/z (ESI): 396.4 [M+1]

Chiral HPLC: retention time 7.153 minutes, chiral purity: 99.9% (chromatographic column: CHIRALPAK OD 4.6× 150 mm 5 m; mobile phase: ethanol (containing 0.1% diethylamine)/n-hexane=20/80 (v/v));

$^1$H NMR (400 MHz, CDCl$_3$) δ 9.01-9.00 (d, 1H), 8.20-8.18 (m, 2H), 8.14-8.11 (m, 1H), 7.44-7.43 (d, 1H), 7.39-7.35 (m, 1H), 7.14-7.12 (d, 1H), 6.97-6.95 (d, 1H), 5.95-5.90 (br, 1H), 5.97-5.51 (br, 1H), 5.09 (s, 1H), 3.65 (s, 1H), 2.42-2.40 (d, 1H), 2.27 (s, 3H), 2.18-2.08 (m, 2H), 1.98-1.96 (m, 1H), 1.69-1.68 (m, 1H), 1.53-1.50 (m, 1H).

Compound in a single configuration (with longer retention time):

MS m/z (ESI): 396.4 [M+1]

Chiral HPLC: retention time 7.992 minutes, chiral purity: 99.1% (chromatographic column: CHIRALPAK OD 4.6× 150 mm 5 μm; mobile phase: ethanol (containing 0.1% diethylamine)/n-hexane=20/80 (v/v));

$^1$H NMR (400 MHz, CDCl$_3$) δ 9.01-9.00 (d, 1H), 8.20-8.18 (m, 2H), 8.14-8.11 (m, 1H), 7.44-7.43 (d, 1H), 7.39-7.35 (m, 1H), 7.14-7.12 (d, 1H), 6.97-6.95 (d, 1H), 5.94-5.90 (br, 1H), 5.97-5.51 (br, 1H), 5.09 (s, 1H), 3.65 (s, 1H), 2.42-2.40 (d, 1H), 2.27 (s, 3H), 2.18-2.08 (m, 2H), 1.98-1.96 (m, 1H), 1.69-1.68 (m, 1H), 1.53-1.50 (m, 1H).

Example 36

6-(2-(6-Methylpyridin-2-yl)-4,5,6,7-tetrahydro-4,7-ethanopyrazolo[1,5-a]pyridin-3-yl)quinoline-4-carboxamide 36

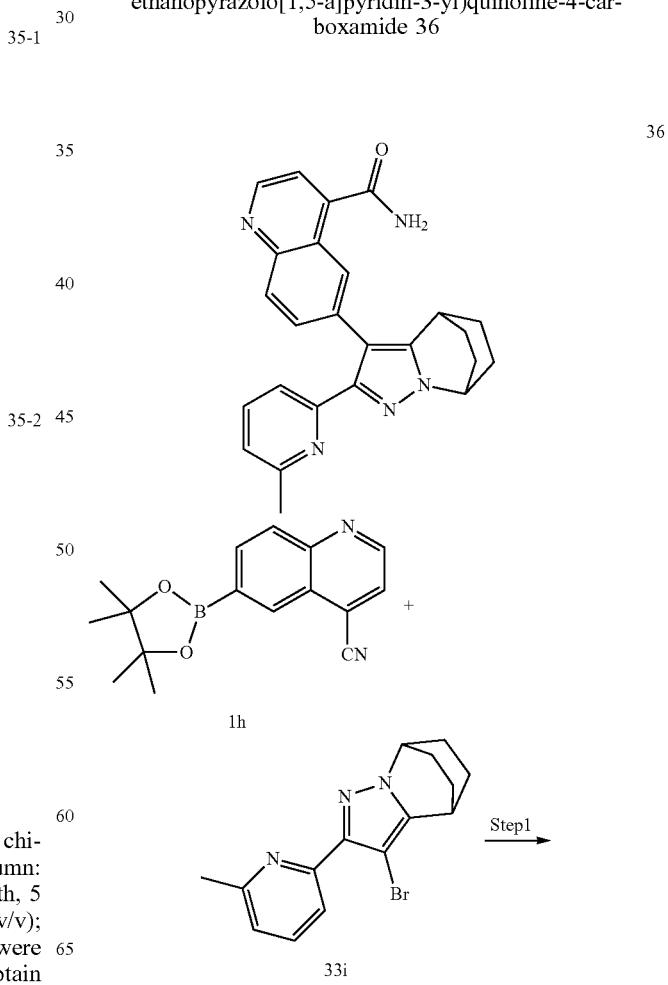

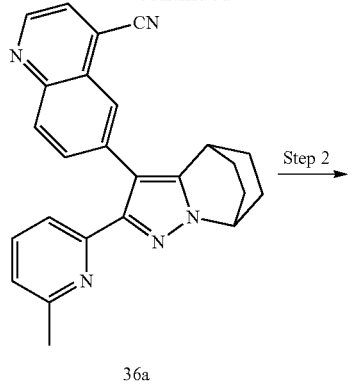

36a

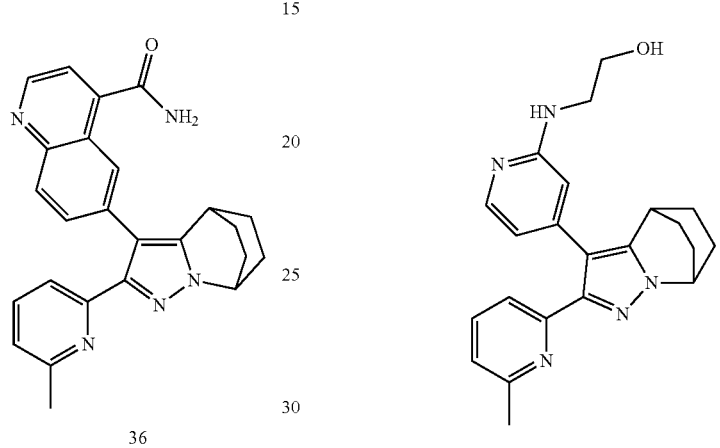

36

Step 1

6-(2-(6-Methylpyridin-2-yl)-4,5,6,7-tetrahydro-4,7-ethanopyrazolo[1,5-a]pyridin-3-yl)quinoline-4-carbonitrile 36a Compound 1h (66 mg, 0.236 mmol), compound 33i (50 mg, 0.157 mmol), [1,1'-bis(diphenylphosphino)ferrocene]dichloropalladium (12 mg, 0.016 mmol) and potassium carbonate (65 mg, 0.471 mmol) were dissolved in 5 mL of a mixed solvent of 1,4-dioxane and water (V/V=4:1), then the reaction solution was warmed up to 85° C. and stirred for 12 hours. The reaction solution was cooled to room temperature, and concentrated under reduced pressure. The resulting residue was purified by silica gel column chromatography with elution system B to obtain the title compound 36a (30 mg, yield: 50%).

Step 2

6-(2-(6-Methylpyridin-2-yl)-4,5,6,7-tetrahydro-4,7-ethanopyrazolo[1,5-a]pyridin-3-yl)quinoline-4-carboxamide 36

Compound 36a (30 mg, 0.077 mmol) was dissolved in 2 mL of dimethyl sulfoxide, then 30% hydrogen peroxide solution (26.063 mg, 0.766 mmol) and potassium carbonate (21.183 mg, 0.153 mmol) were added. After stirring at room temperature for 1 hours, the reaction solution was filtered. The filtrate was purified by high performance liquid chromatography to obtain the title compound 36 (15 mg, yield: 47.8%).

MS m/z (ESI): 410.4 [M+1]

$^1$H NMR (400 MHz, CDCl$_3$) δ 8.95 (d, 1H), 8.29 (d, 1H), 8.09 (d, 1H), 7.72 (dd, 1H), 7.49-7.57 (m, 2H), 7.32 (dd, 1H), 7.08 (d, 1H), 6.04 (s, 1H), 5.92 (s, 1H), 4.91 (s, 1H), 3.57 (s, 1H), 2.52 (s, 3H), 1.91-2.02 (m, 6H), 1.72-1.76 (m, 2H).

Example 37

2-((4-(2-(6-Methylpyridin-2-yl)-4,5,6,7-tetrahydro-4,7-ethanopyrazolo[1,5-a]pyridin-3-yl)pyridin-2-yl)amino)ethanol 37

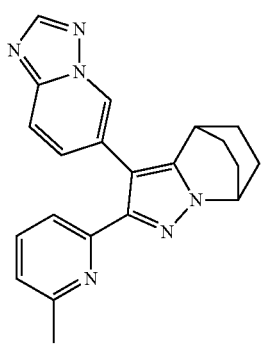

37

In accordance with the synthetic route of Example 5, the starting compound 1f used in Step 1 was replaced with compound 33i, accordingly, the title compound 37 (20 mg) was prepared.

MS m/z (ESI): 376.5 [M+1]

$^1$H NMR (400 MHz, CDCl$_3$) δ 7.99 (d, 1H), 7.52 (t, 1H), 7.14 (d, 1H), 7.18 (d, 1H), 6.47 (dd, 1H), 6.24 (s, 1H), 5.62 (s, 1H), 4.83 (s, 1H), 3.83 (t, 2H), 3.58-3.53 (m, 2H), 3.40 (s, 1H), 2.58 (s, 3H), 1.94-1.88 (m, 4H), 1.77-1.74 (m, 2H), 1.59-1.57 (m, 2H).

Example 38

3-([1,2,4]Triazolo[1,5-a]pyridin-6-yl)-2-(6-methylpyridin-2-yl)-4,5,6,7-tetrahydro-4,7-ethanopyrazolo[1,5-a]pyridine 38

38

151

-continued

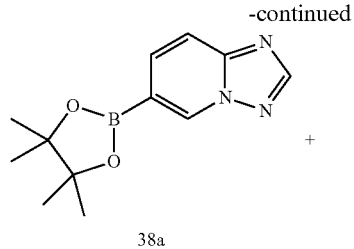

38a

+

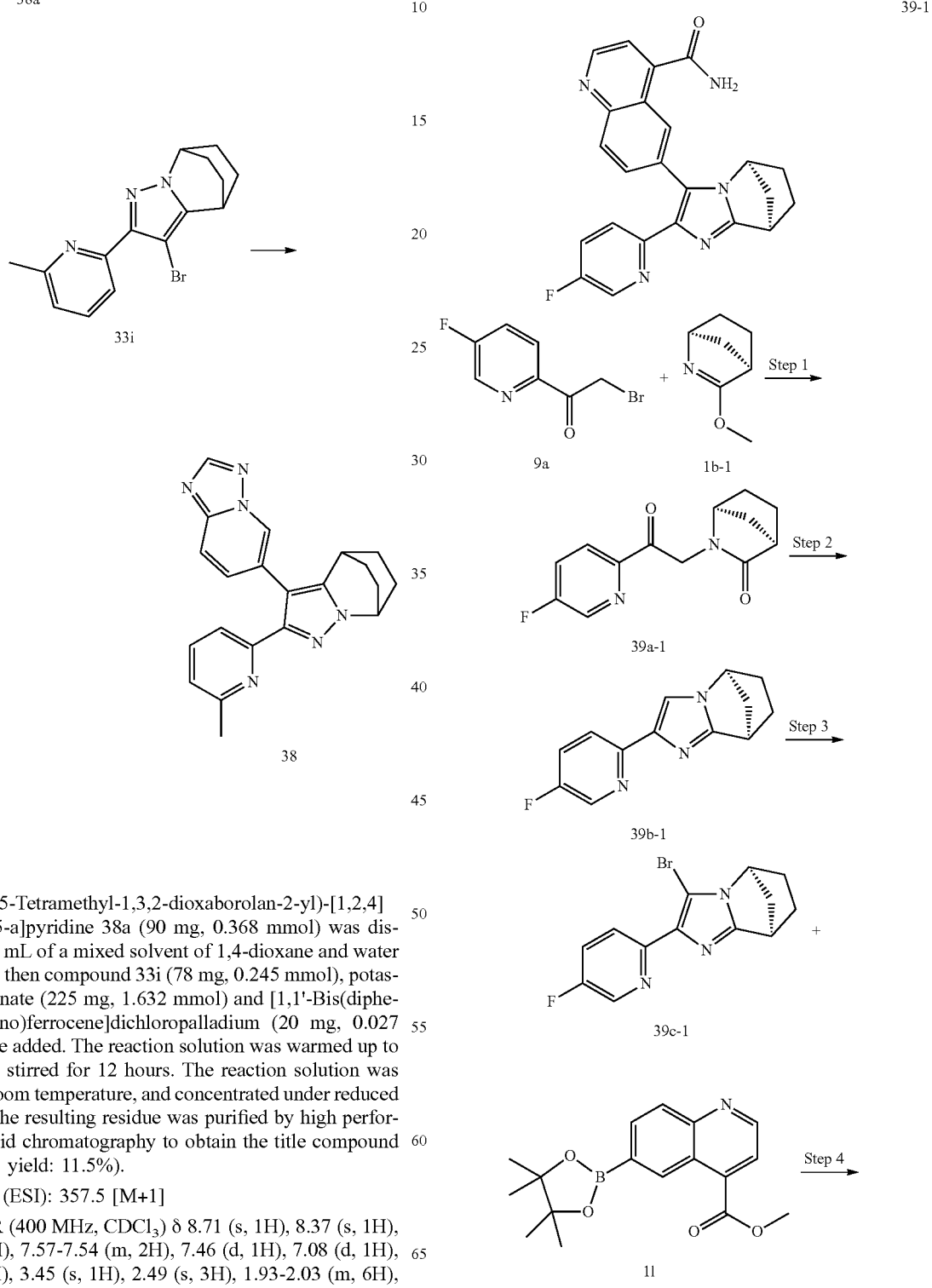

33i

↓

38

6-(4,4,5,5-Tetramethyl-1,3,2-dioxaborolan-2-yl)-[1,2,4] triazolo[1,5-a]pyridine 38a (90 mg, 0.368 mmol) was dissolved in 5 mL of a mixed solvent of 1,4-dioxane and water (V/V=4:1), then compound 33i (78 mg, 0.245 mmol), potassium carbonate (225 mg, 1.632 mmol) and [1,1'-Bis(diphenylphosphino)ferrocene]dichloropalladium (20 mg, 0.027 mmol) were added. The reaction solution was warmed up to 85° C. and stirred for 12 hours. The reaction solution was cooled to room temperature, and concentrated under reduced pressure. The resulting residue was purified by high performance liquid chromatography to obtain the title compound 38 (10 mg, yield: 11.5%).

MS m/z (ESI): 357.5 [M+1]

$^1$H NMR (400 MHz, CDCl$_3$) δ 8.71 (s, 1H), 8.37 (s, 1H), 7.72 (d, 1H), 7.57-7.54 (m, 2H), 7.46 (d, 1H), 7.08 (d, 1H), 4.90 (s, 1H), 3.45 (s, 1H), 2.49 (s, 3H), 1.93-2.03 (m, 6H), 1.69-1.73 (m, 2H).

152

Example 39-1

6-((5S,8R)-2-(5-Fluoropyridin-2-yl)-5,6,7,8-tetrahydro-5,8-methanoimidazo[1,2-a]pyrid in-3-yl)quinoline-4-carboxamide 39-1

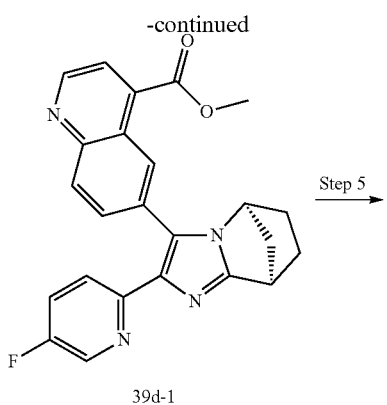

39d-1

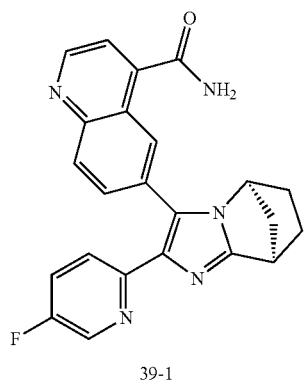 [SMILES: NC(=O)c1ccnc2ccc(-c3c(-c4ccc(F)cn4)nc4n3[C@H]3CC[C@@H]4C3)cc12]

39-1

Step 1

(1S,4R)-2-(2-(5-fluoropyridin-2-yl)-2-oxoethyl)-2-azabicyclo[2.2.1]heptan-3-one 39a-1

Compound 9a (4.5 g, 20.64 mmol) was dissolved in 50 mL of N,N-dimethylformamide, then the crude compound 1b-1 (5.19 g, 41.28 mmol) was added. After stirring at 50° C. for 18 hours under an argon atmosphere, the reaction solution was concentrated under reduced pressure to obtain the crude title compound 39a-1 (5.1 g), which was used directly in the next step without purification.

Step 2

(5S,8R)-2-(5-fluoropyridin-2-yl)-5,6,7,8-tetrahydro-5,8-methanoimidazo[1,2-a]pyridine 39b-1

The crude compound 39a-1 (5 g, 20.14 mmol) and ammonium acetate (1.71 g, 22.16 mmol) were dissolved in 50 mL of acetic acid, then the reaction solution was warmed up to 100° C. and stirred for 18 hours. The reaction solution was cooled to room temperature and concentrated under reduced pressure. Saturated sodium bicarbonate solution was then added dropwise to the resulting residue until the pH is 7. The reaction solution was extracted with dichloromethane, then the organic phases were combined, dried over anhydrous sodium sulfate and filtered. The filtrate was concentrated under reduced pressure, and the resulting residue was purified by silica gel column chromatography with elution system B to obtain the title compound 39b-1 (1.5 g, yield: 29.24%).

Step 3

(5S,8R)-3-Bromo-2-(5-fluoropyridin-2-yl)-5,6,7,8-tetrahydro-5,8-methanoimidazo[1,2-a]pyridine 39c-1

Compound 39b-1 (1.5 g, 6.54 mmol) was dissolved in 10 mL of dichloromethane, then the reaction solution was cooled to 0° C., followed by dropwise addition of liquid bromine (1.15 g, 7.2 mmol), and stirred at room temperature for 1.5 hours. The reaction solution was added with 15 mL of saturated sodium bisulfite solution, and extracted with dichloromethane (20 mL×3). The organic phases were combined, dried over anhydrous sodium sulfate and filtered. The filtrate was concentrated under reduced pressure, and the resulting residue was purified by silica gel column chromatography with elution system A to obtain the title compound 39c-1 (1.3 g, yield: 58.03%).

Step 4

Methyl 6-((5 S,8R)-2-(5-Fluoropyridin-2-yl)-5,6,7,8-tetrahydro-5,8-methanoimidazo[1,2-a]pyridin-3-yl)quinoline-4-carboxylate 39d-1

Compound 11 (121.9 mg, 0.39 mmol), compound 39c-1 (0.1 g, 0.32 mmol), [1,1'-bis(diphenylphosphino)ferrocene]dichloropalladium (12 mg, 0.016 mmol) and potassium carbonate (112.1 g, 0.811 mmol) were dissolved in 11 mL of a mixed solvent of 1,4-dioxane and water (V/V=20:1), then the reaction solution was warmed up to 100° C. and stirred for 16 hours. The reaction solution was cooled to room temperature and filtered through celite. The filtrate was concentrated under reduced pressure, and the resulting residue was purified by high performance liquid chromatography to obtain the title compound 39d-1 (50 mg, yield: 33.4%).

Step 5

6-((5S,8R)-2-(5-Fluoropyridin-2-yl)-5,6,7,8-tetrahydro-5,8-methanoimidazo[1,2-a]pyrid in-3-yl)quinoline-4-carboxamide 39-1

Compound 39d-1 (60 mg, 0.14 mmol) was dissolved in 3 mL of 7 M ammonia in methanol, then the reaction solution was warmed up to 50° C. and stirred for 3 hours under a sealed condition. The reaction solution was cooled to room temperature, and concentrated under reduced pressure. The resulting residue was purified by silica gel column chromatography with elution system A to obtain the title compound 39-1 (30 mg, yield: 51.42%).

MS m/z (ESI): 400.5 [M+1]

$^1$H NMR (400 MHz, CDCl$_3$) δ 9.01-9.00 (m, 1H), 8.56-8.55 (m, 1H), 8.27-8.26 (m, 1H), 8.17-8.15 (m, 1H), 7.95-7.90 (m, 2H), 7.60 (d, 1H), 7.45-7.40 (m, 1H), 6.23 (br, 1H), 5.98 (br, 1H), 4.96 (br, 1H), 3.70 (br, 1H), 2.42-2.40 (m, 1H), 2.13-2.10 (m, 1H), 2.00-1.93 (m, 2H), 1.58-1.55 (m, 1H), 1.44-1.42 (m, 1H).

Example 40-1

(5S,8R)-2-(5-Fluoropyridin-2-yl)-3-(2-(1-methyl-1H-pyrazol-4-yl)pyridin-4-yl)-5,6,7,8-tetrahydro-5,8-methanoimidazo[1,2-a]pyridine 40-1

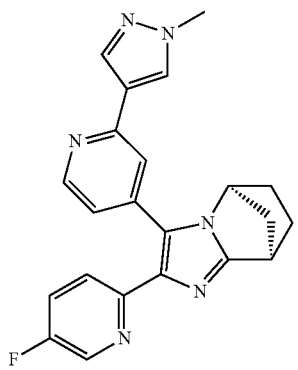

40-1

In accordance with the synthetic route of Example 12, the starting compound 1f used in Step 3 was replaced with compound 39c-1, accordingly, the title compound 40-1 (10 mg) was prepared.

MS m/z (ESI): 387.5 [M+1]

$^1$H NMR (400 MHz, CDCl$_3$) δ 8.59 (d, 1H), 8.33 (d, 1H), 7.96 (s, 1H), 7.93 (s, 1H), 7.89-7.87 (m, 1H), 7.70 (s, 1H), 7.43 (t, 1H), 7.22-7.20 (m, 1H), 4.86 (s, 1H), 4.00 (s, 3H), 3.70 (d, 1H), 2.39 (d, 1H), 2.13-2.10 (m, 1H), 1.98-1.92 (m, 2H), 1.56-1.54 (m, 1H), 1.51-1.42 (m, 1H).

Example 41-1

4-(4-((5S,8R)-2-(5-Fluoropyridin-2-yl)-5,6,7,8-tetrahydro-5,8-methanoimidazo[1,2-a]pyridin-3-yl)pyridin-2-yl)benzamide 41-1

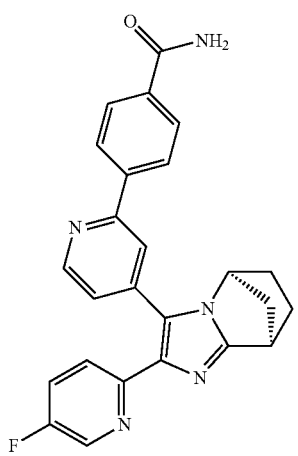

41-1

In accordance with the synthetic route of Example 4, the compound 1f was replaced with compound 39c-1, accordingly, the title compound 41-1 (30 mg) was prepared.

MS m/z (ESI): 424.0 [M+1]

$^1$H NMR (400 MHz, CDCl$_3$) δ 8.78 (d, 1H), 8.33 (br, 1H), 8.12-8.10 (m, 2H), 8.06 (s, 1H), 7.98-7.94 (m, 3H), 7.48-7.41 (m, 2H), 6.23 (br, 1H), 5.84 (br, 1H), 4.89 (br, 1H), 3.75 (br, 1H), 2.42-2.38 (m, 1H), 2.18-2.11 (m, 1H), 2.04-2.00 (m, 2H), 1.57-1.52 (m, 1H), 1.38-1.35 (m, 1H).

Example 42-1

(5S,8R)-2-(5-Fluoropyridin-2-yl)-3-(2-(4-(methylsulfonyl)phenyl)pyridin-4-yl)-5,6,7,8-tetrahydro-5,8-methanoimidazo[1,2-a]pyridine 42-1

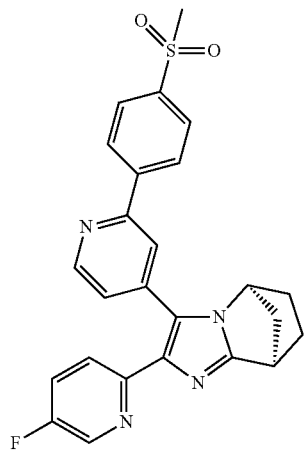

42-1

In accordance with the synthetic route of Example 3, the compound 1f was replaced with compound 39c-1, accordingly, the title compound 42-1 (30 mg) was prepared.

MS m/z (ESI): 461.5 [M+1]

$^1$H NMR (400 MHz, CDCl$_3$) δ 8.78 (d, 1H), 8.30 (d, 1H), 8.21-8.19 (m, 2H), 8.09-8.07 (m, 3H), 7.98-9.98 (m, 1H), 7.48-7.43 (m, 2H), 4.88 (br, 1H), 3.74 (br, 1H), 3.10 (s, 3H), 2.41-2.39 (m, 1H), 2.22-2.14 (m, 1H), 2.01-1.93 (m, 2H), 1.55-1.50 (m, 1H), 1.40-1.35 (m, 1H).

Example 43

2-(6-Methylpyridin-2-yl)-3-(2-(1-(methylsulfonyl)-1H-pyrazol-4-yl)pyridin-4-yl)-5,6,7,8-tetrahydro-5,8-methanoimidazo[1,2-a]pyridine 43

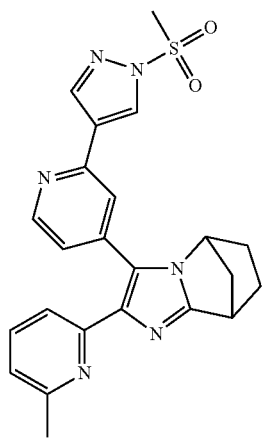

43

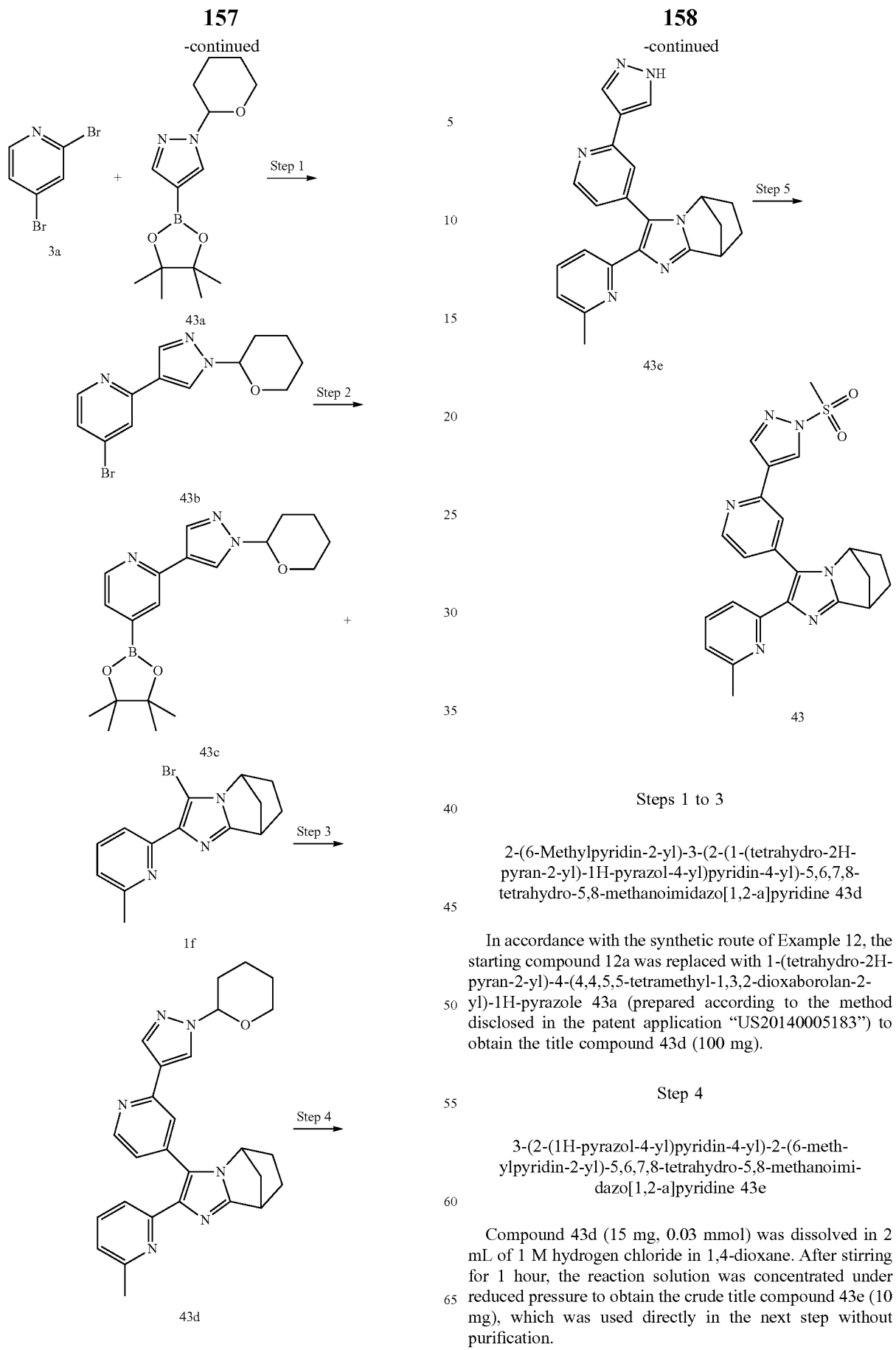

Steps 1 to 3

2-(6-Methylpyridin-2-yl)-3-(2-(1-(tetrahydro-2H-pyran-2-yl)-1H-pyrazol-4-yl)pyridin-4-yl)-5,6,7,8-tetrahydro-5,8-methanoimidazo[1,2-a]pyridine 43d In accordance with the synthetic route of Example 12, the starting compound 12a was replaced with 1-(tetrahydro-2H-pyran-2-yl)-4-(4,4,5,5-tetramethyl-1,3,2-dioxaborolan-2-yl)-1H-pyrazole 43a (prepared according to the method disclosed in the patent application "US20140005183") to obtain the title compound 43d (100 mg).

Step 4

3-(2-(1H-pyrazol-4-yl)pyridin-4-yl)-2-(6-methylpyridin-2-yl)-5,6,7,8-tetrahydro-5,8-methanoimidazo[1,2-a]pyridine 43e Compound 43d (15 mg, 0.03 mmol) was dissolved in 2 mL of 1 M hydrogen chloride in 1,4-dioxane. After stirring for 1 hour, the reaction solution was concentrated under reduced pressure to obtain the crude title compound 43e (10 mg), which was used directly in the next step without purification.

Step 5

2-(6-Methylpyridin-2-yl)-3-(2-(1-(methylsulfonyl)-1H-pyrazol-4-yl)pyridin-4-yl)-5,6,7,8-tetrahydro-5,8-methanoimidazo[1,2-a]pyridine 43

The crude compound 43e (10 mg, 0.03 mmol) was dissolved in 5 mL of dichloromethane, then the reaction solution was cooled to 0° C. Triethylamine (8.24 mg, 0.08 mmol) and methanesulfonyl chloride (4.66 mg, 0.04 mmol) were added. After stirring for 1 hours, the reaction solution was concentrated under reduced pressure. The resulting residue was purified by high performance liquid chromatography to obtain the title compound 43 (10 mg, yield: 82.51%).

MS m/z (ESI): 447.2 [M+1]

$^1$H NMR (400 MHz, CDCl$_3$) δ 8.81 (d, 1H), 8.67 (s, 1H), 8.36 (s, 1H), 7.87 (s, 1H), 7.82 (t, 1H), 7.58 (d, 1H), 7.39 (d, 1H), 7.27 (d, 1H), 4.98 (s, 1H), 4.10 (s, 1H), 3.45 (t, 3H), 2.71 (s, 3H), 2.52 (d, 1H), 2.25-2.30 (m, 1H), 2.05-2.11 (m, 2H), 1.61-1.69 (m, 1H), 1.41-1.49 (m, 1H).

Example 44

2-(6-Methylpyridin-2-yl)-3-(2-(1-(methylsulfonyl)piperidin-4-yl)pyridin-4-yl)-5,6,7,8-tetrahydro-5,8-methanoimidazo[1,2-a]pyridine 44

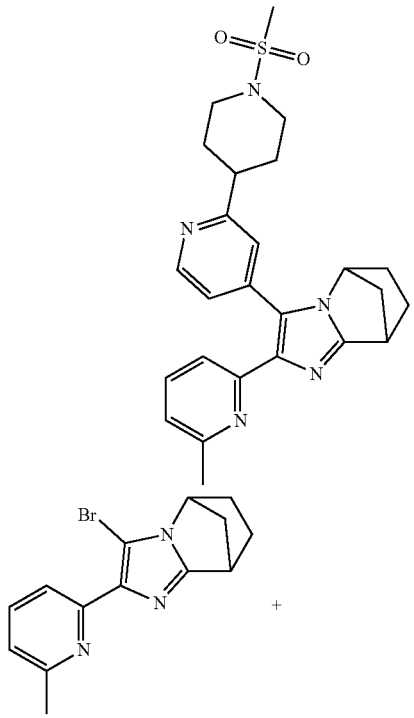

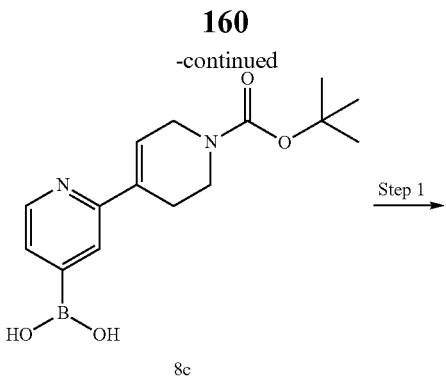

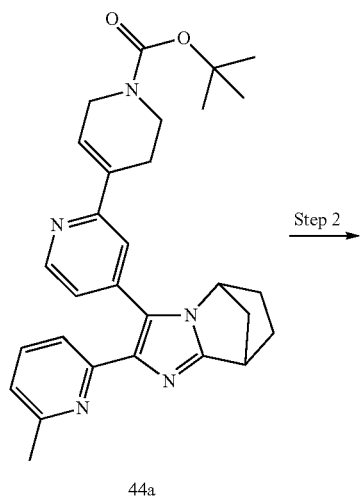

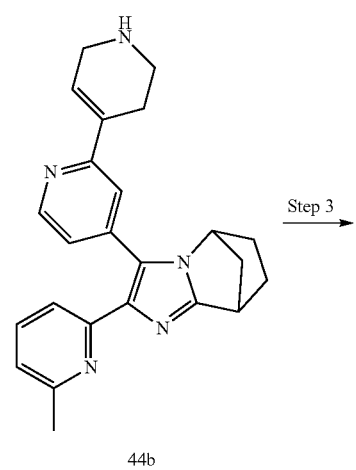

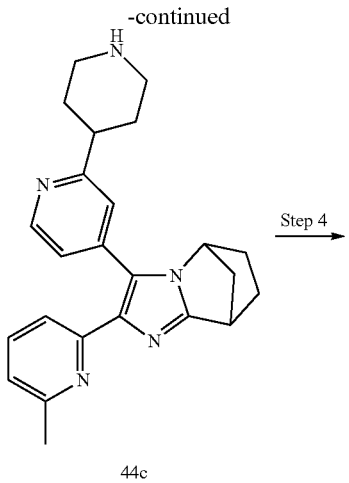

44c

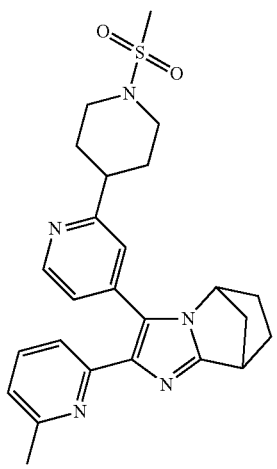

44

Step 1

Tert-butyl 4-(2-(6-methylpyridin-2-yl)-5,6,7,8-tetrahydro-5,8-methanoimidazo[1,2-a]pyridin-3-yl)-5',6'-dihydro-[2,4'-bipyridine]-1'(2'H)-carboxylate 44a Compound 1f (240 mg, 0.79 mmol), compound 44b (237.97 mg, 0.79 mmol), potassium carbonate (218.09 mg, 1.58 mmol) and [1,1'-bis(diphenylphosphino)ferrocene]dichloropalladium (58.53 mg, 0.08 mmol) were dissolved in 15 mL of 1,4-dioxane and 1.5 mL of water, then the reaction solution was warmed up to 100° C. and stirred for 12 hours under an argon atmosphere. The reaction solution was cooled to room temperature, and concentrated under reduced pressure. The resulting residue was purified by combiflash with elution system A to obtain the title compound 44a (300 mg, yield: 78.63%).

Step 2

2-(6-Methylpyridin-2-yl)-3-(5',2',3',6'-tetrahydro-[2,4'-bipyridin]-4-yl)-5,6,7,8-tetrahydro-5,8-methanoimidazo[1,2-a]pyridine 44b Compound 44a (200 mg, 0.41 mmol) and trifluoroacetic acid (6 mg) were added to 10 mL of dichloromethane, then the reaction solution was stirred at room temperature for 12 hours. Stirring was stopped, and the reaction solution was adjusted with saturated sodium bicarbonate solution until the pH was alkaline, and extracted with dichloromethane. The organic phases were combined and concentrated under reduced pressure to obtain the crude title compound 44b (150 mg, yield: 94.58%).

Step 3

2-(6-Methylpyridin-2-yl)-3-(2-(piperidin-4-yl)pyridin-4-bipyridin)-5,6,7,8-tetrahydr-5,8-methanoimidazo[1,2-a]pyridine 44 b Compound 44b (80 mg, 0.210 mmol) was dissolved in 10 mL of methanol, then 10% palladium on carbon (16 mg, 0.470 mmol) was added. The reaction system was purged with hydrogen three times. After stirring at room temperature for 0.5 hours, the reaction solution was filtered. The filtrate was concentrated under reduced pressure to obtain the crude title compound 44c (80 mg, a yellow solid), which was used directly in the next step without purification.

Step 4

2-(6-Methylpyridin-2-yl)-3-(2-(1-(methylsulfonyl)piperidin-4-yl)pyridin-4-yl)-5,6,7,8-tetrahydro-5,8-methanoimidazo[1,2-a]pyridine 44

The crude compound 44c (30 mg, 0.08 mmol) was dissolved in 5 mL of dichloromethane, then N,N-diisopropylethylamine (30.17 mg, 0.23 mmol) and methanesulfonyl chloride (17.83 mg, 0.16 mmol) were added at 0° C. After stirring at 0° C. for 2 hours, the reaction solution was concentrated under reduced pressure. The resulting residue was purified by combiflash with elution system A to obtain the title compound 44 (2 mg, yield: 5.16%).

MS m/z (ESI): 464.5 [M+1]

$^1$H NMR (400 MHz, CD$_3$OD) δ 8.49 (d, 1H), 7.76-7.72 (m, 1H), 7.49 (d, 1H), 7.38 (d, 2H), 7.21 (d, 1H), 3.86 (d, 2H), 3.66 (s, 1H), 2.92-2.86 (m, 5H), 2.43-2.37 (m, 4H), 2.21-2.18 (m, 2H), 2.07-2.00 (m, 4H), 1.83-1.80 (m, 2H), 1.39-1.23 (m, 3H).

Example 45-1

6-((5S,8R)-2-(Pyridin-2-yl)-5,6,7,8-tetrahydro-5,8-methanoimidazo[1,2-a]pyridin-3-yl) quinoline-4-carboxamide 45-1

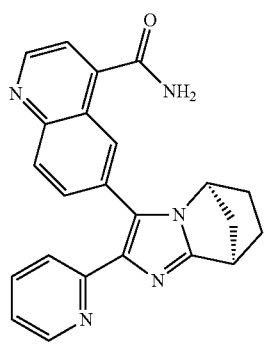

45-1

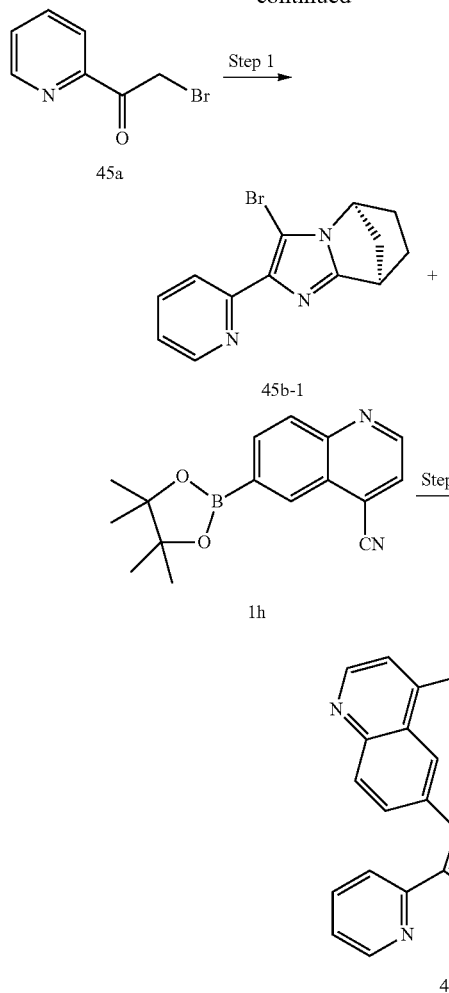

Step 1

(5S,8R)-3-Bromo-2-(pyridin-2-yl)-5,6,7,8-tetrahydro-5,8-methanoimidazo[1,2-a]pyridine 45b-1

In accordance with the synthetic route of steps 1-4 of Example 1, the compound 1c was replaced with 2-bromo-1-(pyridin-2-yl)ethanone 45a, accordingly, the title compound 45b-1 (5 g) was prepared.

Step 2

6-((5S,8R)-2-(Pyridin-2-yl)-5,6,7,8-tetrahydro-5,8-methanoimidazo[1,2-a]pyridin-3-yl) quinoline-4-carboxamide 45-1

In accordance with the synthetic route of Steps 2-3 of Example 36, the compound 33i was replaced with compound 45b-1, accordingly, the title compound 45-1 (15 mg) was prepared.

MS m/z (ESI): 382.4 [M+1]

$^1$H NMR (400 MHz, CD$_3$OD) δ 8.94 (d, 1H), 8.43-8.38 (m, 2H), 8.07 (d, 1H), 7.83-7.80 (m, 2H), 7.73 (d, 1H), 7.66 (d, 1H), 7.30-7.29 (m, 1H), 5.08 (d, 1H), 3.68 (d, 1H), 2.40 (d, 1H), 2.24-2.19 (m, 1H), 2.08-2.02 (m, 2H), 1.47-1.36 (m, 2H).

Example 46-1

(5S,8R)-3-(2-(4-(Methylsulfonyl)phenyl)pyridin-4-yl)-2-(pyridin-2-yl)-5,6,7,8-tetrahydro-5,8-methanoimidazo[1,2-a]pyridine 46-1

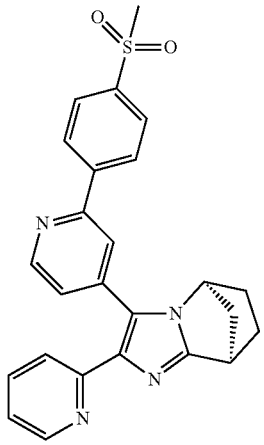

In accordance with the synthetic route of Example 3, the compound 1f was replaced with compound 45b-1, accordingly, the title compound 46-1 (10 mg) was prepared.

MS m/z (ESI): 443.1 [M+1]

$^1$H NMR (400 MHz, CD$_3$OD) δ 8.72 (d, 1H), 8.44 (d, 1H), 8.20-8.18 (m, 2H), 8.09-8.06 (m, 3H), 7.89-7.82 (m, 2H), 7.52-7.51 (m, 1H), 7.34-7.33 (d, 1H), 5.10 (d, 1H), 3.69 (d, 1H), 3.19 (s, 3H), 2.42 (d, 1H), 2.24-2.19 (m, 1H), 2.08-2.01 (m, 2H), 1.42-1.35 (m, 2H).

Example 47-1

7-((5S,8R)-2-(Pyridin-2-yl)-5,6,7,8-tetrahydro-5,8-methanoimidazo[1,2-a]pyridin-3-yl)-[1,2,4]triazolo[4,3-a]pyridine-3-carboxamide 47-1

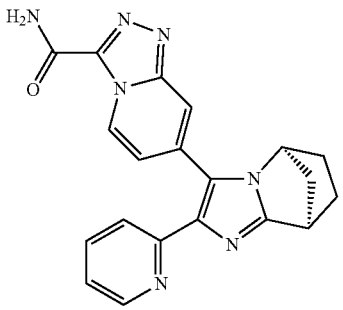

In accordance with the synthetic route of Example 2, the starting compound 1f was replaced with compound 45b-1, accordingly, the title compound 47-1 (10 mg) was prepared.

MS m/z (ESI): 372.1 [M+1]

$^1$H NMR (400 MHz, CD$_3$OD) δ 8.37 (d, 1H), 7.90-7.84 (m, 4H), 7.66-7.63 (m, 1H), 7.28-7.25 (m, 1H), 5.02 (s, 1H), 3.68 (d, 1H), 2.40-2.38 (m, 1H), 2.25-2.19 (m, 1H), 2.12-2.02 (m, 2H), 1.44-1.31 (m, 2H).

TEST EXAMPLES

Biological Assay

Test Example 1. Determination of the Inhibition Effect of the Compounds of the Present Invention on TGFβRI Kinase Activity The inhibition effect of TGFβRI kinase activity in vitro was determined by the following method.

The inhibition effect of the compounds of the present invention on TGFβRI kinase ALK5 activity was determined by the following experimental method:

TGFβRI kinase assay kit (V4093, Promega) was used to assay enzyme activity. 2 µl of enzyme solution (the final concentration of enzyme in the reaction system was 2 ng/µL) formulated with reaction buffer (40 mM Tris pH 7.5, 20 mM MgCl$_2$, 0.1 mg/ml BSA), 1 µl of a 3-fold gradient dilution of the compounds dissolved in 5% DMSO, and 2 µl of a mixed solution of ATP and TGFβRI substrate peptide (the final concentration of ATP was 50 µM, and the final concentration of substrate was 0.2 µg/µL) were added successively to a 384-well plate (4514, Corning). After reaction at 27° C. for 2.5 hours, 5 µl of ADP-Glo solution in the kit was added to each well, then the plate was placed at 27° C. for 40 minutes. 10 µl of kinase assay reagent was then added to each well, then the plate was placed at 27° C. for 30 minutes. The chemiluminescence signal values were measured with a Victor 3 (PerkinElmer) multi-function microplate reader. The IC$_{50}$ values of the compounds for enzyme inhibition were calculated using Graphpad prism software based on each concentration of the compound and the corresponding signal value thereof.

The biological activity of the compounds of the present invention was determined by the above test, and the resulting IC$_{50}$ values are shown in Table 1 below.

TABLE 1

IC$_{50}$ of inhibition effect of the compounds of the present invention on TGFβRI kinase ALK5 activity

| Example No. | IC$_{50}$ (nM) |
|---|---|
| 1-1 | 9 |
| 1-2 | 16 |
| 2-1 | 3 |
| 3-1 | 4 |
| 4 | 29 |
| The compound with retention time of 4.058 minutes among 4-1 and 4-2 | 2 |
| The compound with retention time of 7.204 minutes among 4-1 and 4-2 | 18 |
| 5-1 | 46 |
| 6 | 26 |
| The compound with retention time of 3.747 minutes among 6-1 and 6-2 | 7 |
| The compound with retention time of 5.327 minutes among 6-1 and 6-2 | 8 |
| 7 | 20 |
| 9 | 43 |
| 10 | 25 |
| 11 | 16 |
| 12 | 9 |
| 13-1 | 11 |
| 14 | 31 |
| 15 | 60 |
| 16-1 | 77 |
| 17 | 38 |

TABLE 1-continued

IC$_{50}$ of inhibition effect of the compounds of the present invention on TGFβRI kinase ALK5 activity

| Example No. | IC$_{50}$ (nM) |
|---|---|
| The compound with retention time of 9.196 minutes among 17-1 and 7-2 | 28 |
| The compound with retention time of 5.418 minutes among 17-1 and 7-2 | 28 |
| 18-1 | 80 |
| 5 | 59 |
| 19 | 87 |
| The compound with retention time of 6.631 minutes among 9-1 and 9-2 | 13 |
| The compound with retention time of 13.001 minutes among 9-1 and 9-2 | 13 |
| 29 | 85 |
| 3-2 | 23 |
| 1 | 14 |
| 31 | 55 |
| 32 | 9 |
| 33 | 34 |
| 34 | 12 |
| 35 | 12 |
| The compound with retention time of 7.153 minutes among 35-1 and 35-2 | 39 |
| The compound with retention time of 7.992 minutes among 35-1 and 35-2 | 25 |
| 36 | 21 |
| 37 | 52 |
| 38 | 9 |
| 39-1 | 26 |
| 40-1 | 10 |
| 41-1 | 28 |
| 2-2 | 3 |
| 43 | 21 |
| The compound with retention time of 2.955 minutes among 12-1 and 12-2 | 6 |
| The compound with retention time of 4.695 minutes among 12-1 and 12-2 | 7 |
| 45-1 | 29 |
| 46-1 | 34 |
| 47-1 | 39 |

Conclusion: The compounds of the examples of the present invention have a significant inhibition effect on the TGFβRI kinase ALK5 activity.

Test Example 2. Determination of the Inhibition Effect of the Compounds of the Present Invention on VEGFR2 Kinase Activity The inhibition effect of VEGFR2 kinase activity in vitro was determined by the following method.

The inhibition effect of the compounds of the present invention on VEGFR2 kinase activity was determined by the following experimental method:

Z'-LYTE® Kinase Assay Kit—Tyrosine 1 Peptide (PV3190, Invitrogen) was used to assay enzyme activity. 5 µl of recombinant human VEGFR2 enzyme (PV3660, Invitrogen) and VEGFR2 substrate polypeptide (in the reaction system, the final concentration of enzyme was 0.14 ng/µL, and the final concentration of substrate was 2 NM) formulated with reaction buffer (50 mM HEPES pH7.5, 10 mM MgCl$_2$, 1 mM EGTA, 0.05% BRIJ-35), 2.5 µl of a 2-fold gradient dilution of the compounds dissolved in 5% DMSO, and 2.5 µL of ATP solution (the final concentration of ATP was 50 µM) were added successively to a 384-well plate (4513, Corning). After reaction at 25° C. for 2 hours, 5 µL of detection reagent was added to each well. After the plate was placed at 25° C. for 1 hour, the fluorescence signal values at emission wavelengths of 445 nm and 520 nm were measured with a NOVOstar (BMG) multi-function microplate reader. The IC$_{50}$ values of the compounds for enzyme inhibition were calculated using Graphpad prism software based on each concentration of the compound and the corresponding signal value thereof.

The biological activity of the compounds of the present invention was determined by the above test, and the resulting $IC_{50}$ values are shown in Table 2 below.

TABLE 2

$IC_{50}$ of inhibition effect of the compounds of the present invention on VEGFR2 kinase activity

| Example No. | $IC_{50}$ (nM) |
|---|---|
| 1-1 | 3048 |
| 2-1 | 1156 |
| 3-1 | 2890 |
| 4 | 4055 |
| The compound with retention time of 4.058 minutes among 4-1 and 4-2 | 1052 |
| 5-1 | 3709 |
| 14 | 1001 |
| 16-1 | >10000 |
| 17 | 919 |
| The compound with retention time of 9.196 minutes among 17-1 and 7-2 | 871 |
| The compound with retention time of 5.418 minutes among 17-1 and 7-2 | 960 |
| The compound with retention time of 6.631 minutes among 9-1 and 9-2 | >10000 |
| The compound with retention time of 13.001 minutes among 9-1 and 9-2 | 1346 |
| 3-2 | 928 |
| 32 | 1122 |
| 34 | 1243 |
| The compound wtih retention time of 7.153 minutes among 35-1 and 35-2 | 1711 |
| 36 | 1008 |
| 37 | 2910 |
| 39-1 | 6305 |
| 40-1 | 2083 |
| 42-1 | 9736 |
| 43 | 551 |

Conclusion: The compounds of the examples of the present invention showed no significant inhibition effect on VEGFR2 kinase activity, indicating that the compounds of the examples of the present invention have a selective inhibition effect on TGFβRI kinase.

Test Example 3. Determination of the Inhibition Effect of the Compounds of the Present Invention on p38α Kinase Activity The inhibition of p38α kinase activity in vitro was determined by the following method.

The inhibition effect of the compounds of the present invention on p38a kinase activity was determined by the following experimental method:

p38α kinase assay kit (V9591, Promega) was used to assay enzyme activity. 2 μl of enzyme solution (the final concentration of enzyme in the reaction system was 0.5 ng/μL) formulated with reaction buffer (40 mM Tris pH 7.5, 20 mM $MgCl_2$, 0.1 mg/ml BSA), 1 μl of a 3-fold gradient dilution of the compounds dissolved in 5% DMSO, and 2 μl of a mixed solution of ATP and p38 substrate peptide (the final concentration of ATP was 50 μM, and the final concentration of substrate was 0.2 μg/μL) were added successively to a 384-well plate (4514, Corning). After reaction at 27° C. for 2.5 hours, 5 μl of ADP-Glo solution in the kit was added to each well, then the plate was placed at 27° C. for 40 minutes. 10 μl of kinase assay reagent was then added to each well, then the plate was placed at 27° C. for 30 minutes. The chemiluminescence signal values were measured with a Victor 3 (PerkinElmer) multi-function microplate reader. The $IC_{50}$ values of the compounds on enzyme inhibition were calculated using Graphpad prism software based on each concentration of the compound and the corresponding signal value thereof.

The biological activity of the compounds of the present invention was determined by the above test, and the resulting $IC_{50}$ values are shown in Table 3 below.

TABLE 3

$IC_{50}$ of inhibition effect of the compounds of the present invention on p38α kinase activity

| Example No. | $IC_{50}$ (nM) |
|---|---|
| 1-1 | 618 |
| 2-1 | 1710 |
| 3-1 | 686 |
| 4 | 638 |
| The compound with retention time of 3.747 minutes among 6-1 and 6-2 | 515 |
| 12 | 454 |
| The compound with retention time of 6.631 minutes among 9-1 and 9-2 | 5798 |
| The compound with retention time of 13.001 minutes among 9-1 and 9-2 | 2456 |
| 3-2 | 654 |
| 33 | 563 |
| 36 | 598 |
| 39-1 | 4734 |
| 40-1 | 1362 |
| 42-1 | 7782 |

Conclusion: The compounds of the examples of the present invention showed no significant inhibition effect on p38α kinase activity, indicating that the compounds of the examples of the present invention have a selective inhibition effect on TGFβRI kinase.

Test Example 4. Determination of the Inhibition of the Compounds of the Present Invention on NIH3T3 Cell Proliferation The inhibition effect of the compounds of the present invention on NIH3T3 cell proliferation was determined by the following in vitro test.

The inhibition effect of the compounds of the present invention on NIH3T3 cell proliferation was determined by the following experimental method:

On a 96-well white plate with transparent bottom (3903, Corning), 100 μL of NIH3T3 cell (GNM6, Cell Bank of Typical Culture Collection Committee of Chinese Academy of Sciences) was seeded in a DMEM medium containing 10% FBS in each well. The seeding density is 2000 cells/well. The cells were incubated overnight at 37° C., 5% $CO_2$. After overnight incubation, each well was replaced with 90 μL of DMEM medium containing 0.5% FBS. 10 μl of a 3-fold gradient dilution of the compounds with DMEM medium containing 0.5% FBS was then added, and the plate was incubated for 72 hours in a cell incubator at 37° C., 5% $CO_2$. Finally, 50 μL of CellTiter-Glo (G7573, Promega) was added to each well. After incubation for 10 minutes at room temperature, the chemiluminescence signal values were measured with a Victor 3 microplate reader (PerkinElmer). The $IC_{50}$ values of the compounds were calculated using Graphpad Prism software based on each concentration of the compound and the corresponding signal value thereof.

The biological activity of the compounds of the present invention was determined by the above assay, and the calculated $IC_{50}$ values are shown in Table 4 below:

TABLE 4

$IC_{50}$ of the compounds of the present invention on the inhibition of NIH3T3 cell proliferation

| Example No. | $IC_{50}$ (nM) |
|---|---|
| 1-1 | 89 |
| 2-1 | 44 |
| 3-1 | 28 |
| The compound with retention time of 4.058 minutes among 4-1 and 4-2 | 39 |
| 6 | 22 |
| The compound with retention time of 3.747 minutes among 6-1 and 6-2 | 40 |
| The compound with retention time of 5.327 minutes among 6-1 and 6-2 | 18 |
| 7 | 23 |
| 9 | 91 |
| 10 | 41 |
| 11 | 37 |
| 12 | 13 |
| The compound with retention time of 9.196 minutes among 17-1 and 7-2 | 84 |
| The compound with retention time of 6.631 minutes among 9-1 and 9-2 | 69 |
| 1 | 80 |
| 32 | 19 |
| The compound with retention time of 7.153 minutes among 35-1 and 35-2 | 71 |
| 38 | 33 |
| 39-1 | 88 |
| 40-1 | 42 |
| 43 | 33 |
| The compound with retention time is 2.955 minutes among 12-1 and 12-2 | 37 |
| The compound with retention time is 4.695 minutes among 12-1 and 12-2 | 41 |
| 45-1 | 51 |

Conclusion: The compounds of the present invention have a significant inhibition activity on NIH3T3 cell proliferation.

Test Example 5. Determination of the Inhibition Effect of the Compounds of the Present Invention on Smad Signaling Pathway of TGFβRI The inhibition effect of the compounds of the present invention on Smad signaling pathway of TGFβRI was determined by the following in vitro test.

The inhibition effect of the compounds of the present invention on Smad signaling pathway of TGFβRI was determined by the following experimental method:

On a 96-well plate, 100 μL of HepG2 cell (TCHu 72, Cell Bank of Typical Culture Collection Committee of Chinese Academy of Sciences) was seeded on an EMEM medium containing 10% FBS (42360-099, Gibco) in each well. The seeding density is $2.5 \times 10^4$ cells/well. The cells were incubated overnight at 37° C., 5% $CO_2$. Each well was replaced with fresh EMEM medium containing 10% FBS. 0.1 g of 3TP-lux plasmid (11767, Biovector Science Lab, Inc.) was transfected in each well. The cells were further incubated for 24 hours at 37° C., 5% $CO_2$. Each well was replaced with 90 μL of EMEM medium containing 0.5% FBS, then the cells were starved for 6 hours. The compounds were formulated as a 20 mM stock solution, which was diluted in gradient to a 400× concentration with 100% DMSO, and further 40-fold diluted with EMEM containing 0.5% FBS. The cell culture plate was taken out, then 10 μl of diluted compound or control (0.25% DMSO) was added to each well respectively. The plate was shaken gently, then incubated for 18 hours in an incubator at 37° C., 5% $CO_2$. Finally, 100 μl of detection reagent ONE-Glo™ Luciferase Assay (E6110, Promega) was added to each well, and the plate was placed in dark at room temperature for 10 minutes. The chemiluminescence signal values were measured with a Victor 3.0 (PerkinElmer). The $IC_{50}$ values of the compounds were calculated using Graphpad Prism software based on each concentration of the compound and the corresponding signal value thereof.

The biological activity of the compounds of the present invention was determined by the above assay, and the calculated $IC_{50}$ values are shown in Table 5 below:

TABLE 5

$IC_{50}$ of the compounds of the present invention on the inhibition of Smad signaling pathway of TGFβRI

| Example No. | $IC_{50}$ (nM) |
|---|---|
| 1-1 | 36 |
| 1-2 | 15 |
| 2-1 | 21 |
| 3-1 | 19 |
| 4 | 86 |
| The compound with retention time of 4.058 minutes among 4-1 and 4-2 | 27 |
| The compound with retention time of 7.204 minutes among 4-1 and 4-2 | 60 |
| 5-1 | 75 |
| 6 | 21 |
| The compound with retention time of 3.747 minutes among 6-1 and 6-2 | 4 |
| The compound with retention time of 5.327 minutes among 6-1 and 6-2 | 3 |
| 7 | 6 |
| 9 | 82 |
| 10 | 23 |
| 11 | 26 |
| 12 | 33 |
| 13-1 | 37 |
| 14 | 81 |
| 17 | 96 |
| The compound with retention time of 9.196 minutes among 17-1 and 7-2 | 38 |
| The compound with retention time of 5.418 minutes among 17-1 and 7-2 | 71 |
| 18-1 | 88 |
| 5 | 39 |
| 3 | 58 |
| 20 | 53 |
| 26 | 86 |
| The compound with retention time of 6.631 minutes among 9-1 and 9-2 | 29 |
| The compound with retention time of 13.001 minutes among 9-1 and 9-2 | 94 |
| 3-2 | 31 |
| 1 | 57 |
| 32 | 8 |
| 33 | 87 |
| The compound with retention time of 7.153 minutes among 35-1 and 35-2 | 56 |
| The compound with retention time of 7.992 minutes among 35-1 and 35-2 | 87 |
| 36 | 18 |
| 37 | 61 |
| 38 | 11 |
| 39-1 | 24 |
| 40-1 | 18 |
| 42-1 | 31 |
| 2-2 | 36 |
| 43 | 11 |
| The compound with retention time of 2.955 minutes among 12-1 and 12-2 | 9 |
| The compound with retention time of 4.695 minutes among 12-1 and 12-2 | 13 |
| 45-1 | 32 |
| 46-1 | 79 |
| 47-1 | 53 |

Conclusion: The compounds of the present invention have a significant inhibition activity on Smad signaling pathway of TGFβRI.

Pharmacokinetics Evaluation

Test Example 6. Pharmacokinetics Assay of the Compounds of the Present Invention 1. Abstract Rats were used as test animals. The drug concentration in plasma at different time points was determined by LC/MS/MS method after intragastrical administration of the compounds of Examples 1-1, 1-2, 2-1, 3-1, the compound with retention time of 6.631 minutes among Examples 9-1 and 9-2, and the compounds of Examples 33 and 39-1 to rats. The pharmacokinetic behavior of the compounds of the present invention was studied and evaluated in rats.

2. Test Protocol 2.1 Test Compounds

Compounds of Examples 1-1, 1-2, 2-1, 3-1, compound with retention time of 6.631 minutes among Examples 9-1 and 9-2, and compounds of Examples 33 and 39-1.

2.2 Test Animals

Twenty-eight healthy adult Sprague-Dawley (SD) rats (half male and half female) were purchased from SINO-BRITISH SIPPR/BK LAB. ANIMAL LTD., CO, with Certificate No.: SCXK (Shanghai) 2008-0016, and equally divided into 7 groups (4 rats per group).

2.3 Preparation of the Test Compounds

A certain amount of the test compound was weighed, and added with 5% by volume of DMSO, 5% by volume of Tween 80, and 90% by volume of physiological saline were added to prepare a 0.2 mg/mL colorless, clear and transparent solution.

2.4 Administration

After an overnight fast, SD rats were administered intragastrically the test compounds at an administration dosage of 2.0 mg/kg and an administration volume of 10.0 mL/kg.

3. Process

The rats were intragastrically administered the compounds of Examples 1-1, 1-2, 2-1, 3-1, the compound with retention time of 6.631 minutes among Examples 9-1 and 9-2, and the compounds of Examples 33 and 39-1.0.2 mL of blood was taken from the orbital sinus before administration and at 0.5, 1.0, 2.0, 4.0, 6.0, 8.0, 11.0 and 24.0 hours after administration. The samples were stored in heparinized tubes, and centrifuged for 10 minutes at 4° C. at 3,500 rpm to separate the blood plasma. The plasma samples were stored at −20° C. The rats were fed 2 hours after administration.

The content of the test compounds in the plasma of rats after intragastrical administration of the test compounds at different concentrations was determined: 25 µL of rat plasma at each time after administration was taken, added with 50 µL (100 ng/mL) of the internal standard solution of camptothecin and 175 µL of acetonitrile, shaken vertically for 5 minutes, and centrifuged for 10 minutes (4000 rpm). 3.0 µL of the supernatant was taken from the plasma samples for LC/MS/MS analysis.

4. Results of Pharmacokinetic Parameters

TABLE 6

Pharmacokinetic parameters of the compounds of the present invention are shown below:

| No. | Pharmacokinetics assay (2 mg/kg) | | | | | |
| --- | --- | --- | --- | --- | --- | --- |
| | Plasma concentration Cmax (ng/mL) | Area under curve AUC (ng/mL * h) | Half-life T1/2 (h) | Residence time MRT (h) | Clearance CLz/F (ml/min/kg) | Apparent distribution volume Vz/F (ml/kg) |
| Example 1-1 | 208 ± 61 | 637 ± 355 | 3.42 ± 1.29 | 3.88 ± 0.26 | 68.6 ± 39.2 | 23535 ± 19401 |
| Example 1-2 | 146 ± 81 | 475 ± 267 | 1.92 ± 0.14 | 3.53 ± 0.93 | 89.2 ± 47.4 | 14618 ± 7627 |
| Example 2-1 | 351 ± 52 | 664 ± 93 | 1.77 ± 0.20 | 2.30 ± 0.37 | 50.8 ± 7.2 | 7798 ± 1331 |
| Example 3-1 | 502 ± 128 | 800 ± 208 | 0.868 ± 0.1 | 1.43 ± 0.06 | 43.4 ± 10.4 | 3302 ± 1098 |
| Compound with retention time of 6.631 minutes among Examples 9-1 and 9-2 | 386 ± 148 | 914 ± 410 | 2.39 ± 1.04 | 2.60 ± 0.60 | 43.1 ± 19.8 | 7675 ± 1629 |
| Example 33 | 178 ± 113 | 228 ± 159 | 0.973 ± 0.3 | 1.20 ± 0.35 | 193 ± 95 | 16437 ± 10679 |
| Example 39-1 | 317 ± 269 | 689 ± 609 | 2.06 ± 0.86 | 2.44 ± 1.16 | 121 ± 116 | 18271 ± 17417 |

Conclusion: The compounds of the present invention are well absorbed, and have a significant pharmacokinetic advantage.

What is claimed is:

1. A compound of formula (I):

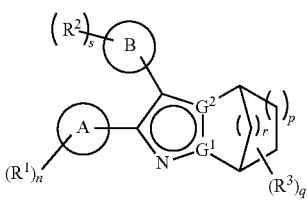

or a tautomer, mesomer, racemate, enantiomer, diastereomer thereof, or mixture thereof, or a pharmaceutically acceptable salt thereof, wherein:

$G^1$ and $G^2$ are each N or C, and when $G^1$ is N, $G^2$ is C; and when $G^1$ is C, $G^2$ is N;

ring A is aryl or heteroaryl;

ring B is selected from the group consisting of aryl, heteroaryl and heterocyclyl;

each $R^1$ is identical or different and each is independently selected from the group consisting of hydrogen, halogen, alkyl, alkoxy, haloalkyl, hydroxy, hydroxyalkyl, cyano, amino, nitro, cycloalkyl and heterocyclyl;

each $R^2$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, oxo, —$OR^4$, —$C(O)R^4$, —$C(O)OR^4$, —$NHC(O)OR^4$, —$O(CH_2)_xOR^4$, —$NH(CH_2)_xOR^4$, —$NR^5R^6$, —$O(CH_2)_xC(O)NR^5R^6$, —$NH(CH_2)_xNR^5R^6$ and —$C(O)NR^5R^6$, wherein the alkyl, alkoxy, cycloalkyl, heterocyclyl, aryl and heteroaryl are each independently optionally substituted by one or more substituents selected from the group consisting of hydrogen, alkyl, alkoxy, halogen, haloalkyl, hydroxy, hydroxyalkyl, cyano, amino, nitro, cycloalkyl, heterocyclyl, aryl, heteroaryl, —$OR^7$, —$C(O)R^7$, —$C(O)OR^7$, —$S(O)_mR^7$, —$S(O)_mNR^8R^9$, —$NR^8R^9$ and —$C(O)NR^8R^9$;

each $R^3$ is identical or different and each is independently selected from the group consisting of hydrogen, halogen, alkyl, alkoxy, haloalkyl, hydroxy, hydroxyalkyl, amino, cyano and nitro;

$R^4$ is selected from the group consisting of hydrogen, alkyl, haloalkyl, amino, alkenyl, alkynyl, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

$R^5$ and $R^6$ are each independently selected from the group consisting of hydrogen, alkyl, haloalkyl, alkoxy, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl, heteroaryl, —$NR^8R^9$, —$C(O)R^7$, —$C(O)OR^7$, —$S(O)_mNR^8R^9$ and —$S(O)_mR^7$;

$R^7$ is selected from the group consisting of hydrogen, alkyl, haloalkyl, hydroxyalkyl, amino, alkenyl, alkynyl, cycloalkyl, heterocyclyl, aryl and heteroaryl;

$R^8$ and $R^9$ are each independently selected from the group consisting of hydrogen, alkyl, haloalkyl, cycloalkyl, heterocyclyl, aryl and heteroaryl;

n is 0, 1 or 2;
s is 0, 1 or 2;
r is 1 or 2;
p is 0, 1 or 2;
q is 0, 1 or 2;
m is 0, 1 or 2; and
x is 0, 1, 2, 3 or 4.

2. The compound of formula (I) according to claim 1, wherein the compound is a compound of formula (II):

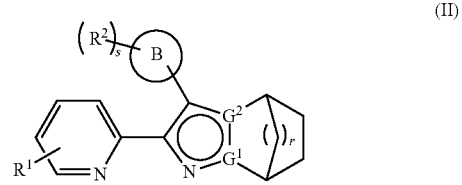

or a tautomer, mesomer, racemate, enantiomer, diastereomer thereof, or mixture thereof, or a pharmaceutically acceptable salt thereof, wherein:

ring B, $G^1$, $G^2$, $R^1$, $R^2$, s and r are as defined in claim 1.

3. The compound of formula (I) according to claim 1, wherein the compound is a compound of formula (II-1):

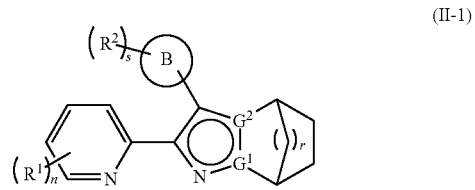

or a tautomer, mesomer, racemate, enantiomer, diastereomer thereof, or mixture thereof, or a pharmaceutically acceptable salt thereof, wherein:

ring B, $G^1$, $G^2$, $R^1$, $R^2$, s, n, and r are as defined in claim 1.

4. The compound of formula (I) according to claim 1, wherein $R^1$ is alkyl or halogen.

5. The compound of formula (I) according to claim 1, wherein ring B is selected from the group consisting of:

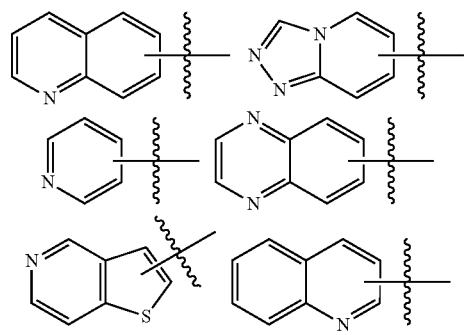

-continued

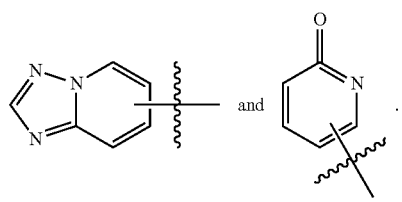 and

6. The compound of formula (I) according to claim 1, wherein the compound is a compound of formula (III) or (IV):

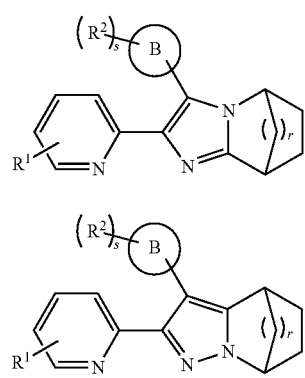

or a tautomer, mesomer, racemate, enantiomer, diastereomer thereof, or mixture thereof, or a pharmaceutically acceptable salt thereof, wherein:

ring B, $R^1$, $R^2$, s and r are as defined in claim 1.

7. The compound of formula (I) according to claim 1, wherein the compound is a compound of formula (V) or (VI):

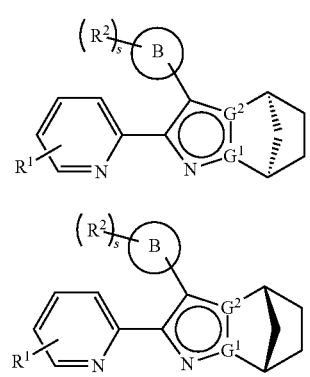

or a tautomer, mesomer, racemate, enantiomer, diastereomer thereof, or mixture thereof, or a pharmaceutically acceptable salt thereof, wherein:

ring B, $G^1$, $G^2$, $R^1$, $R^2$, and s are as defined in claim 1.

8. The compound of formula (I) according to claim 1, wherein the compound is a compound of formula (V-1):

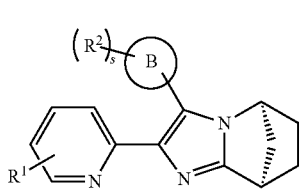

or a tautomer, mesomer, racemate, enantiomer, diastereomer thereof, or mixture thereof, or a pharmaceutically acceptable salt thereof, wherein:

ring B, $R^1$, $R^2$ and s are as defined in claim 1.

9. The compound of formula (I) according to claim 1, selected from the group consisting of:

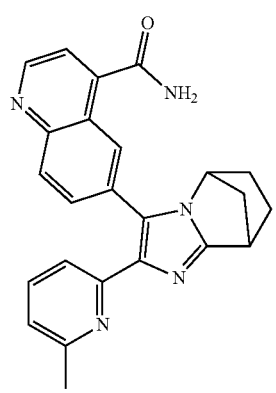

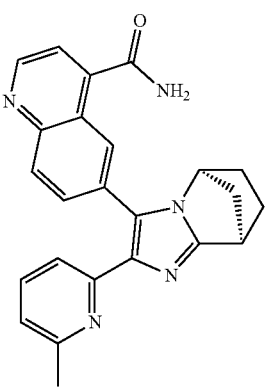

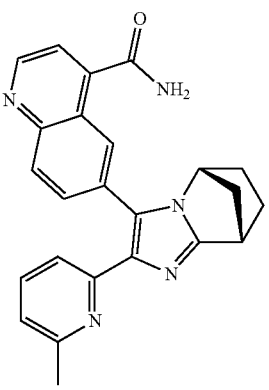

2
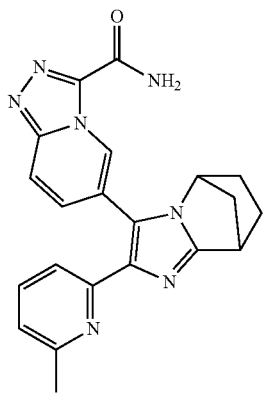
2
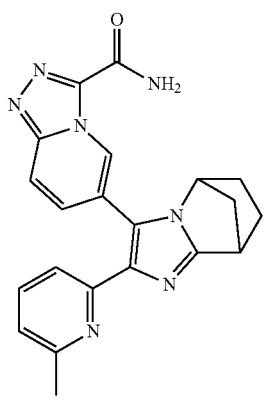
2-1
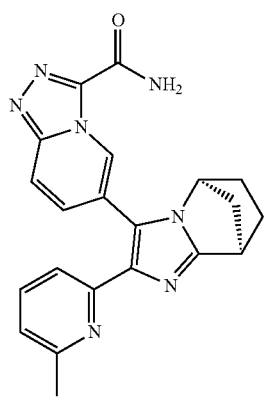
2-2
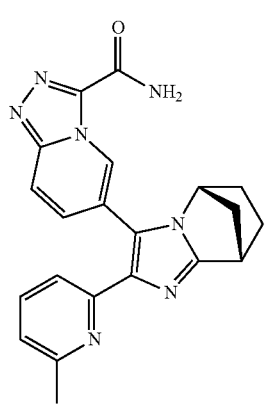
3
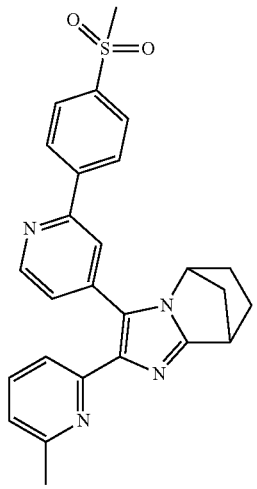
3-1
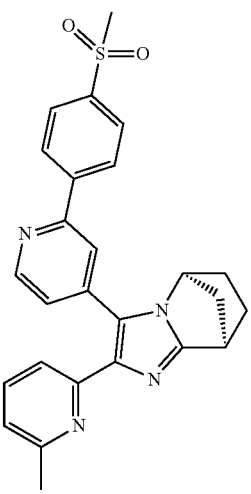
3-2
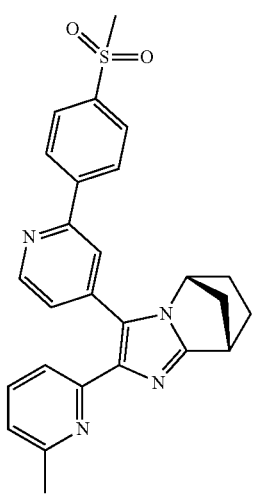

4
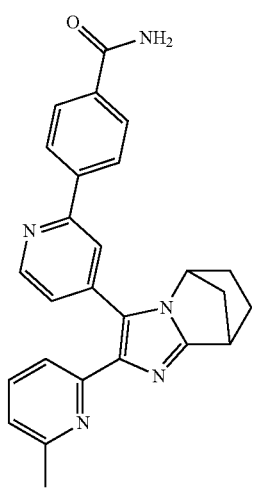
4-1
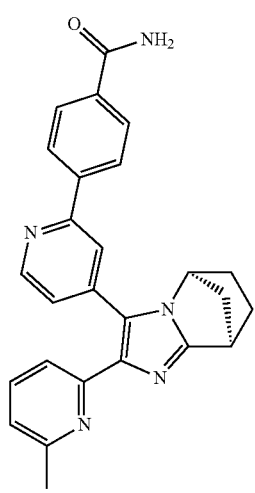
4-2
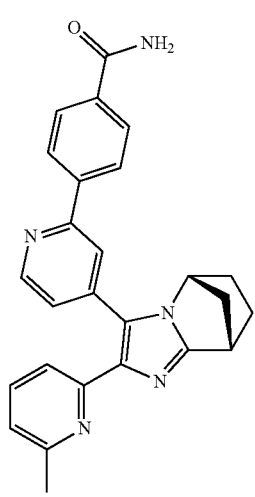
5
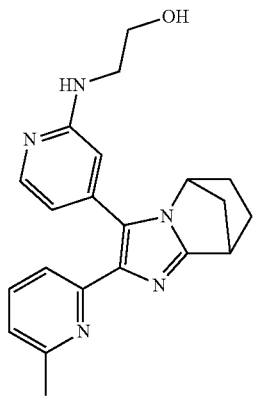
5-1
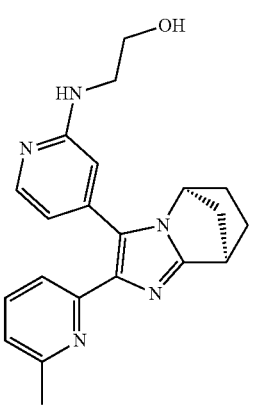
5-2
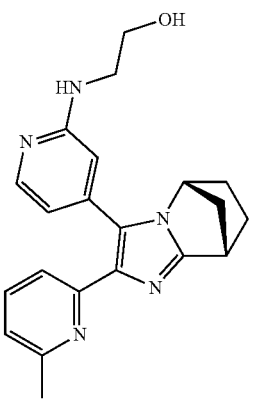
6
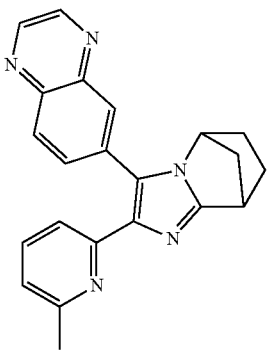

6-1
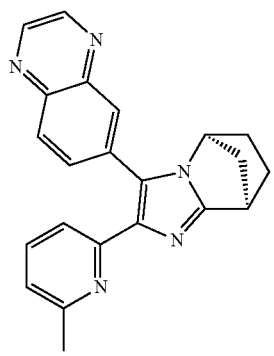
6-2
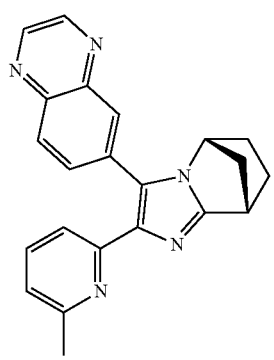
7
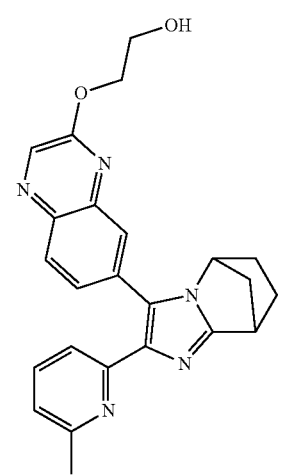
8
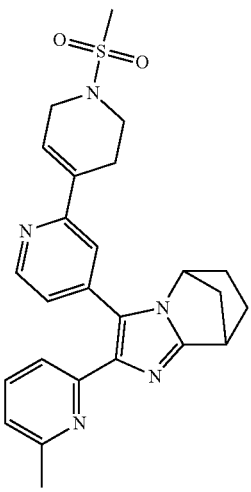
9
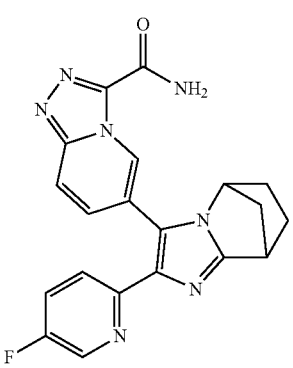
9-1
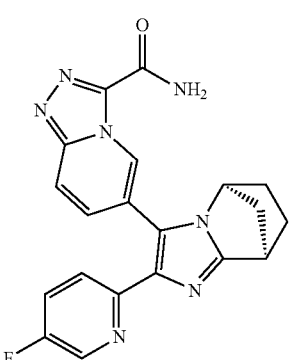
9-2
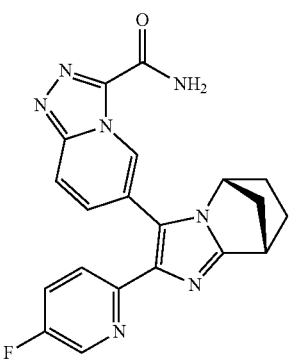

183
-continued
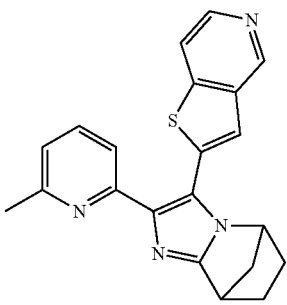
10
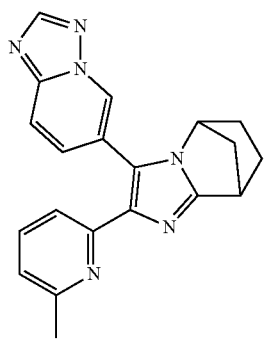
11
12
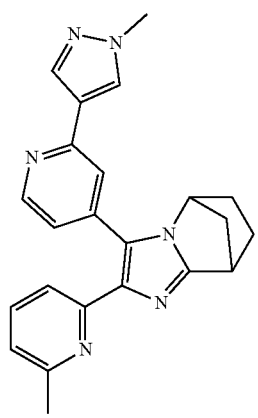
12-1
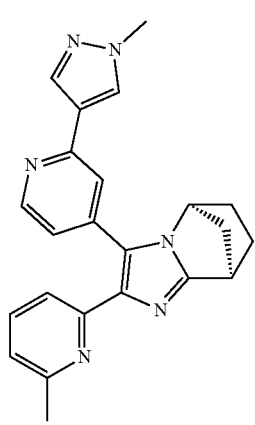
184
-continued
12-2
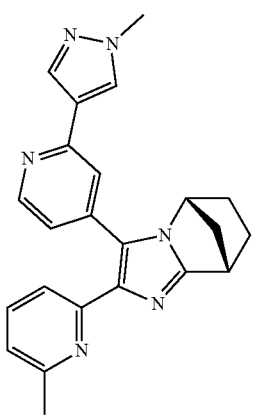
13
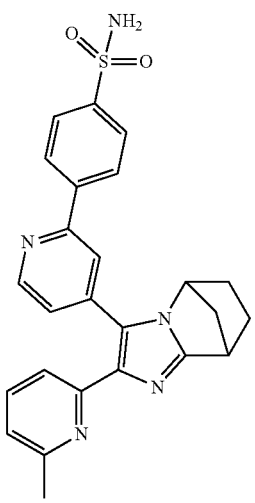
13-1
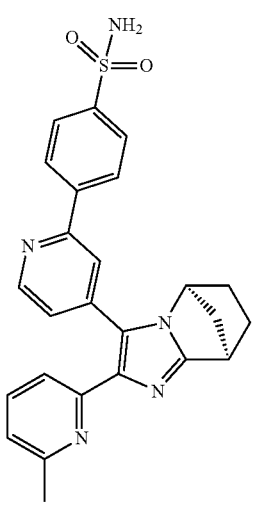

13-2
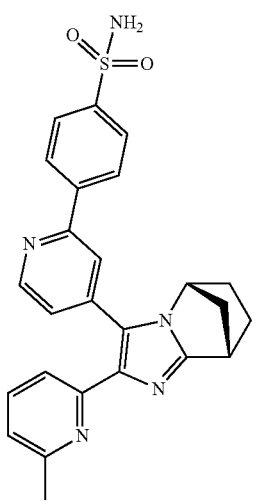
14
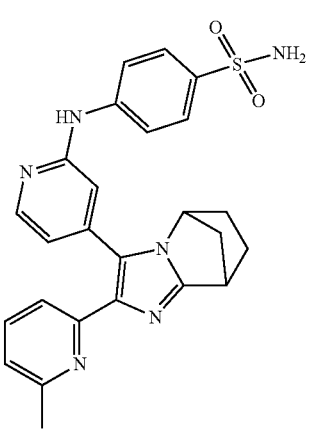
15
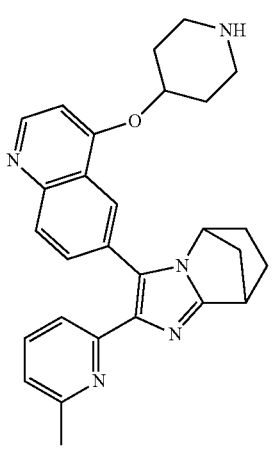
16
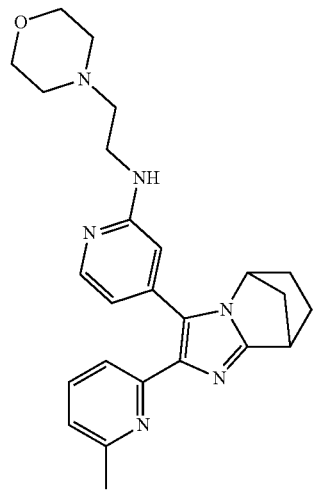
16-1
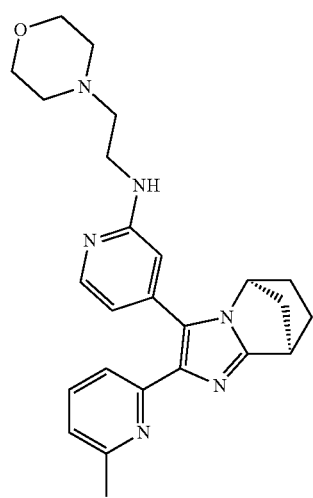
16-2
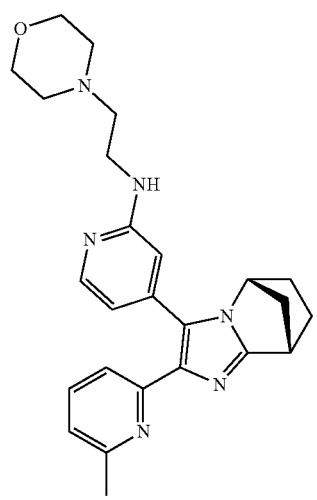

| 187 | 188 |
|---|---|
| -continued | -continued |
| 17 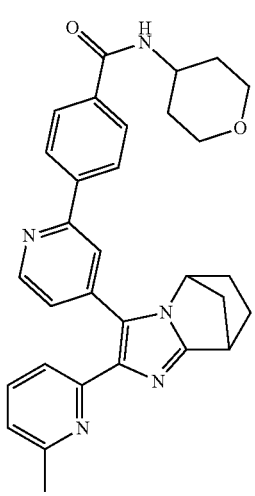 | 18 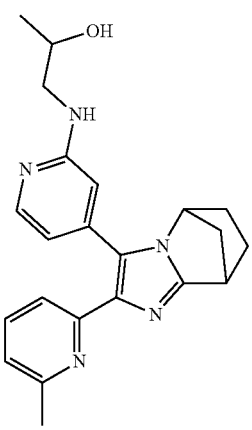 |
| 17-1 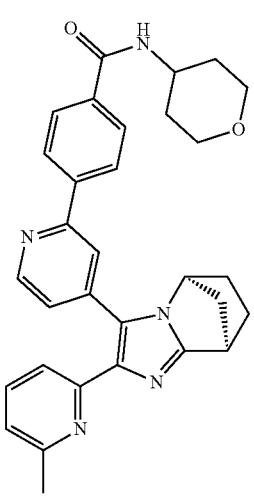 | 18-1 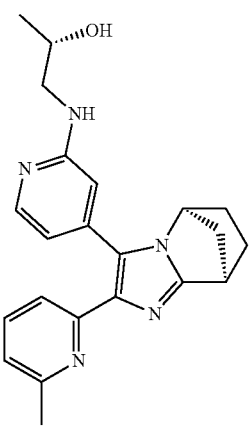 |
| 17-2 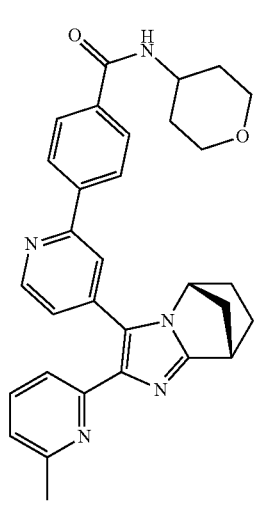 | 18-2 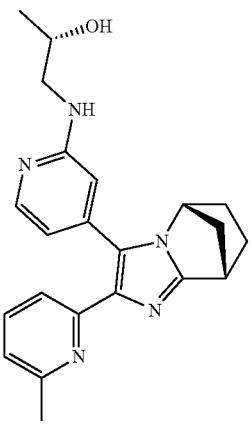 |

189
-continued
| | |
|---|---|
| 19 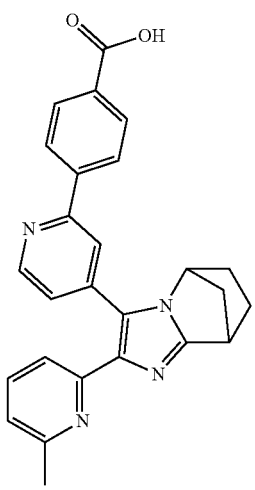 | |
| 20 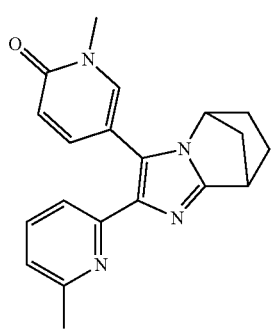 | |
| 21 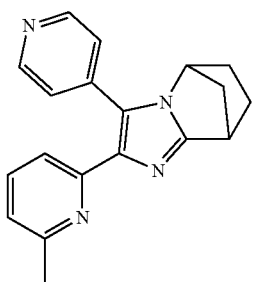 | |
| 22 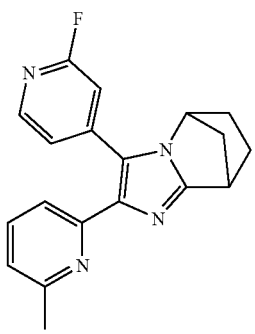 | |
190
-continued
| | |
|---|---|
| 23 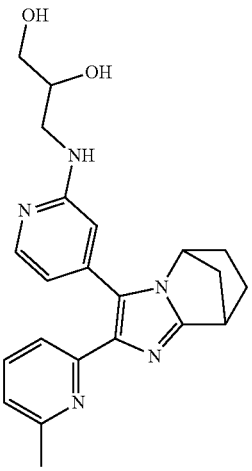 | |
| 23-1 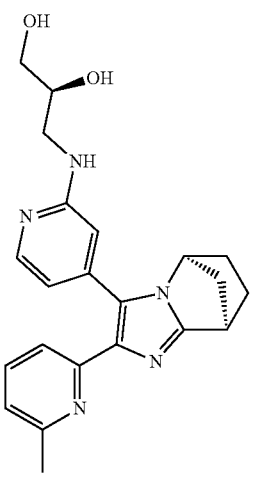 | |
| 23-2 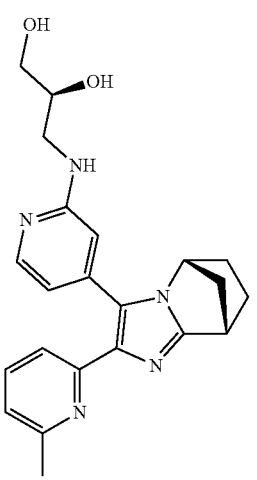 | |

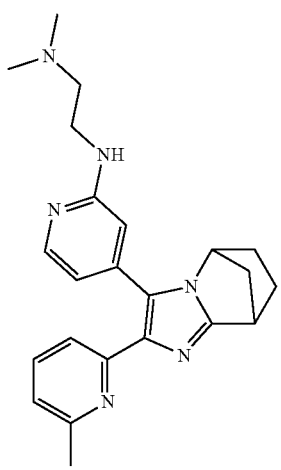
24
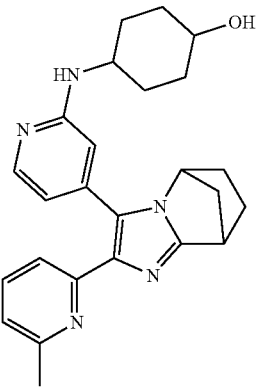
25
24-1
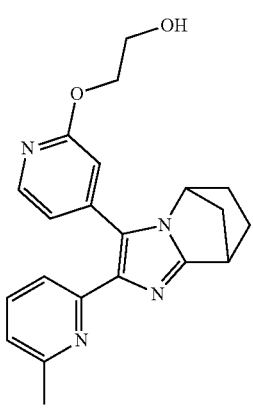
26
24-2
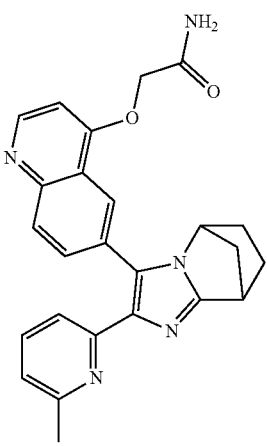
27
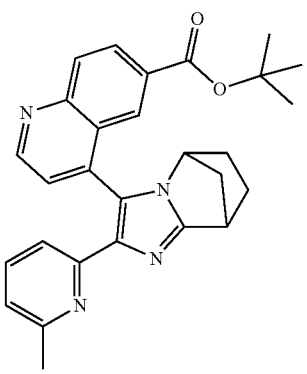
28

29
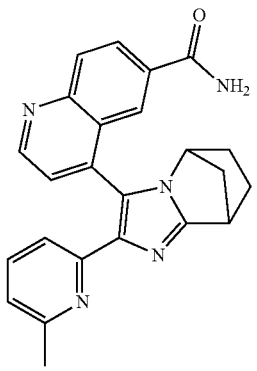
30
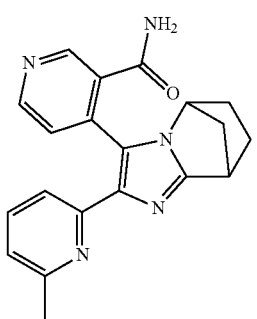
30-1
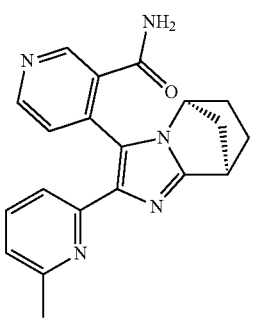
30-2
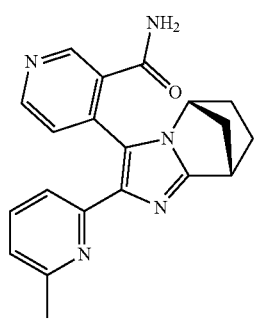
31
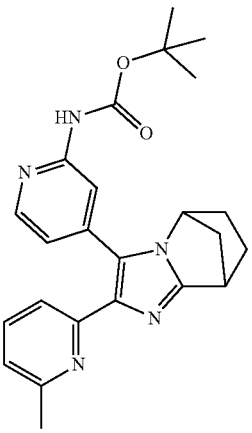
32
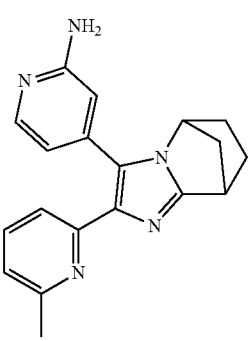
33
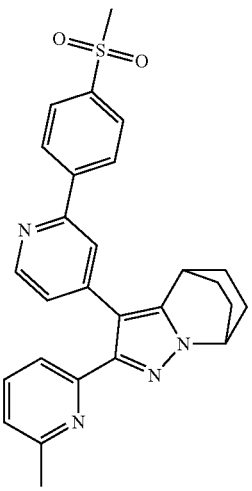
34
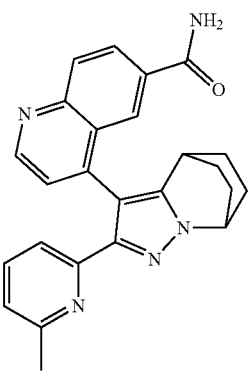

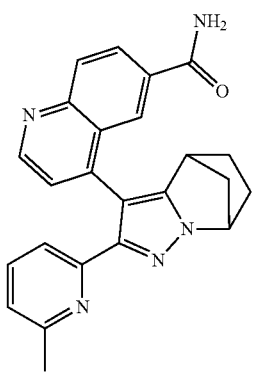
35
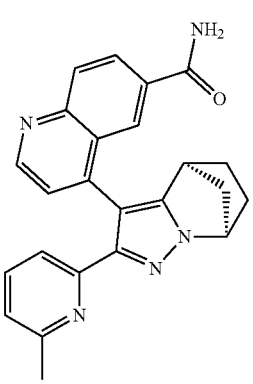
35-1
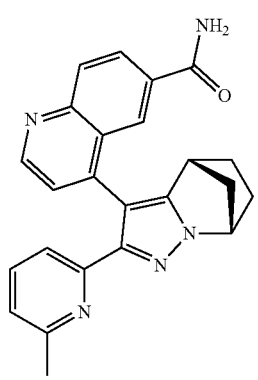
35-2
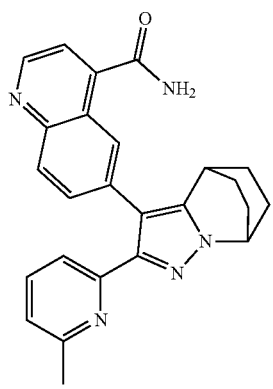
36
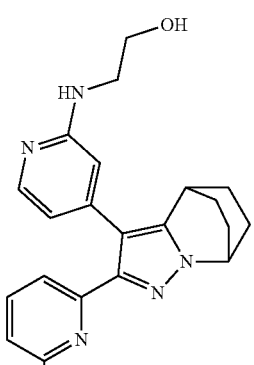
37
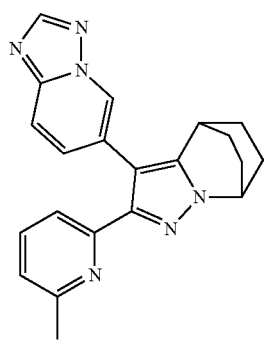
38
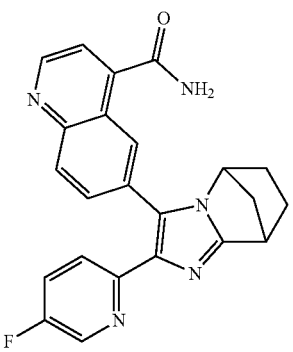
39
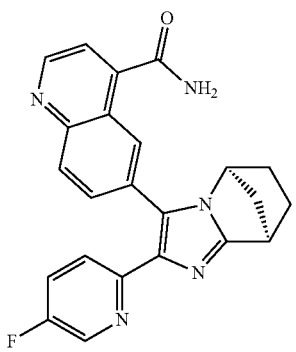
39-1

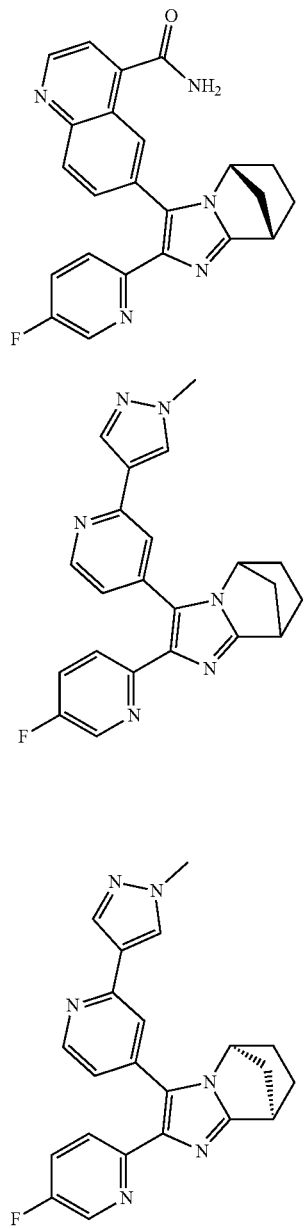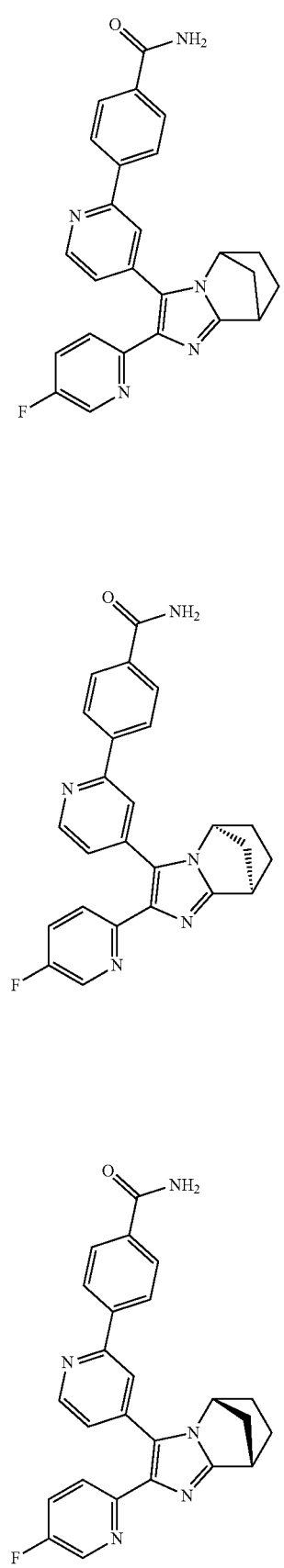

42
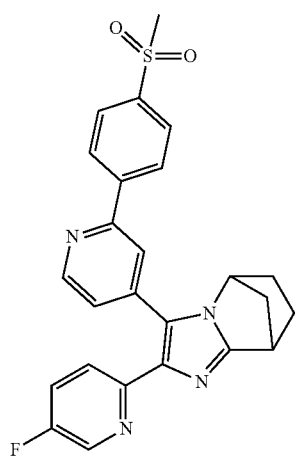
42-1
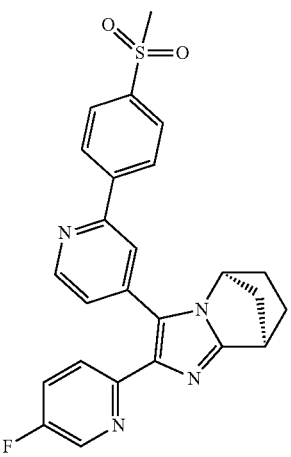
42-2
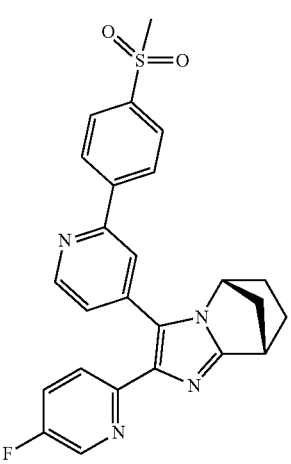
43
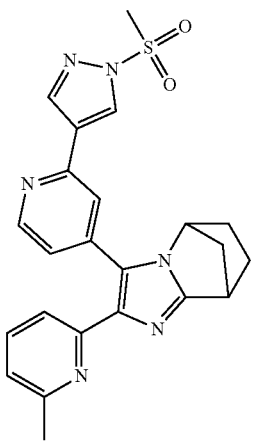
44
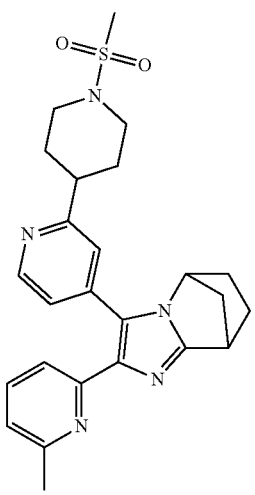
45
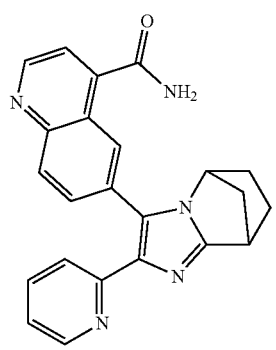
45-1
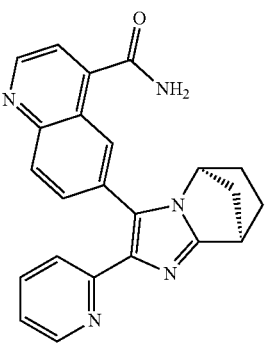

45-2
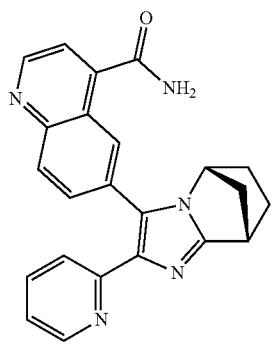
46
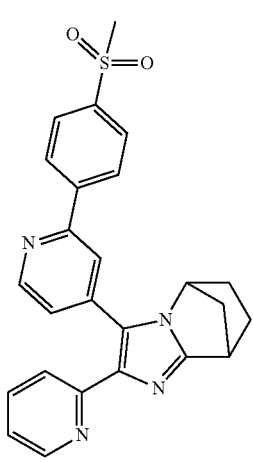
46-1
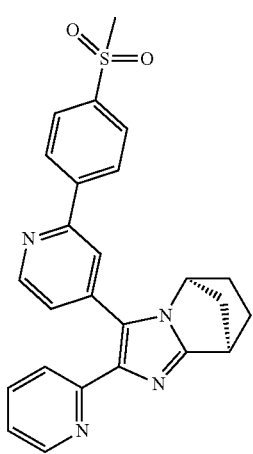
46-2
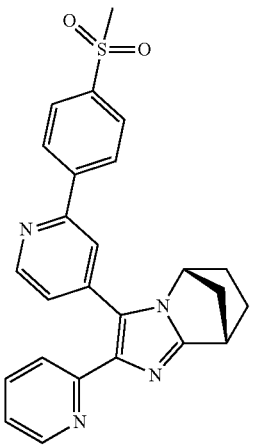
47
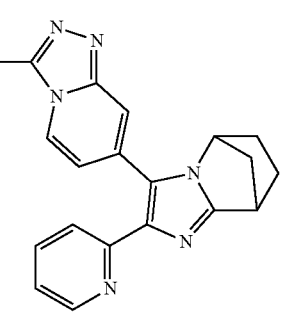
47-1
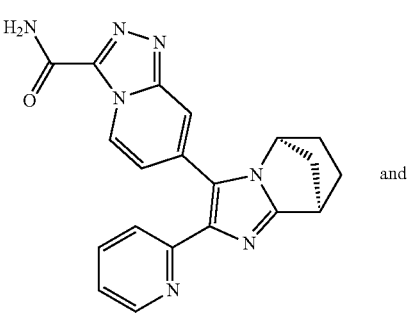
and
47-2
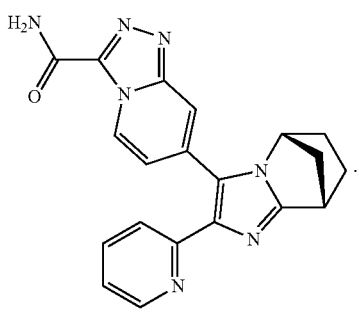

10. A compound of formula (I-B):

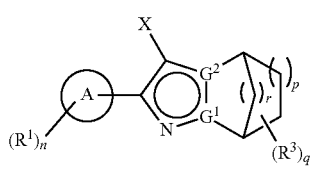
(I-B)

or a tautomer, mesomer, racemate, enantiomer, diastereomer thereof, or mixture thereof, or a pharmaceutically acceptable salt thereof, wherein:

X is halogen;

ring A, $G^1$, $G^2$, $R^1$, $R^3$, r, p, n and q are as defined in claim 1.

11. The compound of formula (I-B) according to claim 10, wherein the compound is a compound of formula (I-Bb):

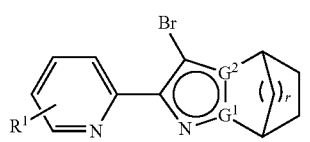
(I-Bb)

wherein:

$G^1$, $G^2$, $R^1$ and r are as defined in claim 10.

12. The compound of formula (I-B) according to claim 10, wherein the compound is a compound of formula (I-Bc):

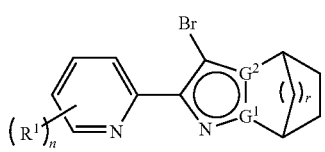
(I-Bc)

wherein:

$G^1$, $G^2$, $R^1$, n and r are as defined in claim 10.

13. The compound of formula (I-B) according to claim 10, selected from the group consisting of:

1f

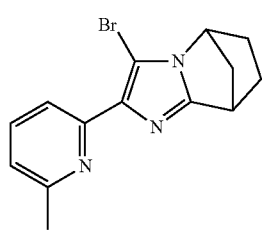

1f-1

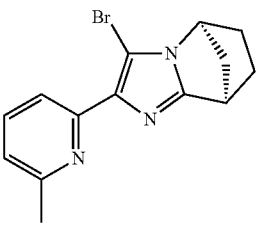

1f-2

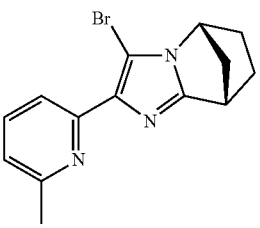

9d

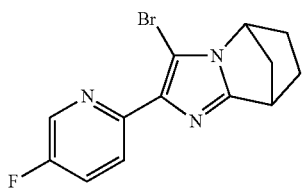

39c-1

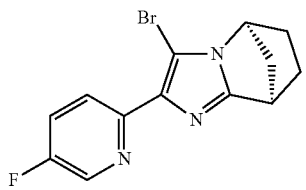

39c-2

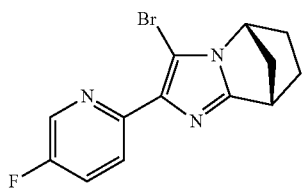

33i

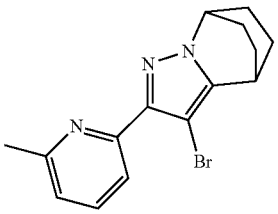

35e

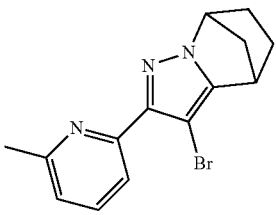

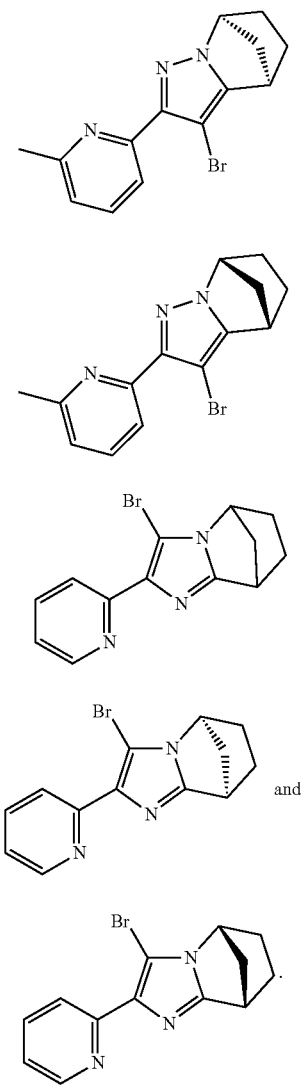

14. A method for preparing the compound of formula (I) according to claim 1, comprising a step of:

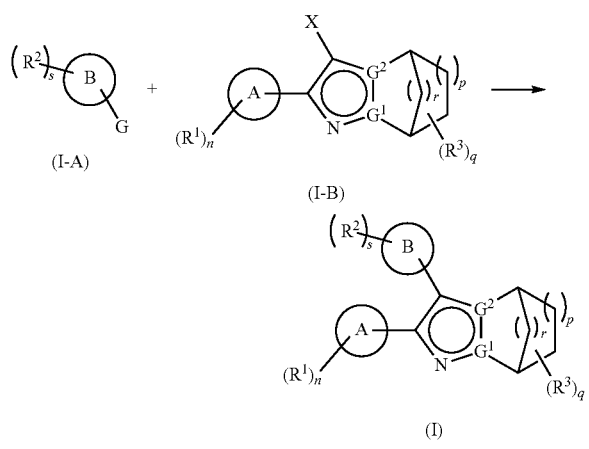

subjecting a compound of formula (I-A) and a compound of formula (I-B) to a Suzuki reaction under an alkaline condition in the presence of a catalyst to obtain the compound of formula (I), wherein:

G is selected from the group consisting of halogen,

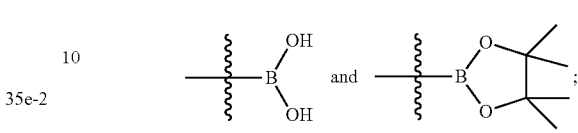

X is halogen;

ring A, ring B, $G^1$, $G^2$, $R^1 \sim R^3$, r, p, n, s and q are as defined in claim 1.

15. A pharmaceutical composition, comprising a therapeutically effective amount of the compound of formula (I), or a tautomer, mesomer, racemate, enantiomer, diastereomer thereof, or mixture thereof, or a pharmaceutically acceptable salt thereof according to claim 1, and one or more pharmaceutically acceptable carriers, diluents or excipients.

16. A method for treating or reducing tumor cell metastasis mediated by TGF-β overexpression, comprising administering to a patient in need thereof a therapeutically effective amount of the compound of formula (I), or a tautomer, mesomer, racemate, enantiomer, diastereomer thereof, or mixture thereof, or a pharmaceutically acceptable salt thereof according to claim 1.

17. A method for treating or reducing cancer mediated by TGF-β overexpression, comprising administering to a patient in need thereof a therapeutically effective amount of the compound of formula (I), or a tautomer, mesomer, racemate, enantiomer, diastereomer thereof, or mixture thereof, or a pharmaceutically acceptable salt thereof according to claim 1.

18. A method for treating or reducing a disease mediated by TGF-β overexpression selected from the group consisting of vascular injury, glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, cystic fibrosis, interstitial lung disease, acute lung injury, adult respiratory distress syndrome, myelodysplastic syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, intimal thickening, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, glaucoma, high intraocular pressure, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, radiation-induced fibrosis, thrombosis, tumor metastasis growth, multiple myeloma, melanoma, glioma, glioblastomas, leukemia, sarcomas, leiomyomas, mesothelioma, breast cancer, cervical cancer, lung cancer, stomach cancer, rectal cancer, colon cancer, pancreatic cancer, brain cancer, skin cancer, oral cancer, prostate cancer, bone cancer, kidney cancer, ovarian cancer, bladder cancer and liver cancer, comprising administering to a patient in need thereof a therapeutically effective amount of the compound of formula (I), or a tautomer, mesomer, racemate, enantiomer, diastereomer thereof, or mixture thereof, or a pharmaceutically acceptable salt thereof according to claim 1.

19. A method for treating or reducing tumor cell metastasis mediated by TGF-β overexpression, comprising administering to a patient in need thereof a therapeutically effective amount of the pharmaceutical composition according to claim 15.

20. A method for treating or reducing cancer mediated by TGF-β overexpression, comprising administering to a patient in need thereof a therapeutically effective amount of the pharmaceutical composition according to claim 15.

* * * * *